US010010535B2

(12) United States Patent
Bergeron, Jr.

(10) Patent No.: US 10,010,535 B2
(45) Date of Patent: Jul. 3, 2018

(54) DESFERRITHIOCIN ANALOGS AND USES THEREOF

(71) Applicant: University of Florida Research Foundation, Incorporated, Gainesville, FL (US)

(72) Inventor: Raymond J. Bergeron, Jr., Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 31 days.

(21) Appl. No.: 15/038,188

(22) PCT Filed: Nov. 21, 2014

(86) PCT No.: PCT/US2014/066965
§ 371 (c)(1),
(2) Date: May 20, 2016

(87) PCT Pub. No.: WO2015/077655
PCT Pub. Date: May 28, 2015

(65) Prior Publication Data
US 2016/0289223 A1    Oct. 6, 2016

Related U.S. Application Data
(60) Provisional application No. 61/907,913, filed on Nov. 22, 2013.

(51) Int. Cl.
*A61K 31/426* (2006.01)
*A61K 31/4439* (2006.01)
(Continued)

(52) U.S. Cl.
CPC ........ *A61K 31/426* (2013.01); *A61K 31/4439* (2013.01); *C07D 277/12* (2013.01); *C07D 417/04* (2013.01); *C07H 15/26* (2013.01)

(58) Field of Classification Search
CPC . A61K 31/4439; A61K 31/426; C07D 271/12
(Continued)

(56) References Cited

U.S. PATENT DOCUMENTS 3,274,207 A    9/1966   Kollonitsch
3,809,754 A    5/1974   Bertrand
(Continued)

FOREIGN PATENT DOCUMENTS

CA    2728636 A1    1/2010
DE    2245560 A1    3/1974
(Continued)

OTHER PUBLICATIONS

Bedford et al, "Iron Chelation in the Treatment of Cancer: A new role for Deferasirox?", Journal of Clinical Pharmacology (Jun. 2013), vol. 53(9), pp. 885-891.*
(Continued)

*Primary Examiner* — Craig D Ricci
*Assistant Examiner* — Janet L. Coppins
(74) *Attorney, Agent, or Firm* — Wolf, Greenfield & Sacks, P.C.

(57) ABSTRACT

Iron overload is associated with pathological conditions such as oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, and reperfusion injury. The present invention provides methods and pharmaceutical compositions using desferrithiocin analogs of Formulae (A) and (J) for treating and/or preventing these pathological conditions, metal (e.g., iron, aluminum, a lanthanide, or an actinide (e.g., uranium)) overload conditions, and infectious diseases (e.g., malaria).

36 Claims, 11 Drawing Sheets

(51) Int. Cl.
  *C07D 277/12* (2006.01)
  *C07D 417/04* (2006.01)
  *C07H 15/26* (2006.01)

(58) Field of Classification Search
  USPC .......................................... 514/365; 548/146
  See application file for complete search history.

(56) References Cited

U.S. PATENT DOCUMENTS

| | | | |
|---|---|---|---|
| 3,882,110 A | 5/1975 | Clemence et al. | |
| 4,367,233 A | 1/1983 | Clark et al. | |
| 4,406,905 A | 9/1983 | Zahner et al. | |
| 4,457,935 A | 7/1984 | Iwao et al. | |
| 4,457,936 A | 7/1984 | Draeger et al. | |
| 4,558,059 A | 12/1985 | Kawasaki et al. | |
| 4,775,675 A | 10/1988 | Gyorgydeak et al. | |
| 4,829,072 A | 5/1989 | Hamprecht et al. | |
| 4,902,700 A | 2/1990 | Hayasi et al. | |
| 4,914,208 A | 4/1990 | Jakob et al. | |
| 5,084,083 A | 1/1992 | Lewis et al. | |
| 5,106,992 A | 4/1992 | Magnin et al. | |
| 5,182,402 A | 1/1993 | Lewis et al. | |
| 5,192,781 A | 3/1993 | Bru-Magniez et al. | |
| 5,385,922 A | 1/1995 | Bron et al. | |
| 5,393,777 A | 2/1995 | Crosa | |
| 5,442,073 A | 8/1995 | Eicken et al. | |
| 5,614,520 A | 3/1997 | Kondo et al. | |
| 5,840,739 A | 11/1998 | Bergeron, Jr. | |
| 6,080,764 A | 6/2000 | Chihiro et al. | |
| 6,083,966 A | 7/2000 | Bergeron, Jr. | |
| 6,147,070 A | 11/2000 | Facchini | |
| 6,159,983 A | 12/2000 | Bergeron, Jr. | |
| 6,251,927 B1 | 6/2001 | Lai et al. | |
| 6,437,143 B2 | 8/2002 | Moinet et al. | |
| 6,521,652 B1 | 2/2003 | Bergeron | |
| 6,525,080 B1 | 2/2003 | Bergeron | |
| 6,559,315 B1 | 5/2003 | Bergeron | |
| 6,864,270 B2* | 3/2005 | Bergeron, Jr. | A61K 31/4164 514/365 |
| RE39,132 E | 6/2006 | Bergeron, Jr. | |
| 7,126,004 B2 | 10/2006 | Bergeron | |
| 7,144,904 B2* | 12/2006 | Bergeron, Jr. | A61K 31/4164 514/365 |
| 7,531,563 B2 | 5/2009 | Bergeron | |
| 7,879,886 B2* | 2/2011 | Bergeron, Jr. | A61K 31/4164 514/226.8 |
| 8,008,502 B2* | 8/2011 | Bergeron | C07D 277/12 548/146 |
| 8,063,227 B2 | 11/2011 | Tapper et al. | |
| 8,278,458 B2 | 10/2012 | Bergeron, Jr. | |
| 8,324,397 B2 | 12/2012 | Bergeron, Jr. | |
| 8,604,216 B2 | 12/2013 | Bergeron, Jr. | |
| 8,722,899 B2 | 5/2014 | Bergeron, Jr. | |
| 9,096,553 B2 | 8/2015 | Bergeron, Jr. | |
| 9,174,948 B2 | 11/2015 | Bergeron, Jr. | |
| 9,567,309 B2 | 2/2017 | Bergeron | |
| 2002/0049316 A1 | 4/2002 | Halbert et al. | |
| 2003/0083349 A1 | 5/2003 | Bergeron, Jr. | |
| 2003/0236417 A1 | 12/2003 | Bergeron | |
| 2004/0044220 A1 | 3/2004 | Bergeron, Jr. | |
| 2004/0132789 A1 | 7/2004 | Bergeron, Jr. | |
| 2005/0033057 A1 | 2/2005 | Bergeron | |
| 2005/0234113 A1 | 10/2005 | Bergeron, Jr. | |
| 2006/0211746 A1 | 9/2006 | Bergeron, Jr. | |
| 2006/0211773 A1 | 9/2006 | Bergeron, Jr. | |
| 2007/0238767 A1 | 10/2007 | Bergeron | |
| 2008/0096974 A2 | 4/2008 | Bergeron, Jr. | |
| 2008/0194518 A1 | 8/2008 | Mookerjee et al. | |
| 2008/0214630 A1 | 9/2008 | Bergeron | |
| 2008/0255081 A1 | 10/2008 | Bergeron, Jr. | |
| 2010/0093812 A1 | 4/2010 | Bergeron, Jr. | |
| 2010/0094016 A1 | 4/2010 | Bergeron | |
| 2010/0137346 A1 | 6/2010 | Bergeron, Jr. | |
| 2010/0137383 A1 | 6/2010 | Tapper et al. | |
| 2011/0053993 A1 | 3/2011 | McCall, Jr. et al. | |
| 2011/0275636 A1 | 11/2011 | Malecha | |
| 2012/0184586 A1 | 7/2012 | Bergeron, Jr. | |
| 2013/0030028 A1 | 1/2013 | Bergeron, Jr. | |
| 2013/0210870 A1 | 8/2013 | Bergeron, Jr. | |
| 2014/0235680 A1 | 8/2014 | Bergeron, Jr. | |
| 2014/0323534 A1 | 10/2014 | Bergeron, Jr. | |
| 2014/0343110 A1 | 11/2014 | Bergeron, Jr. | |
| 2015/0336911 A1 | 11/2015 | Bergeron, Jr. | |
| 2016/0022645 A1 | 1/2016 | Bergeron, Jr. | |
| 2017/0209420 A1 | 7/2017 | Bergeron | |
| 2017/0217912 A1 | 8/2017 | Bergeron | |

FOREIGN PATENT DOCUMENTS

| | | |
|---|---|---|
| DE | 3002989 A1 | 7/1981 |
| EP | 0 214 101 A2 | 3/1987 |
| EP | 0 214 933 A2 | 3/1987 |
| EP | 0 325 559 A2 | 7/1989 |
| EP | 0 513 379 A1 | 11/1992 |
| EP | 2062581 A1 | 5/2009 |
| FR | 2247243 A2 | 5/1975 |
| GB | 1292170 A | 10/1972 |
| GB | 1382887 A | 2/1975 |
| JP | 57-058682 A | 4/1982 |
| JP | 2008-536833 A | 9/2008 |
| JP | 5909473 B2 | 4/2016 |
| WO | WO 1994/011367 A1 | 5/1994 |
| WO | WO 1997/036885 | 10/1997 |
| WO | WO 1999/053039 A1 | 10/1999 |
| WO | WO 2000/012493 | 3/2000 |
| WO | WO 2000/016763 | 3/2000 |
| WO | WO 2001/027119 A2 | 4/2001 |
| WO | WO 2003/078467 A1 | 9/2003 |
| WO | WO 2004/017959 | 3/2004 |
| WO | WO 2005/023310 | 3/2005 |
| WO | WO 2005/034949 A1 | 4/2005 |
| WO | WO 2006/055412 A1 | 5/2006 |
| WO | WO 2006/107626 A1 | 10/2006 |
| WO | WO 2008/115433 | 9/2008 |
| WO | WO 2008/130395 | 10/2008 |
| WO | WO 2009/053628 A2 | 4/2009 |
| WO | WO 2010/009120 A2 | 1/2010 |
| WO | WO 2011/017054 A2 | 2/2011 |
| WO | WO 2011/028255 A2 | 3/2011 |
| WO | WO 2012/027794 A2 | 3/2012 |
| WO | WO 2013/090750 A1 | 6/2013 |
| WO | WO 2013/090766 A1 | 6/2013 |
| WO | WO 2014/134701 A1 | 9/2014 |

OTHER PUBLICATIONS

Bergeron et al, "Substituent Effects on Desferrithiocin and Desferrithiocin Analogue Iron-Clearing and Toxictiy Profiles," J. Med. Chem (2012), vol. 55, pp. 7090-7103.*
Budimir, Ana, "Metal ions, Azlheimer's disease and chelation therapy," Acta Pharm. (2011), vol. 61, pp. 1-14.*
Lui et al, "The Iron Chelator, Deferasirox, as a Novel Strategy for Cancer Treatment," Mol Pharmacol (2013), vol. 83, pp. 179-190.*
Mounsey and Teismann, "Chelators in the Treatment of Iron Accumulation in Parkinson's Diseases," International Journal of Cell Biology (2012), pp. 1-12.*
U.S. Appl. No. 15/428,232, filed Feb. 9, 2017, Bergeron, Jr.
U.S. Appl. No. 15/424,557, filed Feb. 3, 2017, Bergeron, Jr.
EP 16196408.5, dated Mar. 29, 2017, Extended European Search Report.
Extended European Search Report, dated Mar. 29, 2017, in connection with Application No. EP 14864521.1.
Extended European Search Report, dated Jan. 19, 2010, in connection with Application No. EP 07874513.0.
International Search Report and Written Opinion, dated Jan. 8, 2009, in connection with Application No. PCT/US2007/025377.
International Preliminary Report on Patentability, dated Jun. 23, 2009, in connection with Application No. PCT/US2007/025377.
Extended European Search Report, dated Dec. 27, 2010, in connection with Application No. EP 08742093.1.

(56) References Cited

OTHER PUBLICATIONS

International Search Report and Written Opinion, dated Jun. 19, 2008, in connection with Application No. PCT/US2008/003433.
International Preliminary Report on Patentability, dated Sep. 24, 2009, in connection with Application No. PCT/US2008/003433.
Extended European Search Report, dated Mar. 25, 2013, in connection with Application No. EP 10814064.1.
International Search Report and Written Opinion, dated May 23, 2011, in connection with Application No. PCT/US2010/002336.
International Preliminary Report on Patentability, dated Mar. 8, 2012, in connection with Application No. PCT/US2010/002336.
International Search Report and Written Opinion, dated Mar. 5, 2004, in connection with Application No. PCT/US2003/028304.
International Search Report and Written Opinion, dated Aug. 9, 2006, in connection with Application No. PCT/US2006/010945.
International Preliminary Report on Patentability, dated Oct. 18, 2007, in connection with Application No. PCT/US2006/010945.
Supplementary European Search Report, dated Dec. 5, 2001, in connection with Application No. EP 99945267.5.
International Search Report, dated Jan. 19, 2000, in connection with Application No. PCT/US1999/019691.
Written Opinion, dated Aug. 21, 2000, in connection with Application No. PCT/US1999/019691.
International Preliminary Examination Report, dated Feb. 2, 2001, in connection with Application No. PCT/US1999/019691.
International Search Report and Written Opinion, dated Apr. 19, 2013, in connection with Application No. PCT/US2012/069795.
International Preliminary Report on Patentability, dated Jun. 26, 2014, in connection with Application No. PCT/US2012/069795.
International Search Report and Written Opinion, dated Apr. 12, 2013, in connection with Application No. PCT/US2012/069826.
International Preliminary Report on Patentability, dated Jun. 26, 2014, in connection with Application No. PCT/US2012/069826.
European Search Report, dated Mar. 20, 2015, in connection with Application No. EP 12857135.3.
Extended European Search Report, dated Jul. 9, 2015, in connection with Application No. EP 12857135.3.
Invitation to Pay Additional Fees, dated Jan. 27, 2015, in connection with Application No. PCT/US2014/066961.
International Search Report and Written Opinion, dated Apr. 14, 2015, in connection with Application No. PCT/US2014/066961.
Invitation to Pay Additional Fees, dated Jan. 27, 2015, in connection with Application No. PCT/US2014/066965.
International Search Report and Written Opinion, dated Apr. 14, 2015, in connection with Application No. PCT/US2014/066965.
International Search Report and Written Opinion, dated Feb. 25, 2016, in connection with Application No. PCT/US2015/065985.
International Search Report and Written Opinion, dated Jun. 17, 2016, in connection with Application No. PCT/US2016/024239.
PubChem SID 241084044, Feb. 16, 2015.
[No Author Listed] Highlights of Prescribing Information: EXJADE. Novartis Pharma Stein AG. 2010. Available at http://www.pharma.us.novartis.com/product/pi/pdf/exjade.pdf. Last accessed Sep. 9, 2010. 14 pages.
[No Author Listed] "Ion exchanger." Ullmanns Encyclopedia of Industrial Chemistry. 5th Ed. vol. 14A:446-56.
[No Author Listed] Database CHEMCATS, Accession No. 2003:2524667; TimTec Overseas Stock; May 19, 2003.
[No Author Listed] Desferal. Product Information. Novartis Pharmaceuticals Corporation. East Hanover, NJ. 2011. Available at www.pharma.us.novartis.com/product/pi/pdf/desferal.pdf. Last accessed Jan. 25, 2013.
[No Author Listed], Closed head injury. Wikipedia. http://en.wikipedia.org/wiki/Close_head_injury [last accessed Nov. 28, 2011]. 7 pages.
[No Author Listed], Irritable bowel syndrome. Wikipedia. http://en.wikipedia.org/wiki/Irritable_bowel_syndrome [last accessed Nov. 28, 2011]. 24 pages.
[No Author Listed], Macular degeneration. Wikipedia. http://en.wikipedia.org/wiki/Macular_degeneration [last accessed Nov. 28, 2011]. 14 pages.
[No Author Listed], Reperfusion injury. Wikipedia. http://en.wikipedia.org/wiki/Reperfusion_injury [last accessed Nov. 28, 2011]. 7 pages.
[No Author Listed], Stroke. Wikipedia. http://en.wikipedia.org/wiki/Stroke [last accessed Nov. 28, 2011]. 29 pages.
Allgayer, Clinical relevance of oxygen radicals in inflammatory bowel disease—facts and fashion. Klin Wochenschr. Dec. 15, 1991;69(21-23):1001-3.
Al-Refaie et al., Zinc concentration in patients with iron overload receiving oral iron chelator 1,2-dimethyl-3-hydroxypyrid-4-one or desferrioxamine. J Clin Pathol. 1994;47:657-60.
Anderegg et al., Metal Complex Formation of a New Siderophore Desferrithiocin and of Three Related Ligands. J Chem Soc Chem Commun. 1990:1194-6.
Angelucci et al., Hepatic iron concentration and total body iron stores in thalassemia major. N Engl J Med. Aug. 3, 2000;343(5):327-31.
Babbs et al., Oxygen radicals in ulcerative colitis. Free Radic Biol Med. 1992;13(2):169-81.
Bartakke et al., Effect of Deferiprone on Urinary Zinc Excretion in Multiply Transfused Children with Thalassemia Major. Ind Ped. Feb. 17, 2005;42:150-4.
Berge et al., Pharmaceutical salts. J Pharm Sci. Jan. 1977;66(1):1-19.
Bergeron et al., (S)-4,5-dihydro-2-(2-hydroxy-4-hydroxyphenyl)-4-methyl-4-thiazolecarboxylic acid polyethers: a solution to nephrotoxicity. J Med Chem. May 4, 2006;49(9):2772-83.
Bergeron et al., A comparative evaluation of iron clearance models. Ann N Y Acad Sci. 1990;612:378-393.
Bergeron et al., A comparative study of the iron-clearing properties of desferrithiocin analogues with desferrioxamine B in a Cebus monkey model. Blood. Apr. 15, 1993;81(8):2166-73.
Bergeron et al., A comparison of the iron-clearing properties of 1,2-dimethyl-3-hydroxypyrid-4-one, 1,2-diethyl-3-hydroxypyrid-4-one, and deferoxamine. Blood. Apr. 1, 1992;79(7):1882-90.
Bergeron et al., An investigation of desferrithiocin metabolism. J Med Chem. Sep. 2, 1994;37(18):2889-95.
Bergeron et al., Comparison of iron chelator efficacy in iron-overloaded beagle dogs and monkeys (Cebus apella). Comp Med. Dec. 2004;54(6):664-72.
Bergeron et al., Desazadesmethyldesferrithiocin analogues as orally effective iron chelators. J Med Chem. Jan. 14, 1999;42(1):95-108.
Bergeron et al., Desferrithiocin analogue based hexacoordinate iron(III) chelators. J Med Chem. Jan. 2, 2003;46(1):16-24.
Bergeron et al., Desferrithiocin analogue iron chelators: iron clearing efficiency, tissue distribution, and renal toxicity. Biometals. Apr. 2011;24(2):239-58. Epub Nov. 20, 2010.
Bergeron et al., Desferrithiocin analogue uranium decorporation agents. Int J Radiat Biol. Apr. 2009;85(4):348-61.
Bergeron et al., Desferrithiocin analogues and nephrotoxicity. J Med Chem. Oct. 9, 2008;51(19):5993-6004. Epub Sep. 13, 2008.
Bergeron et al., Design, synthesis, and testing of non-nephrotoxic desazadesferrithiocin polyether analogues. J Med Chem. Jul. 10, 2008;51(13):3913-23. Epub Jun. 6, 2008.
Bergeron et al., Design, Synthesis, and Testing of Polyamine Vectored Iron Chelators. Synthesis (Stuttg). 2010;2010(21):3631-3636.
Bergeron et al., Effects of C-4 stereochemistry and C-4' hydroxylation on the iron clearing efficiency and toxicity of desferrithiocin analogues. J Med Chem. Jul. 1, 1999;42(13):2432-40.
Bergeron et al., Evaluation of desferrithiocin and its synthetic analogues as orally effective iron chelators. J Med Chem. Jul. 1991;34(7):2072-8.
Bergeron et al., Evaluation of the desferrithiocin pharmacophore as a vector for hydroxamates. J Med Chem. Jul. 29, 1999;42(15):2881-6.
Bergeron et al., HBED: A potential alternative to deferoxamine for iron-chelating therapy. Blood. Feb. 15, 1998;91(4):1446-52.

(56) References Cited

OTHER PUBLICATIONS

Bergeron et al., Impact of the 3,6,9-Trioxadecyloxy Group on Desazadesferrithiocin Analogue Iron Clearance and Organ Distribution. J Med Chem. 2007 Jul 12;50(14):3302-13. Epub Jun. 12, 2007.

Bergeron et al., Impact of the Lipophilicity of Desferrithiocin Analogues on Iron Clearance. Medicinal Inorg Chem. 2005:366-83.

Bergeron et al., Influence of iron on in vivo proliferation and lethality of L1210 cells. J Nutr. Mar. 1985;115(3):369-74.

Bergeron et al., Iron chelation promoted by desazadesferrithiocin analogs: An enantioselective barrier. Chirality. Aug. 2003;15(7):593-9.

Bergeron et al., Iron Chelators and Therapeutic Uses. In: Burger's Medicinal Chemistry, 6th ed. 2003:479-561.

Bergeron et al., Metabolism and pharmacokinetics of N1,N11-diethylnorspermine in a *Cebus apella* primate model. Cancer Res. Aug. 15, 2000;60(16):4433-9.

Bergeron et al., Metabolism and pharmacokinetics of N1,N14-diethylhomospermine. Drug Metab Dispos. Mar. 1996;24(3):334-43.

Bergeron et al., Methoxylation of desazadesferrithiocin analogues: enhanced iron clearing efficiency. J Med Chem. Apr. 10, 2003;46(8):1470-7.

Bergeron et al., Partition-variant desferrithiocin analogues: organ targeting and increased iron clearance. J Med Chem. Feb. 10, 2005;48(3):821-31.

Bergeron et al., Pharmacokinetics of orally administered desferrithiocin analogs in *Cebus apella* primates. Drug Metab Dispos. Dec. 1999;27(12):1496-8.

Bergeron et al., Polyamine-vectored iron chelators: the role of charge. J Med Chem. Jun. 16, 2005;48(12):4120-37.

Bergeron et al., Prevention of acetic acid-induced colitis by desferrithiocin analogs in a rat model. Dig Dis Sci. Feb. 2003;48(2):399-407.

Bergeron et al., Structure-activity relationships among desazadesferrithiocin analogues. In: Iron Chelation Therapy. Hershko, ed. 2002:167-84.

Bergeron et al., Substituent effects on desferrithiocin and desferrithiocin analogue iron-clearing and toxicity profiles. J Med Chem. Aug. 23, 2012;55(16):7090-103. doi: 10.1021/jm300509y. Epub Aug. 13, 2012.

Bergeron et al., Synthesis and biological evaluation of hydroxamate-based iron chelators. J Med Chem. Nov. 1991;34(11):3182-7.

Bergeron et al., Synthesis and biological evaluation of naphthyldesferrithiocin iron chelators. J Med Chem. Apr. 12, 1996;39(8):1575-81.

Bergeron et al., Synthesis of heterobactins A and B and Nocardia heterobactin. Tetrahedron. 2011:67(18):3163-69.

Bergeron et al., The desferrithiocin pharmacophore. J Med Chem. May 13, 1994;37(10):1411-7.

Bergeron et al., The design, synthesis, and evaluation of organ-specific iron chelators. J Med Chem. Nov. 30, 2006;49(24):7032-43.

Bergeron et al., The impact of polyether chain length on the iron clearing efficiency and physiochemical properties of desferrithiocin analogues. J Med Chem. Apr. 8, 2010;53(7):2843-53.

Bergeron et al., The origin of the differences in (R)- and (S)-desmethyldesferrithiocin. Iron-clearing properties. Ann N Y Acad Sci. Jun. 30, 1998;850:202-16.

Bergeron et al., Vibriobactin antibodies: a vaccine strategy. J Med Chem. Jun. 25, 2009;52(12):3801-13.

Bergeron, Desferrithiocin Polyether Analogue Uranium Decorporation Agents. Quad Chart and White Paper. Research Area #4 Radiological/Nuclear Threat Medical Countermeasures. BARDA CBRN BAA-11-100-SOL-00009. Oct. 27, 2011. 17 pages.

Bergeron, Iron: A controlling micronutrient in proliferative processes. Trends Biochem Sci. 1986;11:133-136.

Bickel et al., [Metabolic Properties of Actinomycetes.] Ferrioxamine B. Helv Chim Acta. 1960;43:2129-38. German.

Bierer et al., The effect of desferrithiocin, an oral iron chelator, on T-cell function. Blood. Nov. 15, 1990;76(10):2052-9.

Boddaert et al., Selective iron chelation in Friedreich ataxia: biologic and clinical implications. Blood. Jul. 1, 2007;110(1):401-8. Epub Mar. 22, 2007.

Bonkovsky et al., Iron-induced liver injury. Clin Liver Dis. May 2000;4(2):409-29, vi-vii.

Brittenham et al., Efficacy of deferoxamine in preventing complications of iron overload in patients with thalassemia major. N Engl J Med. Sep. 1, 1994;331(9):567-73.

Brittenham, Disorders of Iron Metabolism: Iron Deficiency and Overload. In: Hermatology: Basic Principles and Practice. 3d Ed. Hoffman et al., eds., Churchill Livingston. New York. 2000:397-428.

Brittenham, Iron chelators and iron toxicity. Alcohol. Jun. 2003;30(2):151-8.

Brittenham, Pyridoxal isonicotinoyl hydrazone. Effective iron chelation after oral administration. Ann N Y Acad Sci. 1990;612:315-26.

Brittenham, Pyridoxal isonicotinoyl hydrazone: an effective iron-chelator after oral administration. Semin Hematol. Apr. 1990;27(2):112-6.

Brunner et al., Carboplatin-containing Porphyrin-platinum Complexes as Cytotoxic and Phototoxic Antitumor Agents. Inorg Chim Acta. 2004;357:4423-51.

Byers et al., Microbial iron transport: iron acquisition by pathogenic microorganisms. Met Ions Biol Syst. 1998;35:37-66.

Cappellini, Iron-chelating therapy with the new oral agent ICL670 (Exjade). Best Pract Res Clin Haematol. Jun. 2005;18(2):289-98.

Cario, Insulin sensitivity and beta-cell secretion in thalassaemia major with secondary haemochromatosis: assessment by oral glucose tolerance test. Eur J Pediatr. Mar. 2003;162(3):139-46. Epub Jan. 15, 2003.

Cavaliere et al., The biofilm matrix destabilizers, EDTA and DNaseI, enhance the susceptibility of nontypeable Hemophilus influenzae biofilms to treatment with ampicillin and ciprofloxacin. Microbiologyopen. Aug. 2014;3(4):557-67. doi: 10.1002/mbo3.187. Epub Jul. 6, 2014.

Conrad et al., Iron absorption and transport. Am J Med Sci. Oct. 1999;318(4):213-29.

Cragg et al., The iron chelator L1 potentiates oxidative DNA damage in iron-loaded liver cells. Blood. Jul. 15, 1998;92(2):632-8.

Dean et al., The Action of Nine Chelators on Iron-Dependent Radical Damage. Free Rad Res. 1994;20(2):83-101.

Domingo et al., Comparative effects of the chelators sodium 4,5-dihydroxybenzene-1,3-disulfonate (Tiron) and diethylenetriaminepentaacetic acid (DTPA) on acute uranium nephrotoxicity in rats. Toxicology. Mar. 14, 1997;118(1):49-59.

Donovan et al., Preclinical and clinical development of deferitrin, a novel, orally available iron chelator. Ann N Y Acad Sci. 2005;1054:492-4.

Dunaief et al., Macular degeneration in a patient with aceruloplasminemia, a disease associated with retinal iron overload. Ophthalmology. Jun. 2005;112(6):1062-5.

Dunaief, Iron induced oxidative damage as a potential factor in age-related macular degeneration: the Cogan Lecture. Invest Ophthalmol Vis Sci. Nov. 2006;47(11):4660-4.

Durbin et al., Chelating agents for uranium(VI): 2. Efficacy and toxicity of tetradentate catecholate and hydroxypyridinonate ligands in mice. Health Phys. May 2000;78(5):511-21.

Durbin et al., In Vivo Chelation of Am(III), Pu(IV), Np(V), and U(VI) in Mice by TREN-(Me-3,2-HOPO). Radiat Prot Dosimetry. 1994;53:305-09.

Durbin, Lauriston S. Taylor Lecture: the quest for therapeutic actinide chelators. Health Phys. Nov. 2008;95(5):465-92.

Farkas et al., Structure-based differences between the metal ion selectivity of two siderophores desferrioxamine B (DFB) and desferricoprogen (DFC): Why DFC is much better Pb(II) sequestering agent than DFB? J Inorg Biochem. 2008;102;1654-9.

Fedorak et al., Misoprostol provides a colonic mucosal protective effect during acetic acid-induced colitis in rats. Gastroenterology. Mar. 1990;98(3):615-25.

Finch et al., Ferrokinetics in man. Medicine (Baltimore). Jan. 1970;49(1):17-53.

(56) References Cited

OTHER PUBLICATIONS

Finch et al., Iron metabolism. Clin Physiol Biochem. 1986;4(1):5-10.
Finch et al., Perspectives in iron metabolism. N Engl J Med. Jun. 24, 1982;306(25):1520-8.
Fritsch et al., Plasmodium falciparum: inhibition in vitro with lactoferrin, desferriferrithiocin, and desferricrocin. Exp Parasitol. Feb. 1987;63(1):1-9.
Fukuda, Chelating agents used for plutonium and uranium removal in radiation emergency medicine. Curr Med Chem. 2005;12(23):2765-70.
Galanello et al., A dose escalation study of the pharmacokinetics, safety & efficacy of deferitrin, an oral iron chelator in beta thalassaemia patients. ASH Annu Meet Abstr. 2007;110: Abstract 2669.
Galanello et al., Safety, tolerability, and pharmacokinetics of ICL670, a new orally active iron-chelating agent in patients with transfusion-dependent iron overload due to beta-thalassemia. J Clin Pharmacol. Jun. 2003;43(6):565-72.
Galey et al., N,N'-bis-(3,4,5-trimethoxybenzyl) ethylenediamine N,N'-diacetic acid as a new iron chelator with potential medicinal applications against oxidative stress. Biochem Pharmacol. Jan. 26, 1996;51(2):103-15.
Gershon et al., Antifungal activity of 5-, 7-, and 5,7-substituted 2-methyl-8-quinolinols. Antimicrob Agents Chemother. May 1972;1(5):373-5.
Giardina et al., Chelation therapy in beta-thalassemia: an optimistic update. Semin Hematol. Oct. 2001;38(4):360-6.
Gorden et al., Rational design of sequestering agents for plutonium and other actinides. Chem Rev. Nov. 2003;103(11):4207-82.
Grady et al., HBED: a potential oral iron chelator. Ann N Y Acad Sci. 1990;612:361-8.
Grady et al., Rhodotorulic acid—investigation of its potential as an iron-chelating drug. J Pharmacol Exp Ther. Jun. 1979;209(3):342-8.
Graf et al., Iron-catalyzed hydroxyl radical formation. Stringent requirement for free iron coordination site. J Biol Chem. Mar. 25, 1984;259(6):3620-4.
Grishman et al., Neutrophil-mediated mucosal injury. Role of reactive oxygen metabolites. Dig Dis Sci. Mar. 1988;33(3 Suppl):6S-15S.
Guilmette et al., Competitive binding of Pu and Am with bone mineral and novel chelating agents. Radiat Prot Dosimetry. 2003;105(1-4):527-34.
Guterman et al., Feasibility of enterochelin as an iron-chelating drug: studies with human serum and a mouse model system. Gen Pharmacol. 1978;9(2):123-7.
Hadziahmetovic et al., The oral iron chelator deferiprone protects against iron overload-induced retinal degeneration. Invest Ophthalmol Vis Sci. Feb. 16, 2011;52(2):959-68. doi: 10.1167/iovs.10-6207.
Hahn et al., Coordination Chemistry of Microbial Iron Transport. 42. Structural and Spectroscopic Characterization of Diastereomeric Cr(III) and Co(III) Complexes of Desferriferrithiocin. J Am Chem Soc. 1990;112:1854-60.
Hallberg, Bioavailability of dietary iron in man. Ann Rev Nutr. 1981;1:123-47.
Halliwell, Free radicals and antioxidants: a personal view. Nutr Rev. Aug. 1994;52(8 Pt 1):253-65.
Halliwell, Iron, Oxidative Damage and Chelating Agents. In: The Development of Iron Chelators for Clinical Use, Bergeron, ed. 1994:33-56.
Henry, Chemotherapeutic nitroheterocycles. Derivatives of 5-nitrothiazole-2-carboxaldehyde and 5-nitrothiazole-2-carboxylic acid. J Med Chem. Mar. 1969;12(2):303-6.
Hoffbrand et al., Long-term trial of deferiprone in 51 transfusion-dependent iron overloaded patients. Blood. Jan. 1, 1998;91(1):295-300.
Hoffbrand, Transfusion Siderosis and Chelation Therapy. Iron in Biochemistry and Medicine. vol. II. London. 1980: 449-527.
Horackova et al., The antioxidant effects of a novel iron chelator salicylaldehyde isonicotinoyl hydrazone in the prevention of $H_2O_2$ injury in adult cardiomyocytes. Cardiovasc Res. Aug. 18, 2000;47(3):529-36.
Hua et al., Long-term effects of experimental intracerebral hemorrhage: the role of iron. J Neurosurg. Feb. 2006;104(2):305-12.
Iranmanesh et al., Chelation of chromium(VI) by combining deferasirox and deferiprone in rats. Biometals. 2013;26:465-71.
Jalal et al., Structure of Anguibactin, a Unique Plasmid-Related Bacterial Siderophore from the Fish Pathogen Vibrio Anguillarum. J Am Chem Soc. 1989;111(1):292-96.
Jarvis et al., Some correlations involving the stability of complexes of transuranium metal ions and ligands with negatively charged oxygen donors. Inorg Chim Acta. 1991;182:229-32.
Kalinowski et al., The evolution of iron chelators for the treatment of iron overload disease and cancer. Pharmacol Rev. Dec. 2005;57(4):547-83.
Kersten et al., Long-term treatment of transfusional iron overload with the oral iron chelator deferiprone (L1): a Dutch multicenter trial. Ann Hematol. Nov. 1996;73(5):247-52.
Kicic et al., The desferrithiocin (DFT) class of iron chelators: potential as antineoplastic agents. Anticancer Drug Des. Aug.-Oct. 2001;16(4-5):195-207.
Kishore et al., Synthesis of α-Poly-[Nε-2-aryl-Δ2-thiazoline-4-carbonyl-L-lysine] with Antival Activity. Ind J Chem. 1977;15B:255-57.
Kitazawa et al., Reduction of ultraviolet light-induced oxidative stress by amino acid-based iron chelators. Biochim Biophys Acta. Dec. 27, 1999;1473(2-3):400-8.
Kontoghiorghes et al., 1,2-Dimethyl-3-hydroxypyrid-4-one, an orally active chelator for treatment of iron overload. Lancet. Jun. 6, 1987;1(8545):1294-5.
Kontoghiorghes, New Concepts of Iron and Aluminium Chelation Therapy With Oral L1 (Deferiprone) and Other Chelators. Analyst. Mar. 1995;120:845-51.
Koppenol, Kinetics and mechanism of the fenton reaction: implications for iron toxicity, Iron Chelators: New Development Strategies, Badman et al., Eds.; Saratoga, Ponte Vedra Beach, FL, 2000;3-10.
Langer et al., Solid complexes with tetravalent metal ions and ethylenediamime tetra-acetic acid (EDTA). J Inorg Nucl Chem. 1964;26:59-72.
Levien et al., Pentetate Calcium Trisodium (Ca-DTPA) and Pentetate Zinc Trisodium (Zn-DTPA). Formulary Drug Reviews. 2005;40:65-71.
Lieu et al., The roles of iron in health and disease. Mol Aspects Med. Feb.-Apr. 2001;22(1-2):1-87.
Liu et al., Nanoparticle and iron chelators as a potential novel Alzheimer therapy. Methods Mol Biol. 2010;610:123-44. doi: 10.1007/978-1-60327-029-8_8.
Lovejoy et al., Iron chelators as anti-neoplastic agents: current developments and promise of the PIH class of chelators. Curr Med Chem. Jun. 2003;10(12):1035-49.
MacPherson et al., Experimental production of diffuse colitis in rats. Digestion. 1978;17(2):135-50.
Malcovati, Impact of transfusion dependency and secondary iron overload on the survival of patients with myelodysplastic syndromes. Leuk Res. Dec. 2007;31 Suppl 3:S2-6.
Malluche et al., The Use of Deferoxamine in the Management of Aluminum Accumulation in Bone in Patients with Renal Failure. N Engl J Med. Jul. 19, 1984;311(3):140-4.
Millan et al., Biological signatures of brain damage associated with high serum ferritin levels in patients with acute ischemic stroke and thrombolytic treatment. Dis Markers. 2008;25(3):181-8.
Miller et al., Efficacy of orally administered amphipathic polyaminocarboxylic acid chelators for the removal of plutonium and americium: comparison with injected Zn-DTPA in the rat. Radiat Prot Dosimetry. 2006;118(4):412-20. Epub Dec. 6, 2005.
Molina-Jijón et al., Deferoxamine pretreatment prevents Cr(VI)-induced nephrotoxicity and oxidant stress: Role of Cr(VI) chelation. Toxicol. 2012;291:93-101.
Moreau-Marquis et al., Tobramycin and FDA-approved iron chelators eliminate Pseudomonas aeruginosa biofilms on cystic fibrosis

(56) References Cited

OTHER PUBLICATIONS cells. Am J Respir Cell Mol Biol. Sep. 2009;41(3):305-13. doi: 10.1165/rcmb.2008-0299OC. Epub Jan. 23, 2009.

Naegeli et al., Metabolites of Microorganisms. Part 193. Ferrithiocin. Helv Chim Acta. 1980;63:1400-06. German.

Nash et al., Features of the thermodynamics of two-phase distribution reactions of americium(III) and europium(III) nitrates into solutions of 2,6-bis[(bis(2-ethylhexyl)phosphino)methyl]pyridine N,P,P'-trioxide. Inorg Chem. Nov. 4, 2002;41(22):5849-58.

Neu et al., Structural Characterization of a Plutonium(IV) Siderophore Complex: Single-Crystal Structure of Pu-Desferrioxamine E. Angew Chem Int Ed Engl. Apr. 2000;39(8):1442-1444.

Nisbet-Brown et al., Effectiveness and safety of ICL670 in iron-loaded patients with thalassaemia: a randomised, double-blind, placebo-controlled, dose-escalation trial. Lancet. May 10, 2003;361(9369):1597-602.

O'Connell et al., The role of iron in ferritin- and haemosiderin-mediated lipid peroxidation in liposomes. Biochem J. Jul. 1, 1985;229(1):135-9.

Olivieri et al., Iron-chelating therapy and the treatment of thalassemia. Blood. Feb. 1, 1997;89(3):739-61.

Olivieri et al., Long-term safety and effectiveness of iron-chelation therapy with deferiprone for thalassemia major. N Engl J Med. Aug. 13, 1998;339(7):417-23.

Olivieri, Long-term therapy with deferiprone. Acta Haematol. 1996;95(1):37-48.

Olivieri, Progression of iron overload in sickle cell disease. Semin Hematol. Jan. 2001;38(1 Suppl 1):57-62.

Panter et al., Dextran-Coupled Deferoxamine Improves Outcome in a Murine Model of Head Injury. J Neurotrauma. 1992;9(1):47-53.

Paquet et al., Efficacy of 3,4,3-LI(1,2-HOPO) for decorporation of Pu, Am and U from rats injected intramuscularly with high-fired particles of MOX. Radiat Prot Dosimetry. 2003;105(1-4):521-5.

Pashalidis et al., Effective complex formation in the interaction of 1,2-dimethyl-3-hydroxypyrid-4-one (Deferiprone or L1) with uranium (VI). J Radioanal Nucl Chem. 1999;242:181-84.

Pietrangelo, Iron chelation beyond transfusion iron overload. Am J Hematol. Dec. 2007;82(12 Suppl):1142-6.

Pietrangelo, Mechanism of iron toxicity. In: Iron Chelation Therapy. Hershko, ed. 2002:19-43.

Pippard et al., Iron chelation using subcutaneous infusions of diethylene triamine penta-acetic acid (DTPA). Scand J Haematol. May 1986;36(5):466-72.

Pippard, Desferrioxamine-induced iron excretion in humans. Baillieres Clin Haematol. Apr. 1989;2(2):323-43.

Pippard, Iron overload and iron chelation therapy in thalassaemia and sickle cell haemoglobinopathies. Acta Haematol. 1987;78(2-3):206-11.

Ponka et al., Function and regulation of transferrin and ferritin. Semin Hematol. Jan. 1998;35(1):35-54.

Ponka et al., Mobilization of iron from reticulocytes. Identification of pyridoxal isonicotinoyl hydrazone as a new iron chelating agent. FEBS Lett. Jan. 15, 1979;97(2):317-21.

Rao et al., Complexation of Thorium(IV) with Desmethyldesferrithiocin. Radiochim Acta. 2000;88:851-56.

Raymond et al., Coordination Chemistry and Microbial Iron Transport. Acc Chem Res. 1979;12:183-190.

Re et al., Antioxidant activity applying an improved ABTS radical cation decolorization assay. Free Radic Biol Med. May 1999;26(9-10):1231-7.

Richardson et al., Development of potential iron chelators for the treatment of Friedreich's ataxia: ligands that mobilize mitochondrial iron. Biochim Biophys Acta. May 31, 2001;1536(2-3):133-40.

Richardson, The controversial role of deferiprone in the treatment of thalassemia. J Lab Clin Med. May 2001;137(5):324-9.

Saljooghi et al., Clinical evaluation of Deferasirox for removal of cadmium ions in rat. Biometals. 2010;23:707-12.

Saljooghi, Chelation of aluminum by combining deferasirox and deferiprone in rats. Toxicol Ind Health. 2012;28(8):740-5.

Santos et al., A cyclohexane-1, 2-diyldinitrilotetraacetate tetrahydroxamate derivative for actinide complexation: Synthesis and complexation studies. J Chem Soc Dalton Trans. 2000:4398-4402.

Seligman et al., Molecular Mechanisms of Iron Metabolism. The Molecular Basis of Blood Diseases. 1987;219-44.

Shin et al., A novel trivalent cation chelator Feralex dissociates binding of aluminum and iron associated with hyperphosphorylated τ of Alzheimer's disease. Brain Res. 2003;961:139-46.

Stahel et al., Iron chelators: in vitro inhibitory effect on the liver stage of rodent and human malaria. Am J Trop Med Hyg. Sep. 1988;39(3):236-40.

Stradling et al., Recent developments in the decorpoartion of plutonium, americium and thorium. Radiat Prot Dosimetry. 1998;79:445-48.

Streiff et al., Phase 1 study of N1-N11-diethylnorspermine (DENSPM) administered TID for 6 days in patients with advanced malignancies. Invest New Drugs. 2001;19(1):29-39.

Taetle et al., Combination iron depletion therapy. J Natl Cancer Inst. Aug. 16, 1989;81(16):1229-35.

Theil et al., Ferritin Mineralization: Ferroxidation and Beyond. J Inorg Biochem. 1997;67:30. Abstract B13.

Thomas et al., Ferritin and superoxide-dependent lipid peroxidation. J Biol Chem. Mar. 25, 1985;260(6):3275-80.

Uhlir et al., Specific sequestering agents for the actinides. 21. Synthesis and initial biological testing of octadentate mixed catecholate-hydroxypyridinonate ligands. J Med Chem. Feb. 19, 1993;36(4):504-9.

Vichinsky, Current issues with blood transfusions in sickle cell disease. Semin Hematol. Jan. 2001;38(1 Suppl 1):14-22.

Whisenhunt et al., Specific Sequestering Agents for the Actinides. 29. Stability of the Thorium(IV) Complexes of Desferrioxamine B (DFO) and Three Octadentate Catecholate or Hydroxypyridinonate DFO Derivatives: DFOMTA, DFOCAMC, and DFO-1,2-HOPO. Comparative Stability of the Plutonium(IV) DFOMTA Complex(1). Inorg Chem. Jul. 3, 1996;35(14):4128-4136.

White et al., The effect of chelating agents on cellular iron metabolism. Clin Sci Mol Med. Mar. 1976;50(3):145-52.

White et al., The effect of chelating agents on iron mobilization in Chang cell cultures. Blood. Dec. 1976;48(6):923-9.

Wojcik et al., Natural history of C282Y homozygotes for hemochromatosis. Can J Gastroenterol. May 2002;16(5):297-302.

Wolfe et al., A non-human primate model for the study of oral iron chelators. Br J Haematol. Jul. 1989;72(3):456-61.

Wolff et al., A Phase II study of the polyamine analog N1,N11-diethylnorspermine (DENSpm) daily for five days every 21 days in patients with previously treated metastatic breast cancer. Clin Cancer Res. Dec. 1, 2003;9(16 Pt 1):5922-8.

Wong et al., The Friedreich's ataxia mutation confers cellular sensitivity to oxidant stress which is rescued by chelators of iron and calcium and inhibitors of apoptosis. Hum Mol Genet. Mar. 1999;8(3):425-30.

Wood et al., The metabolism of iron-dextran given as a total-dose infusion to iron deficient Jamaican subjects. Br J Haematol. Feb. 1968;14(2):119-29.

Yamada et al., Role of neutrophil-derived oxidants in the pathogenesis of intestinal inflammation. Klin Wochenschr. Dec. 15, 1991;69(21-23):988-94.

Zacharski et al., Reduction of iron stores and cardiovascular outcomes in patients with peripheral arterial disease: a randomized controlled trial. JAMA. Feb. 14, 2007;297(6):603-10.

Zaman et al., Protection from oxidative stress-induced apoptosis in cortical neuronal cultures by iron chelators is associated with enhanced DNA binding of hypoxia-inducible factor-1 and ATF-1/CREB and increased expression of glycolytic enzymes, p21(waf1/cip1), and erythropoietin. J Neurosci. Nov. 15, 1999;19(22):9821-30.

Zecca et al., Neuromelanin can protect against iron-mediated oxidative damage in system modeling iron overload of brain aging and Parkinson's disease. J Neurochem. Aug. 2008;106(4):1866-75. Epub Jul. 4, 2008.

(56) References Cited

OTHER PUBLICATIONS

Zurlo et al., Survival and causes of death in thalassaemia major. Lancet. Jul. 1, 1989;2(8653):27-30.

* cited by examiner

US 10,010,535 B2

DESFERRITHIOCIN ANALOGS AND USES THEREOF

RELATED APPLICATION

The present application is a national stage filing under 35 U.S.C. § 371 of international PCT application, PCT/US2014/066965, filed Nov. 21, 2014, which claims priority under 35 U.S.C. § 119(e) to U.S. provisional patent application, U.S. Ser. No. 61/907,913, filed Nov. 22, 2013, each of which is incorporated herein by reference.

GOVERNMENT SUPPORT

This invention was made with government support under Grant No. DK049108 awarded by the National Institutes of Health. The government has certain rights in the invention.

BACKGROUND OF THE INVENTION

Nearly all life forms require iron as a micronutrient. However, the low solubility of Fe(III) hydroxide ($K_{sp}$=1×10$^{-39}$) (Raymond et al., "Coordination Chemistry and Microbial Iron Transport." *Acc. Chem. Res.* 1979, 12, 183-190), the predominant form of the metal in the biosphere, required the development of sophisticated iron storage and transport systems in nature. Microorganisms utilize low molecular weight, ferric iron-specific chelators, siderophores (Byers et al., "Microbial Iron Transport: Iron Acquisition by Pathogenic Microorganisms." *Met. Ions Biol. Syst.* 1998, 35, 37-66); eukaryotes tend to employ proteins to transport and store iron (Bergeron, "Iron: A Controlling Micronutrient in Proliferative Processes." *Trends Biochem. Sci.* 1986, 11, 133-136; Theil et al., "Ferritin Mineralization: Ferroxidation and Beyond." *J. Inorg. Biochem.* 1997, 67, 30; Ponka et al., "Function and Regulation of Transferrin and Ferritin." *Semin. Hematol.* 1998, 35, 35-54). Humans have evolved a highly efficient iron management system in which we absorb and excrete only about 1 mg of the metal daily; there is no mechanism for the excretion of excess metal (Brittenham, "Disorders of Iron Metabolism: Iron Deficiency and Overload." In *Hematology: Basic Principles and Practice*; 3$^{rd}$ ed.; Hoffman et al., Eds.; Churchill Livingstone: New York, 2000; pp. 397-428). Whether derived from transfused red blood cells (Olivieri et al., "Iron-Chelating Therapy and the Treatment of Thalassemia." *Blood* 1997, 89, 739-761; Vichinsky, "Current Issues with Blood Transfusions in Sickle Cell Disease." *Semin. Hematol.* 2001, 38, 14-22; Kersten et al., "Long-Term Treatment of Transfusional Iron Overload with the Oral Iron Chelator Deferiprone (L1): A Dutch Multicenter Trial." *Ann. Hematol.* 1996, 73, 247-252) or from increased absorption of dietary iron (Conrad et al., "Iron Absorption and Transport." *Am. J. Med. Sci.* 1999, 318, 213-229; Lieu et al., "The Roles of Iron in Health and Disease." *Mol. Aspects Med.* 2001, 22, 1-87), without effective treatment, body iron progressively increases with deposition in the liver, heart, pancreas, and elsewhere (iron overload disease).

In patients with iron overload disease, the toxicity derives from iron's interaction with reactive oxygen species (Graf et al., "Iron-Catalyzed Hydroxyl Radical Formation. Stringent Requirement for Free Iron Coordination Site." *J. Biol. Chem.* 1984, 259, 3620-3624; Halliwell, "Free Radicals and Antioxidants: A Personal View." *Nutr. Rev.* 1994, 52, 253-265; Halliwell, "Oxidative Damage, and Chelating Agents." In *The Development of Iron Chelators for Clinical Use*; Bergeron et al., Eds.; CRC: Boca Raton, Fla., 1994; pp 33-56; Koppenol, "Kinetics and Mechanism of the Fenton Reaction: Implications for Iron Toxicity." In *Iron Chelators: New Development Strategies*; Badman et al., Eds.; Saratoga: Ponte Vedra Beach, Fla., 2000, pp 3-10). For example, in the presence of Fe(II), endogenous $H_2O_2$ is reduced to the hydroxyl radical (HO.), a very reactive species, and HO$^-$, in the Fenton reaction. The hydroxyl radical reacts very quickly with a variety of cellular constituents and can initiate free radicals and radical-mediated chain processes that damage DNA and membranes as well as produce carcinogens (Halliwell, "Free Radicals and Antioxidants: A Personal View." *Nutr. Rev.* 1994, 52, 253-265); Babbs, "Oxygen Radicals in Ulcerative Colitis." *Free Radical Biol. Med.* 1992, 13, 169-181; Hazen et al., "Human Neutrophils Employ the Myeloperoxidase-Hydrogen Peroxide-Chloride System to Oxidize α-Amino Acids to a Family of Reactive Aldehydes. Mechanistic Studies Identifying Labile Intermediates along the Reaction Pathway." *J. Biol. Chem.* 1998, 273, 4997-5005). The liberated Fe(III) is reduced back to Fe(II) via a variety of biological reductants (e.g., ascorbate, glutathione), a problematic cycle.

Iron-mediated damage can be focal, as in reperfusion damage (Millán et al., "Biological Signatures of Brain Damage Associated with High Serum Ferritin Levels in Patients with Acute Ischemic Stroke and Thrombolytic Treatment." *Dis. Markers* 2008, 25, 181-188), Parkinson's (Zecca et al., "Neuromelanin Can Protect Against Iron-Mediated Oxidative Damage in System Modeling Iron Overload of Brain Aging and Parkinson's Disease." *J. Neurochem.* 2008, 106, 1866-1875), Friedreich's ataxia (Pietrangelo, "Iron Chelation Beyond Tranfusion Iron Overload." *Am. J. Hematol.* 2007, 82, 1142-1146), macular degeneration (Dunaief, "Iron Induced Oxidative Damage as a Potential Factor in Age-Related Macular Degeneration: The Cogan Lecture" *Invest. Ophthalmol. Vis. Sci.* 2006, 47, 4660-4664), and hemorrhagic stroke (Hua et al., "Long-Term Effects of Experimental Intracerebral Hemorrhage: The Role of Iron." *J. Neurosurg.* 2006, 104, 305-312), or global, as in transfusional iron overload, e.g., thalassemia (Pippard, "Iron Overload and Iron Chelation Therapy in Thalassaemia and Sickle Cell Haemoglobinopathies." *Acta. Haematol.* 1987, 78, 206-211), sickle cell disease (Pippard, "Iron Overload and Iron Chelation Therapy in Thalassaemia and Sickle Cell Haemoglobinopathies." *Acta. Haematol.* 1987, 78, 206-211; Olivieri, "Progression of Iron Overload in Sickle Cell Disease." *Semin. Hematol.* 2001, 38, 57-62), and myelodysplasia (Malcovati, "Impact of Transfusion Dependency and Secondary Iron Overload on the Survival of Patients with Myelodysplastic Syndromes." *Leukemia Res.* 2007, 31, S2-S6), with multiple organ involvement. The solution in both scenarios is the same: chelate and promote the excretion of excess unmanaged iron.

Treatment with a chelating agent capable of sequestering iron and permitting its excretion from the body is the only therapeutic approach available. Some of the iron chelating agents that are now in use or that have been clinically evaluated include desferrioxamine B mesylate (DFO$^a$) (*Desferal*; Novartis Pharmaceuticals Corporation: East Hanover, N.J., 2008; www.pharma.us.novartis.com/product/pi/pdf/desferal.pdf), 1,2-dimethyl-3-hydroxy-4-pyridinone (deferiprone, L1) (Hoffbrand, "Long-Term Trial of Deferiprone in 51 Transfusion-Dependent Iron Overloaded Patients." *Blood* 1998, 91, 295-300; Olivieri, "Long-Term Therapy with Deferiprone." *Acta Haematol.* 1996, 95, 37-48; Olivieri, "Long-Term Safety and Effectiveness of Iron-Chelation Therapy with Deferiprone from Thalassemia Major." *N. Engl. J. Med.* 1998, 339, 417-423; Richardson, "The Controversial Role of Deferiprone in the Treatment of Thalassemia." *J. Lab. Clin. Med.* 2001, 137, 324-329), and 4-[3,5-bis(2-hydroxyphenyl)-1,2,4-triazol-1-yl]benzoic acid (desferasirox, ICL670A) (Nisbet-Brown et al., "Effectiveness and Safety of ICL670 in Iron-Loaded Patients with Thalassemia: A Randomised, Double-Blind, Placebo-Controlled, Dose-Escalation Trial." *Lancet,* 2003, 361, 1597-1602; Galanello et al., "Safety, Tolerability, and Pharmacokinetics of ICL670, a New Orally Active Iron-Chelating Agent in Patients with Transfusion-Dependent Iron Overload Due to β-Thalassemia." *J. Clin. Pharmacol.* 2003, 43, 565-572; Cappellini, "Iron-Chelating Therapy with the New Oral Agent ICL670 (Exjade)." *Best Pract. Res. Clin. Haematol.* 2005, 18, 289-298). Each of these compounds presents with shortcomings. DFO must be given subcutaneously (sc) for protracted periods of time, e.g., 12 h a day, five days a week, a serious patient compliance issue (Olivieri et al., "Iron-Chelating Therapy and the Treatment of Thalassemia." *Blood* 1997, 89, 739-761; Pippard, "Desferrioxamine-Induced Iron Excretion in Humans." *Bailliere's Clin. Haematol.* 1989, 2, 323-343; Giardina et al., "Chelation Therapy in β-Thalassemia: An Optimistic Update." *Semin. Hematol.* 2001, 38, 360-366). Deferiprone, while orally active, simply does not remove enough iron to maintain patients in a negative iron balance (Hoffbrand, "Long-Term Trial of Deferiprone in 51 Transfusion-Dependent Iron Overloaded Patients." *Blood* 1998, 91, 295-300; Olivieri, "Long-Term Therapy with Deferiprone." *Acta Haematol.* 1996, 95, 37-48; Olivieri, "Long-Term Safety and Effectiveness of Iron-Chelation Therapy with Deferiprone from Thalassemia Major." *N. Engl. J. Med.* 1998, 339, 417-423; Richardson, "The Controversial Role of Deferiprone in the Treatment of Thalassemia." *J. Lab. Clin. Med.* 2001, 137, 324-329). Desferasirox did not show noninferiority to DFO and is associated with numerous side effects, including some renal toxicity (Nisbet-Brown et al., "Effectiveness and Safety of ICL670 in Iron-Loaded Patients with Thalassemia: A Randomised, Double-Blind, Placebo-Controlled, Dose-Escalation Trial." *Lancet,* 2003, 361, 1597-1602; Galanello et al., "Safety, Tolerability, and Pharmacokinetics of ICL670, a New Orally Active Iron-Chelating Agent in Patients with Transfusion-Dependent Iron Overload Due to β-Thalassemia." *J. Clin. Pharmacol.* 2003, 43, 565-572; Cappellini, "Iron-Chelating Therapy with the New Oral Agent ICL670 (Exjade)." *Best Pract. Res. Clin. Haematol.* 2005, 18, 289-298).

Despite the work on metal chelation agents described above, there is still a need for other chelators with more desirable properties (e.g., improved physiochemical, pharmacokinetic, pharmacodynamic, and/or toxicological properties, such as absorption, distribution, metal-clearing efficiency, and toxicity) for a better treatment and/or prevention of pathological conditions in a subject.

SUMMARY OF THE INVENTION

The present invention provides novel desferrithiocin analogs based on desferrithiocin 1 (shown below), and pharmaceutically acceptable salts, tautomers, stereoisomers, solvates, hydrates, and polymorphs thereof, that chelate a metal. The invention also provides methods of using the inventive desferrithiocin analogs, or pharmaceutically acceptable salts, tautomers, stereoisomers, solvates, hydrates, or polymorphs thereof, and pharmaceutical compositions thereof, for the treatment and/or prevention of a pathological condition. Without wishing to be bound by any particular theory, the inventive compounds are thought to chelate iron and/or other metals (e.g., aluminum, thallium, chromium, magnesium, calcium, strontium, nickel, manganese, cobalt, copper, zinc, silver, sodium, potassium, cadmium, mercury, lead, antimony, molybdenum, tungsten, a lanthanide (e.g., cerium), or an actinide (e.g., uranium)). Therefore, a metal overload, metal poisoning, and other pathological conditions (e.g., oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, and reperfusion injury) that are associated with metal overload may be treated and/or prevented by the inventive methods. The methods of the invention may also be useful in treating and/or preventing an infectious disease (e.g., malaria). Iron is usually a nutrient necessary for the growth of microorganisms. Depriving the organisms of iron by chelating and/or removing iron may contribute to the treatment and/or prevention of infectious diseases. Further provided by the invention are kits, containing one or more inventive desferrithiocin analogs, or pharmaceutically acceptable salts, tautomers, stereoisomers, solvates, hydrates, or polymorphs thereof, or pharmaceutical compositions thereof, for treating and/or preventing a pathological condition (e.g., iron overload).

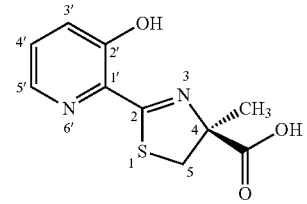

1

In one aspect, provided are compounds of Formula (A), and pharmaceutically acceptable salts, tautomers, stereoisomers, solvates, hydrates, and polymorphs thereof:

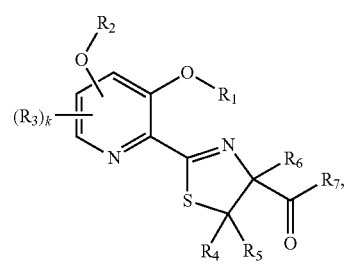

(A)

wherein $R_1$, $R_2$, $R_3$, $R_4$, $R_5$, $R_6$, $R_7$, and k are as described herein. The compounds of Formula (A) include at least one carbohydrate moiety, wherein the C1 position of the carbohydrate moiety is attached to the pyridyl ring or carbonyl group of the compounds of Formula (A), optionally through a linker. In certain embodiments, the linker is a polyethylene glycol (PEG) moiety.

In certain embodiments, the compound of Formula (A) is of the formula:

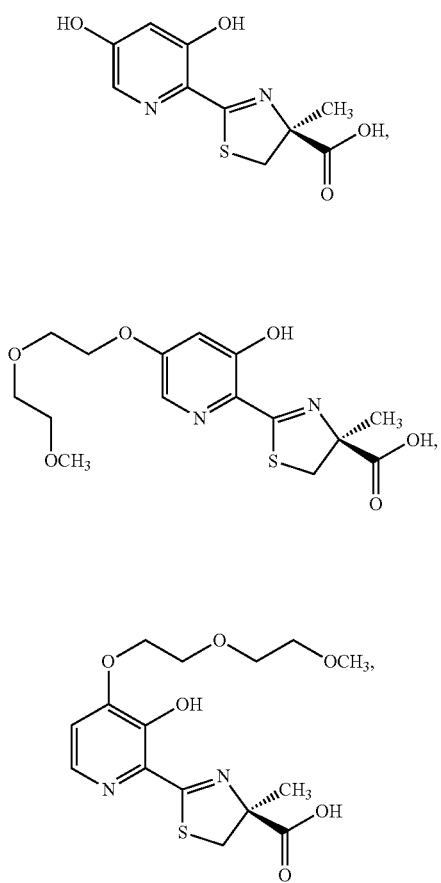

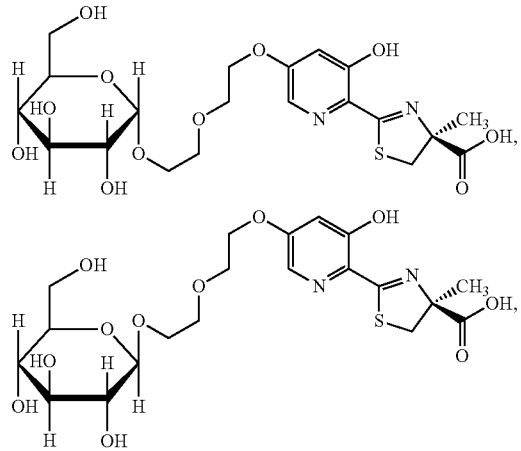

or a pharmaceutically acceptable salt, tautomer, stereoisomer, solvate, hydrate, or polymorph thereof.

In certain embodiments, the compound of Formula (A) is not of Formula (I-1), (I-2), (I-3), or a pharmaceutically acceptable salt, tautomer, stereoisomer, solvate, hydrate, or polymorph thereof. In certain embodiments, the compound of Formula (A) is not of Formula (I-1), (I-2), or (I-3).

In certain embodiments, the compound of Formula (A) is of the formula:

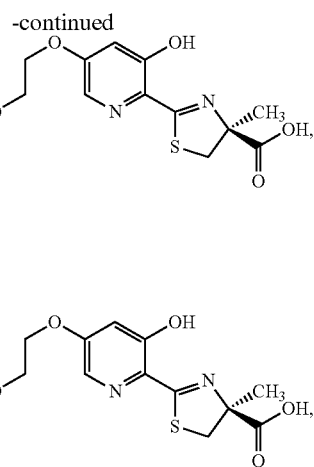

or a pharmaceutically acceptable salt, tautomer, stereoisomer, solvate, hydrate, or polymorph thereof.

Without wishing to be bound by any particular theory, by introducing an —OR$_2$ group on the pyridinyl ring of desferrithiocin 1, the resulting inventive compounds have lower nephrotoxicity and/or improved metal clearance properties than the parent compound 1.

In certain embodiments, the compounds of the invention may also include one or more carbohydrate (e.g., glucose, including α-D-, β-D-, α-L-, and β-L-glucose) moieties. Such compounds are expected to show superior physiochemical, pharmacokinetic, and/or pharmacodynamic properties (e.g., greater solubility, permeability, and bioavailability; improved distribution, absorption, metabolism, and iron-clearing efficiency; and reduced clearance, excretion, and toxicity) compared with the parent compound 1 and/or desferrithiocin analogs that do not include a carbohydrate moiety.

In another aspect, provided are compounds of Formula (J), and pharmaceutically acceptable salts, tautomers, stereoisomers, solvates, hydrates, and polymorphs thereof:

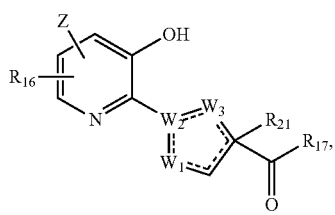

wherein $\mathrel{\text{-----}}$, $W_1$, $W_2$, $W_3$, $Z$, $R_{16}$, $R_{17}$, and $R_{21}$ are as described herein.

In another aspect, the present invention provides pharmaceutical compositions including an inventive compound, or a pharmaceutically acceptable salt, tautomer, stereoisomer, solvate, hydrate, or polymorph thereof, and optionally a pharmaceutically acceptable excipient. The pharmaceutical compositions of the invention may include a therapeutically or prophylactically effective amount of the inventive compound.

In still another aspect, the invention provides methods of using the inventive compounds, or pharmaceutical compositions thereof, for the treatment and/or prevention of a pathological condition in a subject. In certain embodiments, the pathological condition is responsive to the chelation or sequestration of a metal. In certain embodiments, the metal is iron (e.g., Fe(III)). In certain embodiments, the metal is aluminum, thallium, chromium, magnesium, calcium, strontium, nickel, manganese, cobalt, copper, zinc, silver, sodium, potassium, cadmium, mercury, lead, antimony, molybdenum, tungsten, a lanthanide (e.g., cerium), or an actinide (e.g., uranium). In certain embodiments, the metal is a trivalent metal. In certain embodiments, the metal is a monovalent, divalent, tetravalent, pentavalent, or hexavalent metal. In certain embodiments, the subject is a human. In certain embodiments, the pathological condition is metal overload (e.g., iron overload, aluminum overload, chromium overload, magnesium overload, calcium overload, strontium overload, nickel overload, manganese overload, cobalt overload, copper overload, zinc overload, silver overload, sodium overload, potassium overload, cadmium overload, mercury overload, lead overload, molybdenum overload, tungsten overload, or actinide overload (e.g., uranium overload)). In certain embodiments, the pathological condition is iron overload. In certain embodiments, the pathological condition is metal poisoning (e.g., iron poisoning, aluminum poisoning, thallium poisoning, chromium poisoning, magnesium poisoning, calcium poisoning, strontium poisoning, nickel poisoning, manganese poisoning, cobalt poisoning, copper poisoning, zinc poisoning, silver poisoning, sodium poisoning, potassium poisoning, cadmium poisoning, mercury poisoning, lead poisoning, antimony poisoning, molybdenum poisoning, tungsten poisoning, lanthanide poisoning (e.g., cerium poisoning), or actinide poisoning (e.g., uranium poisoning). In certain embodiments, the pathological condition is oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, and reperfusion injury. In certain embodiments, the pathological condition is an infectious disease (e.g., malaria). In certain embodiments, the methods of treatment and/or prevention include administering to the subject a therapeutically or prophylactically effective amount of a compound of the invention, or a pharmaceutically acceptable salt, tautomer, stereoisomer, solvate, hydrate, or polymorph thereof, or a pharmaceutical compositions thereof.

In yet another aspect, the invention provides kits for treating and/or preventing a pathological condition in a subject. The inventive kits include a first container containing a therapeutically effective amount of a compound of the invention, or a pharmaceutically acceptable salt, tautomer, stereoisomer, solvate, hydrate, or polymorph thereof, or a pharmaceutical compositions thereof; and instructions for administering the compound to the subject to treat and/or prevent the pathological condition. A kit may include multiple unit dosages, for example, for multiple days of treatment.

The details of one or more embodiments of the invention are set forth herein. Other features, objects, and advantages of the invention will be apparent from the Detailed Description, Figures, Examples, and Claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers". When a compound has an asymmetric center, for example, a carbon atom of the compound is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates plane polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched" means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}C$ or $^{14}C$ are within the scope of this invention. Such compounds are useful, for example, as analytical tools, as probes in biological assays, or as therapeutic agents in accordance with the present invention.

In a formula, ⁓ is a single bond where the stereochemistry of the moieties immediately attached thereto is not specified, - - - is absent or a single bond, and ═ or ≡ is a single or double bond.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl" refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (-CHO), carboxylic acids (-CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula ($-OR^i$), wherein $R^i$ is an optionally substituted acyl group, as defined herein, and the oxygen moiety is directly attached to the parent molecule.

The term "aliphatic" includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl (e.g., unsubstituted methyl (Me)), ethyl (e.g., unsubstituted ethyl (Et)), propyl (e.g., unsubstituted propyl (Pr)), n-propyl, isopropyl, butyl (e.g., unsubstituted butyl (Bu)), n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl" denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl" refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R")$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR', —SSR$^{ee}$, —C(=O)R$^{ee}$, —CO$_2$H, —CO$_2$R$^{ee}$, —OC(=O)R$^{ee}$, —OCO$_2$R', —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R', —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_6$-10 aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NHC(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_K$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

The term "amino" refers to a group of the formula (—NH$_2$). A "substituted amino" refers either to a mono-substituted amine (—NHR$^h$) of a disubstituted amine (—NR$^h{}_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the disubstituted amino group (—NR$^h{}_2$) form a 5- to 6-membered heterocyclic ring.

The term "alkoxy" refers to a "substituted hydroxyl" of the formula (—OR$^i$), wherein R$^i$ is an optionally substituted alkyl group as defined herein, and the oxygen moiety is directly attached to the parent molecule.

The term "alkylthioxy" refers to a "substituted thiol" of the formula (—SR$^r$), wherein R$^r$ is an optionally substituted alkyl group as defined herein, and the sulfur moiety is directly attached to the parent molecule.

The term "alkylamino" refers to a "substituted amino" of the formula (—NR$^h{}_2$), wherein R$^h$ is, independently, a hydrogen or an optionally substituted alkyl group as defined herein, and the nitrogen moiety is directly attached to the parent molecule.

The term "aryl" refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl" refers to an aryl substituted alkyl group, wherein the terms "aryl" and "alkyl" are defined herein, and wherein the aryl group is attached to the alkyl group, which in turn is attached to the parent molecule. Exemplary arylalkyl groups are benzyl and phenethyl.

The term "aryloxy" refers to a "substituted hydroxyl" of the formula (—OR$^i$), wherein R$^i$ is an optionally substituted aryl group as defined herein, and the oxygen moiety is directly attached to the parent molecule.

The term "arylamino," refers to a "substituted amino" of the formula (—NR$^h{}_2$), wherein R$^h$ is, independently, a hydrogen or an optionally substituted aryl group as defined herein, and the nitrogen moiety is directly attached to the parent molecule.

The term "arylthioxy" refers to a "substituted thiol" of the formula (—SR$^r$), wherein R$^r$ is an optionally substituted aryl group as defined herein, and the sulfur moiety is directly attached to the parent molecule.

The terms "halo" and "halogen" refer to an atom selected from fluorine (fluoro, —F), chlorine (chloro, —Cl), bromine (bromo, —Br), and iodine (iodo, —I).

The term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, the terms "heteroalkyl", "heteroalkenyl", "heteroalkynyl", and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" refers to an alkyl moiety, as defined herein, which contain one or more oxygen, sulfur, nitrogen, phosphorus, or silicon atoms, e.g., in place of carbon atoms.

The term "heteroalkenyl" refers to an alkenyl moiety, as defined herein, which contain one or more oxygen, sulfur, nitrogen, phosphorus, or silicon atoms, e.g., in place of carbon atoms.

The term "heteroalkynyl" refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula ($-NR^h_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula ($-OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula ($-SR^r$), wherein $R^r$ is an optionally substituted heteroalkyl group, as defined herein, and the sulfur moiety is directly attached to the parent molecule.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cyclohep-tenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclic," "heterocycles," or "heterocyclyl" refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl" refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl (pyridyl), pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—NR$^h$$_2$), wherein R$^h$ is, independently, hydrogen or an optionally substituted heteroaryl group, as defined herein, and the nitrogen moiety is directly attached to the parent molecule.

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "heteroarylthioxy" refers to a "substituted thiol" of the formula (—SR$^r$), wherein R$^r$ is an optionally substituted heteroaryl group, as defined herein, and the sulfur moiety is directly attached to the parent molecule.

The term "hydroxy" or "hydroxyl" refers to a group of the formula (—OH). A "substituted hydroxyl" refers to a group of the formula (—OR$^i$), wherein R$^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino" refers to a group of the formula (=NR'), wherein R$^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein R$^r$ is hydrogen.

The term "nitro" refers to a group of the formula (—NO$_2$).

The term "oxo" refers to a group of the formula (=O).

A "protecting group" is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference. Suitable "amino-protecting groups" (also referred to as "nitrogen protecting groups") include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(ptoluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(mphenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "hydroxyl protecting group" (also referred to as an "oxygen protecting group") is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})^2$, —$P(=O)(OR^{cc})_2$, —$P(=O)_2N(R^{bb})_2$, and —$P(=O)(NR^{bb})_2$, wherein $R^{aa}$, $R^{bb}$, and $R^{CC}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the —$CH_2OH$ side branch. The alternative form, in which the —$CH_2OH$ substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, and rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

The term "pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., $Ca(OH)_2$), magnesium (by using, e.g., $Mg(OH)_2$ and magnesium acetate), zinc, (by using, e.g., $Zn(OH)_2$ and zinc acetate), and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N-diethylethanolamine, N,N-dimethylethanolamine, triethanolamine, and tromethamine. Basic amino acids (e.g., l-glycine and l-arginine) and amino acids which may be zwitterionic at neutral pH (e.g., betaine (N,N,N-trimethylglycine)) are also contemplated.

The term "tautomer" refers to a particular isomer of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, lactam-lactim forms, ketene-ynol forms, enamine-enamine forms, and pyridione-hydroxypyridine forms.

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.xH_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "subject" refers to any animal. In certain embodiments, the subject is a mammal. In certain embodiments, the subject is a human (e.g., a man, a woman, or a child). The human may be of either sex and may be at any stage of development. In certain embodiments, the subject has been diagnosed with the condition or disease to be treated. In other embodiments, the subject is at risk of developing the condition or disease. In certain embodiments, the subject is an experimental animal (e.g., mouse, rat, rabbit, dog, pig, or primate). The experimental animal may be genetically engineered. In certain embodiments, the subject is a domesticated animal (e.g., dog, cat, bird, horse, cow, goat, sheep).

The terms "administer," "administering," or "administration" refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of the present invention or a pharmaceutical composition thereof refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound of the present invention or a pharmaceutical composition thereof is an amount sufficient to provide a therapeutic benefit in the treatment of a condition, e.g., iron overload, or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent. In certain embodiments, a therapeutically effective amount is an amount sufficient for chelating a metal described herein. In certain embodiments, a therapeutically effective amount is an amount sufficient for treating a pathological condition described herein. In certain embodiments, a therapeutically effective amount is an amount sufficient for chelating a metal described herein and for treating a pathological condition described herein.

A "prophylactically effective amount" of a compound of the present invention is an amount sufficient to prevent a condition, e.g., iron overload, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for chelating a metal described herein. In certain embodiments, a prophylactically effective amount is an amount sufficient for preventing a pathological condition described herein. In certain embodiments, a prophylactically effective amount is an amount sufficient for chelating a metal described herein and for preventing a pathological condition described herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

"Chelation," "chelating," "sequestration," or "sequestering" is the formation or presence of two or more separate coordinate bonds between a polydentate (multiple-bonded) compound and a single central atom. The polydentate compound is typically an organic compound and referred to as a "chelator," "chelant," "chelating agent," "sequestrator," "sequestering agent," or "ligand." The central atom is usually a metal atom or metal ion (e.g., a metal atom or metal ion described herein, such as iron (e.g., Fe(III)), Al(III), chromium (e.g., Cr(III) or Cr(VI)), and uranium (e.g., U(VI)), etc.). The chelator may form a stable complex with the central atom through coordinate bonds, inactivating the central atom so that the central atom is less likely to react with other molecules or atoms.

The term "metal-clearing efficiency" or "MCE" refers to the efficacy of a given concentration of chelator in clearing a metal atom or metal ion (e.g., a metal atom or metal ion described herein, such as iron (e.g., Fe(III)), Al(III), chromium (e.g., Cr(III) or Cr(VI)), and uranium (e.g., U(VI)) from the body or one of its organs or parts. Efficaciousness in turn concerns quantity of the metal atom or metal ion removed from a target system (e.g., a whole body, an organ, or a tissue) in a unit of time. Chelators of a metal atom or metal ion are needed in one or more of three clinical situations: (1) for acute metal toxicity from ingestion or infusion of the metal atom or metal ion; (2) to reduce total body metal secondary to transfusion or excess metal absorption; and (3) for the maintenance of metal balance after total body metal has been satisfactorily reduced and only daily dietary metal needs to be excreted. In practical terms, therefore, for chronic metal overload secondary to transfusion, the recommendation is that 0.3-0.5 mg/kg/d (i.e., mg iron per kg body weight of the subject per day) need be excreted. For the maintenance treatment, 0.25-1 mg/kg/d is sufficient. Other ranges are also possible. In certain embodiments, the metal-clearing efficiency is iron-clearing efficiency or "ICE." In certain embodiments, the metal-clearing efficiency is aluminum-clearing efficiency. In certain embodiments, the metal-clearing efficiency is chromium-clearing efficiency. In certain embodiments, the metal-clearing efficiency is uranium-clearing efficiency.

The term "focal iron overload" refers to any disease or condition that involves the accumulation of unmanaged iron in a tissue or organ. Focal iron overload typically involves less than the subject's whole body but may involve more than one organ or tissue. Unmanaged iron in any tissue or organ is typically undesired and can be the focus of the treatments of the present invention. The treatment may involve the removal of as much iron as possible from the tissue or organ or may only involve the removal of excess iron. Examples of disease and conditions associated with focal iron overload include, but are not limited to, macular degeneration, IBD, reperfusion injury, stroke including hemorrhagic stroke, and closed head injury; however, any disease or condition of focal iron overload may be treated as described herein. In certain embodiments, the term "focal iron overload" does not include diseases or conditions associated with global iron overload (e.g., global iron overload associated with chronic transfusion therapy, hereditary hemochromatosis, etc.). The treatment of focal iron overload may be systemic or local administration of an effective amount of an inventive compound, or a pharmaceutical composition thereof.

The term "reactive oxygen species" or "ROS" refers to molecules or ions formed by the incomplete reduction of oxygen. Reactive oxygen species include superoxide anion ($O_2.^-$), peroxides such as hydrogen peroxide ($H_2O_2$), hydroxyl radical (HO.), and hypochlorous acid (HClO). These molecules are typically chemically reactive. Reactive oxygen species may be formed by any number of mechanisms (e.g., enzymatically, by ionizing radiation, by reaction oxygen with a metal). In certain embodiments, the reactive oxygen species are formed by the reduction of oxygen by an iron ion, such as $Fe^{+2}$.

"Primary hemochromatosis" is a genetic disorder characterized by excessive iron accumulation that results in tissue damage. Manifestations include systemic symptoms, liver disorders, cardiomyopathy, diabetes, erectile dysfunction, and arthropathy. Normal total body iron content is about 2.5 g in women and 3.5 g in men. Because symptoms may be delayed until iron accumulation is excessive, hemochromatosis may not be recognized until total body iron content is >10 g, or often several times greater. In women, clinical manifestations are uncommon before menopause because iron loss due to menses (and sometimes pregnancy and childbirth) tends to offset iron accumulation. One mechanism for iron overload is increased iron absorption from the gastrointestinal tract, leading to chronic deposition of iron in the tissues. Hepcidin, a liver-derived peptide, is the critical control mechanism for iron absorption. Hepcidin, along with the normal HFE gene, prevents excessive iron absorption and storage in normal people. Tissue injury in a subject with primary hemochromatosis may result from reactive free hydroxyl radicals generated when iron deposition in tissues catalyzes their formation. Other mechanisms may affect particular organs (e.g., skin hyperpigmentation can result from increased melanin as well as iron accumulation).

"Secondary hemochromatosis" is a condition acquired as a consequence of another disease that causes iron overload, or blood transfusions, or both, and typically characterized by increased hepatic and total body iron content and unequivocal portal cirrhosis of the liver. Secondary hemochromatosis is usually caused by disorders of erythropoiesis (e.g., thalassemia, sickle cell anemia, X-linked sideroblastic anemia, pyruvate kinase deficiency, hereditary spherocytosis, and congenital dyserythropoietic anemia (CDA)) and the treatment of these diseases with blood transfusions. After damaging the transfused erythrocytes by macrophages, iron freed from the heme is accumulated in the body (e.g., in the liver, heart, or skin).

"Diabetes" or "diabetes mellitus" is a metabolic disorder in which there are high levels of glucose in the blood. Diabetes can be caused by insufficient amount of insulin (a hormone produced by the pancreas to control blood glucose) or resistance to insulin in a subject, or both. There are three major types of diabetes: Type 1, Type 2, and gestational diabetes. Type 1 diabetes is usually diagnosed in children and young adults, and was previously known as juvenile diabetes. In type 1 diabetes, the body does not produce insulin, which may be a result of the destruction of islet cells in the pancreas. Type 2 diabetes, or non-insulin-dependent diabetes mellitus (NIDDM) or adult-onset diabetes, is the most common form of diabetes. Type 2 diabetes is characterized by high blood glucose in the context of insulin resistance and relative insulin deficiency. This is in contrast to Type 1 diabetes in which there is an absolute insulin deficiency. Obesity is thought to be one of the primary causes of Type 2 diabetes in subjects who are genetically predisposed to obesity. Gestational diabetes is characterized by high blood glucose that develops during pregnancy in a woman who does not have diabetes prior to the pregnancy. Gestational diabetes may be caused by various pregnancy hormones that may interfere with the body's response to insulin.

The term "closed head injury" refers to any injury to the head that does not penetrate the skull. Closed head injuries may result from falls, blasts, accidents including vehicular accidents, and assaults. Closed head injuries can lead to hemorrhage or brain swelling, which can result in increased intracranial pressure, which can in turn lead to permanent brain damage or even death. Various types of closed head injury include concussions, brain contusions, diffuse axonal injury, and hematomas.

"Thalassemia" is a group of inherited autosomal recessive blood disorders that originated in the Mediterranean region. In a subject with thalassemia, the genetic defect, which could be either mutation or deletion, results in reduced rate of synthesis or no synthesis of one of the globin chains that make up hemoglobin. This can cause the formation of abnormal hemoglobin molecules, thus causing anemia. There are two main types of thalassemia: alpha and beta thalassemias. Alpha thalassemia occurs when a gene or genes related to the alpha globin protein are missing or changed (i.e., mutated). Beta thalassemia occurs when similar gene defects affect production of the beta globin protein. Each of alpha and beta thalassemias includes two forms: thalassemia major and thalassemia minor. Beta thalassemia major is also referred to as Cooley's anemia or Mediterranean anemia.

"Friedreich's ataxia" or "FRDA" is an inherited disease that causes progressive damage to the nervous system of a subject resulting in symptoms including muscle weakness, speech problems, and heart disease. In a subject with Friedreich's ataxia, the spinal cord and peripheral nerves degenerate and become thinner. The cerebellum, part of the brain that coordinates balance and movement, also degenerates to a lesser extent. This damage results in awkward, unsteady movements and impaired sensory functions. Friedreich's ataxia also causes problems in the heart and spine, and some subjects with the condition develop diabetes. However, this disorder usually does not affect cognitive functions, such as thinking and reasoning. Friedreich's ataxia is caused by a defect, which may be a result of mutation, in a gene labeled as FXN. This disorder is recessive, meaning it occurs only in someone who inherits two defective copies of the gene, one from each parent.

"Macular degeneration" is a disease that affects the retina of a subject. The retina is a thin tissue lining the back of the eye. Light-sensitive cells in the retina are responsible for converting light into electrical impulses, which are then sent via the optic nerve to the brain for interpretation. In the center of the retina is the macula. The macula contains the highest concentration of the light-sensitive cells, called cones, which are responsible for sharp, detailed, and central vision. In macular degeneration, cells in the macular region begin to die, which results in blind spots and distorted vision. Macular degeneration is the leading cause of vision loss in humans over the age of 60. There are two forms of macular degeneration: dry and wet macular degenerations. It is possible for a subject to suffer from both forms, for it to affect one or both eyes, and for the disease to progress slowly or rapidly. Dry macular degeneration is the most common type of macular degeneration, in which the photosensitive cells of the macula slowly break down. Yellow deposits called drusen (extracellular waste products from metabolism) form and accumulate under the retina between the retinal pigmented epithelium (RPE) layer and the Bruch's membrane, which supports the retina. Over time, drusen are associated with deterioration of the macula and the death of RPE and photoreceptor cells, resulting in a blurring or spotty loss of clear, straight-ahead vision. This process does not cause any pain. In the early stages of the disease, the subject may notice slightly blurry vision. However, as more and more of the cells die, central vision worsens. Dry macular degeneration may advance and cause loss of vision without turning into the wet form of the disease. However, it is also possible for the early-stage dry form to change into the wet form of macular degeneration. Wet macular degeneration occurs when abnormal blood vessels grow behind the macula as RPE and photoreceptor cells die. The Bruch's membrane begins to break down, usually near drusen deposits, and new blood vessels grow. These vessels are very fragile and can leak fluid and blood. Scarring of and severe damage to the macula may result. Straight-ahead vision can become distorted or lost entirely in a short period of time.

BRIEF DESCRIPTION OF THE DRAWINGS

FIG. 1 shows the chemical structures of certain chelating compounds.

DETAILED DESCRIPTION OF CERTAIN EMBODIMENTS OF THE INVENTION

Figure 1A:
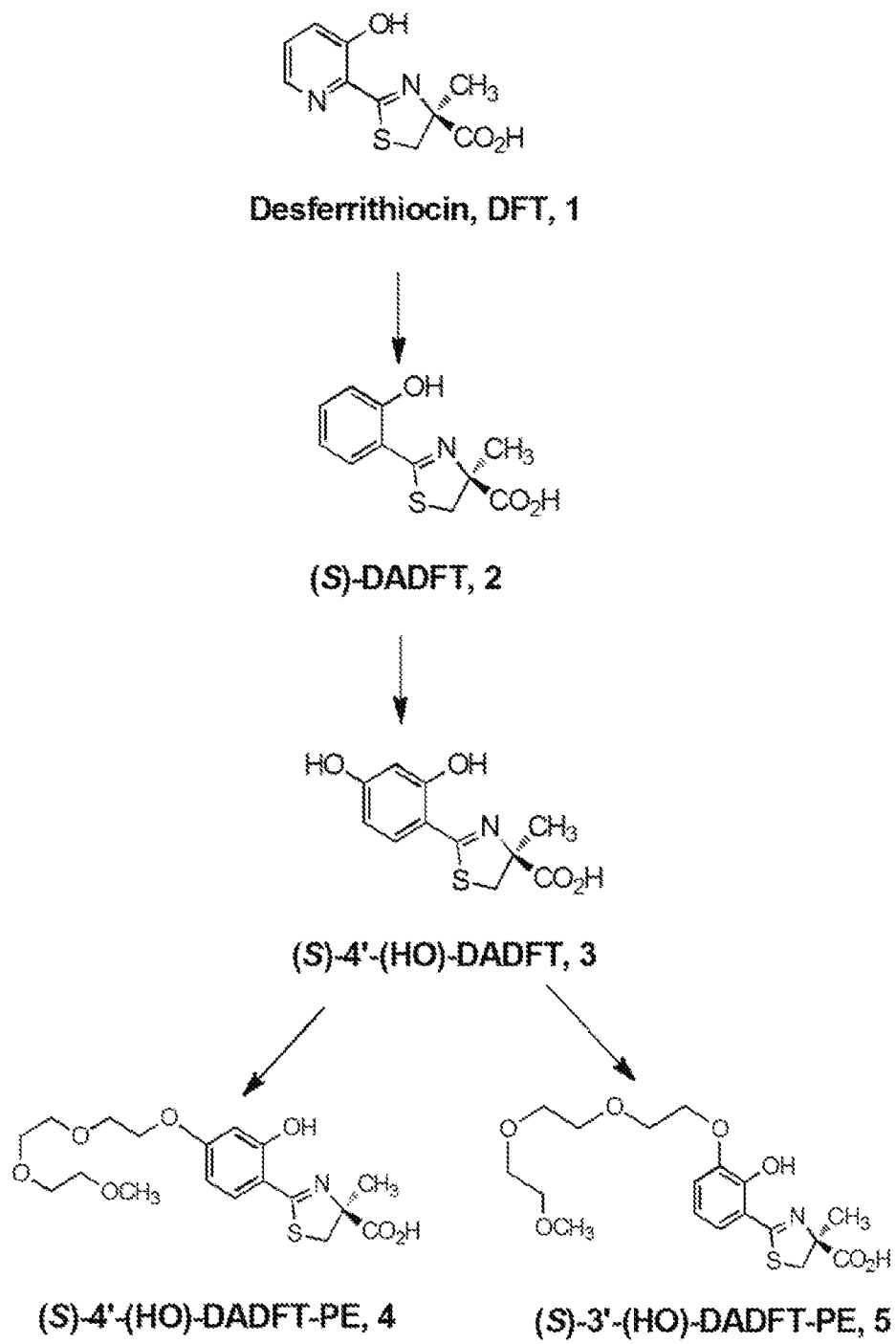
FIG. 1A illustrates that the desferrithiocin (DFT, 1) has been structurally modified to give desazadesferrithiocin (DADFT) analogs 2-5.

Various desazadesferrithiocin analogs have been described for use in the treatment of iron overload, which results from transfusion therapy, high-iron diet, acute iron ingestion, or malabsorption. Such analogs may also be used to treat focal iron overload, where the local concentration of iron in a particular tissue or organ contributes to the pathological process. For instance, the unmanaged $Fe^{+2}$ ions in a tissue or organ may result in the production of hydroxyl radicals or other reactive oxygen species that lead to tissue or cell damage. Structural modification of a desazadesferrithiocin analog by replacing the phenyl ring of the analog with a pyridinyl ring gives rise to a desferrithiocin analog, such as desferrithiocin (1). Structural modification of 1 by, among other things, attaching one or more carbohydrate (e.g., a sugar, such as glucose, including α-D-, β-D-, α-L-, and β-L-glucose) moieties, optionally through linkers, to 1 gives rise to novel desferrithiocin analogs of Formula (A) or (J). These inventive compounds may have one or more superior properties (such as greater solubility, permeability, and bioavailability; improved distribution, absorption, metabolism, and iron-clearing efficiency; and reduced clearance, excretion, and toxicity) compared with the parent compound 1 and/or other desferrithiocin analogs. The inventive compounds may also be efficiently delivered into cells or taken up by cells and be retained inside cells, which is desired for the treatment and/or prevention of pathological conditions in a subject using the inventive compounds. For example, the carbohydrate moieties are hydrophilic, and the inventive compounds bearing these moieties may be more soluble and/or have a greater ability to get into a cell. Moreover, the carbohydrate moieties may be recognized by membrane transport proteins that lead to the uptake of the inventive compounds into cells. As a result, the inventive compounds with carbohydrate moieties attached may be more efficiently transported into the cells of a subject. Additionally, the linker connecting the carbohydrate moiety and desferrithiocin 1 may be hydrolyzed in a cell to give rise to a desferrithiocin analog without a carbohydrate moiety. This analog may no longer be recognized by membrane transport proteins and, therefore, may be retained inside the cell. This analog may also remain in the cell because the analog is too polar to pass through the cell membrane to get out of the cell. Any linkers capable of hydrolysis under physiological conditions may be used in the present invention. For example, when -polyether- (e.g., a PEG moiety) is employed as the linker, the compound of the invention is of the formula:

Desferrithiocin-polyether-carbohydrate.

In certain embodiments, one of the oxygen atoms of the polyether linker is attached to the anomeric carbon (i.e., C1) of the carbohydrate moiety. The polyether-C1 bond may hydrolyze under physiological conditions, and a hydrolysis product desferrithiocin-polyether-H, which is an alcohol, may be generated.

In certain embodiments, -polyether-NHC(=O)O— is used as the linker, and the compound of the invention is of the formula:

Desferrithiocin-polyether-NHC(=O)O-carbohydrate.

The carbamate moiety —NHC(=O)O— may hydrolyze under physiological conditions, and a positively-charged hydrolysis product desferrithiocin-polyether-$NH_3^+$ may be formed.

Desferrithiocin analogs of Formulae (A) and (J) are expected to be useful in the treatment and/or prevention of a wide range of pathological conditions, including, but not limited to, metal overload (e.g., iron overload, aluminum overload, chromium overload, magnesium overload, calcium overload, strontium overload, nickel overload, manganese overload, cobalt overload, copper overload, zinc overload, silver overload, sodium overload, potassium overload, cadmium overload, mercury overload, lead overload, molybdenum overload, tungsten overload, or actinide overload (e.g., uranium overload)), metal poisoning (e.g., iron poisoning, aluminum poisoning, thallium poisoning, chromium poisoning, magnesium poisoning, calcium poisoning, strontium poisoning, nickel poisoning, manganese poisoning, cobalt poisoning, copper poisoning, zinc poisoning, silver poisoning, sodium poisoning, potassium poisoning, cadmium poisoning, mercury poisoning, lead poisoning, antimony poisoning, molybdenum poisoning, tungsten poisoning, lanthanide poisoning (e.g., cerium poisoning), or actinide poisoning (e.g., uranium poisoning)), oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, and reperfusion injury. Without wishing to be bound by any particular theory, the compounds of the invention are thought to chelate a metal (e.g., iron, aluminum, thallium, chromium, magnesium, calcium, strontium, nickel, manganese, cobalt, copper, zinc, silver, sodium, potassium, cadmium, mercury, lead, antimony, molybdenum, tungsten, a lanthanide (e.g., cerium), or an actinide (e.g., uranium)). The inventive compounds may prevent iron from participating in the generation of reactive oxygen species. Moreover, the inventive compounds may act as free radical scavengers thereby limiting the damage of reactive oxygen species or other radicals.

The inventive compounds may also be useful in the treatment and/or prevention of infectious diseases (e.g., malaria). Infectious diseases are caused by microbes such as bacteria, fungi, and parasites. These pathogenic micobes typically require one or more metals (e.g., iron, calcium, magnesium, strontium, potassium, sodium, chromium, copper, manganese, molybdenum, zinc, and tungsten) to sustain life. For example, iron is used by cytochromes and as a cofactor for enzymes in electron-transport proteins. Without wishing to be bound by any particular theory, the compounds of the invention are thought to deprive the microbes of the iron needed for their metabolic processes by chelating iron.

The invention, therefore, provides novel carbohydrate-modified desferrithiocin analogs; as well as methods of treating and/or preventing pathological conditions, pharmaceutical compositions, uses, and kits, each involving the inventive compounds.

Compounds

Desferrithiocin (DFT) 1 (FIG. 1A) is a natural product iron chelator isolated from Streptomyces antibioticus (Nae-geli et al., "Metabolites of Microorganisms. Part 193. Ferrithiocin." Helv. Chim. Acta 1980, 63, 1400-1406). It forms a 2:1 complex with Fe(III) with a cumulative formation constant of $4 \times 10^{29}$ $M^{-1}$ (Hahn et al., "Coordination Chemistry of Microbial Iron Transport. 42. Structural and Spectroscopic Characterization of Diastereomeric Cr(III) and Co(III) Complexes of Desferriferrithiocin." J. Am. Chem. Soc. 1990, 112, 1854-1860; Anderegg et al., "Metal Complex Formation of a New Siderophore Desferrithiocin and of Three Related Ligands." J. Chem. Soc., Chem. Commun. 1990, 1194-1196). Although the compound was shown to be an excellent deferration agent when administered orally (po) to rats (Bergeron et al., "Evaluation of Desferrithiocin and Its Synthetic Analogs as Orally Effective Iron Chelators." J. Med. Chem. 1991, 34, 2072-2078) and primates (Bergeron et al., "A Comparative Evaluation of Iron Clearance Models." Ann. N.Y. Acad. Sci. 1990, 612, 378-393; Wolfe et al., "A Non-Human Primate Model for the Study of Oral Iron Chelators." Br. J. Haematol. 1989, 72, 456-461), it caused severe nephrotoxicity in rats (Bergeron et al., "A Comparative Study of the Iron-Clearing Properties of Desferrithiocin Analogs with Desferrioxamine B in a Cebus Monkey Model." Blood 1993, 81, 2166-2173). However, the compound's oral activity spurred SAR studies focused on the DFT platform aimed at identifying an orally active and safe DFT analog (Bergeron et al., "Effects of C-4 Stereochemistry and C-4' Hydroxylation on the Iron Clearing Efficiency and Toxicity of Desferrithiocin Analogs." J. Med. Chem. 1999, 42, 2432-2440; Bergeron et al., "Methoxylation of Desazadesferrithiocin Analogs: Enhanced Iron Clearing Efficiency." J. Med. Chem. 2003, 46, 1470-1477; Bergeron et al., "Desazadesmethyldesferrithiocin Analogs as Orally Effective Iron Chelators." J. Med. Chem. 1999, 42, 95-108). Various desazadesferrithiocin analogs have been developed that effectively chelate and remove metals from biological systems. See International PCT Application Publications, WO 1997/036885, published Oct. 9, 1997; WO 2000/016763, published Mar. 30, 2000; WO 2000/012493, published Mar. 9, 2000; WO 2004/017959, published Mar. 4, 2004; WO 2005/034949, published Apr. 21, 2005; WO 2005/023310, published Mar. 17, 2005; WO 2006/107626, published Oct. 12, 2006; WO 2008/130395, published Oct. 30, 2008; WO 2008/115433, published Sep. 25, 2008; WO 2011/028255, published Mar. 10, 2011; WO 2013/090750, published Jun. 20, 2013; and WO 2013/090766, published Jun. 20, 2013; each of which is incorporated herein by reference. Also see U.S. Pat. Nos. 5,840,739; 6,864,270; 7,144,904; 7,879,886, US RE39,132; U.S. Pat. Nos. 6,083, 966; 6,521,652; 6,525,080; 6,559,315; 8,278,458; and 8,324,397; each of which is incorporated herein by reference. Also see U.S. Patent Application Publications, US 2004/044220, US 2004/132789, US 2005/234113, US 2008/255081, US 2006/211746, US 2006/211773, US 2008/096974, US 2013/030028, US 2010/137346, US 2013/210870, and US 2012/184586, each of which is incorporated herein by reference.

Removal of the pyridine nitrogen of 1 provided 2 (FIG. 1A), the parent compound of the desazadesferrithiocin (DADFT) series (Bergeron et al., "Desazadesmethyldesferrithiocin Analogs as Orally Effective Iron Chelators." J. Med. Chem. 1999, 42, 95-108). Interestingly, although 2 was not overtly nephrotoxic, it elicited serious gastrointestinal (GI) problems (Bergeron et al., "A Comparative Study of the Iron-Clearing Properties of Desferrithiocin Analogs with Desferrioxamine B in a Cebus Monkey Model." Blood 1993, 81, 2166-2173; Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Desazadesmethyldesferrithiocin Analogs as Orally Effective Iron Chelators." *J. Med. Chem.* 1999, 42, 95-108). In spite of its GI toxicity, the compound's excellent iron-clearing efficiency (ICE) and the absence of nephrotoxicity prompted further SAR studies predicated on this pharmacophore. This led to the discovery that the lipophilicity (partition between octanol and water, expressed as the log of the fraction in the octanol layer, log $P_{app}$) (Sangster, *Octanol-Water Partition Coefficients: Fundamentals and Physical Chemistry*; John Wiley and Sons: West Sussex, England, 1997; Vol. 2) of the DADFT analogs could have a profound effect on the compound's ICE, organ distribution, and toxicity profile (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Iron Chelators and Therapeutic Uses." In: Abraham, ed. *Burger's Medicinal Chemistry.* 6th. Wiley; New York: 2003. pp. 479-561; Bergeron et al., "Desferrithiocin Analogs and Nephrotoxicity." *J. Med. Chem.* 2008, 51, 5993-6004). Desferrithiocin analogs have been reported to chelate and remove iron or other metals. See International PCT Application Publications, WO 1997/036885, published Oct. 9, 1997; WO 2000/016763, published Mar. 30, 2000; WO 2000/012493, published Mar. 9, 2000; and WO 2004/017959, published Mar. 4, 2004; each of which is incorporated herein by reference. Also see U.S. Pat. Nos. 5,840,739; 6,864,270; 7,144,904; 7,879,886; US RE39,132; U.S. Pat. Nos. 6,083,966; 6,521,652 6,525,080; and 6,559,315; each of which is incorporated herein by reference. Also see U.S. Patent Application Publications, US 2004/044220, US 2004/132789, US 2005/234113, and US 2008/255081, each of which is incorporated herein by reference.

Ultimately, it was determined that hydroxylation of DADFT and a number of different analogs at the 3'-, 4'-, or 5'-position allowed for compounds that were very efficient, orally active iron chelators with less toxicity than 1 or 2 (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Iron Chelators and Therapeutic Uses." In: Abraham, ed. *Burger's Medicinal Chemistry.* 6th. Wiley; New York: 2003. pp. 479-561). Hydroxylation had a significant effect on toxicity reduction. One of these compounds, 3, was studied in human clinical trials by Genzyme (Galanello et al., "A Dose Escalation Study of the Pharmacokinetics, Safety, and Efficacy of Deferitrin, an Oral Iron Chelator in Beta Thalassaemia Patients." *ASH Annu. Meet. Abstr.* 2007, 110, 2669).

Compound 3 was reengineered, by introducing a 3,6,9-trioxadecyloxy group at the 4'-position, to yield 4 (FIG. 1A) (Bergeron et al., "(S)-4,5-Dihydro-2-(2-hydroxy-4-hydroxyphenyl)-4-methyl-4-thiazolecarboxylic Acid Polyethers: A Solution to Nephrotoxicity." *J. Med. Chem.* 2006, 49, 2772-2783). This provided a remarkably efficient orally active iron chelator which, given to rats orally once or twice daily, was virtually nephrotoxicity-free (Bergeron et al., "(S)-4,5-Dihydro-2-(2-hydroxy-4-hydroxyphenyl)-4-methyl-4-thiazolecarboxylic Acid Polyethers: A Solution to Nephrotoxicity." *J. Med. Chem.* 2006, 49, 2772-2783). This turned out to also be true when a variety of polyether backbones were fixed at the 3'-, 4'-, or 5'-position of the DADFT pharmacophore (Bergeron, R. J.; Wiegand, J.; Bharti, N.; Singh, S.; Rocca, J. R. Impact of 3,6,9-Trioxadecyloxy Group on Desazadesferrithiocin Analog Iron Chelators and Organ Distribution. *J. Med. Chem.* 2007, 50, 3302-3313; Bergeron et al., "Design, Synthesis, and Testing of Non-Nephrotoxic Desazadesferrithiocin Polyether Analogs." *J. Med. Chem.* 2008, 51, 3913-3923; Bergeron et al., "The Impact of Polyether Chain Length on the Iron Clearing Efficiency and Physiochemical Properties of Desferrithiocin Analogs." *J. Med. Chem.* 2010, 53, 2843-2853; Bergeron et al., "Desferrithiocin Analog Iron Chelators: Iron Clearing Efficiency, Tissue Distribution, and Renal Toxicity." *Biometals,* 2011, 24, 239-258). In fact, (S)-4,5-dihydro-2-[2-hydroxy-3-(3,6,9-trioxadecyloxy)]-4-methyl-4-thiazolecarboxylic acid ((S)-3'-(HO)-DADFT-PE, 5; FIG. 1A) has now been moved forward to clinical trials. Thus, it appeared as though fixing a polyether fragment to the DADFT framework was also a uniformly effective tool in further reducing the nephrotoxicity induced by 3.

Although DFT and DADFT analogs as a class of compounds appear promising as metal chelating agents, much work remains to be done to improve these compounds' physiochemical, pharmacokinetic, pharmacodynamic, and/or toxicological properties, such as absorption, distribution, metal-clearing efficiency, and toxicity, for the purpose of providing safe and effective compounds for a better treatment and/or prevention of pathological conditions in a subject. Provided by the present invention are novel DFT analogs that include one or more carbohydrate (e.g., a sugar, such as glucose, including α-D-, β-D-, α-L-, and β-L-glucose) moieties. The carbohydrate moieties may be attached directly to or through a linker moiety at different positions on the parent compound DFT 1, for example, at the 2'-, 3'-, 4'-, and/or 5'-position on the pyridinyl ring, and/or at the carboxyl group. The compounds of the invention may be useful in the treatment and/or prevention of a variety of pathological conditions.

In one aspect of the present invention, provided are compounds of Formula (A):

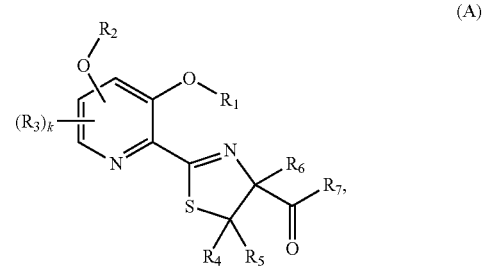

(A)

and pharmaceutically acceptable salts, tautomers, stereoisomers, solvates, hydrates, and polymorphs thereof, wherein:

$R_1$ is hydrogen, alkyl, acyl, an oxygen protecting group,

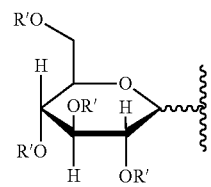

or

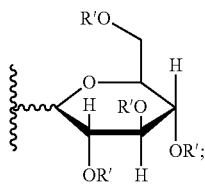

R$_2$ is hydrogen, alkyl, acyl, an oxygen protecting group, —[(CH$_2$)$_n$—O]$_x$—[(CH$_2$)$_x$—O]$_y$—R″, or —[(CH$_2$)$_n$—O]$_x$—[(CH$_2$)$_n$—O]$_y$—(CH$_2$)$_n$—NR$_{10}$—C(=O)O—R″;

each occurrence of R$_3$ is independently alkyl, arylalkyl, or —OR$_8$;

R$_4$ is hydrogen or alkyl;
R$_5$ is hydrogen or alkyl;
R$_6$ is hydrogen or alkyl;
R$_7$ is —OR$_9$ or —SR$_9$;
R$_8$ is hydrogen, alkyl, acyl, an oxygen protecting group,

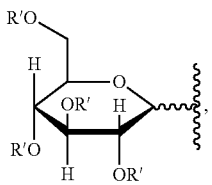

or

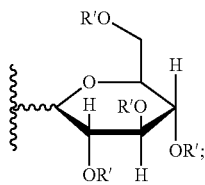

R$_9$ is hydrogen, alkyl,

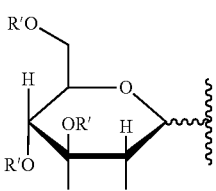

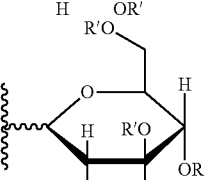

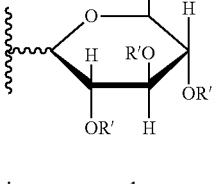

an oxygen protecting group when attached to an oxygen atom, or a sulfur protecting group when attached to a sulfur atom;

R$_{10}$ is hydrogen, alkyl, acyl, or a nitrogen protecting group;

R' is hydrogen or an oxygen protecting group;
R″ is hydrogen, alkyl, acyl, an oxygen protecting group,

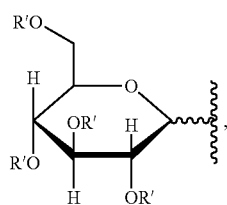

or

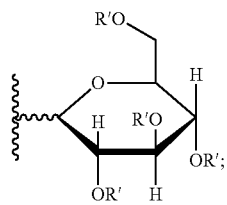

each occurrence of n is independently an integer from 1 to 8, inclusive;
k is an integer from 0 to 2, inclusive;
x is an integer from 1 to 8, inclusive; and
y is an integer from 0 to 8, inclusive.

In certain embodiments, at least one of R$_1$ and R$_9$ is

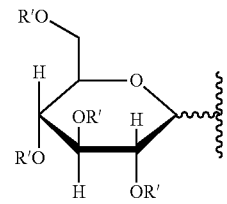

or

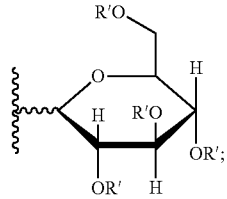

or R$_2$ is —[(CH$_2$)$_n$—O]$_x$—[(CH$_2$)$_n$—O]$_y$—R″ or —[(CH$_2$)$_n$—O]$_x$—[(CH$_2$)$_n$—O]$_y$—(CH$_2$)$_n$—NR$_{10}$—C(=O)O—R″, and R″ is

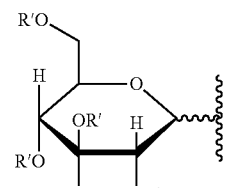

or

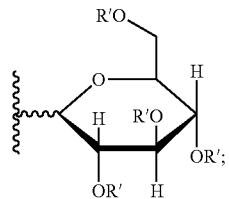

or $R_3$ is —$OR_8$, $R_8$ is

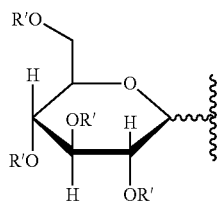

or

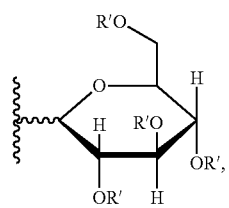

and k is 1 or 2.

In certain embodiments, $R_1$ is hydrogen, alkyl, acyl, or an oxygen protecting group;

$R_2$ is hydrogen, alkyl, acyl, an oxygen protecting group, —[(CH$_2$)$_n$—O]$_x$—[(CH$_2$)$_n$—O]$_y$—R", or —[(CH$_2$)$_n$—O]—[(CH$_2$)$_n$—O]$_y$—(CH$_2$)$_n$—NR$_{10}$—C(=O)O—R";

each occurrence of $R_3$ is independently alkyl, arylalkyl, or —$OR_8$;

$R_4$, $R_5$, and $R_6$ are each independently hydrogen or alkyl;

$R_7$ is —$OR_9$ or —$SR_9$;

$R_8$ is hydrogen, alkyl, acyl, or an oxygen protecting group;

$R_9$ is hydrogen, alkyl, an oxygen protecting group when attached to an oxygen atom, or a sulfur protecting group when attached to a sulfur atom;

$R_{10}$ is hydrogen, alkyl, acyl, or a nitrogen protecting group;

R' is hydrogen or an oxygen protecting group;

R" is hydrogen, alkyl, acyl, or an oxygen protecting group;

each occurrence of n is independently an integer from 1 to 8, inclusive;

k is an integer from 0 to 2, inclusive;

x is an integer from 1 to 8, inclusive; and y is an integer from 0 to 8, inclusive.

In compounds of Formula (A), $R_1$ is hydrogen, alkyl, acyl, an oxygen protecting group,

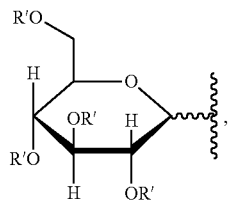

or

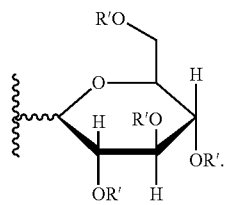

In certain embodiments, $R_1$ is hydrogen. In certain embodiments, $R_1$ is alkyl. In certain embodiments, $R_1$ is $C_{1-6}$ alkyl. In certain embodiments, $R_1$ is methyl. In certain embodiments, $R_1$ is ethyl. In certain embodiments, $R_1$ is propyl. In certain embodiments, $R_1$ is butyl. In certain embodiments, $R_1$ is acyl. In certain embodiments, $R_1$ is acetyl. In certain embodiments, $R_1$ is pivaloyl. In certain embodiments, $R_1$ is an oxygen protecting group. In certain embodiments, $R_1$ is silyl. In certain embodiments, $R_1$ is TBDPS, TBDMS, TIPS, TES, or TMS. In certain embodiments, $R_1$ is MOM, THP, t-Bu, Bn, allyl, acetyl, pivaloyl, or Bz. In certain embodiments, $R_1$ is

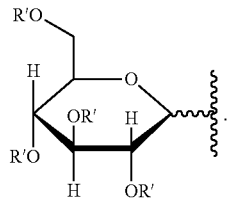

In certain embodiments, $R_1$ is

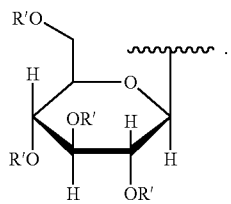

In certain embodiments, $R_1$ is

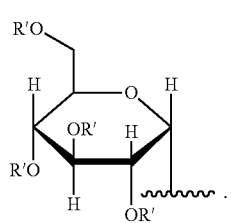

In certain embodiments, $R_1$ is

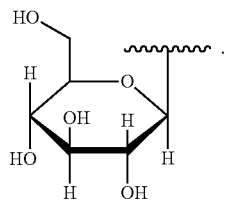

In certain embodiments, $R_1$ is

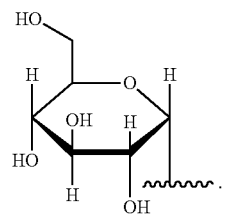

In certain embodiments, $R_1$ is

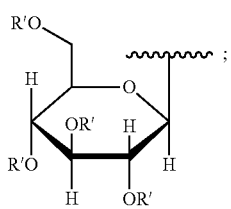

wherein all R' are oxygen protecting groups. In certain embodiments, $R_1$ is

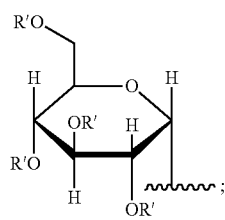

wherein all R' are oxygen protecting groups. In certain embodiments, $R_1$ is

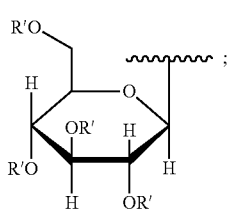

wherein all R' are silyl, TBDPS, TBDMS, TIPS, TES, TMS, MOM, THP, t-Bu, Bn, allyl, acetyl, pivaloyl, or Bz. In certain embodiments, $R_1$

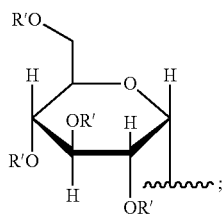

is wherein all R' are silyl, TBDPS, TBDMS, TIPS, TES, TMS, MOM, THP, t-Bu, Bn, allyl, acetyl, pivaloyl, or Bz. In certain embodiments, $R_1$ is

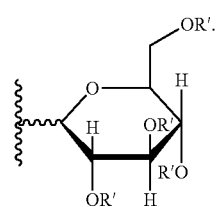

In certain embodiments, $R_1$ is

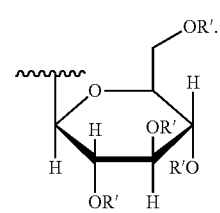

In certain embodiments, $R_1$ is

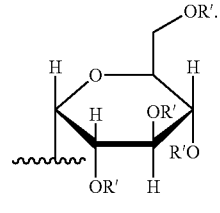

In certain embodiments, $R_1$ is

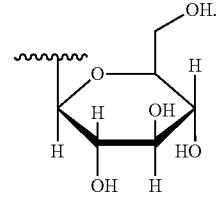

In certain embodiments, $R_1$ is

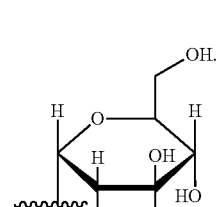

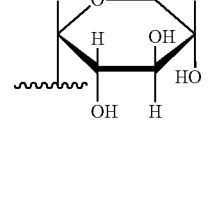

In certain embodiments, $R_1$ is

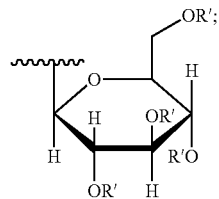

wherein all R' are oxygen protecting groups. In certain embodiments, $R_1$ is

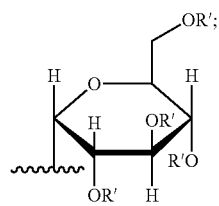

wherein all R' are oxygen protecting groups. In certain embodiments, $R_1$ is

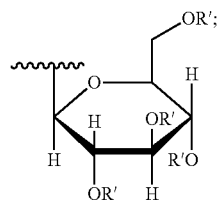

wherein all R' are silyl, TBDPS, TBDMS, TIPS, TES, TMS, MOM, THP, t-Bu, Bn, allyl, acetyl, pivaloyl, or Bz. In certain embodiments, $R_1$ is

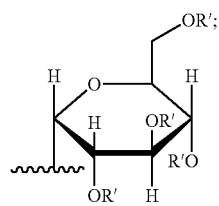

wherein all R' are silyl, TBDPS, TBDMS, TIPS, TES, TMS, MOM, THP, t-Bu, Bn, allyl, acetyl, pivaloyl, or Bz.

In compounds of Formula (A), $R_2$ is hydrogen, alkyl, acyl, an oxygen protecting group, $-[(CH_2)_n-O]_x-[(CH_2)_n-O]_y-R''$, or $-[(CH_2)_n-O]_x-[(CH_2)_n-O]_y-(CH_2)_n-NR_{10}-C(=O)O-R''$. In certain embodiments, $R_2$ is hydrogen. In certain embodiments, $R_2$ is alkyl. In certain embodiments, $R_2$ is $C_{1-12}$ alkyl optionally substituted with one or more substituents independently selected from the group consisting of hydroxyl, alkyloxy, and $-CO_2H$. In certain embodiments, $R_2$ is $-(CH_2)_2-OH$, $-(CH_2)_3-OH$, $-(CH_2)_4-OH$, $-(CH_2)_5-OH$, $-(CH_2)_6-OH$, $-(CH_2)_7-OH$, or $-(CH_2)_8-OH$. In certain embodiments, $R_2$ is $-(CH_2)_2-OCH_3$, $-(CH_2)_3-OCH_3$, $-(CH_2)_4-OCH_3$, $-(CH_2)_5-OCH_3$, $-(CH_2)_6-OCH_3$, $-(CH_2)_7-OCH_3$, or $-(CH_2)_8-OCH_3$. In certain embodiments, $R_2$ is $-CH_2-CO_2H$, $-(CH_2)_2-CO_2H$, $-(CH_2)_3-CO_2H$, $-(CH_2)_4-CO_2H$, $-(CH_2)_5-CO_2H$, $-(CH_2)_6-CO_2H$, or $-(CH_2)_7-CO_2H$. In certain embodiments, $R_2$ is $C_{1-12}$ alkyl substituted at least with $-CO_2R_{31}$, wherein $R_{31}$ is substituted or unsubstituted $C_{1-6}$ alkyl (e.g., $-CH_3$). In certain embodiments, $R_2$ is $-CH_2-CO_2R_{31}$, $-(CH_2)_2-CO_2R_{31}$, $-(CH_2)_3-CO_2R_{31}$, $-(CH_2)_4-CO_2R_{31}$, $-(CH_2)_5-CO_2R_{31}$, $-(CH_2)_6-CO_2R_{31}$, or $-(CH_2)_7-CO_2R_{31}$. In certain embodiments, $R_2$ is $C_{1-6}$ alkyl. In certain embodiments, $R_2$ is methyl. In certain embodiments, $R_2$ is ethyl. In certain embodiments, $R_2$ is propyl. In certain embodiments, $R_2$ is butyl. In certain embodiments, $R_2$ is acyl. In certain embodiments, $R_2$ is acetyl. In certain embodiments, $R_2$ is pivaloyl. In certain embodiments, $R_2$ is an oxygen protecting group. In certain embodiments, $R_2$ is silyl. In certain embodiments, $R_2$ is TBDPS, TBDMS, TIPS, TES, or TMS. In certain embodiments, $R_2$ is MOM, THP, t-Bu, Bn, allyl, acetyl, pivaloyl, or Bz. In certain embodiments, $R_2$ is $-[(CH_2)_n-O]_x-[(CH_2)_n-O]_y-R''$. In certain embodiments, $R_2$ is

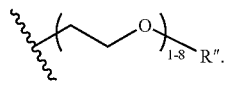

In certain embodiments, $R_2$ is

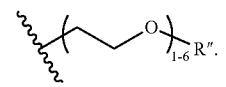

In certain embodiments, $R_2$ is

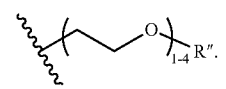

In certain embodiments, $R_2$ is

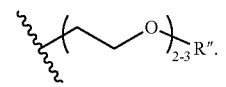

In certain embodiments, $R_2$ is

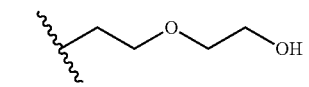 [SMILES: *CCOCCO]

or

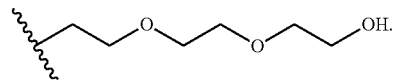 [SMILES: *CCOCCOCCO]

In certain embodiments, $R_2$ is

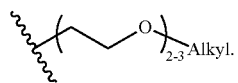

In certain embodiments, $R_2$ is

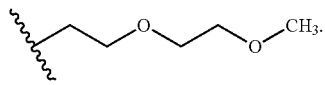 [SMILES: *CCOCCOC]

In certain embodiments, $R_2$ is

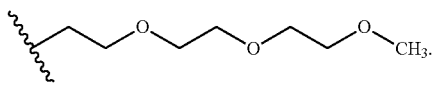 [SMILES: *CCOCCOCCOC]

In certain embodiments, $R_2$ is

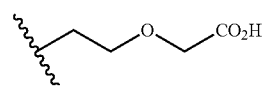 [SMILES: *CCOCC(=O)O]

or

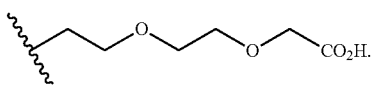 [SMILES: *CCOCCOCC(=O)O]

In certain embodiments, $R_2$ is

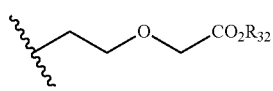

or

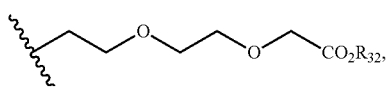

wherein $R_{32}$ is substituted or unsubstituted $C_{1-6}$ alkyl (e.g., —$CH_3$). In certain embodiments, $R_2$ is

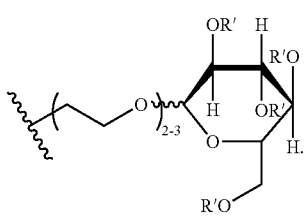

In certain embodiments, $R_2$ is

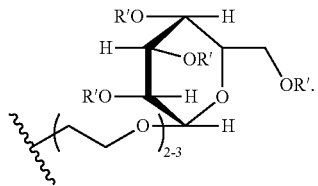

In certain embodiments, $R_2$ is

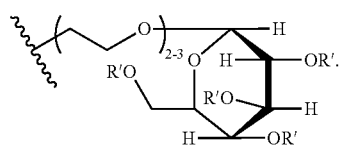

In certain embodiments, $R_2$ is

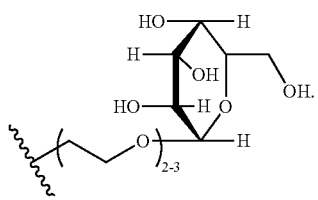

In certain embodiments, $R_2$ is

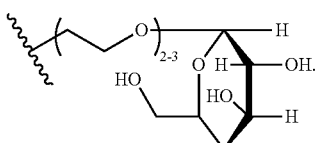

In certain embodiments, $R_2$ is

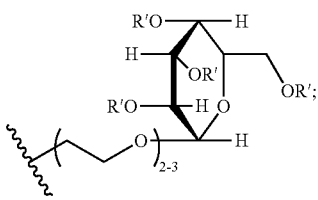

wherein all R' are oxygen protecting groups. In certain embodiments, $R_2$ is

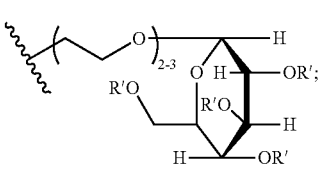

wherein all R' are oxygen protecting groups. In certain embodiments, $R_2$ is

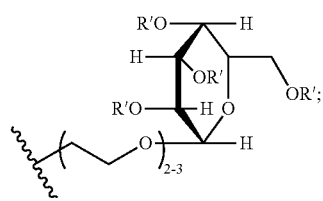

wherein all R' are silyl, TBDPS, TBDMS, TIPS, TES, TMS, MOM, THP, t-Bu, Bn, allyl, acetyl, pivaloyl, or Bz. In certain embodiments, $R_2$ is

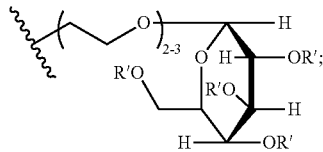

wherein all R' are silyl, TBDPS, TBDMS, TIPS, TES, TMS, MOM, THP, t-Bu, Bn, allyl, acetyl, pivaloyl, or Bz. In certain embodiments, $R_2$ is

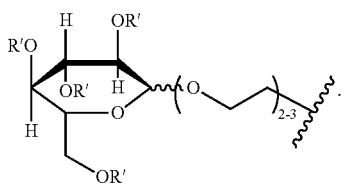

In certain embodiments, $R_2$ is

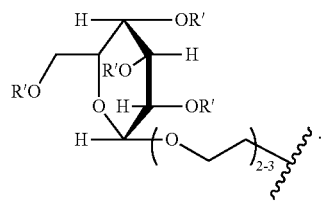

In certain embodiments, $R_2$ is

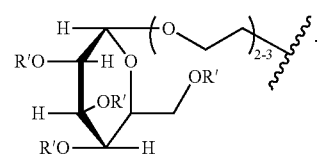

In certain embodiments, $R_2$ is

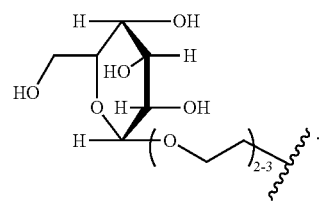

In certain embodiments, $R_2$ is

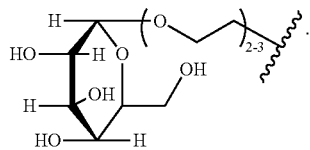

In certain embodiments, $R_2$ is

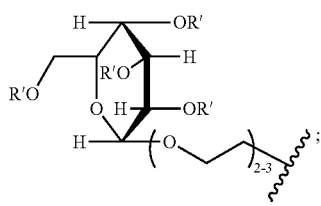

wherein all R' are oxygen protecting groups. In certain embodiments, $R_2$ is

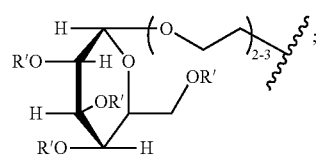

wherein all R' are oxygen protecting groups. In certain embodiments, $R_2$ is

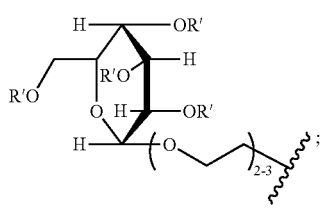

wherein all R' are silyl, TBDPS, TBDMS, TIPS, TES, TMS, MOM, THP, t-Bu, Bn, allyl, acetyl, pivaloyl, or Bz. In certain embodiments, $R_2$ is

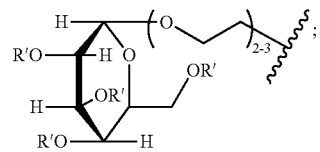

wherein all R' are silyl, TBDPS, TBDMS, TIPS, TES, TMS, MOM, THP, t-Bu, Bn, allyl, acetyl, pivaloyl, or Bz. In certain embodiments, $R_2$ is $-[(CH_2)_n-O]_y-[(CH_2)_n-O]_y-(CH_2)_n-NR_{10}-C(=O)O-R''$. In certain embodiments, $R_2$ is $-[(CH_2)_n-O]_y-[(CH_2)_n-O]_y-(CH_2)_n-NH-C(=O)O-R''$. In certain embodiments, $R_2$ is

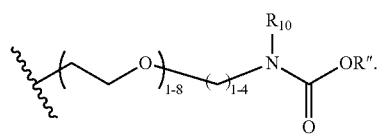

In certain embodiments, $R_2$ is

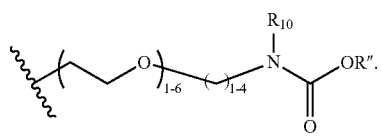

In certain embodiments, $R_2$ is

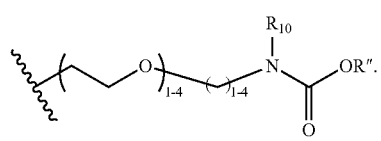

In certain embodiments, $R_2$ is

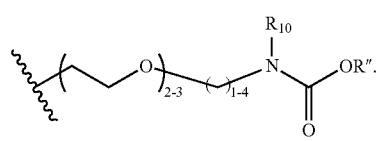

In certain embodiments, $R_2$ is

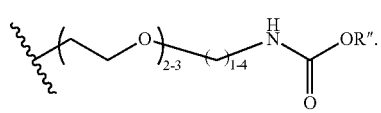

In certain embodiments, $R_2$ is

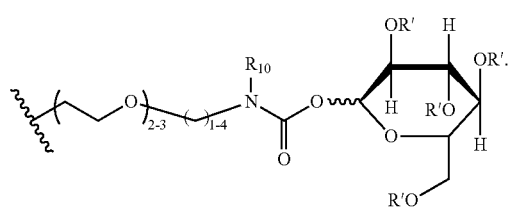

In certain embodiments, $R_2$ is

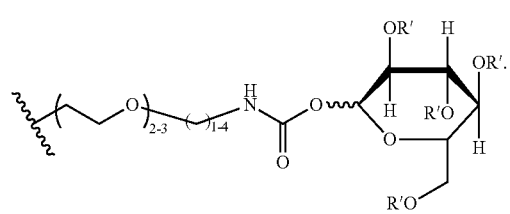

In certain embodiments, $R_2$ is

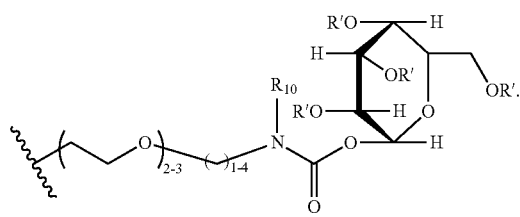

In certain embodiments, $R_2$ is

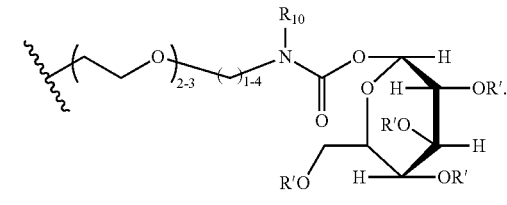

In certain embodiments, $R_2$ is

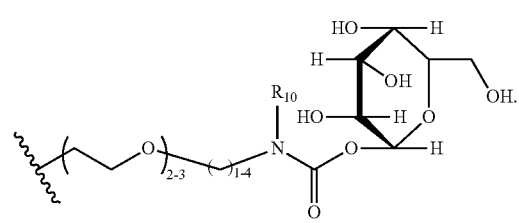

In certain embodiments, $R_2$ is

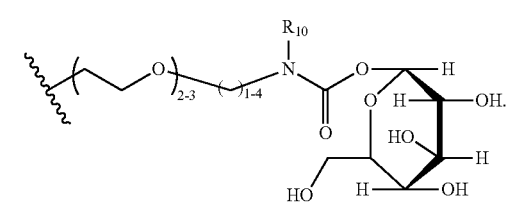

In certain embodiments, $R_2$ is

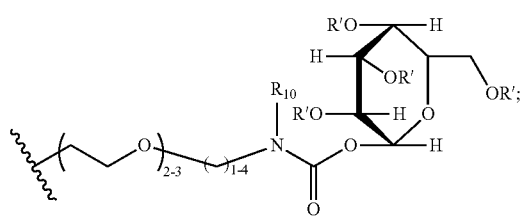

wherein all R' are oxygen protecting groups. In certain embodiments, $R_2$ is

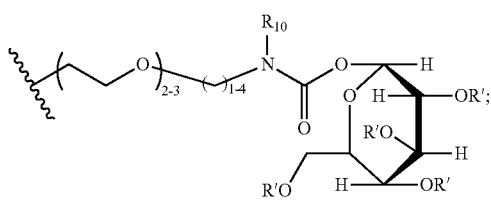

wherein all R' are oxygen protecting groups. In certain embodiments, $R_2$ is

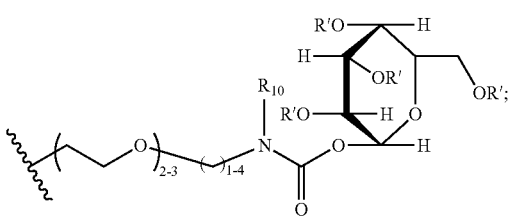

wherein all R' are silyl, TBDPS, TBDMS, TIPS, TES, TMS, MOM, THP, t-Bu, Bn, allyl, acetyl, pivaloyl, or Bz. In certain embodiments, $R_2$ is

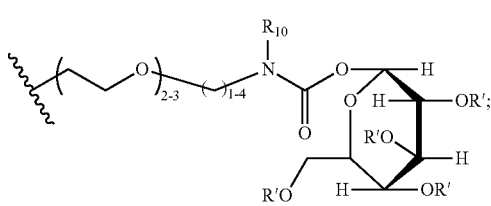

wherein all R' are silyl, TBDPS, TBDMS, TIPS, TES, TMS, MOM, THP, t-Bu, Bn, allyl, acetyl, pivaloyl, or Bz. In certain embodiments, $R_2$ is

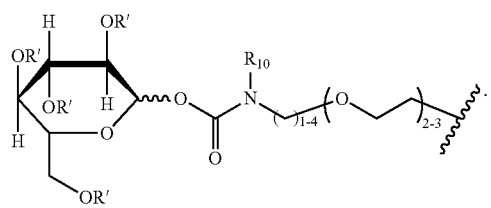

In certain embodiments, $R_2$ is

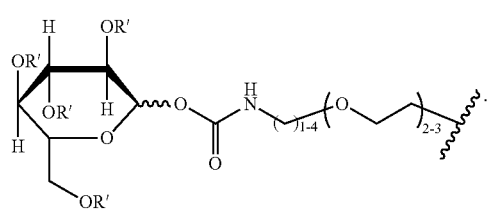

In certain embodiments, $R_2$ is

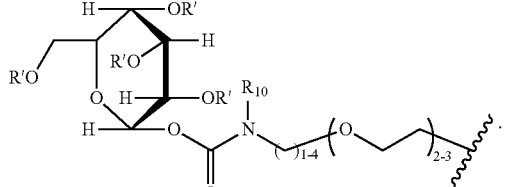

In certain embodiments, $R_2$ is

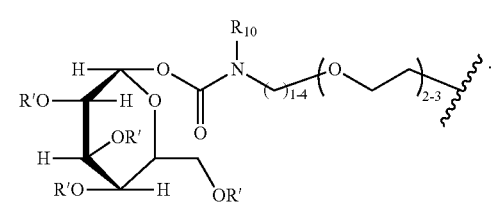

In certain embodiments, $R_2$ is

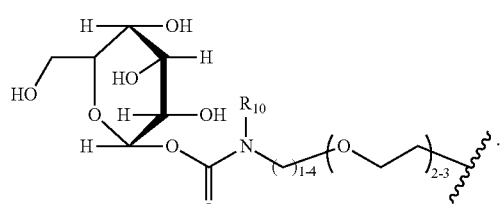

In certain embodiments, $R_2$ is

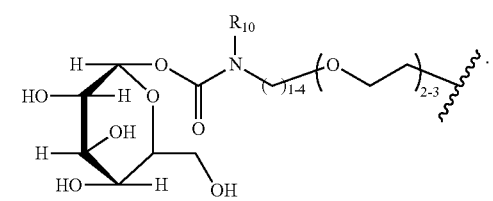

In certain embodiments, $R_2$ is

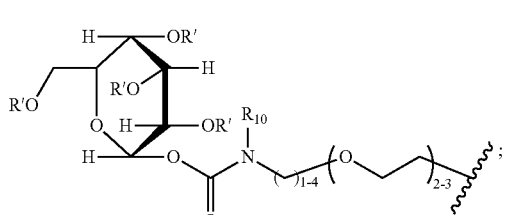

wherein all R' are oxygen protecting groups. In certain embodiments, $R_2$ is

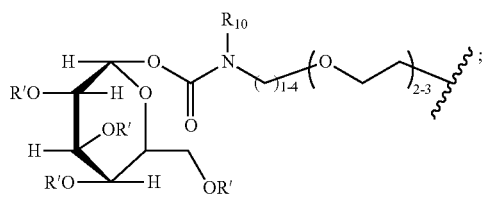

wherein all R' are oxygen protecting groups. In certain embodiments, $R_2$ is

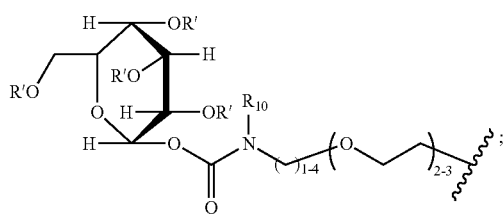

wherein all R' are silyl, TBDPS, TBDMS, TIPS, TES, TMS, MOM, THP, t-Bu, Bn, allyl, acetyl, pivaloyl, or Bz. In certain embodiments, $R_2$ is

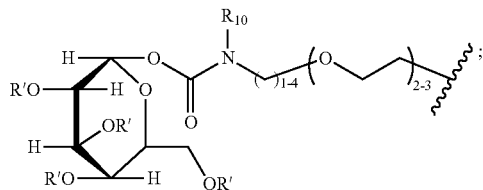

wherein all R' are silyl, TBDPS, TBDMS, TIPS, TES, TMS, MOM, THP, t-Bu, Bn, allyl, acetyl, pivaloyl, or Bz.

In certain embodiments, both $R_1$ and $R_2$ are hydrogen.

In compounds of Formula (A), each occurrence of $R_3$ is independently alkyl, arylalkyl, or —$OR_8$. In certain embodiments, at least one occurrence of $R_3$ is alkyl. In certain embodiments, at least one occurrence of $R_3$ is $C_{1-6}$ alkyl. In certain embodiments, at least one occurrence of $R_3$ is methyl. In certain embodiments, at least one occurrence of $R_3$ is ethyl. In certain embodiments, at least one occurrence of $R_3$ is propyl. In certain embodiments, at least one occurrence of $R_3$ is butyl. In certain embodiments, at least one occurrence of $R_3$ is arylalkyl. In certain embodiments, at least one occurrence of $R_3$ is benzyl. In certain embodiments, at least one occurrence of $R_3$ is —$OR_8$. In certain embodiments, at least one occurrence of $R_3$ is —OH. In certain embodiments, at least one occurrence of $R_3$ is —O-alkyl. In certain embodiments, at least one occurrence of $R_3$ is —O—($C_{1-6}$ alkyl). In certain embodiments, at least one occurrence of $R_3$ is —OMe. In certain embodiments, at least one occurrence of $R_3$ is —OEt. In certain embodiments, at least one occurrence of $R_3$ is —OPr. In certain embodiments, at least one occurrence of $R_3$ is —OBu. In certain embodiments, at least one occurrence of $R_3$ is —O-acyl. In certain embodiments, at least one occurrence of $R_3$ is —O—C(=O)—$CH_3$. In certain embodiments, at least one occurrence of $R_3$ is

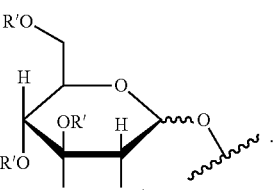

In certain embodiments, at least one occurrence of $R_3$ is

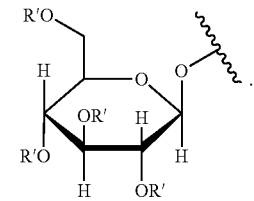

In certain embodiments, at least one occurrence of $R_3$ is

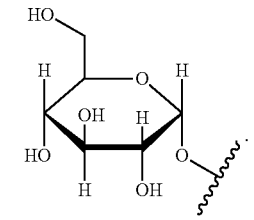

In certain embodiments, at least one occurrence of $R_3$ is

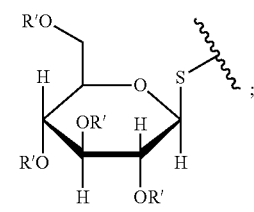

In certain embodiments, at least one occurrence of $R_3$ is wherein all R' are oxygen protecting groups. In certain embodiments, at least one occurrence of $R_3$ is

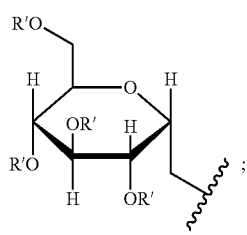

wherein all R' are oxygen protecting groups. In certain embodiments, at least one occurrence of $R_3$ is

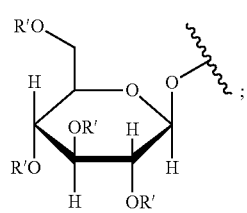

wherein all R' are silyl, TBDPS, TBDMS, TIPS, TES, TMS, MOM, THP, t-Bu, Bn, allyl, acetyl, pivaloyl, or Bz. In certain embodiments, at least one occurrence of $R_3$ is

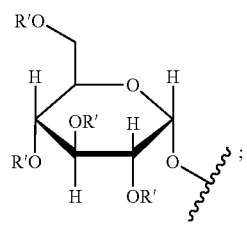

wherein all R' are silyl, TBDPS, TBDMS, TIPS, TES, TMS, MOM, THP, t-Bu, Bn, allyl, acetyl, pivaloyl, or Bz. In certain embodiments, at least one occurrence of $R_3$ is

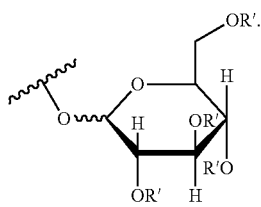

In certain embodiments, at least one occurrence of $R_3$ is

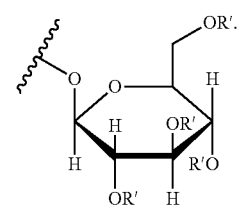

In certain embodiments, at least one occurrence of $R_3$ is

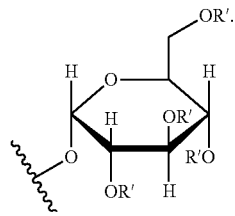

In certain embodiments, at least one occurrence of $R_3$ is

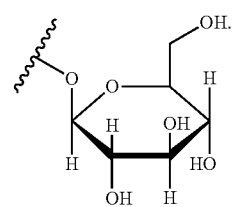

In certain embodiments, at least one occurrence of $R_3$ is

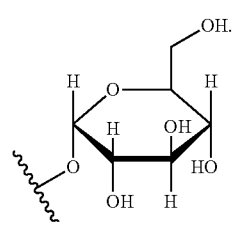

In certain embodiments, at least one occurrence of $R_3$ is

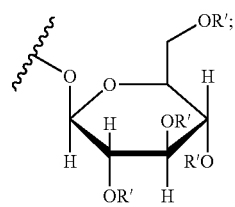

wherein all R' are oxygen protecting groups. In certain embodiments, at least one occurrence of $R_3$ is

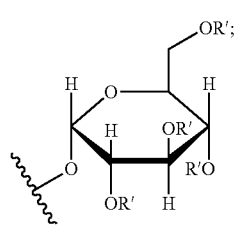

wherein all R' are oxygen protecting groups. In certain embodiments, at least one occurrence of $R_3$ is

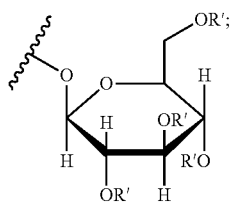

wherein all R' are silyl, TBDPS, TBDMS, TIPS, TES, TMS, MOM, THP, t-Bu, Bn, allyl, acetyl, pivaloyl, or Bz. In certain embodiments, at least one occurrence of $R_3$ is

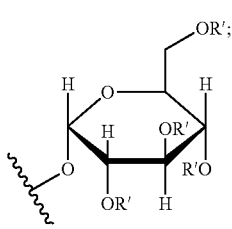

wherein all R' are silyl, TBDPS, TBDMS, TIPS, TES, TMS, MOM, THP, t-Bu, Bn, allyl, acetyl, pivaloyl, or Bz.

In compounds of Formula (A), $R_4$ is hydrogen or alkyl. In certain embodiments, $R_4$ is hydrogen. In certain embodiments, $R_4$ is alkyl. In certain embodiments, $R_4$ is $C_{1-6}$ alkyl. In certain embodiments, $R_4$ is methyl. In certain embodiments, $R_4$ is ethyl. In certain embodiments, $R_4$ is propyl. In certain embodiments, $R_4$ is butyl.

In compounds of Formula (A), $R_5$ is hydrogen or alkyl. In certain embodiments, $R_5$ is hydrogen. In certain embodiments, $R_5$ is alkyl. In certain embodiments, $R_5$ is $C_{1-6}$ alkyl. In certain embodiments, $R_5$ is methyl. In certain embodiments, $R_5$ is ethyl. In certain embodiments, $R_5$ is propyl. In certain embodiments, $R_5$ is butyl.

In certain embodiments, $R_4$ and $R_5$ are each hydrogen. In certain embodiments, $R_4$ and $R_5$ are each alkyl. In certain embodiments, $R_4$ and $R_5$ are each $C_{1-6}$ alkyl. In certain embodiments, $R_4$ and $R_5$ are each methyl. In certain embodiments, $R_4$ and $R_5$ are each ethyl.

In compounds of Formula (A), $R_6$ is hydrogen or alkyl. In certain embodiments, $R_6$ is hydrogen. In certain embodiments, $R_6$ is alkyl. In certain embodiments, $R_6$ is $C_{1-6}$ alkyl. In certain embodiments, $R_6$ is methyl. In certain embodiments, $R_6$ is ethyl. In certain embodiments, $R_6$ is propyl. In certain embodiments, $R_6$ is butyl.

In certain embodiments, $R_4$ and $R_5$ are each hydrogen; and $R_6$ is alkyl. In certain embodiments, $R_4$ and $R_5$ are each hydrogen; and $R_6$ is $C_{1-6}$ alkyl. In certain embodiments, $R_4$ and $R_5$ are each hydrogen; and $R_6$ is methyl. In certain embodiments, $R_4$ and $R_5$ are each hydrogen; and $R_6$ is ethyl. In certain embodiments, $R_4$ and $R_5$ are each hydrogen; and $R_6$ is propyl. In certain embodiments, $R_4$ and $R_5$ are each hydrogen; and $R_6$ is butyl.

In certain embodiments, $R_4$ and $R_5$ are each alkyl; and $R_6$ is methyl. In certain embodiments, $R_4$ and $R_5$ are each $C_{1-6}$ alkyl; and $R_6$ is methyl. In certain embodiments, $R_4$ and $R_5$ are each methyl; and $R_6$ is methyl. In certain embodiments, $R_4$ and $R_5$ are each ethyl; and $R_6$ is methyl.

In certain embodiments, $R_4$ and $R_5$ are each alkyl; and $R_6$ is hydrogen. In certain embodiments, $R_4$ and $R_5$ are each $C_{1-6}$ alkyl; and $R_6$ is hydrogen. In certain embodiments, $R_4$ and $R_5$ are each methyl; and $R_6$ is hydrogen. In certain embodiments, $R_4$ and $R_5$ are each ethyl; and $R_6$ is hydrogen. In certain embodiments, $R_4$, $R_5$, and $R_6$ are each hydrogen.

In compounds of Formula (A), $R_7$ is —$OR_9$ or —$SR_9$. In certain embodiments, $R_7$ is —$OR_9$. In certain embodiments, $R_7$ is —OH. In certain embodiments, $R_7$ is —O-alkyl. In certain embodiments, $R_7$ is —O—($C_{1-6}$ alkyl). In certain embodiments, $R_7$ is —OMe. In certain embodiments, $R_7$ is —OEt. In certain embodiments, $R_7$ is —OPr. In certain embodiments, $R_7$ is

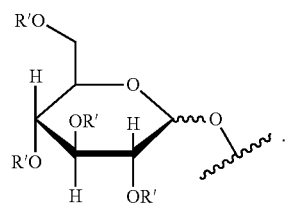

In certain embodiments, $R_7$ is

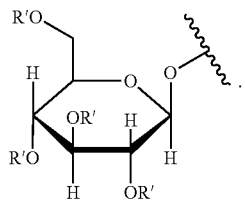

In certain embodiments, $R_7$ is

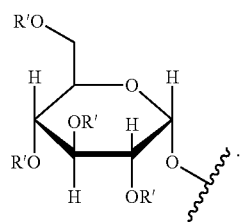

In certain embodiments, $R_7$ is

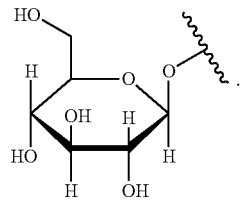

In certain embodiments, $R_7$ is

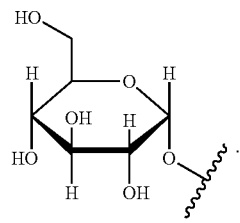

In certain embodiments, R₇ is

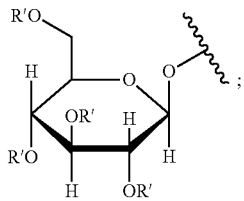;

wherein all R' are oxygen protecting groups. In certain embodiments, R₇ is

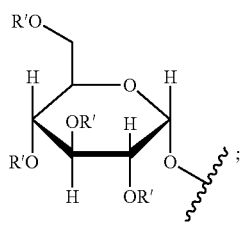;

wherein all R' are oxygen protecting groups. In certain embodiments, R₇ is

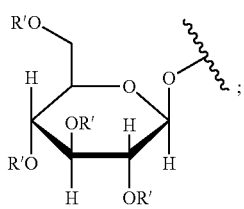;

wherein all R' are silyl, TBDPS, TBDMS, TIPS, TES, TMS, MOM, THP, t-Bu, Bn, allyl, acetyl, pivaloyl, or Bz. In certain embodiments, R₇ is

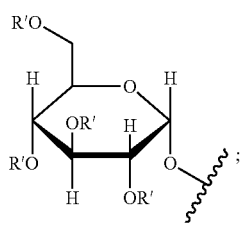;

wherein all R' are silyl, TBDPS, TBDMS, TIPS, TES, TMS, MOM, THP, t-Bu, Bn, allyl, acetyl, pivaloyl, or Bz. In certain embodiments, R₇ is

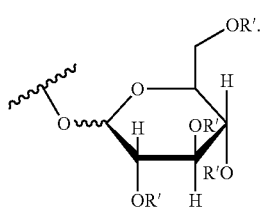

In certain embodiments, R₇ is

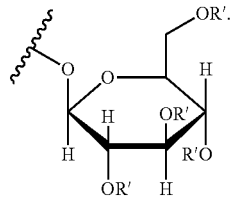

In certain embodiments, R₇ is

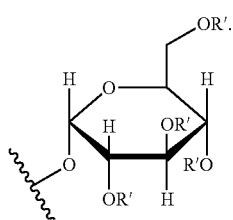

In certain embodiments, R₇ is

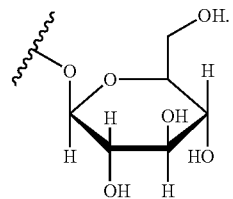

In certain embodiments, R₇ is

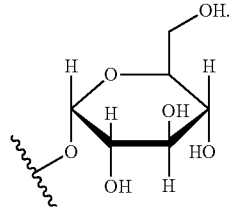

In certain embodiments, R₇ is

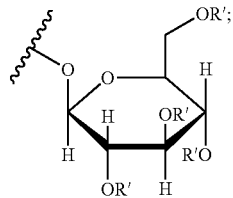

wherein all R' are oxygen protecting groups. In certain embodiments, R₇ is

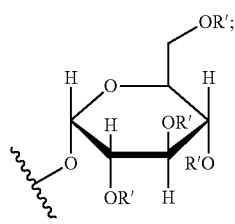

wherein all R' are oxygen protecting groups. In certain embodiments, $R_7$ is

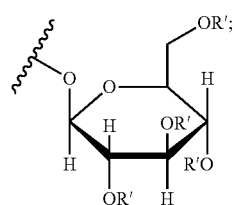

wherein all R' are silyl, TBDPS, TBDMS, TIPS, TES, TMS, MOM, THP, t-Bu, Bn, allyl, acetyl, pivaloyl, or Bz. In certain embodiments, $R_7$ is

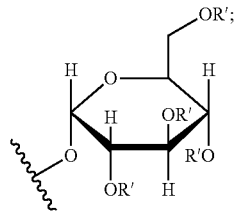

wherein all R' are silyl, TBDPS, TBDMS, TIPS, TES, TMS, MOM, THP, t-Bu, Bn, allyl, acetyl, pivaloyl, or Bz. In certain embodiments, $R_7$ is

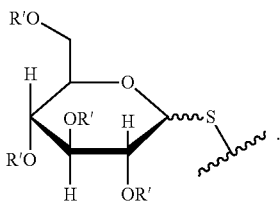

In certain embodiments, $R_7$ is

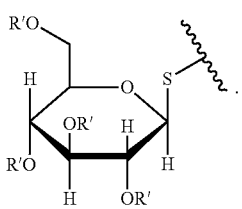

In certain embodiments, $R_7$ is

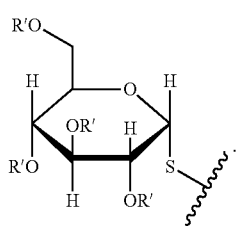

In certain embodiments, $R_7$ is

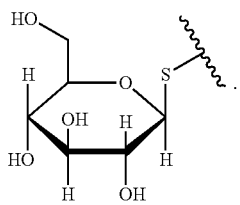

In certain embodiments, $R_7$ is

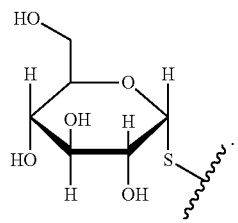

In certain embodiments, $R_7$ is

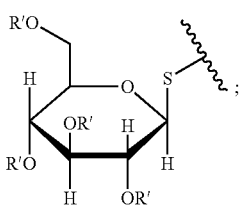

wherein all R' are oxygen protecting groups. In certain embodiments, $R_7$ is

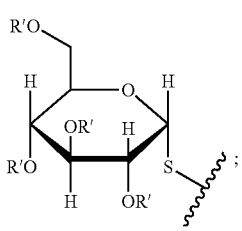

wherein all R' are oxygen protecting groups. In certain embodiments, $R_7$ is

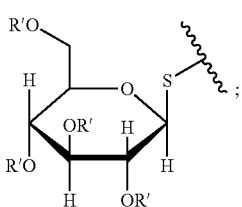

wherein all R' are silyl, TBDPS, TBDMS, TIPS, TES, TMS, MOM, THP, t-Bu, Bn, allyl, acetyl, pivaloyl, or Bz. In certain embodiments, $R_7$ is

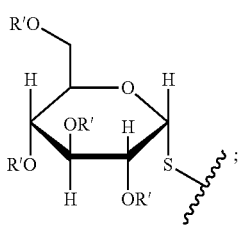

wherein all R' are silyl, TBDPS, TBDMS, TIPS, TES, TMS, MOM, THP, t-Bu, Bn, allyl, acetyl, pivaloyl, or Bz. In certain embodiments, $R_7$ is

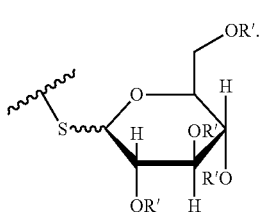

In certain embodiments, $R_7$ is

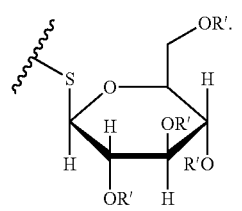

In certain embodiments, $R_7$ is

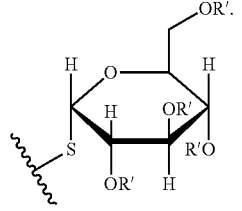

In certain embodiments, $R_7$ is

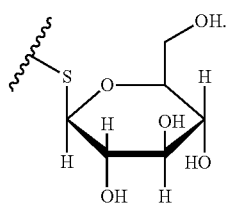

In certain embodiments, $R_7$ is

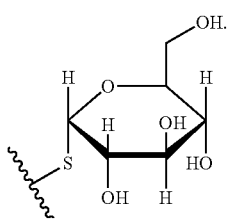

In certain embodiments, $R_7$ is

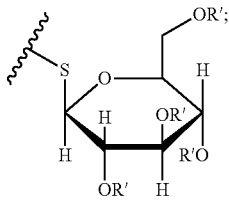

wherein all R' are oxygen protecting groups. In certain embodiments, $R_7$ is

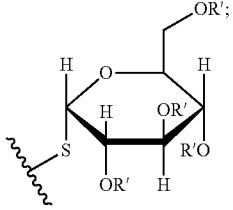

wherein all R' are oxygen protecting groups. In certain embodiments, $R_7$ is

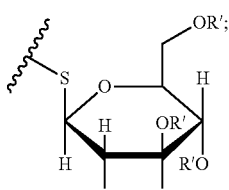

wherein all R' are silyl, TBDPS, TBDMS, TIPS, TES, TMS, MOM, THP, t-Bu, Bn, allyl, acetyl, pivaloyl, or Bz. In certain embodiments, $R_7$ is

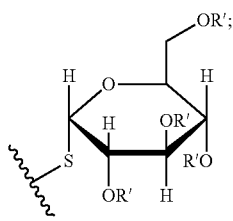

wherein all R' are silyl, TBDPS, TBDMS, TIPS, TES, TMS, MOM, THP, t-Bu, Bn, allyl, acetyl, pivaloyl, or Bz.

In compounds of Formula (A), $R_8$ is hydrogen, alkyl, acyl, an oxygen protecting group,

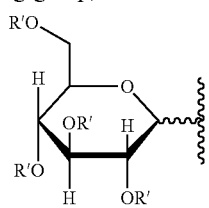

or

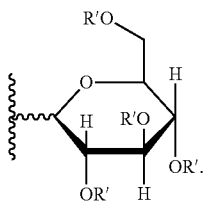

In certain embodiments, $R_8$ is hydrogen. In certain embodiments, $R_8$ is alkyl. In certain embodiments, $R_8$ is $C_{1-6}$ alkyl. In certain embodiments, $R_8$ is methyl. In certain embodiments, $R_8$ is ethyl. In certain embodiments, $R_8$ is propyl. In certain embodiments, $R_8$ is butyl. In certain embodiments, $R_8$ is acyl. In certain embodiments, $R_8$ is acetyl. In certain embodiments, $R_8$ is pivaloyl. In certain embodiments, $R_8$ is an oxygen protecting group. In certain embodiments, $R_8$ is silyl. In certain embodiments, $R_8$ is TBDPS, TBDMS, TIPS, TES, or TMS. In certain embodiments, $R_8$ is MOM, THP, t-Bu, Bn, allyl, acetyl, pivaloyl, or Bz. In certain embodiments, $R_8$ is

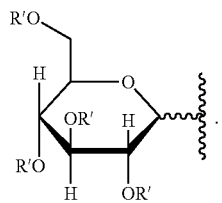

In certain embodiments, $R_8$ is

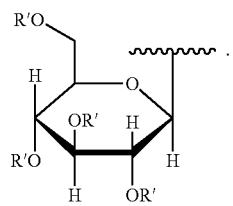

In certain embodiments, $R_8$ is

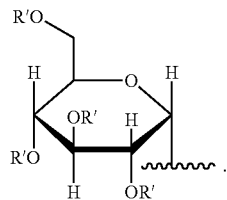

In certain embodiments, $R_8$ is

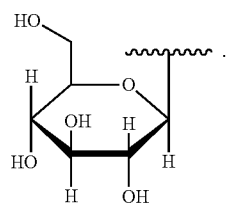

In certain embodiments, $R_8$ is

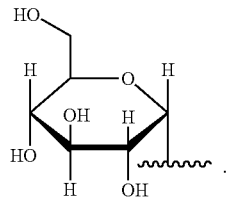

In certain embodiments, $R_8$ is

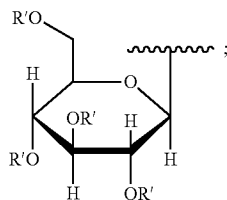

wherein all R' are oxygen protecting groups. In certain embodiments, $R_8$ is

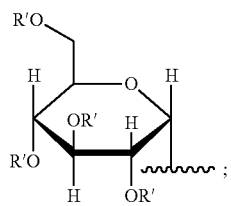

wherein all R' are oxygen protecting groups. In certain embodiments, $R_8$ is

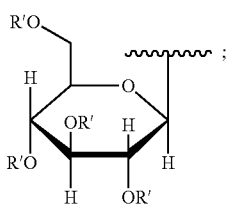

wherein all R' are silyl, TBDPS, TBDMS, TIPS, TES, TMS, MOM, THP, t-Bu, Bn, allyl, acetyl, pivaloyl, or Bz. In certain embodiments, $R_8$ is

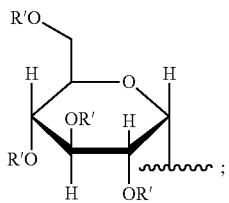

wherein all R' are silyl, TBDPS, TBDMS, TIPS, TES, TMS, MOM, THP, t-Bu, Bn, allyl, acetyl, pivaloyl, or Bz. In certain embodiments, $R_8$ is

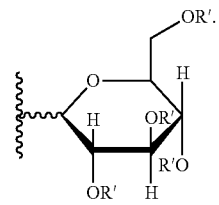

In certain embodiments, $R_8$ is

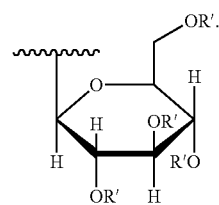

In certain embodiments, $R_8$ is

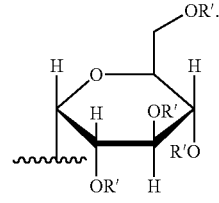

In certain embodiments, $R_8$ is

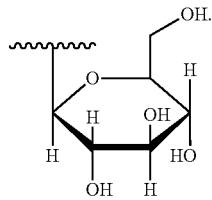

In certain embodiments, $R_8$ is

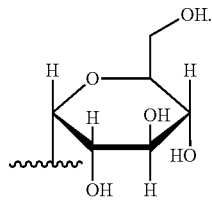

In certain embodiments, $R_8$ is

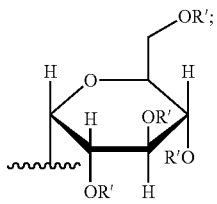

wherein all R' are oxygen protecting groups. In certain embodiments, $R_8$ is

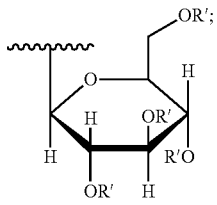

wherein all R' are oxygen protecting groups. In certain embodiments, $R_8$ is

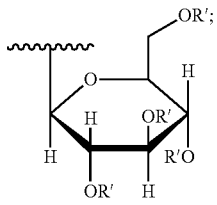

wherein all R' are silyl, TBDPS, TBDMS, TIPS, TES, TMS, MOM, THP, t-Bu, Bn, allyl, acetyl, pivaloyl, or Bz. In certain embodiments, $R_8$ is

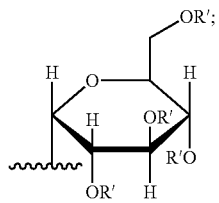

wherein all R' are silyl, TBDPS, TBDMS, TIPS, TES, TMS, MOM, THP, t-Bu, Bn, allyl, acetyl, pivaloyl, or Bz.

In compounds of Formula (A), $R_9$ is hydrogen, alkyl,

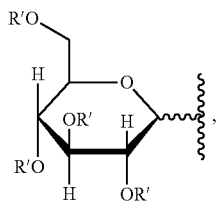

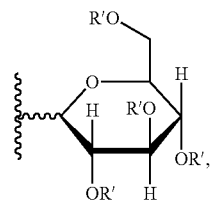

an oxygen protecting group when attached to an oxygen atom, or a sulfur protecting group when attached to a sulfur atom. In certain embodiments, $R_9$ is hydrogen. In certain embodiments, $R_9$ is alkyl. In certain embodiments, $R_9$ is $C_{1-6}$ alkyl. In certain embodiments, $R_9$ is methyl. In certain embodiments, $R_9$ is ethyl. In certain embodiments, $R_9$ is propyl. In certain embodiments, $R_9$ is butyl. In certain embodiments, $R_9$ is

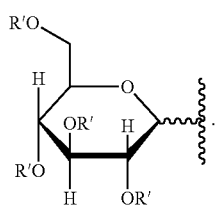

In certain embodiments, $R_9$ is

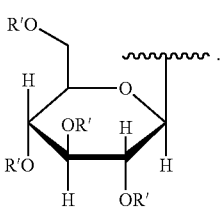

In certain embodiments, $R_9$ is

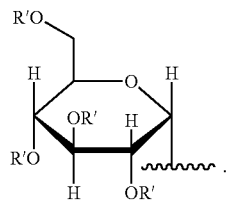

In certain embodiments, $R_9$ is

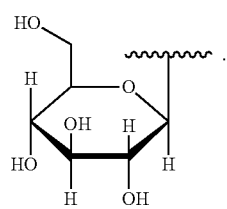

In certain embodiments, $R_9$ is

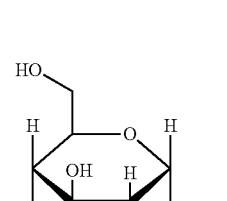

In certain embodiments, $R_9$ is

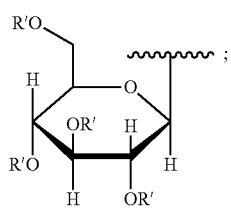

wherein all R' are oxygen protecting groups. In certain embodiments, $R_9$ is

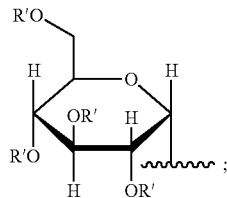

wherein all R' are oxygen protecting groups. In certain embodiments, $R_9$ is

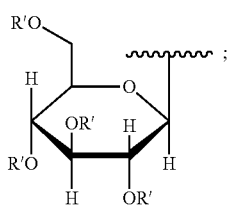

wherein all R' are silyl, TBDPS, TBDMS, TIPS, TES, TMS, MOM, THP, t-Bu, Bn, allyl, acetyl, pivaloyl, or Bz. In certain embodiments, $R_9$ is

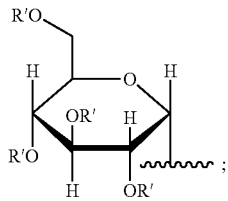

wherein all R' are silyl, TBDPS, TBDMS, TIPS, TES, TMS, MOM, THP, t-Bu, Bn, allyl, acetyl, pivaloyl, or Bz. In certain embodiments, $R_9$ is

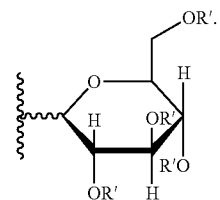

In certain embodiments, $R_9$ is

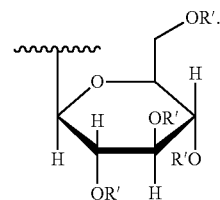

In certain embodiments, $R_9$ is

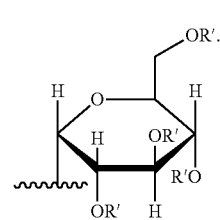

In certain embodiments, $R_9$ is

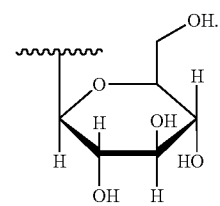

In certain embodiments, $R_9$ is

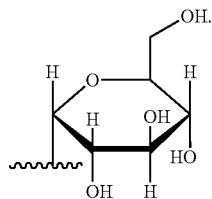

In certain embodiments, $R_9$ is

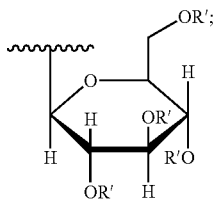

wherein all R' are oxygen protecting groups. In certain embodiments, $R_9$ is

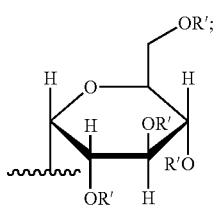

wherein all R' are oxygen protecting groups. In certain embodiments, $R_9$ is

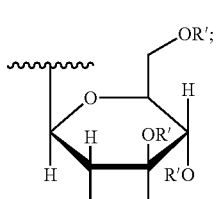

wherein all R' are silyl, TBDPS, TBDMS, TIPS, TES, TMS, MOM, THP, t-Bu, Bn, allyl, acetyl, pivaloyl, or Bz. In certain embodiments, $R_9$ is

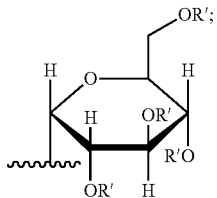

wherein all R' are silyl, TBDPS, TBDMS, TIPS, TES, TMS, MOM, THP, t-Bu, Bn, allyl, acetyl, pivaloyl, or Bz. In certain embodiments, $R_9$ is an oxygen protecting group when attached to an oxygen atom. In certain embodiments, when attached to an oxygen atom, $R_9$ is silyl. In certain embodiments, when attached to an oxygen atom, $R_9$ is TBDPS, TBDMS, TIPS, TES, or TMS. In certain embodiments, when attached to an oxygen atom, $R_9$ is MOM, THP, t-Bu, Bn, allyl, acetyl, pivaloyl, or Bz. In certain embodiments, $R_9$ is a sulfur protecting group when attached to a sulfur atom. In certain embodiments, when attached to a sulfur atom, $R_9$ is acetamidomethyl, t-Bu, 3-nitro-2-pyridine sulfenyl, 2-pyridine-sulfenyl, or triphenylmethyl.

In compounds of Formula (A), $R_{10}$ is hydrogen, alkyl, acyl, or a nitrogen protecting group. In certain embodiments, $R_{10}$ is hydrogen. In certain embodiments, $R_{10}$ is alkyl. In certain embodiments, $R_{10}$ is $C_{1-6}$ alkyl. In certain embodiments, $R_{10}$ is methyl. In certain embodiments, $R_{10}$ is ethyl. In certain embodiments, $R_{10}$ is propyl. In certain embodiments, $R_{10}$ is butyl. In certain embodiments, $R_{10}$ is acyl. In certain embodiments, $R_{10}$ is acetyl. In certain embodiments, $R_{10}$ is pivaloyl. In certain embodiments, $R_{10}$ is a nitrogen protecting group. In certain embodiments, $R_{10}$ is Bn, Boc, Cbz, Fmoc, trifluoroacetyl, triphenylmethyl, or Ts.

In compounds of Formula (A), at least one R' is hydrogen or an oxygen protecting group. In certain embodiments, at least one R' is hydrogen. In certain embodiments, at least one R' is an oxygen protecting group. In certain embodiments, at least one R' is silyl. In certain embodiments, at least one R' is TBDPS. In certain embodiments, at least one R' is TBDMS. In certain embodiments, at least one R' is TIPS. In certain embodiments, at least one R' is TES. In certain embodiments, at least one R' is TMS. In certain embodiments, at least one R' is MOM. In certain embodiments, at least one R' is THP. In certain embodiments, at least one R' is t-Bu. In certain embodiments, at least one R' is Bn. In certain embodiments, at least one R' is allyl. In certain embodiments, at least one R' is acetyl. In certain embodiments, at least one R' is pivaloyl. In certain embodiments, at least one R' is Bz. In certain embodiments, all R' are hydrogen. In certain embodiments, all R' are oxygen protecting groups. In certain embodiments, all R' are silyl. In certain embodiments, all R' are TBDPS. In certain embodiments, all R' are TBDMS. In certain embodiments, all R' are TIPS. In certain embodiments, all R' are TES. In certain embodiments, all R' are TMS. In certain embodiments, all R' are MOM. In certain embodiments, all R' are THP. In certain embodiments, all R' are t-Bu. In certain embodiments, all R' are Bn. In certain embodiments, all R' are allyl. In certain embodiments, all R' are acetyl. In certain embodiments, all R' are pivaloyl. In certain embodiments, all R' are Bz.

In compounds of Formula (A), R" is hydrogen, alkyl, acyl, an oxygen protecting group,

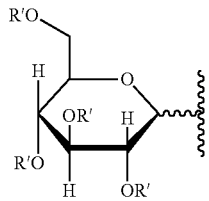

or

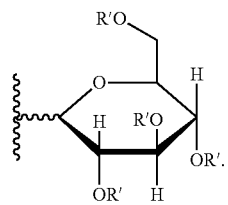

In certain embodiments, R" is hydrogen. In certain embodiments, R" is alkyl. In certain embodiments, R" is $C_{1-6}$ alkyl. In certain embodiments, R" is methyl. In certain embodiments, R" is substituted methyl. In certain embodiments, R" is —$CH_2$—$CO_2H$. In certain embodiments, R" is —$CH_2$—$CO_2$ (substituted or unsubstituted $C_{1-6}$ alkyl) (e.g., —$CH_2$—$CO_2Me$). In certain embodiments, R" is ethyl. In certain embodiments, R" is propyl. In certain embodiments, R" is butyl. In certain embodiments, R" is acyl. In certain embodiments, R" is acetyl. In certain embodiments, R" is pivaloyl. In certain embodiments, R" is an oxygen protecting group. In certain embodiments, R" is silyl. In certain embodiments, R" is TBDPS, TBDMS, TIPS, TES, or TMS. In certain embodiments, R" is MOM, THP, t-Bu, Bn, allyl, acetyl, pivaloyl, or Bz. In certain embodiments, R" is

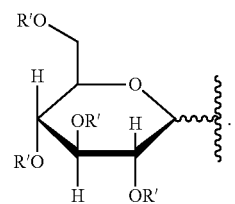

In certain embodiments, R" is

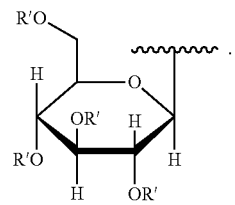

In certain embodiments, R" is

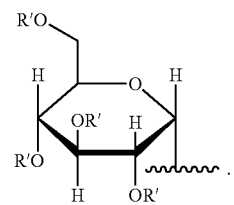

In certain embodiments, R" is

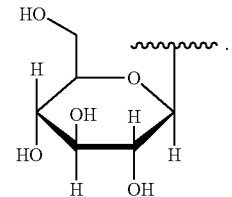

In certain embodiments, R" is

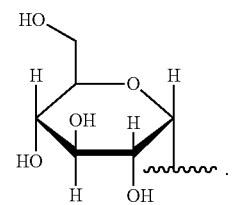

In certain embodiments, R" is

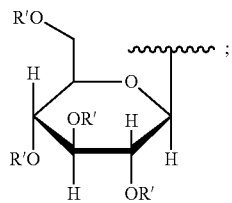

wherein all R' are oxygen protecting groups. In certain embodiments, R" is

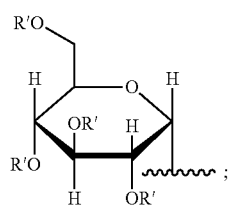

wherein all R' are oxygen protecting groups. In certain embodiments, R" is

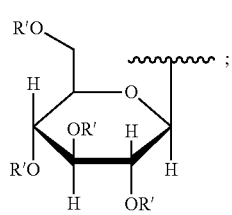

wherein all R' are silyl, TBDPS, TBDMS, TIPS, TES, TMS, MOM, THP, t-Bu, Bn, allyl, acetyl, pivaloyl, or Bz. In certain embodiments, R" is

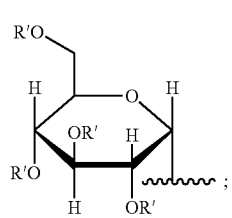

wherein all R' are silyl, TBDPS, TBDMS, TIPS, TES, TMS, MOM, THP, t-Bu, Bn, allyl, acetyl, pivaloyl, or Bz. In certain embodiments, R" is

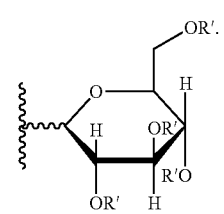

In certain embodiments, R" is

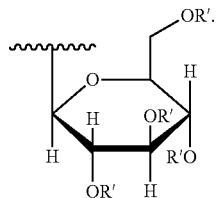

In certain embodiments, R" is

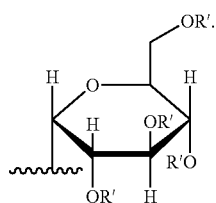

In certain embodiments, R" is

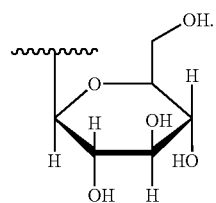

In certain embodiments, R" is

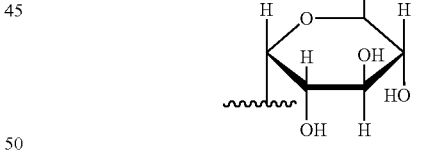

In certain embodiments, R" is

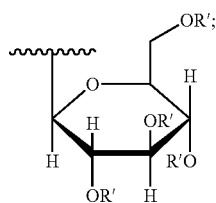

wherein all R' are oxygen protecting groups. In certain embodiments, R" is

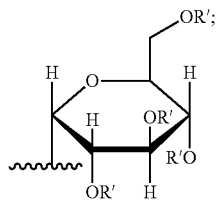

wherein all R' are oxygen protecting groups. In certain embodiments, R" is

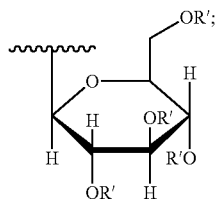

wherein all R' are silyl, TBDPS, TBDMS, TIPS, TES, TMS, MOM, THP, t-Bu, Bn, allyl, acetyl, pivaloyl, or Bz. In certain embodiments, R" is

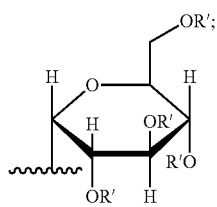

wherein all R' are silyl, TBDPS, TBDMS, TIPS, TES, TMS, MOM, THP, t-Bu, Bn, allyl, acetyl, pivaloyl, or Bz.

In compounds of Formula (A), each occurrence of n is independently an integer from 1 to 8, inclusive. In certain embodiments, at least one occurrence of n is 1. In certain embodiments, at least one occurrence of n is 2. In certain embodiments, at least one occurrence of n is 3. In certain embodiments, at least one occurrence of n is 4. In certain embodiments, at least one occurrence of n is 5. In certain embodiments, at least one occurrence of n is 6. In certain embodiments, at least one occurrence of n is 7. In certain embodiments, at least one occurrence of n is 8.

In compounds of Formula (A), k is an integer from 0 to 2, inclusive. In certain embodiments, k is 0. In certain embodiments, k is 1. In certain embodiments, k is 2.

In compounds of Formula (A), x is an integer from 1 to 8, inclusive. In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8.

In compounds of Formula (A), y is an integer from 0 to 8, inclusive. In certain embodiments, y is 0. In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8.

In compounds of Formula (A), all combinations of n, x, and y are contemplated. In certain embodiments, n is 2; x is 0; and y is 1. In certain embodiments, n is 2; x is 0; and y is 2. In certain embodiments, n is 2; x is 0; and y is 3. In certain embodiments, n is 2; x is 0; and y is 4.

The compound of Formula (A) may have one or more chiral centers. In certain embodiments, the compound of Formula (A) is of Formula (B):

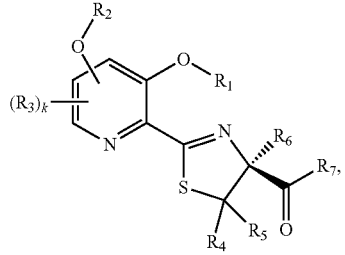

(B)

or a pharmaceutically acceptable salt, tautomer, stereoisomer, solvate, hydrate, or polymorph thereof.

In other embodiments, the compound of Formula (A) is of the formula:

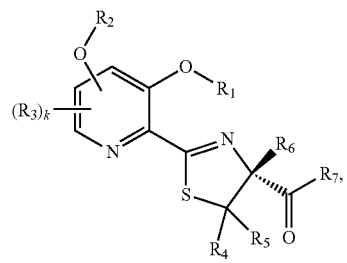

or a pharmaceutically acceptable salt, tautomer, stereoisomer, solvate, hydrate, or polymorph thereof.

In certain embodiments, the compound of Formula (A) is of the formula:

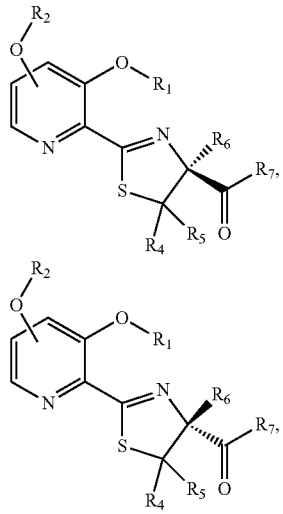

or a pharmaceutically acceptable salt, tautomer, stereoisomer, solvate, hydrate, or polymorph thereof.

The group $-OR_2$ of Formula (A) may be at any position, as valency permits, of the pyridyl ring of Formula (A). In certain embodiments, —OR$_2$ of Formula (A) is at the 3'-position of the pyridyl ring of Formula (A), and the compound of Formula (A) is of Formula (C):

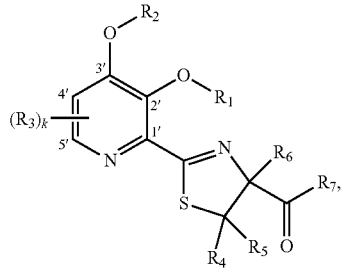
(C)

or a pharmaceutically acceptable salt, tautomer, stereoisomer, solvate, hydrate, or polymorph thereof.

In certain embodiments, —OR2 of Formula (A) is at the 4'-position of the pyridyl ring of Formula (A), and the compound of Formula (A) is of Formula (D):

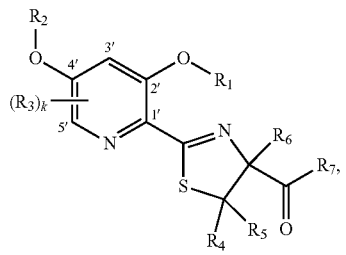
(D)

or a pharmaceutically acceptable salt, tautomer, stereoisomer, solvate, hydrate, or polymorph thereof.

In certain embodiments, the compound of Formula (A) is of the formula:

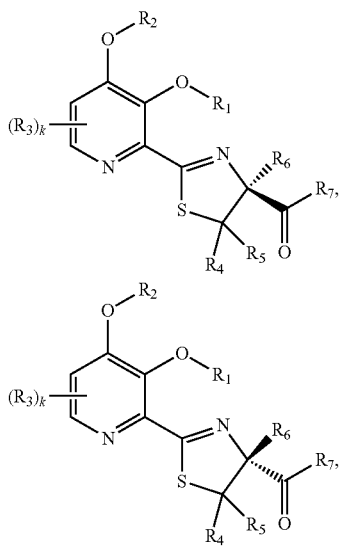

or a pharmaceutically acceptable salt, tautomer, stereoisomer, solvate, hydrate, or polymorph thereof.

In certain embodiments, the compound of Formula (A) is of the formula:

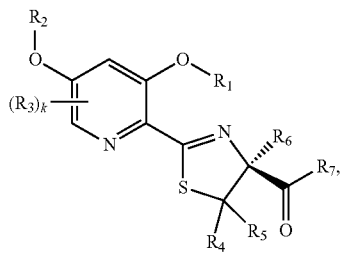

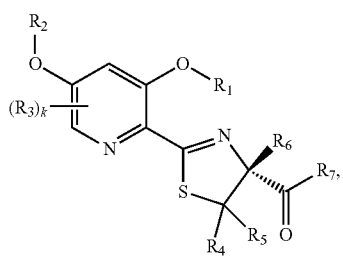

or a pharmaceutically acceptable salt, tautomer, stereoisomer, solvate, hydrate, or polymorph thereof.

In certain embodiments, the compound of Formula (A) is of the formula:

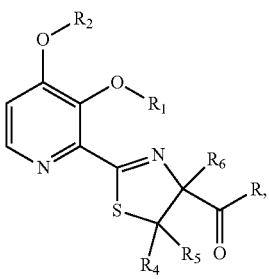

or a pharmaceutically acceptable salt, tautomer, stereoisomer, solvate, hydrate, or polymorph thereof.

In certain embodiments, the compound of Formula (A) is of the formula:

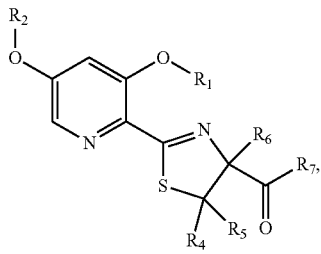

or a pharmaceutically acceptable salt, tautomer, stereoisomer, solvate, hydrate, or polymorph thereof.

In certain embodiments, the compound of Formula (A) is of the formula:

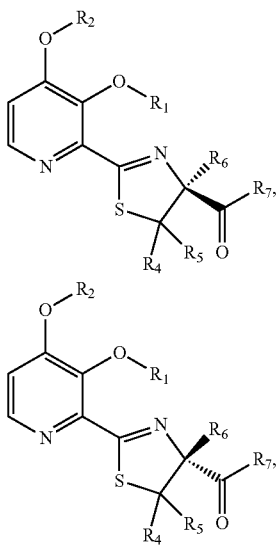

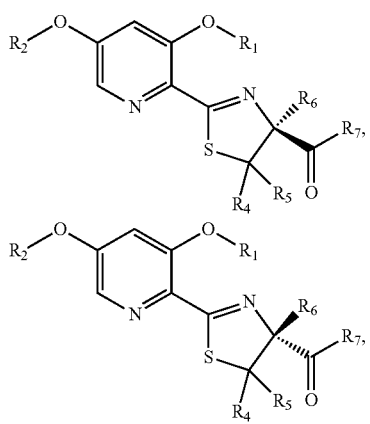

or a pharmaceutically acceptable salt, tautomer, stereoisomer, solvate, hydrate, or polymorph thereof.

In certain embodiments, the compound of Formula (A) is of the formula:

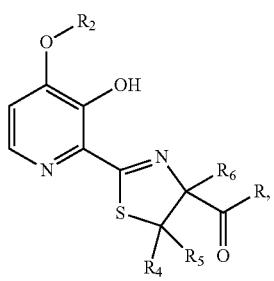

or a pharmaceutically acceptable salt, tautomer, stereoisomer, solvate, hydrate, or polymorph thereof.

In certain embodiments, the compound of Formula (A) is of Formula (E):

(E)

or a pharmaceutically acceptable salt, tautomer, stereoisomer, solvate, hydrate, or polymorph thereof.

In certain embodiments, the compound of Formula (A) is of Formula (F):

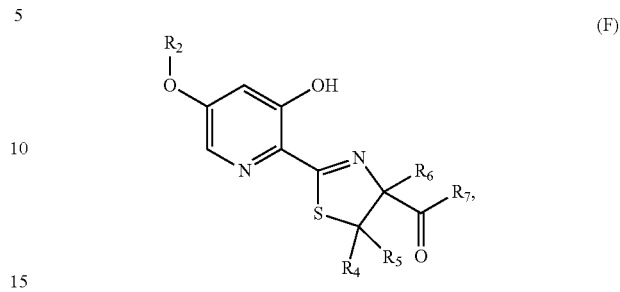

(F)

or a pharmaceutically acceptable salt, tautomer, stereoisomer, solvate, hydrate, or polymorph thereof.

In certain embodiments, the compound of Formula (A) is of the formula:

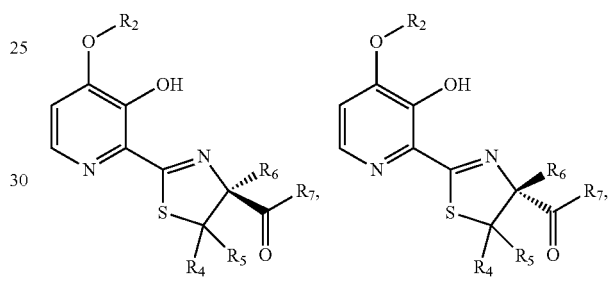

or a pharmaceutically acceptable salt, tautomer, stereoisomer, solvate, hydrate, or polymorph thereof.

In certain embodiments, the compound of Formula (A) is of the formula:

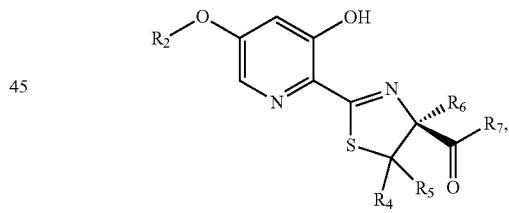

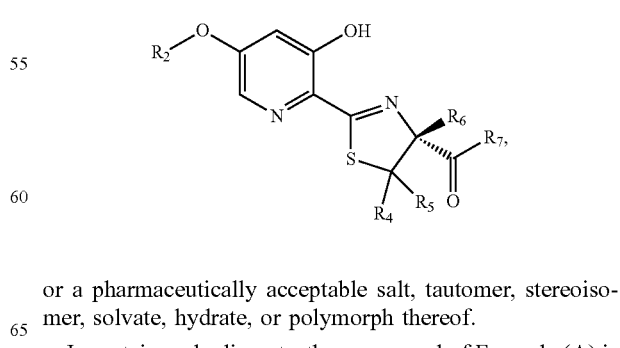

or a pharmaceutically acceptable salt, tautomer, stereoisomer, solvate, hydrate, or polymorph thereof.

In certain embodiments, the compound of Formula (A) is of the formula:

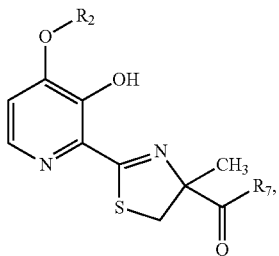

or a pharmaceutically acceptable salt, tautomer, stereoisomer, solvate, hydrate, or polymorph thereof.

In certain embodiments, the compound of Formula (A) is of the formula:

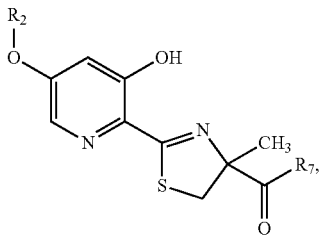

or a pharmaceutically acceptable salt, tautomer, stereoisomer, solvate, hydrate, or polymorph thereof.

In certain embodiments, the compound of Formula (A) is of Formula (G):

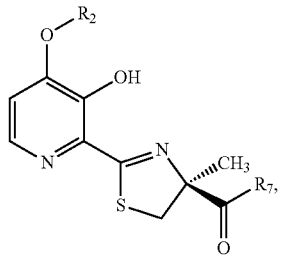

(G)

or a pharmaceutically acceptable salt, tautomer, stereoisomer, solvate, hydrate, or polymorph thereof.

In certain embodiments, the compound of Formula (A) is of the formula:

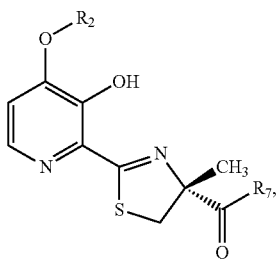

or a pharmaceutically acceptable salt, tautomer, stereoisomer, solvate, hydrate, or polymorph thereof.

In certain embodiments, the compound of Formula (A) is of Formula (H):

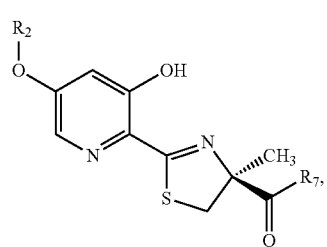

(H)

or a pharmaceutically acceptable salt, tautomer, stereoisomer, solvate, hydrate, or polymorph thereof.

In certain embodiments, the compound of Formula (A) is of the formula:

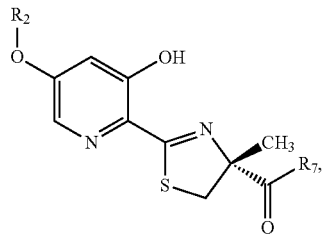

or a pharmaceutically acceptable salt, tautomer, stereoisomer, solvate, hydrate, or polymorph thereof.

In certain embodiments, the compound of Formula (A) is of the formula:

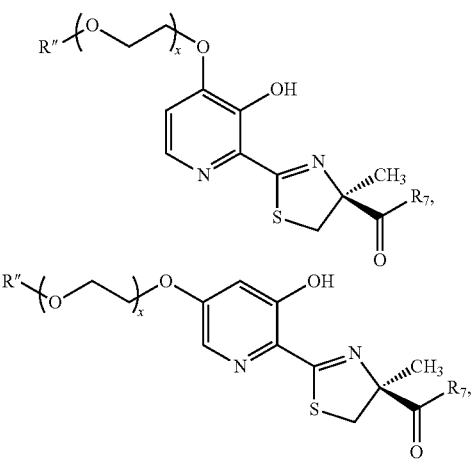

or a pharmaceutically acceptable salt, tautomer, stereoisomer, solvate, hydrate, or polymorph thereof.

In certain embodiments, the compound of Formula (A) is of the formula:

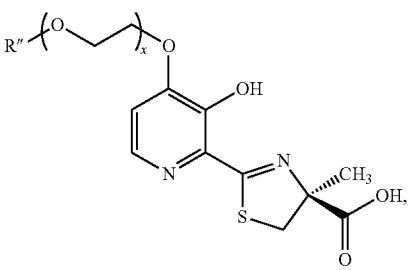

-continued

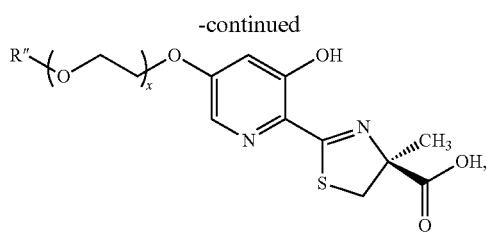

or a pharmaceutically acceptable salt, tautomer, stereoisomer, solvate, hydrate, or polymorph thereof.

In certain embodiments, the compound of Formula (A) is of the formula:

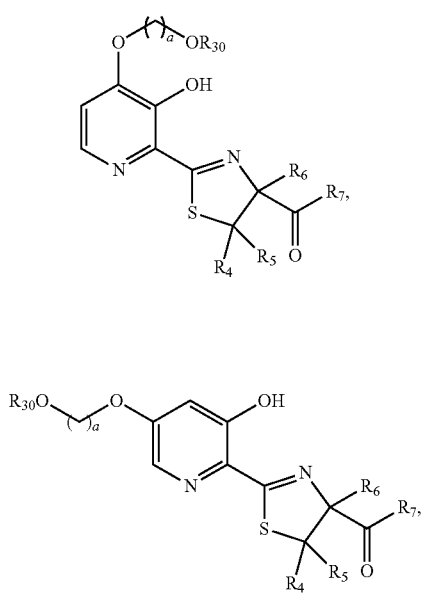

or a pharmaceutically acceptable salt, tautomer, stereoisomer, solvate, hydrate, or polymorph thereof, wherein $R_{30}$ is H, substituted or unsubstituted $C_{1-6}$ alkyl (e.g., —CH$_3$), or an oxygen protecting group; and a is 2, 3, 4, 5, 6, 7, 8, 9, or 10 (e.g., 4, 5, 6, 7, or 8).

In certain embodiments, the compound of Formula (A) is of the formula:

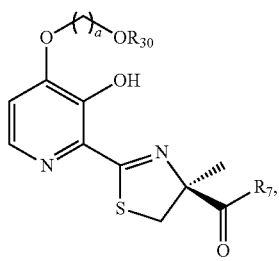

-continued

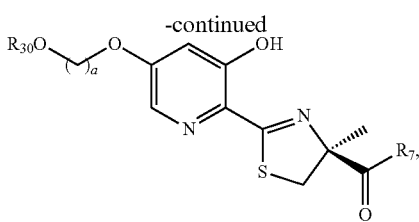

or a pharmaceutically acceptable salt, tautomer, stereoisomer, solvate, hydrate, or polymorph thereof.

In certain embodiments, the compound of Formula (A) is of the formula:

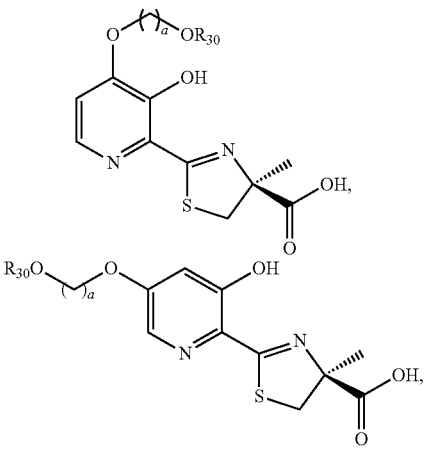

or a pharmaceutically acceptable salt, tautomer, stereoisomer, solvate, hydrate, or polymorph thereof.

In certain embodiments, the compound of Formula (A) is of the formula:

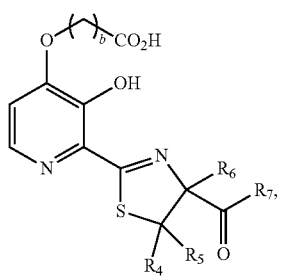

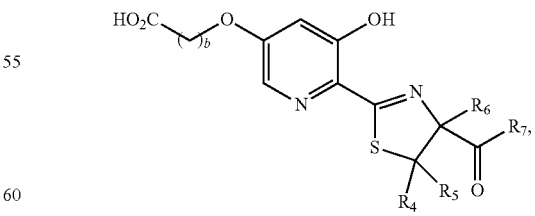

or a pharmaceutically acceptable salt, tautomer, stereoisomer, solvate, hydrate, or polymorph thereof, wherein b is 1, 2, 3, 4, 5, 6, 7, 8, 9, or 10 (e.g., 1, 2, 3, 4, or 5).

In certain embodiments, the compound of Formula (A) is of the formula:

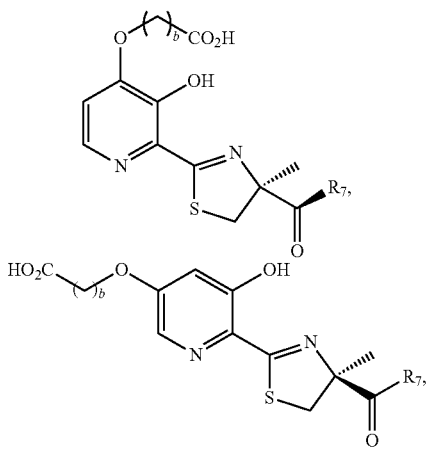
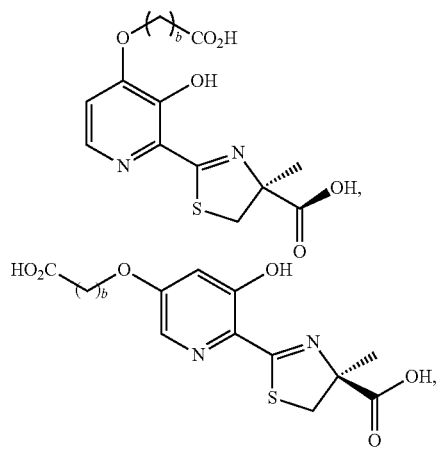
or a pharmaceutically acceptable salt, tautomer, stereoisomer, solvate, hydrate, or polymorph thereof.
In certain embodiments, the compound of Formula (A) is of the formula:
or a pharmaceutically acceptable salt, tautomer, stereoisomer, solvate, hydrate, or polymorph thereof.
In certain embodiments, the compound of Formula (A) is of the formula:
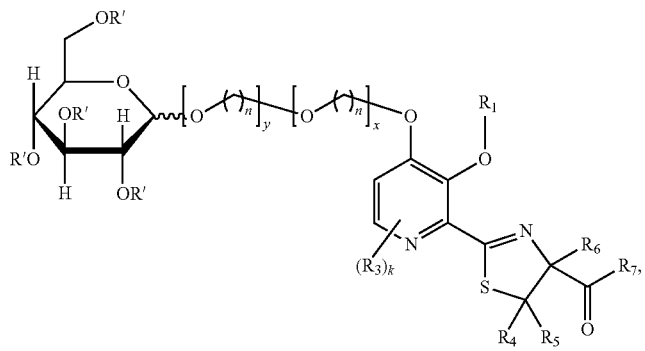
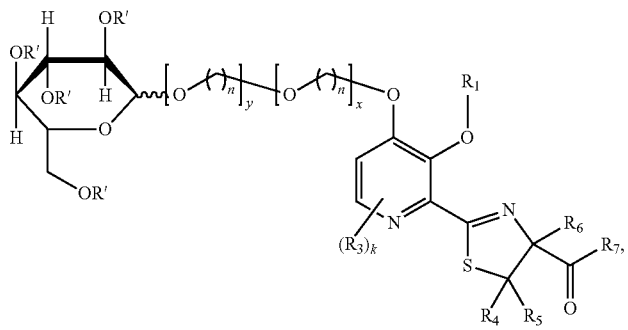
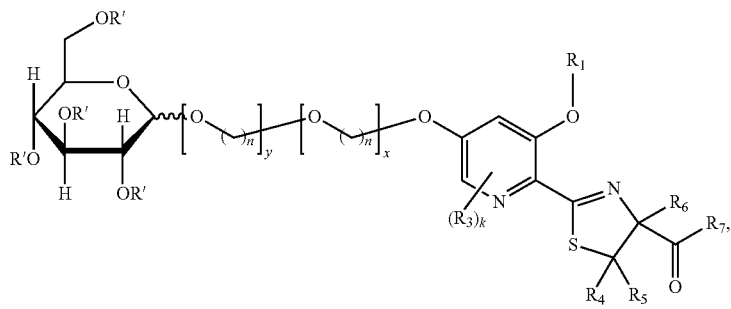

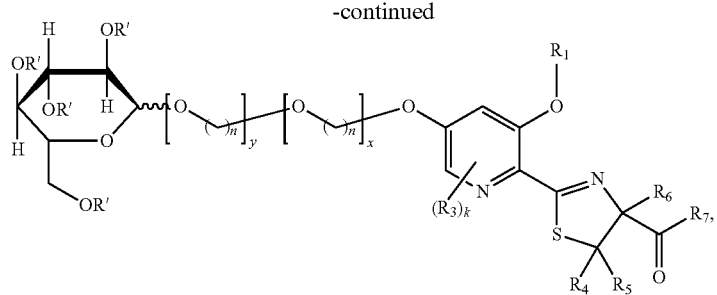
or a pharmaceutically acceptable salt, tautomer, stereoisomer, solvate, hydrate, or polymorph thereof.
In certain embodiments, the compound of Formula (A) is of the formula:
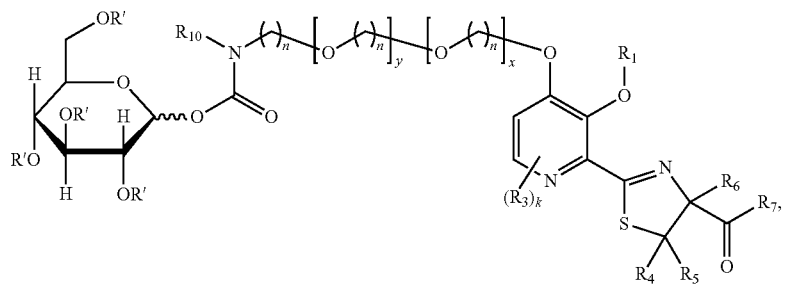
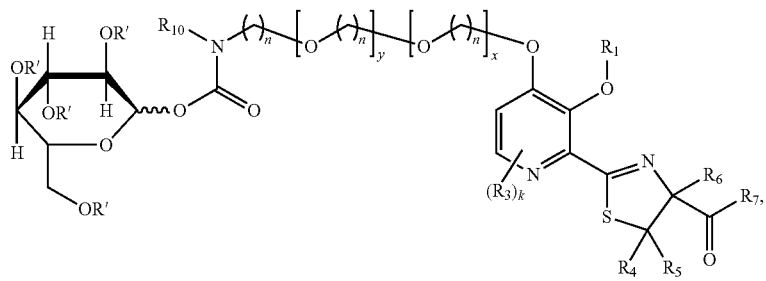
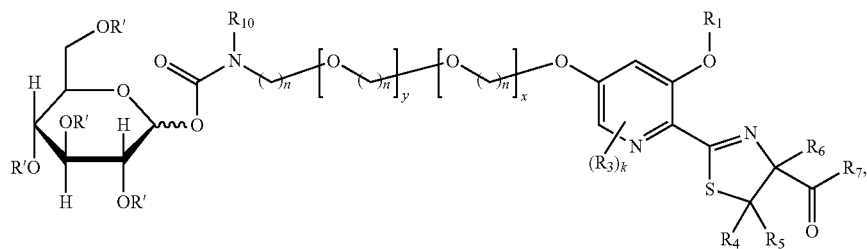
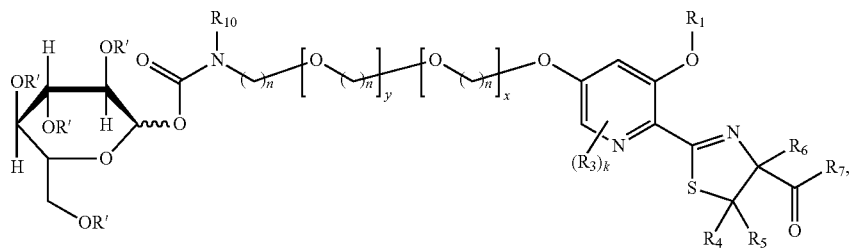

or a pharmaceutically acceptable salt, tautomer, stereoisomer, solvate, hydrate, or polymorph thereof.

In certain embodiments, the compound of Formula (A) is of the formula:

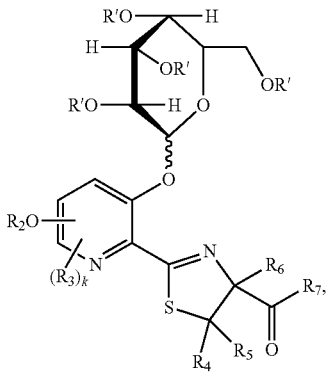

or a pharmaceutically acceptable salt, tautomer, stereoisomer, solvate, hydrate, or polymorph thereof.

In certain embodiments, the compound of Formula (A) is of the formula:

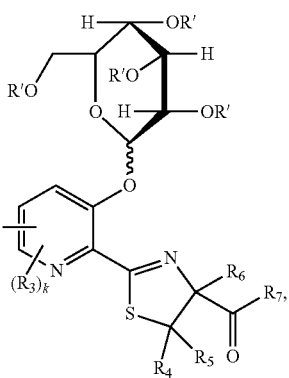

or a pharmaceutically acceptable salt, tautomer, stereoisomer, solvate, hydrate, or polymorph thereof.

In certain embodiments, the compound of Formula (A) is of the formula:

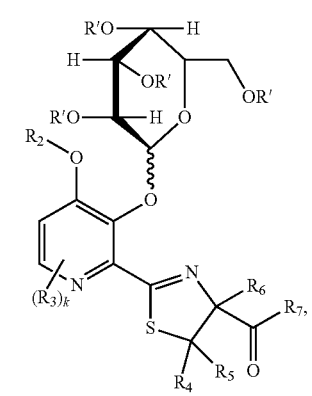

-continued

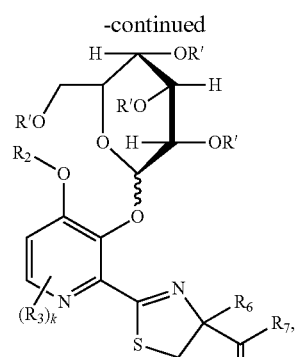

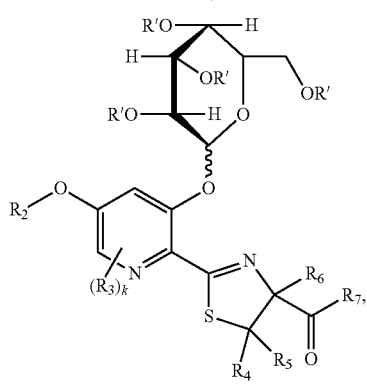

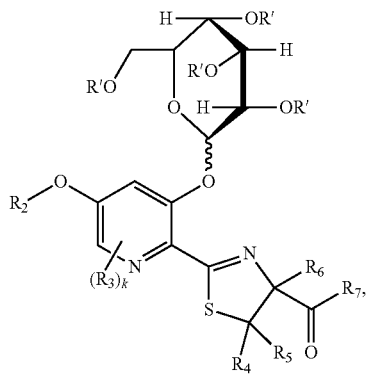

or a pharmaceutically acceptable salt, tautomer, stereoisomer, solvate, hydrate, or polymorph thereof.

In certain embodiments, the compound of Formula (A) is of the formula:

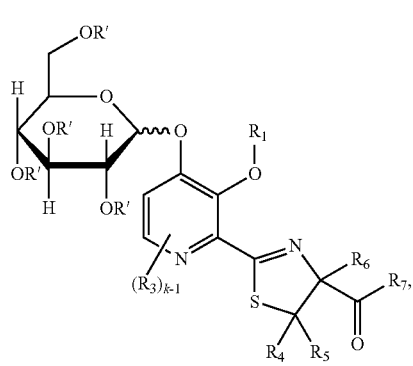

-continued

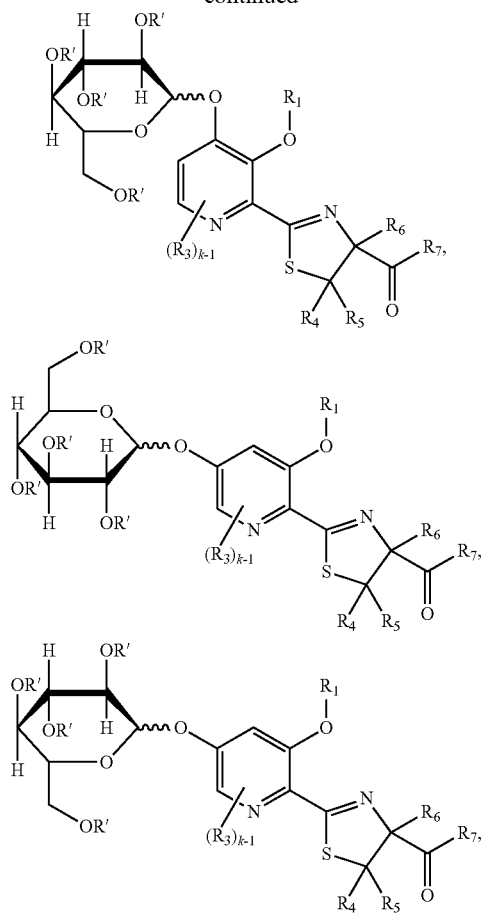

or a pharmaceutically acceptable salt, tautomer, stereoisomer, solvate, hydrate, or polymorph thereof.

In certain embodiments, the compound of Formula (A) is of the formula:

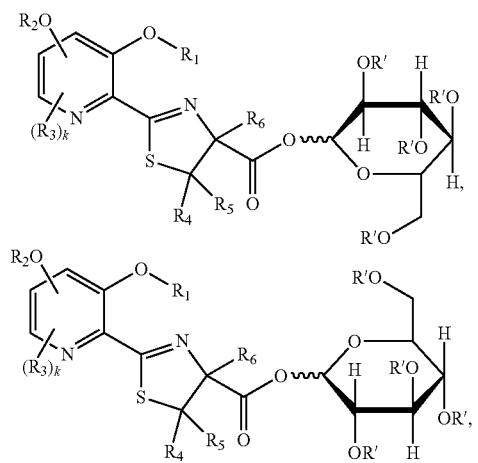

or a pharmaceutically acceptable salt, tautomer, stereoisomer, solvate, hydrate, or polymorph thereof.

In certain embodiments, the compound of Formula (A) is of the formula:

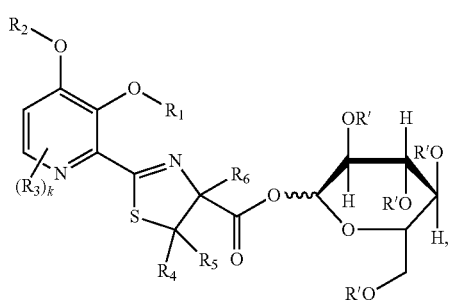

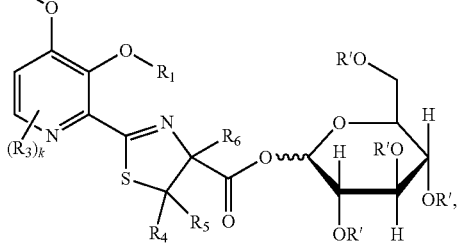

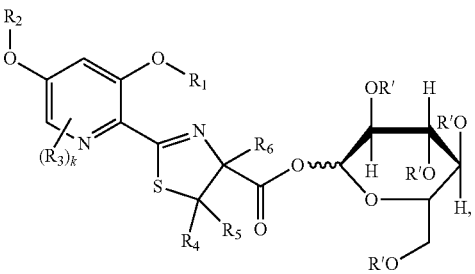

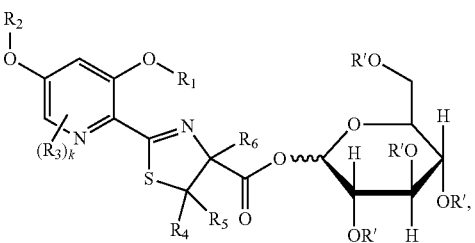

or a pharmaceutically acceptable salt, tautomer, stereoisomer, solvate, hydrate, or polymorph thereof.

In certain embodiments, the compound of Formula (A) is not of the formula:

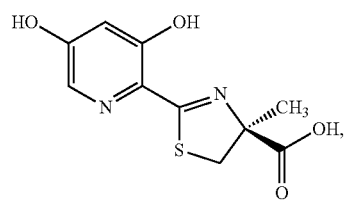

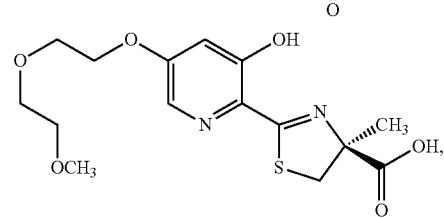

-continued

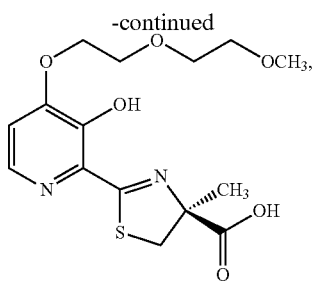

or a pharmaceutically acceptable salt, tautomer, stereoisomer, solvate, hydrate, or polymorph thereof.

In certain embodiments, when $R_7$ is —OH, $R_2$ is not H or —(CH$_2$CH$_2$O)$_2$CH$_3$. In certain embodiments, when $R_7$ is —OH, $R_2$ is not H or —[(CH$_2$)$_n$—O]$_x$—[(CH$_2$)$_n$—O]$_y$—R''. In certain embodiments, when $R_7$ is —OH, —OR$_2$ is attached to the 5'-position of the pyridinyl ring.

In another aspect, novel DFT analogs are obtained by, among other things, changing the thiazolinyl ring of DFT 1 to other 5-membered rings. In certain embodiments, compounds useful in the present invention are of Formula (J):

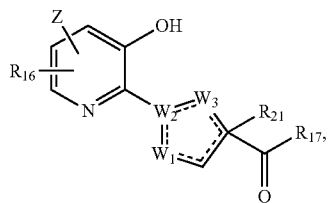

(J)

wherein:

⎯⎯ represents a single bond or double bond;

$W_1$-$W_3$ are independently $CR_{22}$, $NR_{23}$, oxygen, or sulfur, provided that:

when $W_3$ is nitrogen, $R_{23}$ is null, and when $R_{21}$ is methyl or hydrogen, $W_1$ is not sulfur;

Z is —OR$_{11}$, —NR$_{12}$R$_{13}$, morpholine, or optionally substituted piperazinyl;

$R_{11}$ is —[(CH$_2$)$_p$—O]$_u$—[(CH$_2$)$_q$—O]$_v$—R$_{14}$, —[(CH$_2$)$_p$—O]$_u$—[(CH$_2$)$_q$—NR$_{14}$]$_v$—R$_{15}$, or —[(CH$_2$)$_p$—O]$_u$—[(CH$_2$)$_q$—NR$_{14}$]$_v$—R$_{15}$;

$R_{12}$ is hydrogen, alkyl, —[(CH$_2$)$_p$—O]$_u$—[(CH$_2$)$_q$—O]$_v$—R$_{14}$, —[(CH$_2$)$_p$—NH]$_u$—[(CH$_2$)$_q$—NR$_{14}$]$_v$—R$_{15}$, or —[(CH$_2$)$_p$—O]$_u$—[(CH$_2$)$_q$—NR$_{14}$]$_v$—R$_{15}$;

$R_{13}$ is hydrogen or alkyl;

p and q are independently an integer from 1 to 8, inclusive;

u is an integer from 0 to 8, inclusive;

v is an integer from 1 to 8, inclusive;

$R_{14}$ and $R_{15}$ are independently hydrogen, alkyl, or acyl;

$R_{16}$ is hydrogen, alkyl, or alkoxyl;

$R_{17}$ is —OR$_{18}$ or —N(OH)R$_{19}$;

$R_{18}$ is hydrogen, alkyl, or arylalkyl;

$R_{19}$ is alkyl or —(CH$_2$)$_s$—N(OH)C(=O)R$_{20}$;

s is an integer from 1 to 8;

$R_{20}$ is alkyl;

$R_{21}$ is hydrogen or alkyl;

each occurrence of $R_{22}$ is independently null, hydrogen, or alkyl; and each occurrence of $R_{23}$ is independently null, hydrogen, or alkyl;

or a pharmaceutically acceptable salt, tautomer, stereoisomer, solvate, hydrate, or polymorph thereof.

In compounds of Formula (J), Z is —OR$_{11}$, —NR$_{12}$R$_{13}$, morpholine, or optionally substituted piperazinyl. In certain embodiments, Z is —OR$_{11}$. In certain embodiments, Z is —O—[(CH$_2$)$_p$—O]$_u$—[(CH$_2$)$_q$—O]$_v$—R$_{14}$. In certain embodiments, Z is

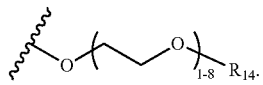

In certain embodiments, Z is

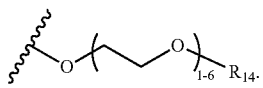

In certain embodiments, Z is

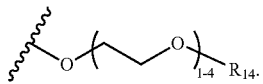

In certain embodiments, Z is

In certain embodiments, Z is

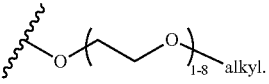

In certain embodiments, Z is

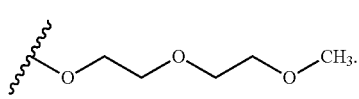 [SMILES: *OCCOCCOC]

In certain embodiments, Z is

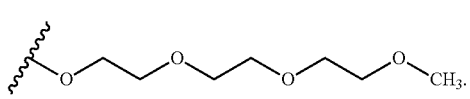 [SMILES: *OCCOCCOCCOC]

In certain embodiments, Z is —O—[(CH$_2$)$_p$—NH]$_u$—[(CH$_2$)$_q$—NR$_{14}$]$_v$—R$_{15}$. In certain embodiments, Z is —O—[(CH$_2$)$_p$—O]$_u$—[(CH$_2$)$_q$—NR$_{14}$]$_v$—R$_{15}$. In certain embodiments, Z is —NR$_{12}$R$_{13}$. In certain embodiments, Z is morpholine. In certain embodiments, Z is unsubstituted piperazinyl. In certain embodiments, Z is substituted piperazinyl. In certain embodiments, Z is piperazinyl substituted at the 4-position with an optionally substituted alkyl. In certain embodiments, Z is 4-(2-hydroxyethyl)-piperazin-1-yl.

In compounds of Formula (J), $R_{11}$ is —$[(CH_2)_p—O]_u$—$[(CH_2)_q—O]_v$—$R_{14}$, —$[(CH_2)_p—NH]_u$—$[(CH_2)_q—NR_{14}]_v$—$R_{15}$, or —$[(CH_2)_p—O]_u$—$[(CH_2)_q—NR_{14}]_v$—$R_{15}$. In certain embodiments, $R_{11}$ is —$[(CH_2)_p—O]_u$—$[(CH_2)_q—O]_v$—$R_{14}$. In certain embodiments, $R_{11}$ is

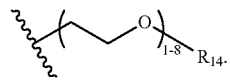

In certain embodiments, $R_{11}$ is

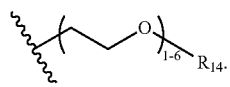

In certain embodiments, $R_{11}$ is

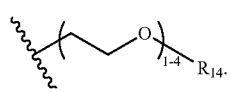

In certain embodiments, $R_{11}$ is

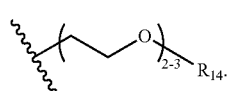

In certain embodiments, $R_{11}$ is

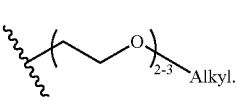

In certain embodiments, $R_{11}$ is

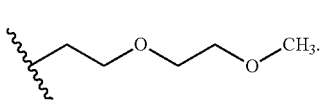 [SMILES: *CCOCCOC]

In certain embodiments, $R_{11}$ is

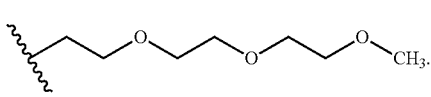 [SMILES: *CCOCCOCCOC]

In certain embodiments, $R_{11}$ is —$[(CH_2)_p—NH]_u$—$[(CH_2)_q—NR_{14}]_v$—$R_{15}$. In certain embodiments, $R_{11}$ is —$[(CH_2)_p—O]_u$—$[(CH_2)_q—NR_{14}]_v$—$R_{15}$.

In compounds of Formula (J), $R_{12}$ is hydrogen, alkyl, —$[(CH_2)_p—O]_u$—$[(CH_2)_q—O]_v$—$R_{14}$, —$[(CH_2)_p—NH]_u$—$[(CH_2)_q—NR_{14}]_v$—$R_{15}$, or —$[(CH_2)_p—O]_u$—$[(CH_2)_q—NR_{14}]_v$—$R_{15}$. In certain embodiments, $R_{12}$ is hydrogen. In certain embodiments, $R_{12}$ is alkyl. In certain embodiments, $R_{12}$ is $C_{1-6}$ alkyl. In certain embodiments, $R_{12}$ is methyl. In certain embodiments, $R_{12}$ is ethyl. In certain embodiments, $R_{12}$ is propyl. In certain embodiments, $R_{12}$ is butyl. In certain embodiments, $R_{12}$ is —$[(CH_2)_p—O]_u$—$[(CH_2)_q—O]_v$—$R_{14}$. In certain embodiments, $R_{12}$ is

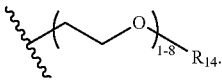

In certain embodiments, $R_{12}$ is

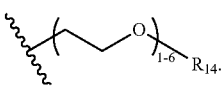

In certain embodiments, $R_{12}$ is

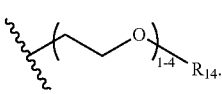

In certain embodiments, $R_{12}$ is

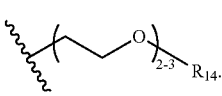

In certain embodiments, $R_{12}$ is

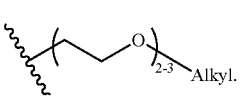

In certain embodiments, $R_{12}$ is

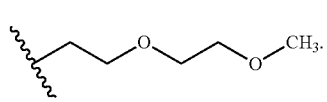 [SMILES: *CCOCCOC]

In certain embodiments, $R_{12}$ is

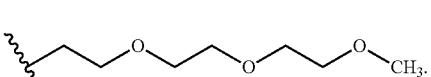

In certain embodiments, $R_{12}$ is —$[(CH_2)_p—NH]_u$—$[(CH_2)_q—NR_{14}]_v$—$R_{15}$. In certain embodiments, $R_{12}$ is —$[(CH_2)_p—O]_u$—$[(CH_2)_q—NR_{14}]_v$—$R_{15}$.

In compounds of Formula (J), $R_{13}$ is hydrogen or alkyl. In certain embodiments, $R_{13}$ is hydrogen. In certain embodiments, $R_{13}$ is alkyl. In certain embodiments, $R_{13}$ is $C_{1-6}$ alkyl. In certain embodiments, $R_{13}$ is methyl. In certain embodiments, $R_{13}$ is ethyl. In certain embodiments, $R_{13}$ is propyl. In certain embodiments, $R_{13}$ is butyl.

In compounds of Formula (J), p is an integer from 1 to 8, inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8.

In compounds of Formula (J), q is an integer from 1 to 8, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8.

In compounds of Formula (J), u is an integer from 0 to 8, inclusive. In certain embodiments, u is 0. In certain embodiments, u is 1. In certain embodiments, u is 2. In certain embodiments, u is 3. In certain embodiments, u is 4. In certain embodiments, u is 5. In certain embodiments, u is 6. In certain embodiments, u is 7. In certain embodiments, u is 8.

In compounds of Formula (J), v is an integer from 1 to 8, inclusive. In certain embodiments, v is 1. In certain embodiments, v is 2. In certain embodiments, v is 3. In certain embodiments, v is 4. In certain embodiments, v is 5. In certain embodiments, v is 6. In certain embodiments, v is 7. In certain embodiments, v is 8.

In compounds of Formula (J), $R_{14}$ is hydrogen, alkyl, or acyl. In certain embodiments, $R_{14}$ is hydrogen. In certain embodiments, $R_{14}$ is alkyl. In certain embodiments, $R_{14}$ is $C_{1-6}$ alkyl. In certain embodiments, $R_{14}$ is methyl. In certain embodiments, $R_{14}$ is ethyl. In certain embodiments, $R_{14}$ is propyl. In certain embodiments, $R_{14}$ is butyl. In certain embodiments, $R_{14}$ is acyl. In certain embodiments, $R_{14}$ is acetyl.

In compounds of Formula (J), $R_{15}$ is hydrogen, alkyl, or acyl. In certain embodiments, $R_{15}$ is hydrogen. In certain embodiments, $R_{15}$ is alkyl. In certain embodiments, $R_{15}$ is $C_{1-6}$ alkyl. In certain embodiments, $R_{15}$ is methyl. In certain embodiments, $R_{15}$ is ethyl. In certain embodiments, $R_{15}$ is propyl. In certain embodiments, $R_{15}$ is butyl. In certain embodiments, $R_{15}$ is acyl. In certain embodiments, $R_{15}$ is acetyl.

In compounds of Formula (J), $R_{16}$ is hydrogen, alkyl, or alkoxyl. In certain embodiments, $R_{16}$ is hydrogen. In certain embodiments, $R_{16}$ is alkyl. In certain embodiments, $R_{16}$ is $C_{1-6}$ alkyl. In certain embodiments, $R_{16}$ is methyl. In certain embodiments, $R_{16}$ is ethyl. In certain embodiments, $R_{16}$ is propyl. In certain embodiments, $R_{16}$ is butyl. In certain embodiments, $R_{16}$ is alkoxyl. In certain embodiments, $R_{16}$ is $C_{1-6}$ alkoxyl. In certain embodiments, $R_{16}$ is methoxyl. In certain embodiments, $R_{16}$ is ethoxyl. In certain embodiments, $R_{16}$ is propoxyl. In certain embodiments, $R_{16}$ is butoxyl.

In compounds of Formula (J), $R_{17}$ is —$OR_{18}$ or —N(OH)$R_{19}$. In certain embodiments, $R_{17}$ is —$OR_{18}$. In certain embodiments, $R_{17}$ is —OH. In certain embodiments, $R_{17}$ is —O-alkyl. In certain embodiments, $R_{17}$ is —O—($C_{1-6}$ alkyl). In certain embodiments, $R_{17}$ is —OMe. In certain embodiments, $R_{17}$ is —OEt. In certain embodiments, $R_{17}$ is —OPr. In certain embodiments, $R_{17}$ is —OBu. In certain embodiments, $R_{17}$ is —O-arylalkyl. In certain embodiments, $R_{17}$ is —O-phenalkyl. In certain embodiments, $R_{17}$ is —O—Bn. In certain embodiments, $R_{17}$ is —O-phenethyl. In certain embodiments, $R_{17}$ is —N(OH)$R_{19}$. In certain embodiments, $R_{17}$ is —N(OH)-alkyl. In certain embodiments, $R_{17}$ is —N(OH)—($C_{1-6}$ alkyl). In certain embodiments, $R_{17}$ is —N(OH)—$(CH_2)_s$—N(OH)C(=O)$R_{20}$.

In compounds of Formula (J), $R_{18}$ is hydrogen, alkyl, or arylalkyl. In certain embodiments, $R_{18}$ is hydrogen. In certain embodiments, $R_{18}$ is alkyl. In certain embodiments, $R_{18}$ is $C_{1-6}$ alkyl. In certain embodiments, $R_{18}$ is methyl. In certain embodiments, $R_{18}$ is ethyl. In certain embodiments, $R_{18}$ is propyl. In certain embodiments, $R_{18}$ is butyl. In certain embodiments, $R_{18}$ is arylalkyl. In certain embodiments, $R_{18}$ is aryl-($C_{1-6}$ alkyl). In certain embodiments, $R_{18}$ is phenyl-($C_{1-6}$ alkyl). In certain embodiments, $R_{18}$ is Bn. In certain embodiments, $R_{18}$ is phenethyl.

In compounds of Formula (J), $R_{19}$ is alkyl or —$(CH_2)_s$—N(OH)C(=O)$R_{20}$.

In certain embodiments, $R_{19}$ is alkyl. In certain embodiments, $R_{19}$ is $C_{1-6}$ alkyl. In certain embodiments, $R_{19}$ is methyl. In certain embodiments, $R_{19}$ is ethyl. In certain embodiments, $R_{19}$ is propyl. In certain embodiments, $R_{19}$ is butyl. In certain embodiments, $R_{19}$ is —$(CH_2)_s$—N(OH)C(=O)$R_{20}$.

In compounds of Formula (J), s is an integer from 1 to 8, inclusive. In certain embodiments, s is 1. In certain embodiments, s is 2. In certain embodiments, s is 3. In certain embodiments, s is 4. In certain embodiments, s is 5. In certain embodiments, s is 6. In certain embodiments, s is 7. In certain embodiments, s is 8.

In compounds of Formula (J), $R_{20}$ is alkyl. In certain embodiments, $R_{20}$ is $C_{1-6}$ alkyl. In certain embodiments, $R_{20}$ is methyl. In certain embodiments, $R_{20}$ is ethyl. In certain embodiments, $R_{20}$ is propyl. In certain embodiments, $R_{20}$ is butyl.

In compounds of Formula (J), $R_{21}$ is hydrogen or alkyl. In certain embodiments, $R_{21}$ is hydrogen. In certain embodiments, $R_{21}$ is alkyl. In certain embodiments, $R_{21}$ is $C_{1-6}$ alkyl. In certain embodiments, $R_{21}$ is methyl. In certain embodiments, $R_{21}$ is ethyl. In certain embodiments, $R_{21}$ is propyl. In certain embodiments, $R_{21}$ is butyl.

In compounds of Formula (J), each occurrence of $R_{22}$ is independently null, hydrogen, or alkyl. In certain embodiments, at least one $R_{22}$ is null. In certain embodiments, at least one $R_{22}$ is hydrogen. In certain embodiments, at least one $R_{22}$ is alkyl. In certain embodiments, at least one $R_{22}$ is $C_{1-6}$ alkyl. In certain embodiments, at least one $R_{22}$ is methyl. In certain embodiments, at least one $R_{22}$ is ethyl. In certain embodiments, at least one $R_{22}$ is propyl. In certain embodiments, at least one $R_{22}$ is butyl.

In compounds of Formula (J), each occurrence of $R_{23}$ is independently null, hydrogen, or alkyl. In certain embodiments, at least one $R_{23}$ is null. In certain embodiments, at least one $R_{23}$ is hydrogen. In certain embodiments, at least one $R_{23}$ is alkyl. In certain embodiments, at least one $R_{23}$ is $C_{1-6}$ alkyl. In certain embodiments, at least one $R_{23}$ is methyl. In certain embodiments, at least one $R_{23}$ is ethyl. In certain embodiments, at least one $R_{23}$ is propyl. In certain embodiments, at least one $R_{23}$ is butyl.

In certain embodiments, the compound of Formula (J) is of the formula:

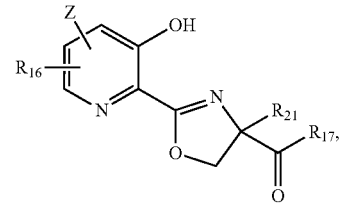

-continued

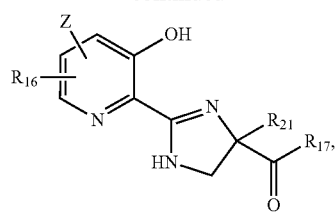

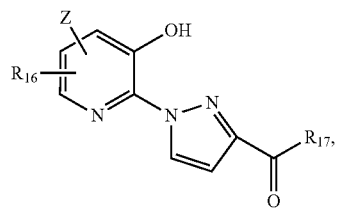

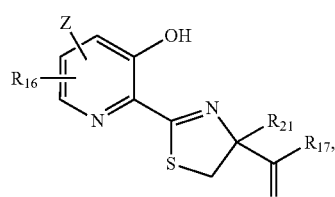

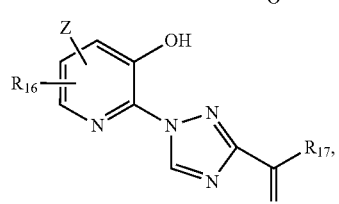

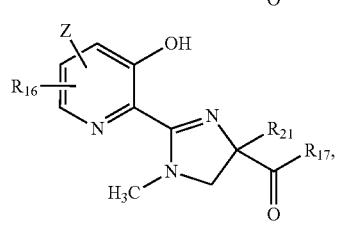

or a pharmaceutically acceptable salt, tautomer, stereoisomer, solvate, hydrate, or polymorph thereof.

The compound of Formula (J) may have one or more chiral centers. In certain embodiments, the compound of Formula (J) is of Formula (K):

(K)

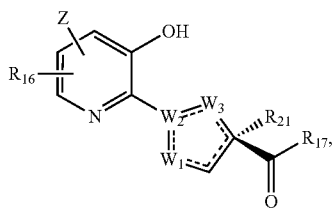

or a pharmaceutically acceptable salt, tautomer, stereoisomer, solvate, hydrate, or polymorph thereof.

In certain embodiments, the compound of Formula (J) is of the formula:

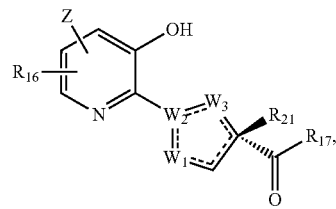

or a pharmaceutically acceptable salt, tautomer, stereoisomer, solvate, hydrate, or polymorph thereof.

In certain embodiments, the compound of Formula (J) is of the formula:

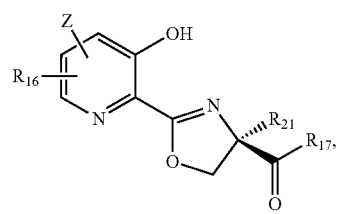

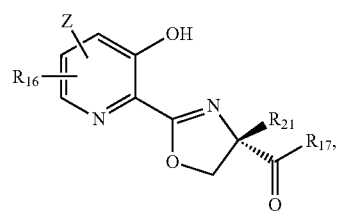

or a pharmaceutically acceptable salt, tautomer, stereoisomer, solvate, hydrate, or polymorph thereof.

In certain embodiments, the compound of Formula (J) is of the formula:

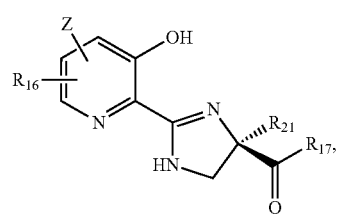

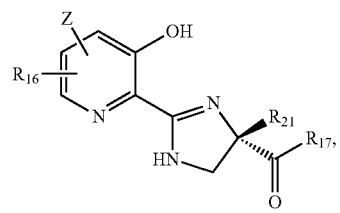

or a pharmaceutically acceptable salt, tautomer, stereoisomer, solvate, hydrate, or polymorph thereof.

In certain embodiments, the compound of Formula (J) is of the formula:

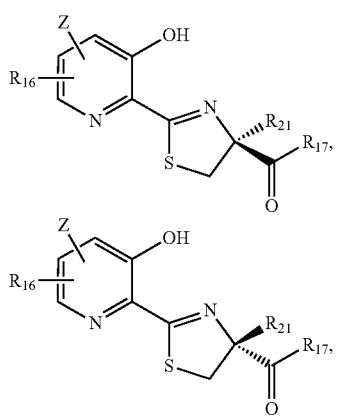

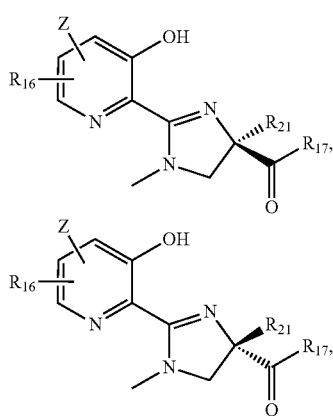

or a pharmaceutically acceptable salt, tautomer, stereoisomer, solvate, hydrate, or polymorph thereof.

In certain embodiments, the compound of Formula (J) is of the formula:

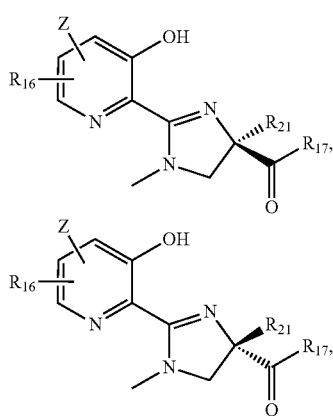

or a pharmaceutically acceptable salt, tautomer, stereoisomer, solvate, hydrate, or polymorph thereof.

The compounds of the invention may be provided in various salts forms. In certain embodiments, the inventive compounds are provided as alkali metal salts. In certain embodiments, the inventive compounds are provided as alkaline earth metal salts. In certain embodiments, when $R_9$ is —OH, the compound may be provided as a carboxylate salt with a positively charged counterion. In certain embodiments, the counterion is betaine, choline hydroxide, diethanolamine, diethylamine, ethanolamine, hydroxyethylmorpholine, 4-(2-hydroxyethyl morpholine), 1-(2-hydroxyethyl pyrrolidine), 1-(2-hydroxyethyl)-piperidine, 1,2-EDSA, HCl, $H_2SO_4$, MSA, p-TSA, hydroxyethyl pyrroldine, imidazone, lysine (e.g., L-lysine), arginine (e.g., L-arginine), histidine (e.g., L-histidine)N-methyl-D-glucamine (NMG), N, N'-dibenzyl-ethylenediamine, N, N'-diethyl-ethanolamine, triethanolamine, tromethamine, calcium (e.g., $Ca(OH)_2$), magnesium (e.g., $Mg(OH)_2$, magnesium acetate), potassium (e.g., KOH, potassium 2-ethylhexanoate), sodium (e.g., NaOH, sodium acetate, sodium 2-ethylhexanoate), zinc (e.g., $Zn(OH)_2$, zinc acetate), $Zn(OH)_2/Mg(OH)_2$, EDA, or piperazinyl. In certain embodiments, the counterion is lysine. In certain embodiments, the counterion is N-methyl-D-glucamine (NMG). In certain embodiments, the counterion is tromethamine. In certain embodiments, the counterion is calcium. In certain embodiments, the counterion is magnesium. In certain embodiments, the counterion is cesium. In certain embodiments, the counterion is potassium. In certain embodiments, the counterion is sodium. In certain embodiments, the counterion is lithium. In certain embodiments, the counterion is zinc. In certain embodiments, the counterion is piperzine. In certain embodiments, the counterion is $MgOH^+$. In certain embodiments, the counterion is $ZnOH^+$.

In certain embodiments, a polymorph of a salt of a compound of the invention is provided. In certain embodiments, a polymorph of a magnesium salt of a compound of the invention is provided. In certain embodiments, a polymorph of a $Na^+$ salt of a compound of the invention is provided. In certain embodiments, a polymorph of a salt of a carboxylate compound of the invention, wherein $R_9$ is —OH, is provided. In certain embodiments, a polymorph of a magnesium salt of a carboxylate compound of the invention, wherein $R_9$ is —OH, is provided. In certain embodiments, a polymorph of a $Na^+$ salt of a carboxylate compound of the invention, wherein $R_9$ is —OH, is provided.

The cation and anion in a salt disclosed herein may combine in a 1:1 molar ratio. Other molar ratios (e.g., 1:1.5, 1:2, 1:6, and 2:1) are also possible. Salts shown herein may be, for the sole purpose of convenience in notation, shown in a 1:1 ratio. All possible stoichiometric arrangements are encompassed by the scope of the present invention.

In certain embodiments, the compound of Formula (A) is of the Formula (I-1):

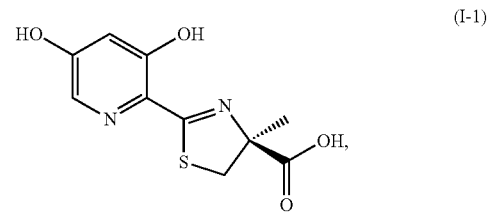 [SMILES: C[C@]1(C(=O)O)CSC(c2ncc(O)cc2O)=N1]

(I-1)

or a pharmaceutically acceptable salt, tautomer, stereoisomer, solvate, hydrate, or polymorph thereof.

In certain embodiments, a salt of a compound of the Formula (I-1) is provided. In certain embodiments, a salt of the Formula (I-1) is provided as shown in the Formula (I-1-i):

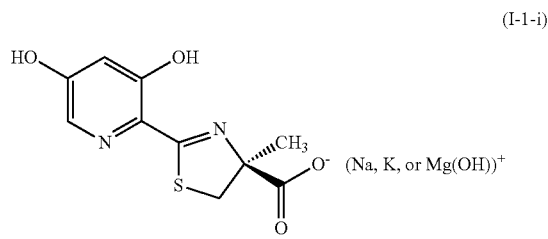 [SMILES: C[C@]1(C(=O)[O-])CSC(c2ncc(O)cc2O)=N1]

(I-1-i)

or a pharmaceutically acceptable salt, tautomer, stereoisomer, solvate, hydrate, or polymorph thereof.

In certain embodiments, the compound of the Formula (A) is of the Formula (I-1-ii):

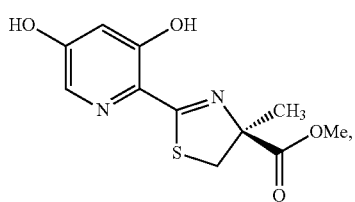

(I-1-ii)

or a pharmaceutically acceptable salt, tautomer, stereoisomer, solvate, hydrate, or polymorph thereof.

In certain embodiments, the compound of the Formula (A) is of the Formula (I-1-iii):

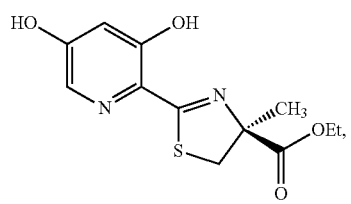

(I-1-iii)

or a pharmaceutically acceptable salt, tautomer, stereoisomer, solvate, hydrate, or polymorph thereof.

In certain embodiments, the compound of the Formula (A) is of the Formula (I-1-iv):

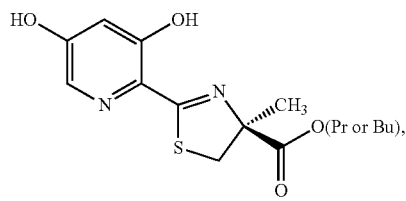

(I-1-iv)

or a pharmaceutically acceptable salt, tautomer, stereoisomer, solvate, hydrate, or polymorph thereof.

In certain embodiments, the compound of the Formula (A) is of the Formula (I-2):

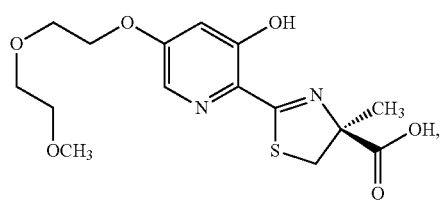

(I-2)

or a pharmaceutically acceptable salt, tautomer, stereoisomer, solvate, hydrate, or polymorph thereof.

In certain embodiments, a salt of a compound of the Formula (I-2) is provided. In certain embodiments, a salt of the Formula (I-2) is provided as shown in the Formula (I-2-i):

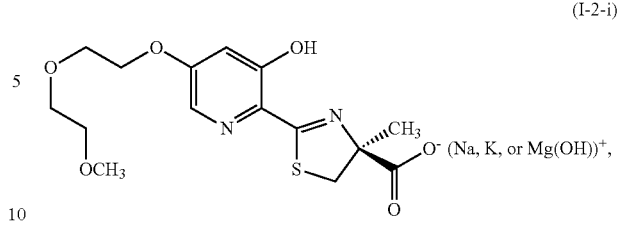

(I-2-i)

or a pharmaceutically acceptable salt, tautomer, stereoisomer, solvate, hydrate, or polymorph thereof.

In certain embodiments, the compound of the Formula (A) is of the Formula (I-2-ii):

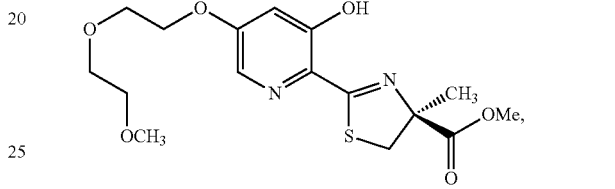

(I-2-ii)

or a pharmaceutically acceptable salt, tautomer, stereoisomer, solvate, hydrate, or polymorph thereof.

In certain embodiments, the compound of the Formula (A) is of the Formula (I-2-iii):

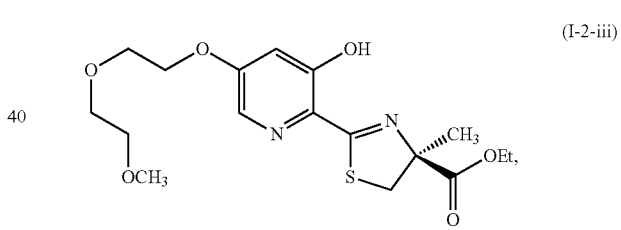

(I-2-iii)

or a pharmaceutically acceptable salt, tautomer, stereoisomer, solvate, hydrate, or polymorph thereof.

In certain embodiments, the compound of the Formula (A) is of the Formula (I-2-iv):

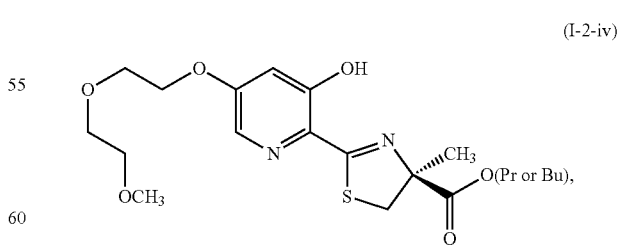

(I-2-iv)

or a pharmaceutically acceptable salt, tautomer, stereoisomer, solvate, hydrate, or polymorph thereof.

In certain embodiments, the compound of the Formula (A) is of the Formula (I-3):

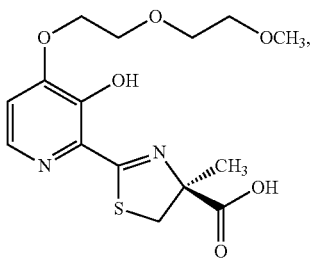

(I-3)

or a pharmaceutically acceptable salt, tautomer, stereoisomer, solvate, hydrate, or polymorph thereof.

In certain embodiments, a salt of a compound of the Formula (I-3) is provided. In certain embodiments, a salt of the Formula (I-3) is provided as shown in the Formula (I-3-i):

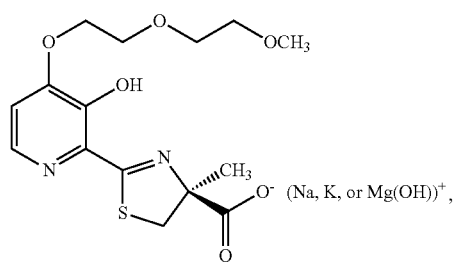

(I-3-i)

or a pharmaceutically acceptable salt, tautomer, stereoisomer, solvate, hydrate, or polymorph thereof.

In certain embodiments, the compound of the Formula (A) is of the Formula (I-3-ii):

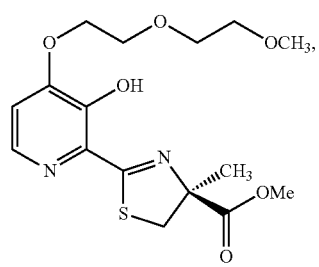

(I-3-ii)

or a pharmaceutically acceptable salt, tautomer, stereoisomer, solvate, hydrate, or polymorph thereof.

In certain embodiments, the compound of the Formula (A) is of the Formula (I-3-iii):

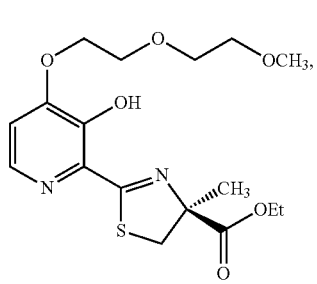

(I-3-iii)

or a pharmaceutically acceptable salt, tautomer, stereoisomer, solvate, hydrate, or polymorph thereof.

In certain embodiments, the compound of the Formula (A) is of the Formula (I-3-iv):

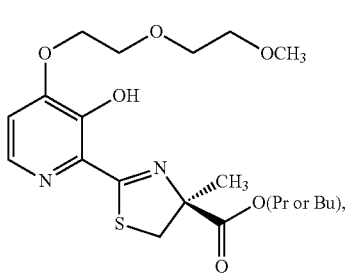

(I-3-iv)

or a pharmaceutically acceptable salt, tautomer, stereoisomer, solvate, hydrate, or polymorph thereof.

In certain embodiments, the compound of Formula (A) is of the formula:

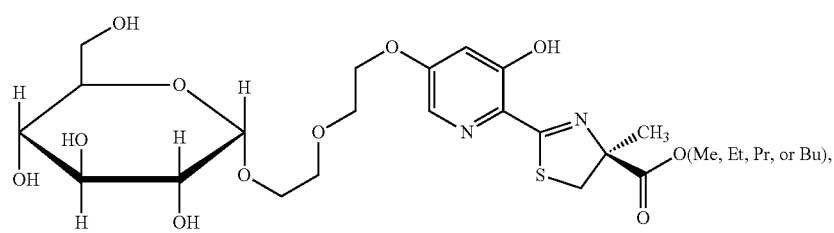

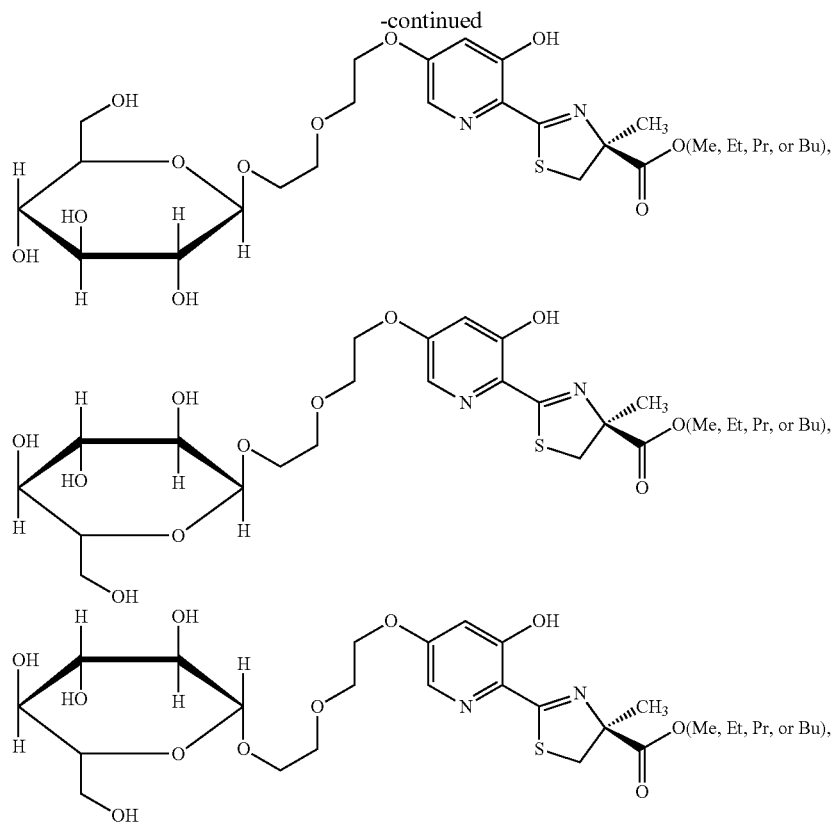
or a pharmaceutically acceptable salt, tautomer, stereoisomer, solvate, hydrate, or polymorph thereof.
In certain embodiments, the compound of Formula (A) is of the formula:
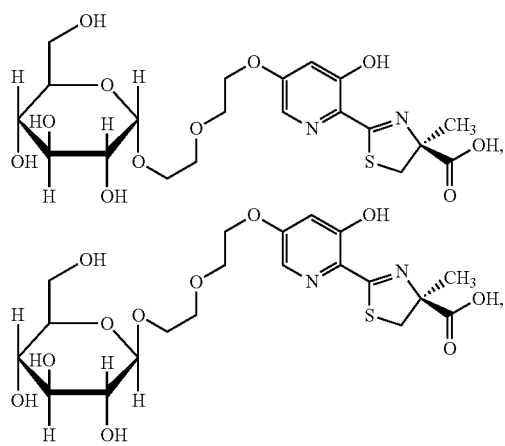
or a pharmaceutically acceptable salt, tautomer, stereoisomer, solvate, hydrate, or polymorph thereof.
In certain embodiments, the salt of a compound of Formula (A) is of the formula:
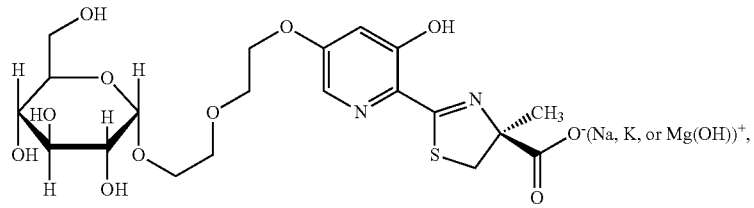

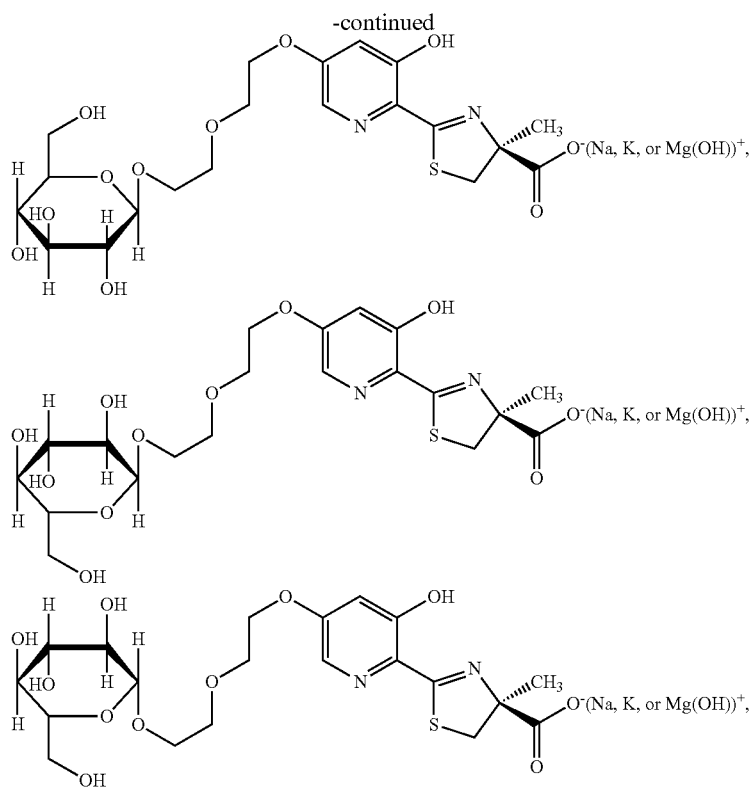
or a pharmaceutically acceptable salt, tautomer, stereoisomer, solvate, hydrate, or polymorph thereof.
In certain embodiments, the compound of Formula (A) is of the formula:
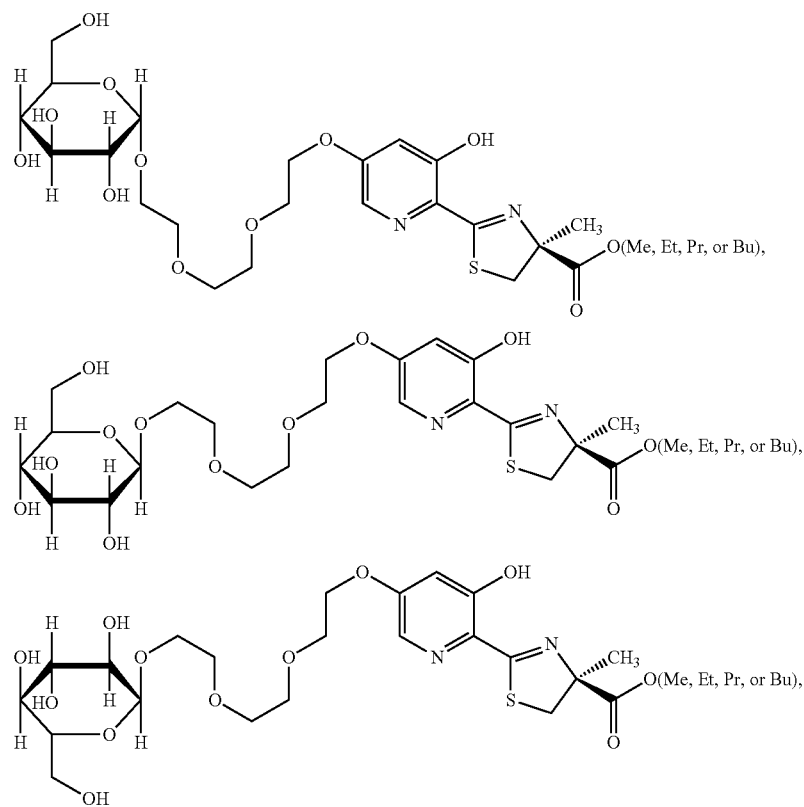

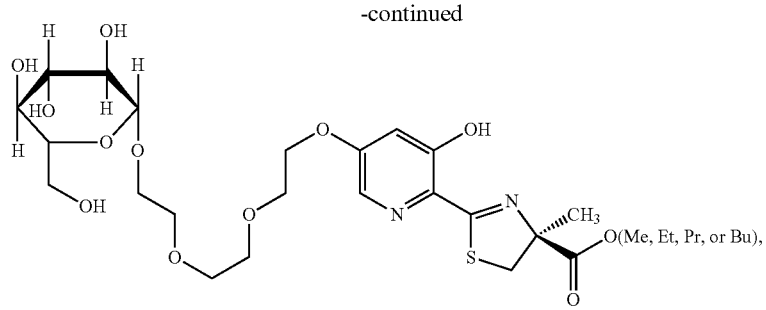
or a pharmaceutically acceptable salt, tautomer, stereoisomer, solvate, hydrate, or polymorph thereof.
In certain embodiments, the compound of Formula (A) is of the formula:
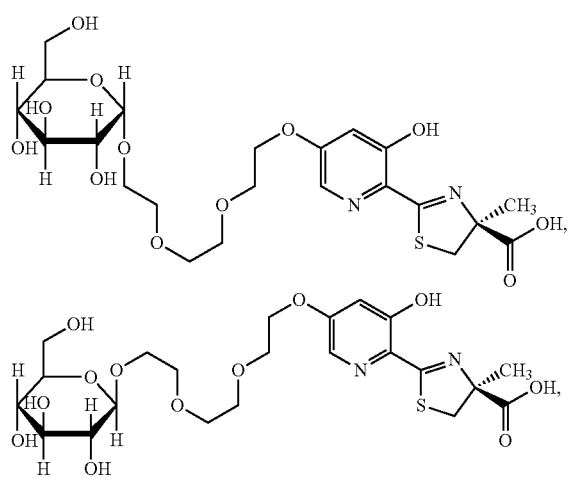
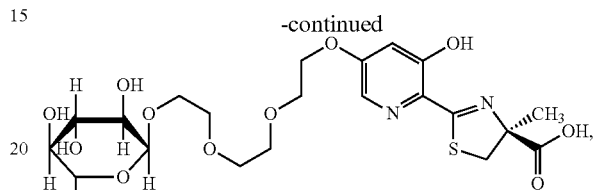
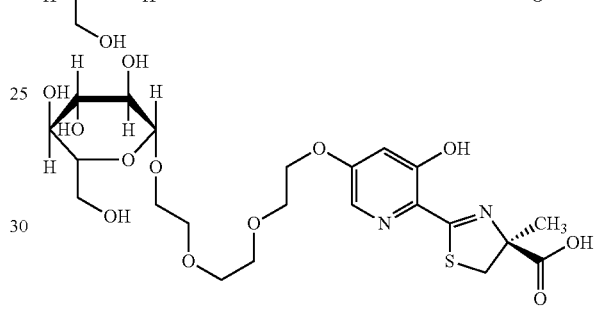
or a pharmaceutically acceptable salt, tautomer, stereoisomer, solvate, hydrate, or polymorph thereof.
In certain embodiments, the salt of a compound of Formula (A) is of the formula:
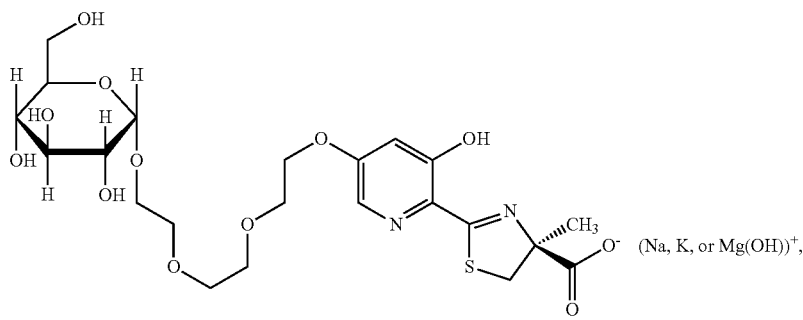
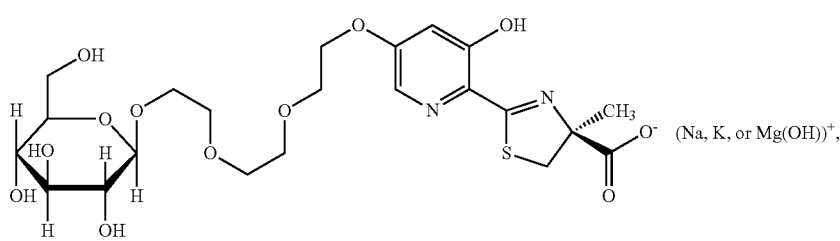

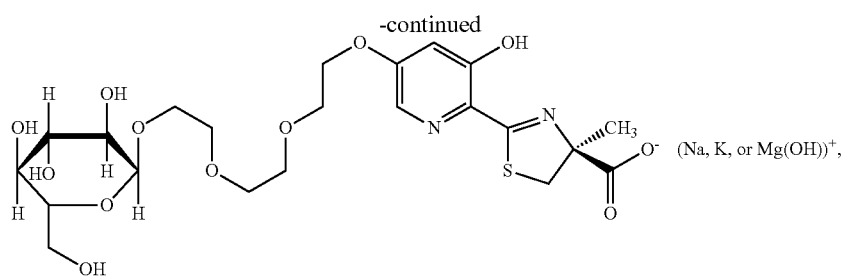
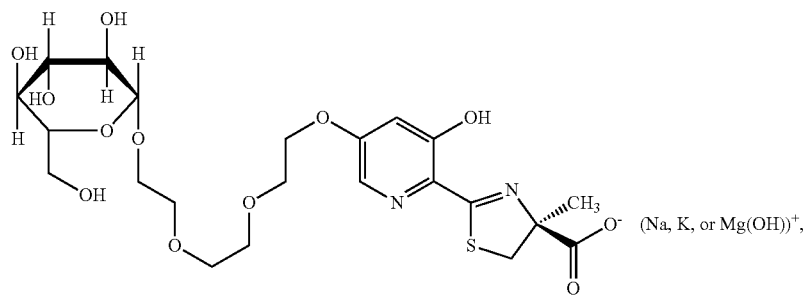
or a pharmaceutically acceptable salt, tautomer, stereoisomer, solvate, hydrate, or polymorph thereof.
Additional exemplary compounds of Formula (A) include, but are not limited to:
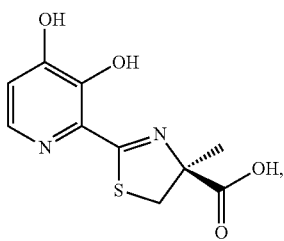
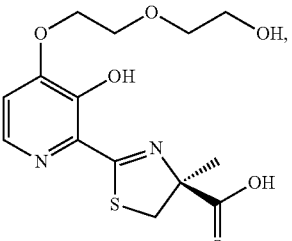
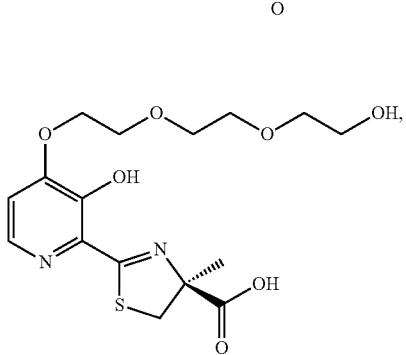
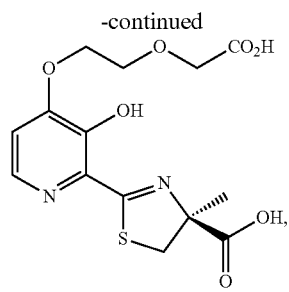
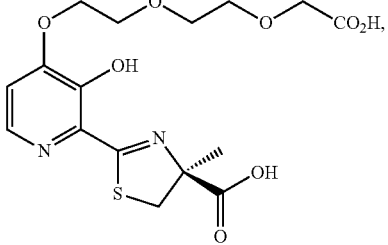
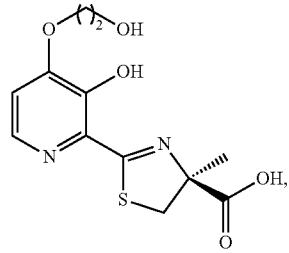
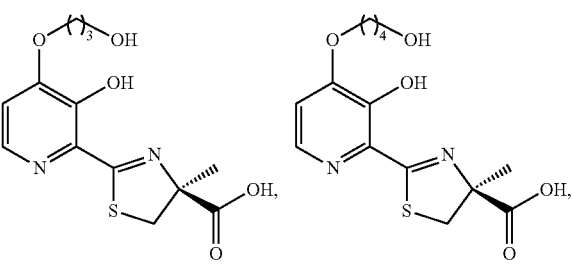

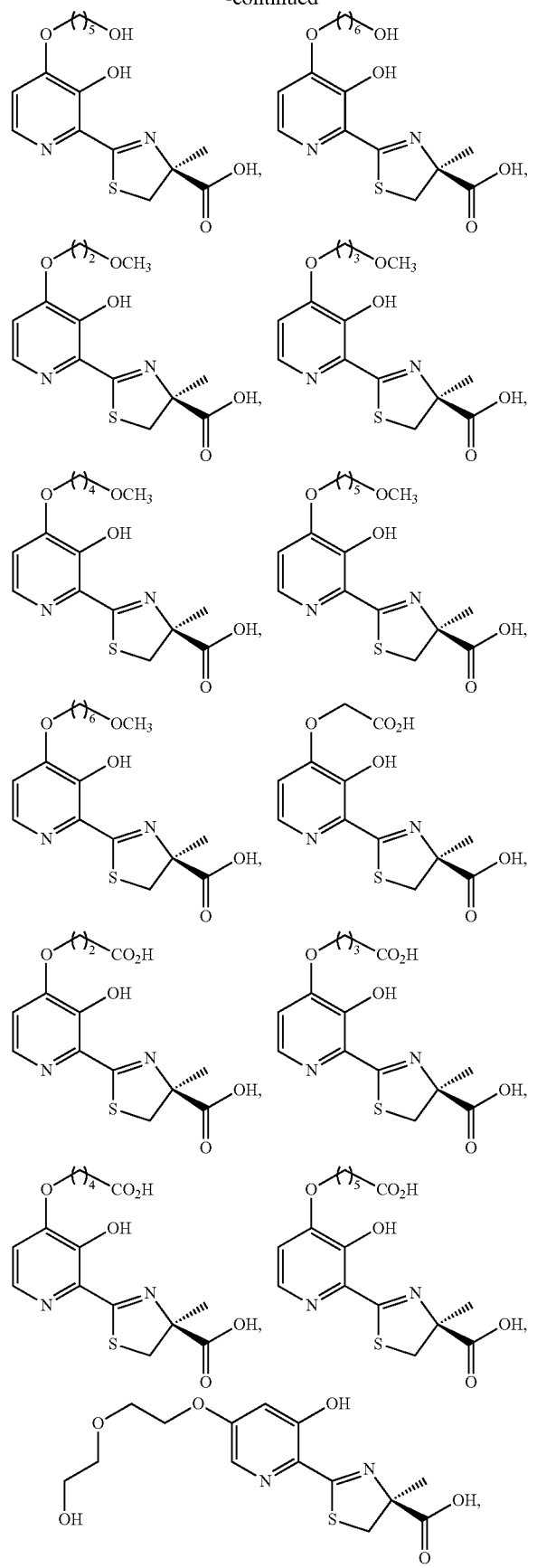
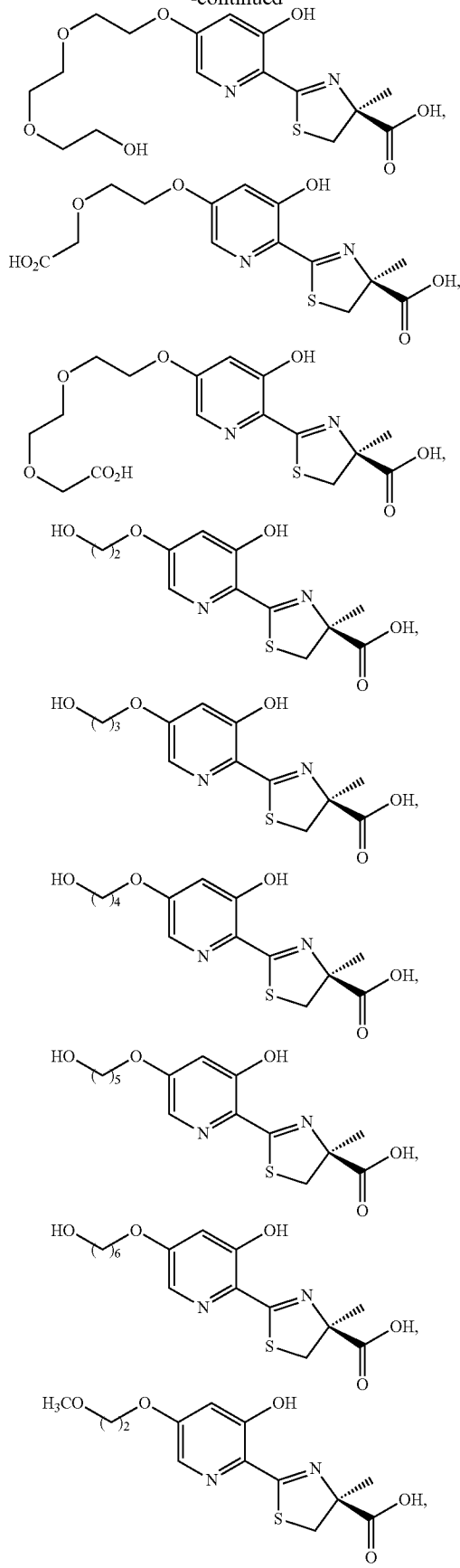

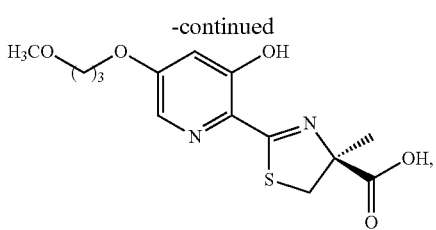

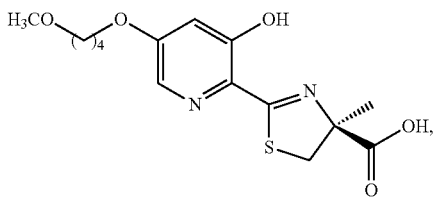

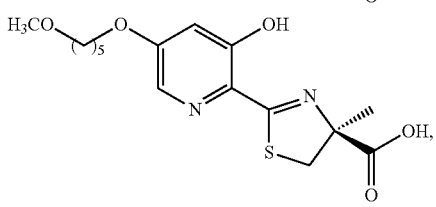

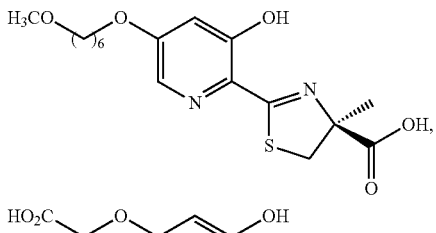

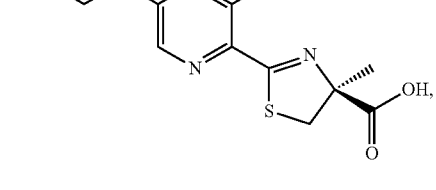

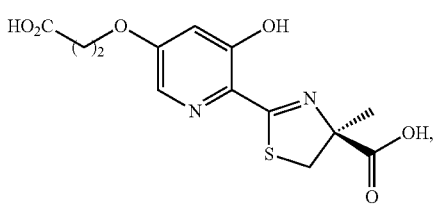

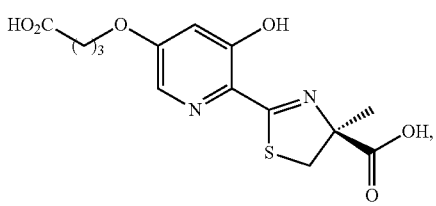

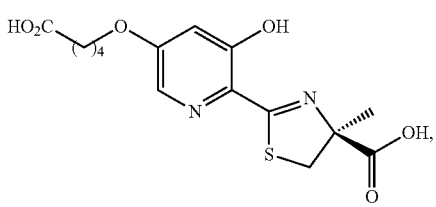

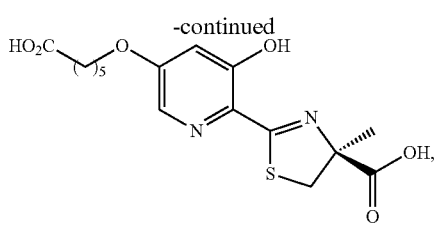

and pharmaceutically acceptable salts, tautomers, stereoisomers, solvates, hydrates, and polymorphs thereof.

In certain embodiments, the compound of Formula (J) is of the Formula (J-1):

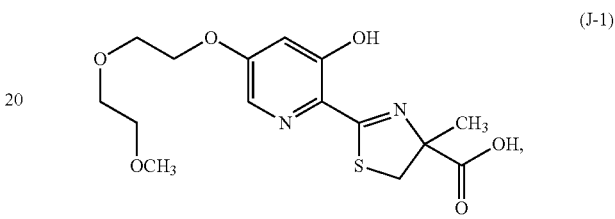

(J-1)

or a pharmaceutically acceptable salt, tautomer, stereoisomer, solvate, hydrate, or polymorph thereof.

In certain embodiments, a salt of a compound of the Formula (J-1) is provided. In certain embodiments, a salt of the Formula (J-1) is provided as shown in the Formula (J-1-i):

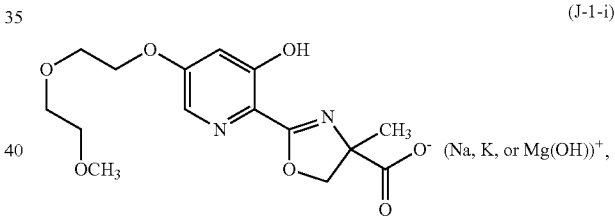

(J-1-i)

or a pharmaceutically acceptable salt, tautomer, stereoisomer, solvate, hydrate, or polymorph thereof.

In certain embodiments, the compound of the Formula (J) is of any one of the Formulae (J-1-ii) to (J-1-iv):

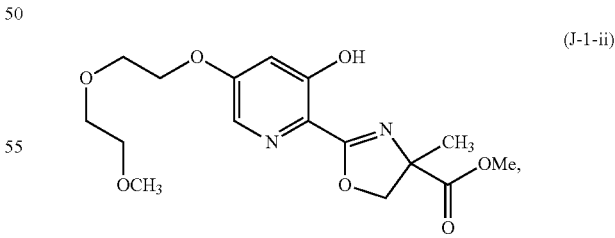

(J-1-ii)

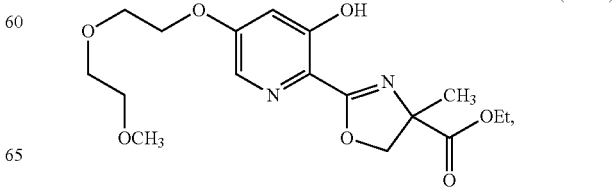

(J-1-iii)

(J-1-iv)

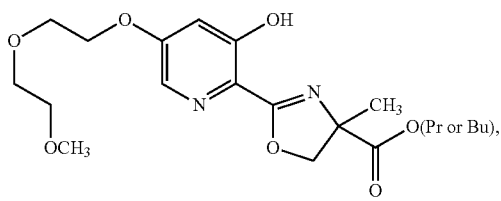

or a pharmaceutically acceptable salt, tautomer, stereoisomer, solvate, hydrate, or polymorph thereof.

In certain embodiments, the compound of Formula (J) is of the Formula (J-2):

(J-2)

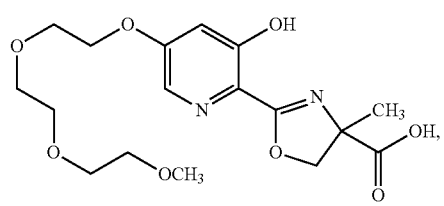

or a pharmaceutically acceptable salt, tautomer, stereoisomer, solvate, hydrate, or polymorph thereof.

In certain embodiments, a salt of a compound of the Formula (J-2) is provided. In certain embodiments, a salt of the Formula (J-2) is provided as shown in the Formula (J-2-i):

(J-2-i)

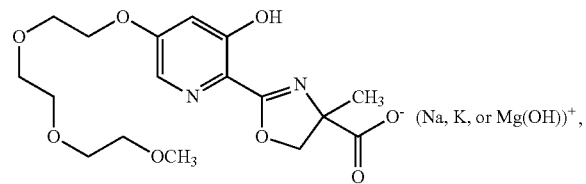

or a pharmaceutically acceptable salt, tautomer, stereoisomer, solvate, hydrate, or polymorph thereof.

In certain embodiments, the compound of the Formula (J) is of any one of the Formulae (J-2-ii) to (J-2-iv):

(J-2-ii)

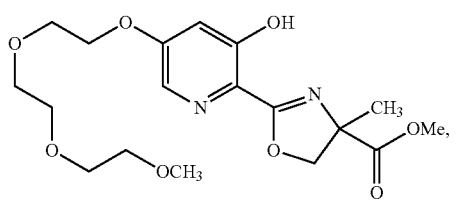

(J-2-iii)

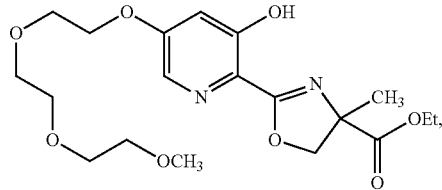

(J-2-iv)

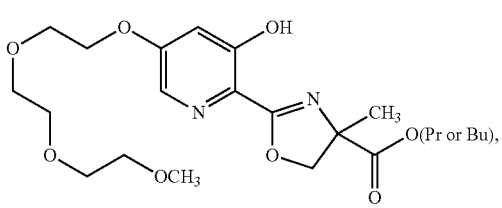

or a pharmaceutically acceptable salt, tautomer, stereoisomer, solvate, hydrate, or polymorph thereof In certain embodiments, the compound of Formula (J) is of the Formula (J-3):

(J-3)

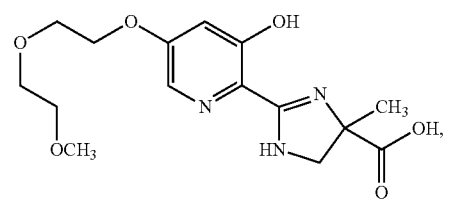

or a pharmaceutically acceptable salt, tautomer, stereoisomer, solvate, hydrate, or polymorph thereof.

In certain embodiments, a salt of a compound of the Formula (J-3) is provided. In certain embodiments, a salt of the Formula (J-3) is provided as shown in the Formula (J-3-i):

(J-3-i)

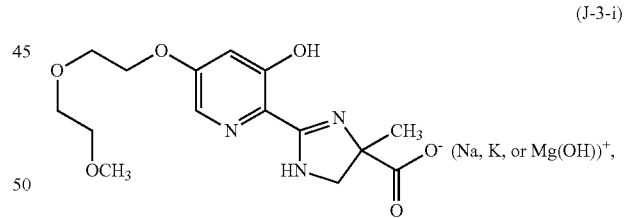

or a pharmaceutically acceptable salt, tautomer, stereoisomer, solvate, hydrate, or polymorph thereof.

In certain embodiments, the compound of the Formula (J) is of any one of the Formulae (J-3-ii) to (J-3-iv):

(J-3-ii)

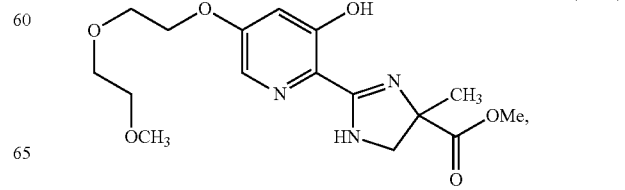

-continued

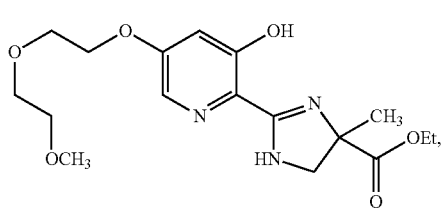
(J-3-iii)

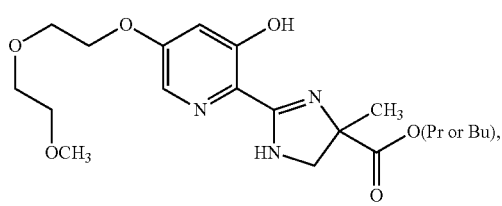
(J-3-iv)

or a pharmaceutically acceptable salt, tautomer, stereoisomer, solvate, hydrate, or polymorph thereof.

In certain embodiments, the compound of Formula (J) is of the Formula (J-4):

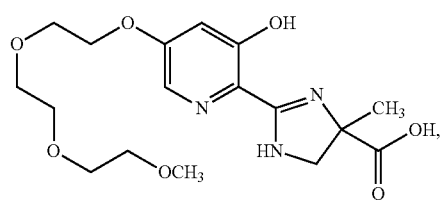
(J-4)

or a pharmaceutically acceptable salt, tautomer, stereoisomer, solvate, hydrate, or polymorph thereof.

In certain embodiments, a salt of a compound of the Formula (J-4) is provided. In certain embodiments, a salt of the Formula (J-4) is provided as shown in the Formula (J-4-i):

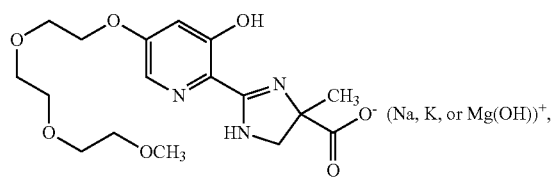
(J-4-i)

or a pharmaceutically acceptable salt, tautomer, stereoisomer, solvate, hydrate, or polymorph thereof.

In certain embodiments, the compound of the Formula (J) is of any one of the Formulae (J-4-ii) to (J-4-iv):

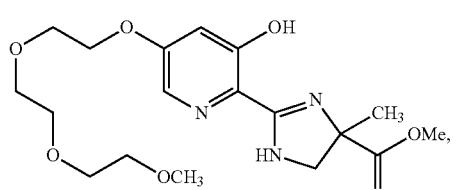
(J-4-ii)

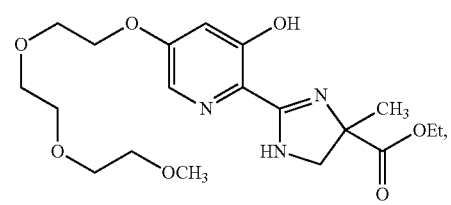
(J-4-iii)

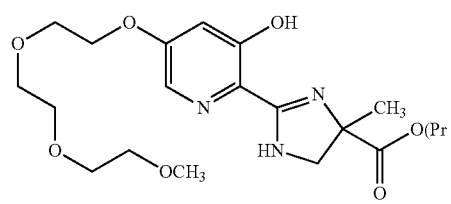
(J-4-iv)

or a pharmaceutically acceptable salt, tautomer, stereoisomer, solvate, hydrate, or polymorph thereof.

In certain embodiments, the compound of Formula (J) is of the Formula (J-5):

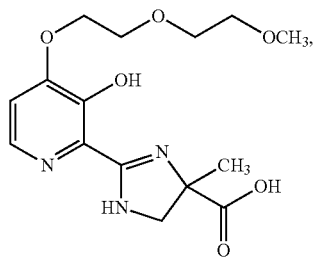
(J-5)

or a pharmaceutically acceptable salt, tautomer, stereoisomer, solvate, hydrate, or polymorph thereof.

In certain embodiments, a salt of a compound of the Formula (J-5) is provided. In certain embodiments, a salt of the Formula (J-5) is provided as shown in the Formula (J-5-i):

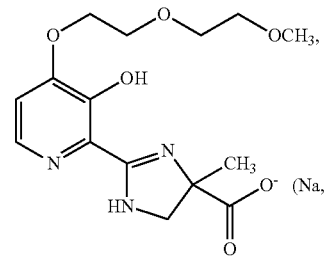
(J-5-i)

or a pharmaceutically acceptable salt, tautomer, stereoisomer, solvate, hydrate, or polymorph thereof.

In certain embodiments, the compound of the Formula (J) is of any one of the Formulae (J-5-ii) to (J-5-iv):

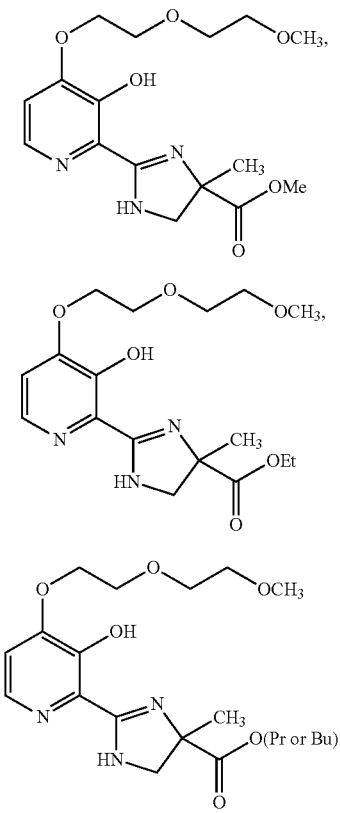

(J-5-ii)

(J-5-iii)

(J-5-iv)

or a pharmaceutically acceptable salt, tautomer, stereoisomer, solvate, hydrate, or polymorph thereof.

In certain embodiments, the compound of Formula (J) is of the Formula (J-6):

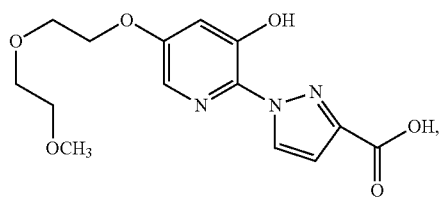

(J-6)

or a pharmaceutically acceptable salt, tautomer, stereoisomer, solvate, hydrate, or polymorph thereof.

In certain embodiments, a salt of a compound of the Formula (J-6) is provided. In certain embodiments, a salt of the Formula (J-6) is provided as shown in the Formula (J-6-i):

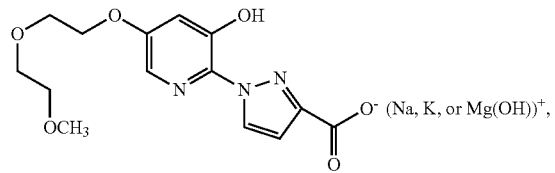

(J-6-i)

or a pharmaceutically acceptable salt, tautomer, stereoisomer, solvate, hydrate, or polymorph thereof.

In certain embodiments, the compound of the Formula (J) is of any one of the Formulae (J-6-ii) to (J-6-iv):

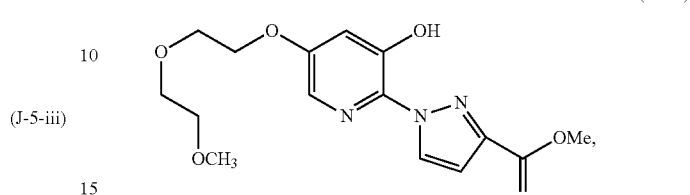

(J-6-ii)

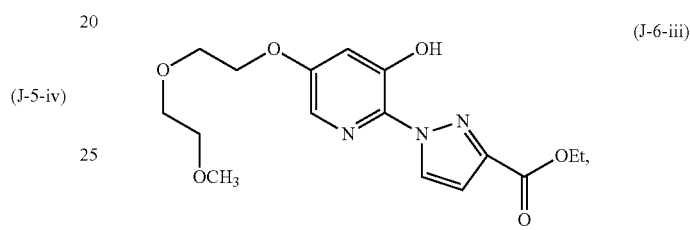

(J-6-iii)

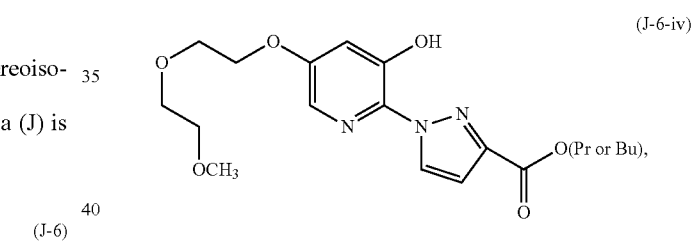

(J-6-iv)

or a pharmaceutically acceptable salt, tautomer, stereoisomer, solvate, hydrate, or polymorph thereof.

In certain embodiments, the compound of Formula (J) is of the Formula (J-7):

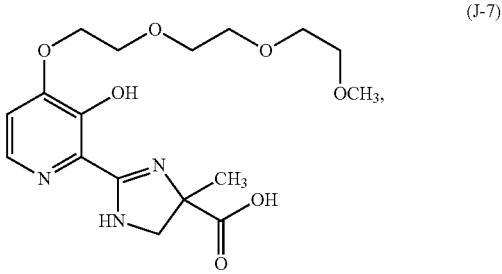 [SMILES: COCCOCCOCCOc1ccnc(C2=NC(C)(C(=O)O)CN2)c1O]

(J-7)

or a pharmaceutically acceptable salt, tautomer, stereoisomer, solvate, hydrate, or polymorph thereof.

In certain embodiments, a salt of a compound of the Formula (J-7) is provided. In certain embodiments, a salt of the Formula (J-7) is provided as shown in the Formula (J-7-i):

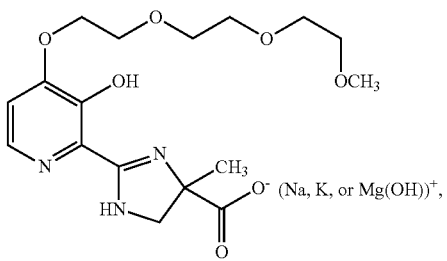
(J-7-i)

or a pharmaceutically acceptable salt, tautomer, stereoisomer, solvate, hydrate, or polymorph thereof.

In certain embodiments, the compound of the Formula (J) is of any one of the Formulae (J-7-ii) to (J-7-iv):

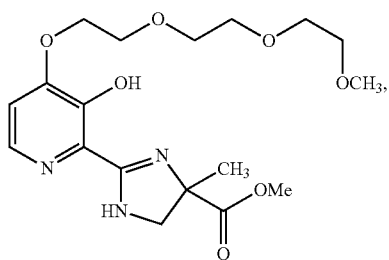
(J-7-ii)

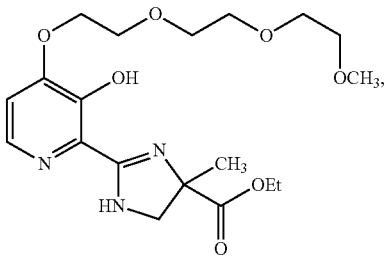
(J-7-iii)

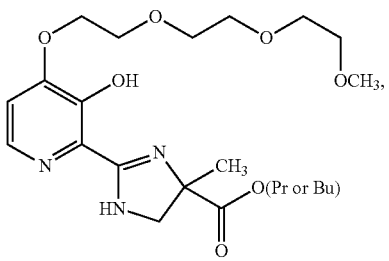
(J-7-iv)

or a pharmaceutically acceptable salt, tautomer, stereoisomer, solvate, hydrate, or polymorph thereof.

In certain embodiments, the compound of Formula (J) is of the Formula (J-8):

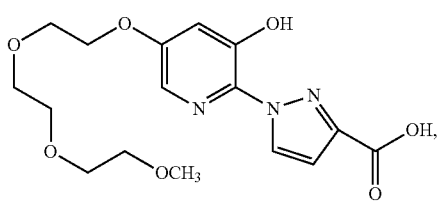
(J-8)

or a pharmaceutically acceptable salt, tautomer, stereoisomer, solvate, hydrate, or polymorph thereof.

In certain embodiments, a salt of a compound of the Formula (J-8) is provided. In certain embodiments, a salt of the Formula (J-8) is provided as shown in the Formula (J-8-i):

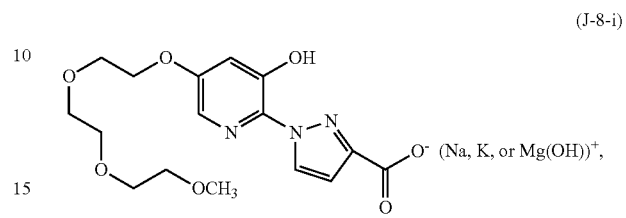
(J-8-i)

or a pharmaceutically acceptable salt, tautomer, stereoisomer, solvate, hydrate, or polymorph thereof.

In certain embodiments, the compound of the Formula (J) is of any one of the Formulae (J-8-ii) to (J-8-iv):

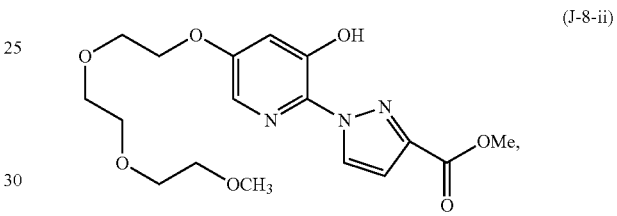
(J-8-ii)

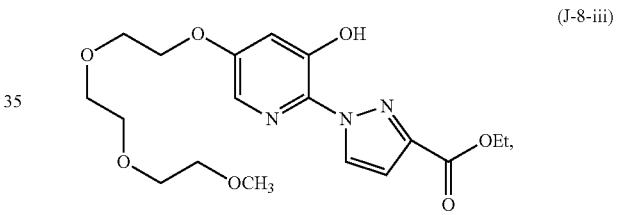
(J-8-iii)

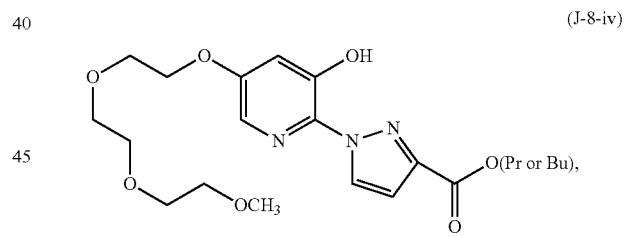
(J-8-iv)

or a pharmaceutically acceptable salt, tautomer, stereoisomer, solvate, hydrate, or polymorph thereof.

In certain embodiments, the compound of Formula (J) is of the Formula (J-9):

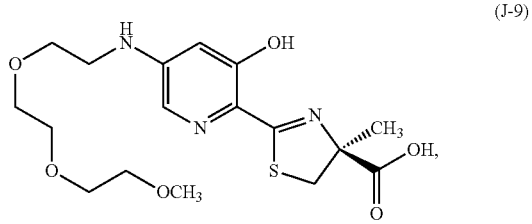 [SMILES: COCCOCCOCCNc1cnc(C2=N[C@@](C)(C(=O)O)CS2)c(O)c1]
(J-9)

or a pharmaceutically acceptable salt, tautomer, stereoisomer, solvate, hydrate, or polymorph thereof.

In certain embodiments, a salt of a compound of the Formula (J-9) is provided. In certain embodiments, a salt of the Formula (J-9) is provided as shown in the Formula (J-9-i):

(J-9-i)

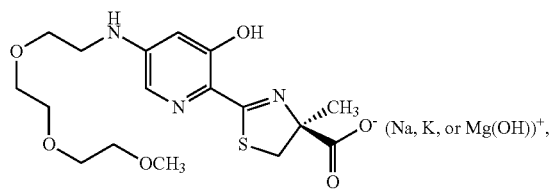

or a pharmaceutically acceptable salt, tautomer, stereoisomer, solvate, hydrate, or polymorph thereof.

In certain embodiments, the compound of the Formula (J) is of any one of the Formulae (J-9-ii) to (J-9-iv):

(J-9-ii)

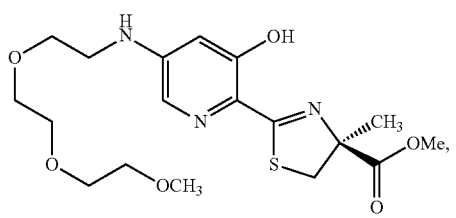

(J-9-iii)

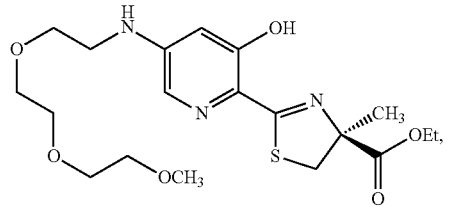

(J-9-iv)

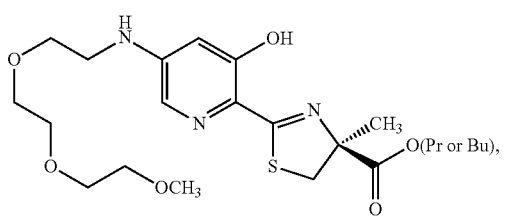

or a pharmaceutically acceptable salt, tautomer, stereoisomer, solvate, hydrate, or polymorph thereof.

In certain embodiments, the compound of Formula (J) is of the Formula (J-10):

(J-10)

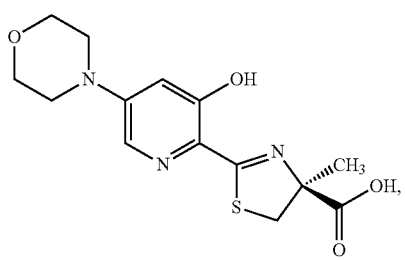

or a pharmaceutically acceptable salt, tautomer, stereoisomer, solvate, hydrate, or polymorph thereof.

In certain embodiments, a salt of a compound of the Formula (J-10) is provided. In certain embodiments, a salt of the Formula (J-10) is provided as shown in the Formula (J-10-i):

(J-10-i)

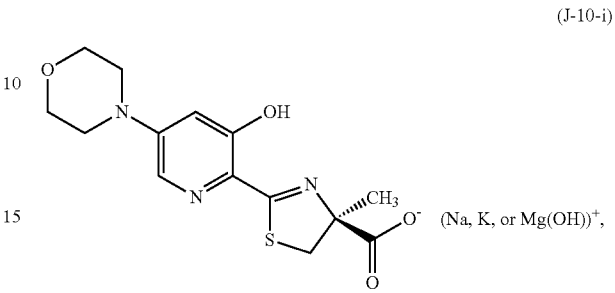

or a pharmaceutically acceptable salt, tautomer, stereoisomer, solvate, hydrate, or polymorph thereof.

In certain embodiments, the compound of the Formula (A) is of any one of the Formulae (J-10-ii) to (J-10-iv):

(J-10-ii)

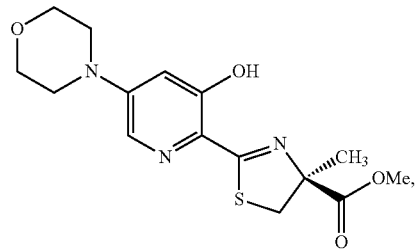

(J-10-iii)

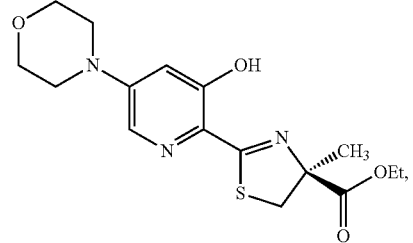

(J-10-iv)

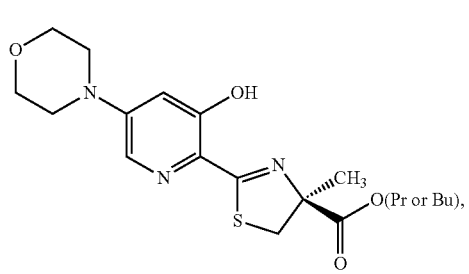

or a pharmaceutically acceptable salt, tautomer, stereoisomer, solvate, hydrate, or polymorph thereof.

In certain embodiments, the compound of Formula (J) is of the Formula (J-11):

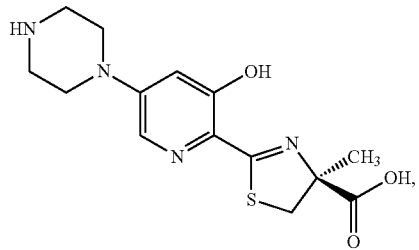
(J-11)

or a pharmaceutically acceptable salt, tautomer, stereoisomer, solvate, hydrate, or polymorph thereof.

In certain embodiments, a salt of a compound of the Formula (J-11) is provided. In certain embodiments, a salt of the Formula (J-11) is provided as shown in the Formula (J-11-i):

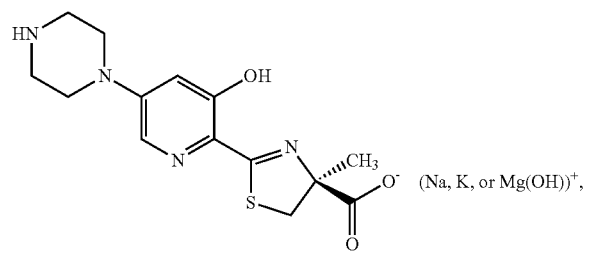
(J-11-i)

or a pharmaceutically acceptable salt, tautomer, stereoisomer, solvate, hydrate, or polymorph thereof.

In certain embodiments, the compound of the Formula (A) is of any one of the Formulae (J-11-ii) to (J-11-iv):

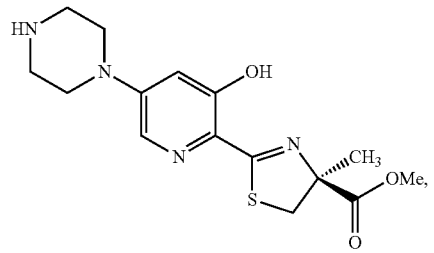
(J-11-ii)

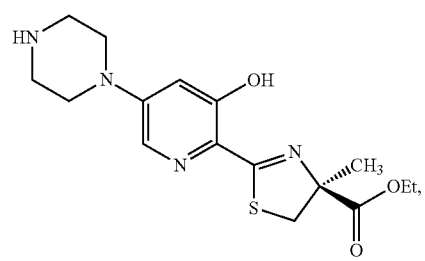
(J-11-iii)

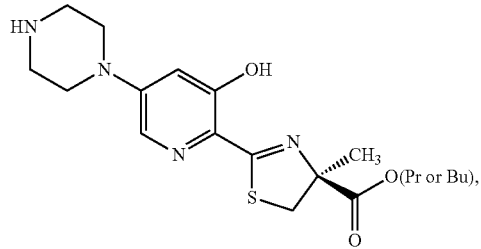
(J-11-iv)

or a pharmaceutically acceptable salt, tautomer, stereoisomer, solvate, hydrate, or polymorph thereof In certain embodiments, the compound of Formula (J) is of the Formula (J-12):

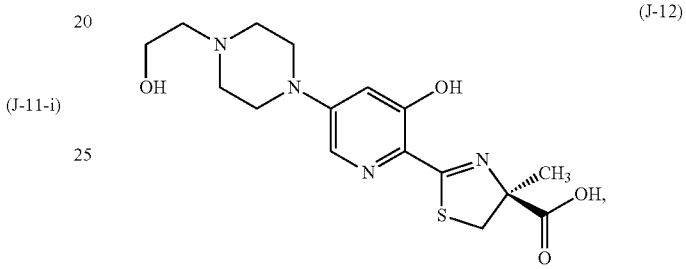
(J-12)

or a pharmaceutically acceptable salt, tautomer, stereoisomer, solvate, hydrate, or polymorph thereof.

In certain embodiments, a salt of a compound of the Formula (J-12) is provided. In certain embodiments, a salt of the Formula (J-12) is provided as shown in the Formula (J-12-i):

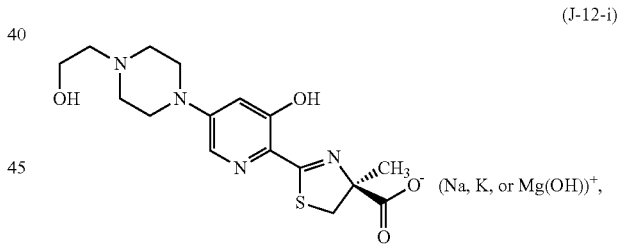
(J-12-i)

or a pharmaceutically acceptable salt, tautomer, stereoisomer, solvate, hydrate, or polymorph thereof.

In certain embodiments, the compound of the Formula (A) is of any one of the Formulae (J-12-ii) to (J-12-iv):

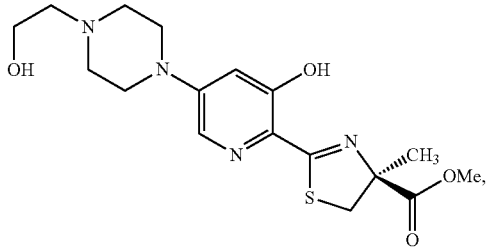
(J-12-ii)

(J-12-iii)

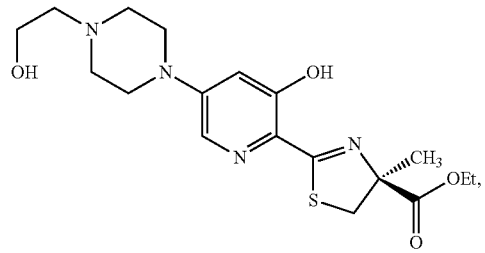

(J-12-iv)

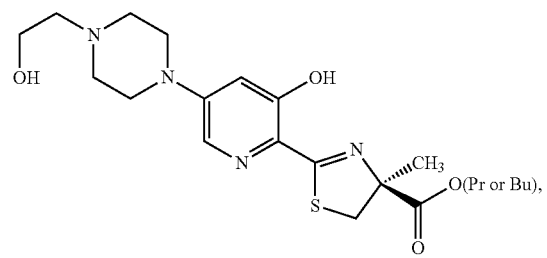

or a pharmaceutically acceptable salt, tautomer, stereoisomer, solvate, hydrate, or polymorph thereof.

In certain embodiments, the compound of Formula (J) is of the Formula (J-13):

(J-13)

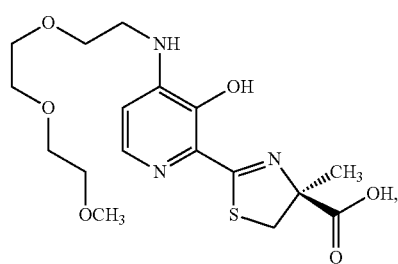

or a pharmaceutically acceptable salt, tautomer, stereoisomer, solvate, hydrate, or polymorph thereof.

In certain embodiments, a salt of a compound of the Formula (J-13) is provided. In certain embodiments, a salt of the Formula (J-13) is provided as shown in the Formula (J-13-i):

(J-13-i)

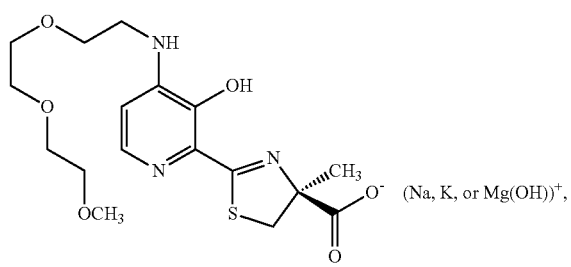

or a pharmaceutically acceptable salt, tautomer, stereoisomer, solvate, hydrate, or polymorph thereof.

In certain embodiments, the compound of the Formula (A) is of any one of the Formulae (J-13-ii) to (J-13-iv):

(J-13-ii)

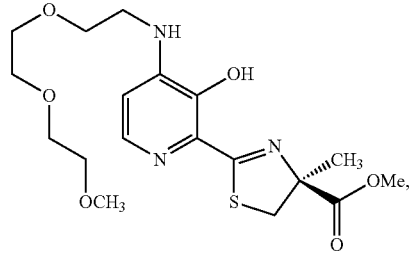

(J-13-iii)

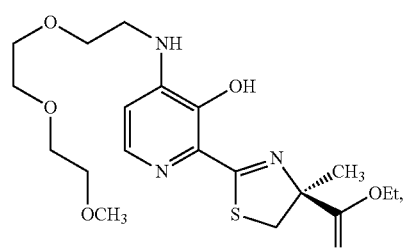

(J-13-iv)

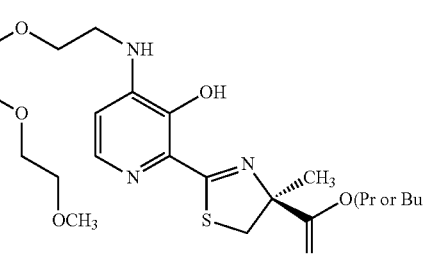

or a pharmaceutically acceptable salt, tautomer, stereoisomer, solvate, hydrate, or polymorph thereof.

In certain embodiments, the compound of Formula (J) is of the Formula (J-14):

(J-14)

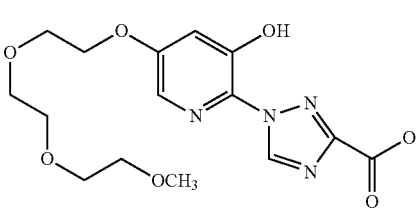

or a pharmaceutically acceptable salt, tautomer, stereoisomer, solvate, hydrate, or polymorph thereof.

In certain embodiments, a salt of a compound of the Formula (J-14) is provided. In certain embodiments, a salt of the Formula (J-14) is provided as shown in the Formula (J-14-i):

(J-14-i)

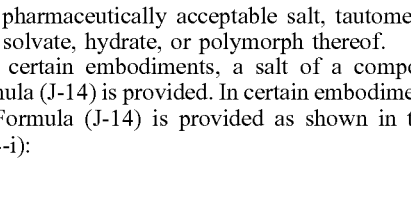

or a pharmaceutically acceptable salt, tautomer, stereoisomer, solvate, hydrate, or polymorph thereof.

In certain embodiments, the compound of the Formula (J) is of any one of the Formulae (J-14-ii) to (J-14-iv):

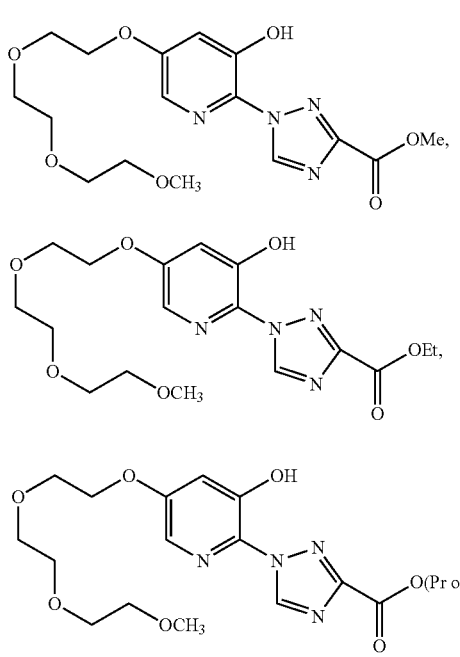

(J-14-ii)

(J-14-iii)

(J-14-iv)

or a pharmaceutically acceptable salt, tautomer, stereoisomer, solvate, hydrate, or polymorph thereof.

In certain embodiments, the compound of Formula (J) is of the Formula (J-15):

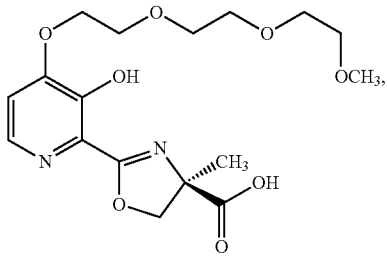

(J-15)

or a pharmaceutically acceptable salt, tautomer, stereoisomer, solvate, hydrate, or polymorph thereof.

In certain embodiments, a salt of a compound of the Formula (J-15) is provided. In certain embodiments, a salt of the Formula (J-15) is provided as shown in the Formula (J-15-i):

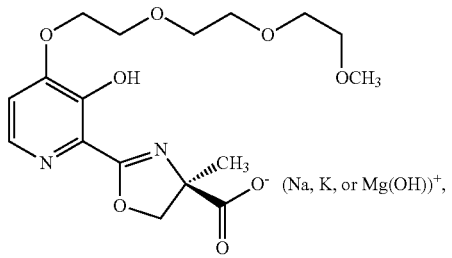

(J-15-i)

or a pharmaceutically acceptable salt, tautomer, stereoisomer, solvate, hydrate, or polymorph thereof.

In certain embodiments, the compound of the Formula (J) is of any one of the Formulae (J-15-ii) to (J-15-iv):

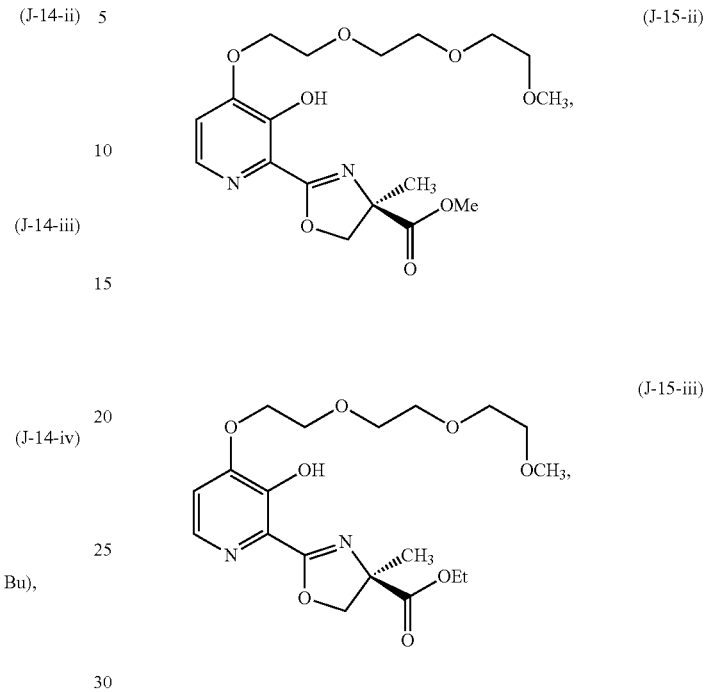

(J-15-ii)

(J-15-iii)

(J-15-iv)

or a pharmaceutically acceptable salt, tautomer, stereoisomer, solvate, hydrate, or polymorph thereof.

In certain embodiments, the compound of Formula (J) is of the Formula (J-16):

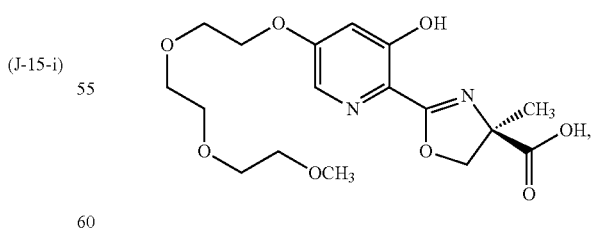

(J-16)

or a pharmaceutically acceptable salt, tautomer, stereoisomer, solvate, hydrate, or polymorph thereof.

In certain embodiments, a salt of a compound of the Formula (J-16) is provided. In certain embodiments, a salt of the Formula (J-16) is provided as shown in the Formula (J-16-i):

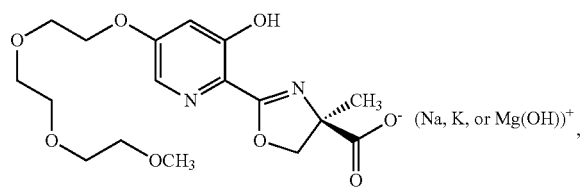
(J-16-i)

or a pharmaceutically acceptable salt, tautomer, stereoisomer, solvate, hydrate, or polymorph thereof.

In certain embodiments, the compound of the Formula (J) is of any one of the Formulae (J-16-ii) to (J-16-iv):

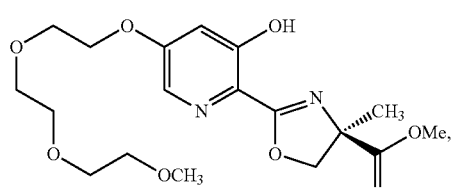
(J-16-ii)

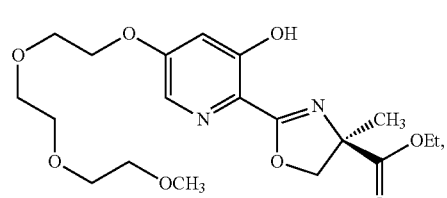
(J-16-iii)

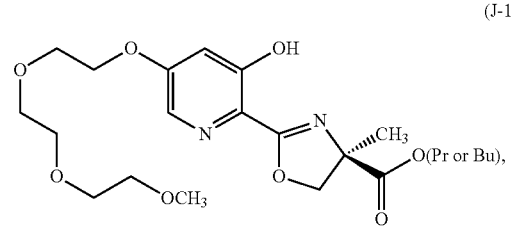
(J-16-iv)

or a pharmaceutically acceptable salt, tautomer, stereoisomer, solvate, hydrate, or polymorph thereof.

In certain embodiments, the compound of Formula (J) is of the Formula (J-17):

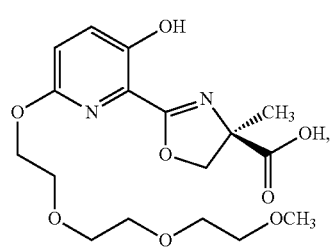
(J-17)

or a pharmaceutically acceptable salt, tautomer, stereoisomer, solvate, hydrate, or polymorph thereof.

In certain embodiments, a salt of a compound of the Formula (J-17) is provided. In certain embodiments, a salt of the Formula (J-17) is provided as shown in the Formula (J-17-i):

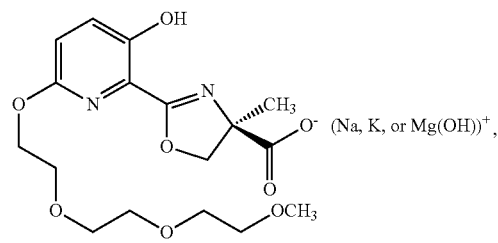
(J-17-i)

or a pharmaceutically acceptable salt, tautomer, stereoisomer, solvate, hydrate, or polymorph thereof.

In certain embodiments, the compound of the Formula (J) is of any one of the Formulae (J-17-ii) to (J-17-iv):

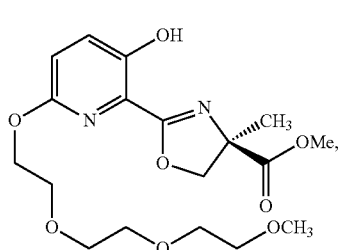
(J-17-ii)

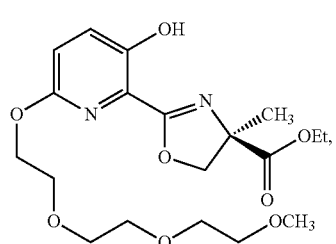
(J-17-iii)

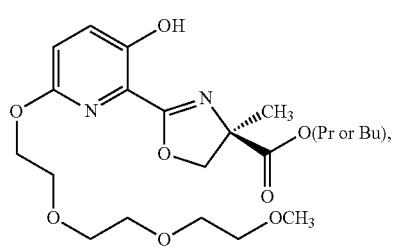
(J-17-iv)

or a pharmaceutically acceptable salt, tautomer, stereoisomer, solvate, hydrate, or polymorph thereof.

In certain embodiments, the compound of Formula (J) is of the Formula (J-18):

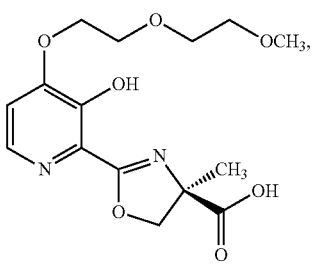
(J-18)

or a pharmaceutically acceptable salt, tautomer, stereoisomer, solvate, hydrate, or polymorph thereof.

In certain embodiments, a salt of a compound of the Formula (J-18) is provided. In certain embodiments, a salt of the Formula (J-18) is provided as shown in the Formula (J-18-i):

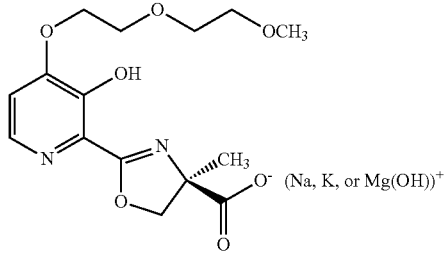
(J-18-i)

or a pharmaceutically acceptable salt, tautomer, stereoisomer, solvate, hydrate, or polymorph thereof.

In certain embodiments, the compound of the Formula (J) is of any one of the Formulae (J-18-ii) to (J-18-iv):

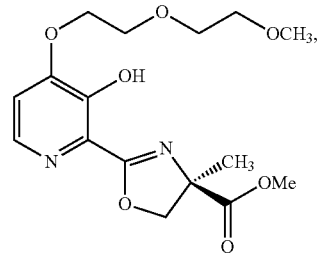
(J-18-ii)

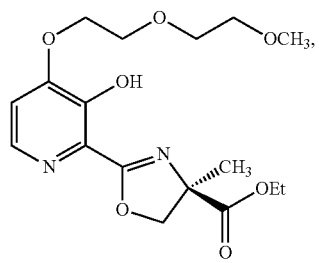
(J-18-iii)

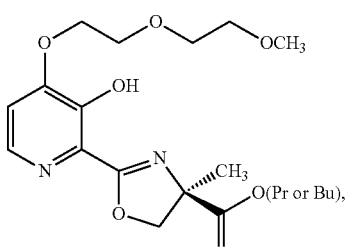
(J-18-iv)

or a pharmaceutically acceptable salt, tautomer, stereoisomer, solvate, hydrate, or polymorph thereof.

In certain embodiments, the compound of Formula (J) is of the Formula (J-19):

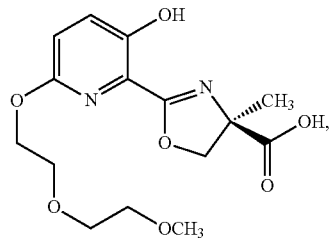
(J-19)

or a pharmaceutically acceptable salt, tautomer, stereoisomer, solvate, hydrate, or polymorph thereof.

In certain embodiments, a salt of a compound of the Formula (J-19) is provided. In certain embodiments, a salt of the Formula (J-19) is provided as shown in the Formula (J-19-i):

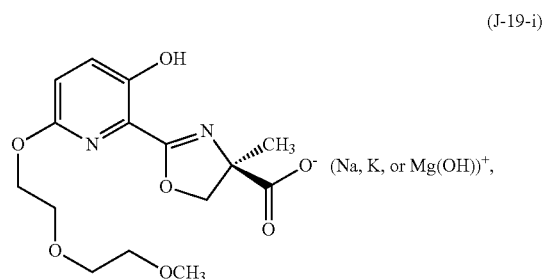
(J-19-i)

or a pharmaceutically acceptable salt, tautomer, stereoisomer, solvate, hydrate, or polymorph thereof.

In certain embodiments, the compound of the Formula (J) is of any one of the Formulae (J-19-ii) to (J-19-iv):

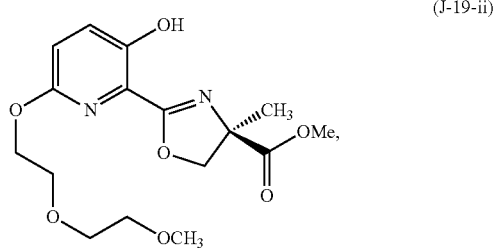
(J-19-ii)

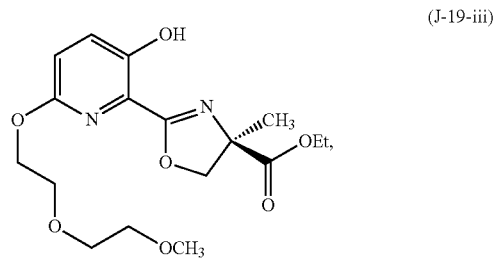
(J-19-iii)

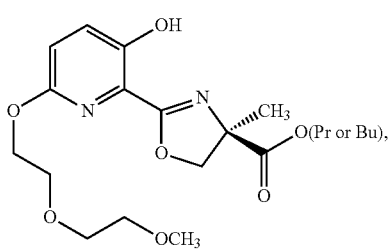
(J-19-iv)

or a pharmaceutically acceptable salt, tautomer, stereoisomer, solvate, hydrate, or polymorph thereof.

In certain embodiments, the compound of Formula (J) is of the Formula (J-20):

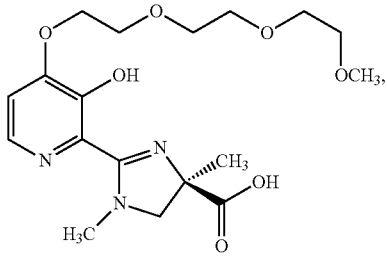
(J-20)

or a pharmaceutically acceptable salt, tautomer, stereoisomer, solvate, hydrate, or polymorph thereof.

In certain embodiments, a salt of a compound of the Formula (J-20) is provided. In certain embodiments, a salt of the Formula (J-20) is provided as shown in the Formula (J-20-i):

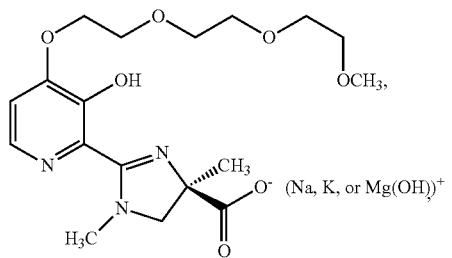
(J-20-i)

or a pharmaceutically acceptable salt, tautomer, stereoisomer, solvate, hydrate, or polymorph thereof.

In certain embodiments, the compound of the Formula (J) is of any one of the Formulae (J-20-ii) to (J-20-iv):

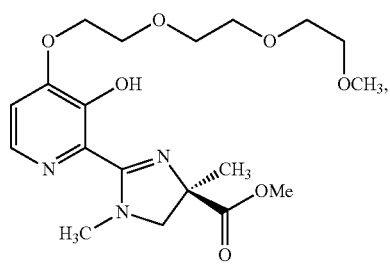
(J-20-ii)

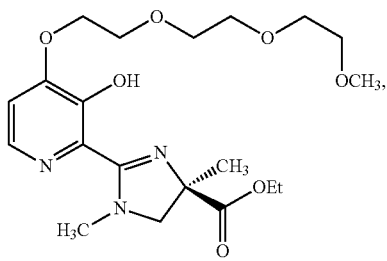
(J-20-iii)

(J-20-iv)

or a pharmaceutically acceptable salt, tautomer, stereoisomer, solvate, hydrate, or polymorph thereof.

In certain embodiments, the compound of Formula (J) is of the Formula (J-21):

(J-21)

or a pharmaceutically acceptable salt, tautomer, stereoisomer, solvate, hydrate, or polymorph thereof.

In certain embodiments, a salt of a compound of the Formula (J-21) is provided. In certain embodiments, a salt of the Formula (J-21) is provided as shown in the Formula (J-21-i):

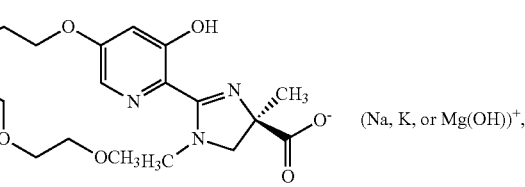
(J-21-i)

or a pharmaceutically acceptable salt, tautomer, stereoisomer, solvate, hydrate, or polymorph thereof.

In certain embodiments, the compound of the Formula (J) is of any one of the Formulae (J-21-ii) to (J-21-iv):

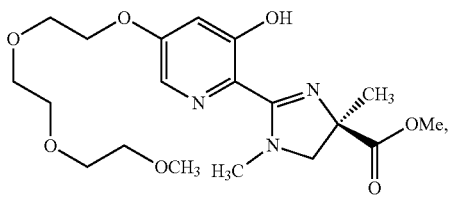
(J-21-ii)

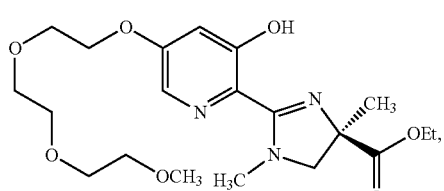
(J-21-iii)

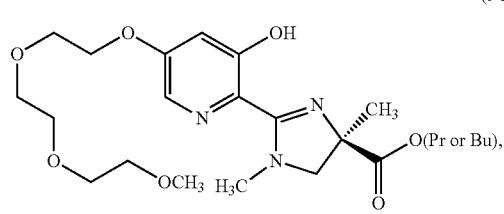
(J-21-iv)

or a pharmaceutically acceptable salt, tautomer, stereoisomer, solvate, hydrate, or polymorph thereof.

Pharmaceutical Compositions, Kits, and Administration

The present invention provides pharmaceutical compositions comprising a compound of the invention, and pharmaceutically acceptable salts, tautomers, stereoisomers, solvates, hydrates, and polymorphs thereof, and optionally a pharmaceutically acceptable excipient. In certain embodiments, the compound of the present invention, or a pharmaceutically acceptable salt thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of the present invention (the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

While it may be possible for the compounds disclosed herein, or pharmaceutically acceptable salts, tautomers, stereoisomers, solvates, hydrates, or polymorphs thereof, to be administered orally as they are, it is also possible to present them as a pharmaceutical formulation or dosage. Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in international PCT Application Publication No. WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and international PCT Application Publication Nos. WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi-liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. The inventive compounds and compositions may also be mixed with blood ex vivo, and the resulting mixture may be administered (e.g., intravenously) to a subject. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents in combination be utilized at levels that do not exceed the levels at which they are utilized individually. In some embodiments, the levels utilized in combination will be lower than those utilized individually.

Exemplary additional therapeutically active agents include, but are not limited to, anti-cancer agents, anti-diabetic agents, anti-inflammatory agents, immunosuppressant agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in another aspect, provided are kits for treating and/or preventing a pathological condition of a subject. In certain embodiments, the kits include a first container comprising a compound of the present invention, or a pharmaceutically acceptable salt, tautomer, stereoisomer, solvate, hydrate, polymorph, or composition thereof; and an instruction for administering the compound, or a pharmaceutically acceptable salt, tautomer, stereoisomer, solvate, hydrate, polymorph, or composition thereof, to the subject to treat and/or prevent the pathological condition. In certain embodiments, the kits of the present invention include one or more additional approved therapeutic agents for use as a combination therapy. In certain embodiments, the instruction includes a notice in the form prescribed by a governmental agency regulating the manufacture, use, or sale of pharmaceutical products, which notice reflects approval by the agency of manufacture, use, or sale for human administration.

Methods of Treatment and Uses

The compounds of the invention and pharmaceutical compositions thereof are expected to be useful in the treatment and/or prevention of a pathological condition in a subject. In one aspect, provided herein are methods of treating and/or preventing a pathological condition in a subject, the methods including administering to the subject a therapeutically or prophylactically effective amount of a compound of the invention, or a pharmaceutically acceptable salt, tautomer, stereoisomer, solvate, hydrate, or polymorph thereof, and optionally a pharmaceutically acceptable excipient.

In another aspect of the present invention, provided are methods of treating and/or preventing a pathological condition, the methods including mixing blood or a component thereof (e.g., red blood cells) with a therapeutically or prophylactically effective amount of a compound of the invention, or a pharmaceutically acceptable salt, tautomer, stereoisomer, solvate, hydrate, or polymorph thereof, or a pharmaceutical composition of the invention; and administering to the subject the mixture of blood or a component thereof (e.g., red blood cells) and the compound, or the pharmaceutically acceptable salt, tautomer, stereoisomer, solvate, hydrate, or polymorph thereof, or the pharmaceutical composition. The blood may be whole blood or a fluid comprising one or more components of whole blood (e.g., red blood cells, white blood cells, plasma, clotting factors, and platelets). In certain embodiments, the mixture is administered intravenously to the subject.

In another aspect of the present invention, provided are compounds of the invention, and pharmaceutically acceptable salts, tautomers, stereoisomers, solvates, hydrates, and polymorphs thereof, for use in treatment and/or prevention of a pathological condition.

The present invention stems from the recognition that the pathogenesis of various pathological conditions, including oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, reperfusion injury, and other pathological conditions, involves free iron and the generation of reactive oxygen species (ROS), including superoxide anion, hydrogen peroxide, hypochlorous acid, and hydroxyl radicals, and other longer lived, free radicals. Such radicals are now realized to be important contributors to these pathological conditions. Free iron is known to contribute to the formation of reactive oxygen species. For example, $Fe^{+2}$ ions in biological systems react with oxygen species to produce highly reactive hydroxyl radicals via the Fenton reaction (see scheme below). The hydroxyl radical is a highly effective oxidizing agent, reacting at a diffusion-controlled rate with most organic species, such as nucleic acids, proteins, and lipids. Furthermore, superoxide anions or a biological reductant (e.g., ascorbic acid) can reduce the resulting $Fe^{+3}$ ion back to $Fe^{+2}$ for continued peroxide reduction, thus a problematic cycle.

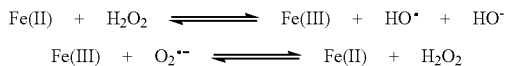

Therefore, pathological conditions that lead to bleeding and/or an inflammatory response involve the possibility that reactive oxygen species will come in contact with $Fe^{+2}$ ions to produce highly reactive and damaging hydroxyl radicals. That is, the iron released from red blood cells react with oxygen species produced by inflammatory cells such as neutrophils to produce hydroxyl radicals that cause cell and tissue injury. The solution, therefore, is chelation and removal of the unmanaged iron.

Without wishing to be bound by any particular theory, the compounds of the invention are thought to chelate or sequestrate a metal, and, in certain embodiments, the pathological condition is responsive to chelation or sequestration of the metal. In certain embodiments, the metal is iron (e.g., Fe(II) or Fe(III)), aluminum, thallium (e.g., Tl(I) or Tl(III)), chromium (e.g., Cr(III) or Cr(VI)), magnesium, calcium, strontium, nickel (e.g., Ni(II)), manganese (e.g., Mn(II)), cobalt (e.g., Co(II) or Co(III)), copper (e.g., Cu(I) or Cu(II)), zinc, silver (e.g., Ag(I)), sodium, potassium, cadmium (e.g., Cd(II)), mercury (e.g., Hg(I) or Hg(II)), lead (e.g., Pb(II) or Pb(IV)), antimony (e.g., Sb(III) or Sb(V)), molybdenum (e.g., Mo(III) or Mo(VI)), tungsten (e.g., W(VI)), a lanthanide (e.g., cerium, such as Ce(III) or Ce(IV)), or an actinide (e.g., uranium, such as U(VI)). In certain embodiments, the metal is a trivalent metal. In certain embodiments, the metal is iron (e.g., Fe(III)). In certain embodiments, the metal is aluminum. In certain embodiments, the metal is Tl(III), Cr(III), Co(III), Sb(III), Mo(III), or Ce(III). In certain embodiments, the metal is a monovalent metal (e.g., Tl(I), Cu(I), Ag(I), Na(I), K(I), or Hg(I)). In certain embodiments, the metal is a divalent metal (e.g., Fe(II), Mg(II), Ca(II), Sr(II), Ni(II), Mn(II), Co(II), Cu(II), Zn(II), Cd(II), Hg(II), or Pb(II)). In certain embodiments, the metal is a tetravalent metal (e.g., Pb(IV) or Ce(IV)). In certain embodiments, the metal is a pentavalent metal (e.g., Sb(V)). In certain embodiments, the metal is a hexavalent metal (e.g., Cr(VI), Mo(VI), W(VI), or U(VI)).

In certain embodiments, the subject administered the inventive compound or pharmaceutical composition is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is an experimental animal such as a rodent or non-human primate.

The inventive compounds, pharmaceutical compositions, and methods may also be useful for the treatment and/or prevention of infectious diseases in a subject. Infectious diseases are typically caused by microbial pathogens (e.g., viruses, bacteria, parasites (e.g., protozoa and multicellular parasites), and fungi) into the cells ("host cells") of a subject ("host"). Iron is an oxidant as well as a nutrient for many microorganisms. To survive and replicate, microbial pathogens must acquire iron from their host. Highly virulent microbial strains usually possess powerful mechanisms for obtaining iron from their host. Depriving the pathogenic microbes of iron may inhibit their activities and may be useful for the treatment and/or prevention of the infectious diseases caused by microbes. In certain embodiments, the pathological condition that is treated and/or prevented by the compounds, pharmaceutical compositions, and methods of the invention is a viral infection. In certain embodiments, the pathological condition is a bacterial infection. In certain embodiments, the pathological condition is a parasitic infection. In certain embodiments, the pathological condition is a protozoan infection. In certain embodiments, the pathological condition is malaria. Malaria is typically caused by parasites of the genus *Plasmodium* (phylum Apicomplexa), including, but not limited to, the species *P. falciparum, P. malariae, P. ovale, P. vivax,* and *P. knowlesi*. In certain embodiments, the pathological condition is a multicellular-parasitic infection. In certain embodiments, the pathological condition is a fungal infection.

In certain embodiments, methods are provided herein that are useful in the treatment and/or prevention of metal overload in a subject. The amount of free metal (e.g., a trivalent metal, such as iron(III) or aluminum) may be elevated in the subject (e.g., in the serum or in a cell), such as when there is insufficient storage capacity for the metal or an abnormality in the metal storage system that leads to metal release. In certain embodiments, the metal overload is iron overload (e.g., Fe(III) overload or Fe(II) overload).

Iron overload conditions or diseases can be characterized by global iron overload or focal iron overload. Global iron overload conditions generally involve an excess of iron in multiple tissues or excess iron located throughout an organism. Global iron overload conditions can result from excess uptake of iron by a subject, excess storage and/or retention of iron, from, for example, dietary iron or blood transfusions. One global iron overload condition is primary hemochromatosis, which is typically a genetic disorder. A second global iron overload condition is secondary hemochromatosis, which is typically the result of receiving multiple (chronic) blood transfusions. Blood transfusions are often required for subjects suffering from thalassemia or sickle cell anemia. A type of dietary iron overload is referred to as Bantu siderosis, which is associated with the ingestion of homebrewed beer with high iron content. In certain embodiments, the pathological condition that may be treated and/or prevented by the compounds, pharmaceutical compositions, and methods of the invention is global iron overload. In certain embodiments, the pathological condition that may be treated and/or prevented by the compounds, pharmaceutical compositions, and methods of the invention is focal iron overload. In certain embodiments, the pathological condition that may be treated and/or prevented by the compounds, pharmaceutical compositions, and methods of the invention is primary hemochromatosis. In certain embodiments, the pathological condition that may be treated and/or prevented by the compounds, pharmaceutical compositions, and methods of the invention is secondary hemochromatosis. In certain embodiments, the pathological condition that may be treated and/or prevented by the compounds, pharmaceutical compositions, and methods of the invention is Bantu siderosis.

In focal iron overload conditions, the excess iron is limited to one or a few cell types or tissues or a particular organ. Alternatively, symptoms associated with the excess iron are limited to a discrete organ, such as the heart, lungs, liver, pancreas, kidneys, or brain. It is believed that focal iron overload can lead to neurological or neurodegenerative disorders such as Parkinson's disease, Alzheimer's disease, Huntington's disease, neuroferritinopathy, amyotrophic lateral sclerosis, and multiple sclerosis. Pathological conditions that benefit from metal chelation or sequestration are often associated with deposition of the metal in the tissues of a subject. Deposition can occur globally or focally. In certain embodiments, the pathological condition that may be treated and/or prevented by the compounds, pharmaceutical compositions, and methods of the invention is a neurological or neurodegenerative disorder. In certain embodiments, the pathological condition that may be treated and/or prevented by the compounds, pharmaceutical compositions, and methods of the invention is a neurological disorder. In certain embodiments, the pathological condition that may be treated and/or prevented by the compounds, pharmaceutical compositions, and methods of the invention is a neurodegenerative disorder. In certain embodiments, the pathological condition that may be treated and/or prevented by the compounds, pharmaceutical compositions, and methods of the invention is Parkinson's disease. In certain embodiments, the pathological condition that may be treated and/or prevented by the compounds, pharmaceutical compositions, and methods of the invention is Alzheimer's disease. In certain embodiments, the pathological condition that may be treated and/or prevented by the compounds, pharmaceutical compositions, and methods of the invention is Huntington's disease. In certain embodiments, the pathological condition that may be treated and/or prevented by the compounds, pharmaceutical compositions, and methods of the invention is neuroferritinopathy. In certain embodiments, the pathological condition that may be treated and/or prevented by the compounds, pharmaceutical compositions, and methods of the invention is amyotrophic lateral sclerosis. In certain embodiments, the pathological condition that may be treated and/or prevented by the compounds, pharmaceutical compositions, and methods of the invention is multiple sclerosis.

While humans have a highly efficient iron management system in which they absorb and excrete about 1 mg of iron daily, there is no conduit for the excretion of excess metal. Transfusion-dependent anemias, like thalassemia, lead to a build up of iron in the liver, heart, pancreas, and elsewhere resulting in (i) liver disease that may progress to cirrhosis (Angelucci et al., "Hepatic Iron Concentration and Total Body Iron Stores in Thalassemia Major." N. Engl. J. Med. 2000, 343, 327-331; Bonkovsky et al., "Iron-Induced Liver Injury." Clin. Liver Dis. 2000, 4, 409-429; Peitrangelo, "Mechanism of Iron Toxicity." Adv. Exp. Med. Biol. 2002, 509, 19-43), (ii) diabetes related both to iron-induced decreases in pancreatic beta-cell secretion and to increases in hepatic insulin resistance (Cario et al., "Insulin Sensitivity and β-Cell Secretion in Thalassemia Major with Secondary Haemochromatosis: Assessment by Oral Glucose Tolerance Test." Eur. J. Pediatr. 2004, 162, 139-146; Wojcik et al., "Natural History of C282Y Homozygotes for Haemochromatosis." Can. J. Gastroenterol. 2002, 16, 297-302), and (iii) heart disease. Relative excess iron has been associated with increased risk of heart disease. Cardiac failure is still the leading cause of death in thalassemia major and related forms of transfusional iron overload (Brittenham, "Disorders of Iron Metabolism: Iron Deficiency and Overload." In: Hoffman et al., editors. Hematology: Basic Principles and Practice. 3. Churchill Livingstone; New York: 2000. pp. 397-428; Brittenham et al., "Efficacy of Deferoxamine in Preventing Complications of Iron Overload in Patients with Thalassemia Major." N. Engl. J. Med. 1994, 331, 567-573; Zurlo et al., "Survival and Causes of Death in Thalassemia Major." Lancet. 1989, 2, 27-30). There is a strong correlation between serum ferritin levels, inflammatory biomarkers such as C-reactive protein and interleukin-1, and mortality is a subset of patients with peripheral arterial disease; phlebotomy and iron chelation has been used to mitigate that risk. Treatment with an iron chelator would reduce iron stores, reduce serum ferritin and potentially reduce the incidence of heart disease and stroke. In certain embodiments, the pathological condition that is treated and/or prevented by the compounds, pharmaceutical compositions, and methods of the invention is transfusional iron overload. In certain embodiments, the pathological condition that is treated and/or prevented by the compounds, pharmaceutical compositions, and methods of the invention is transfusion-dependent anemia. In certain embodiments, the pathological condition that is treated and/or prevented by the compounds, pharmaceutical compositions, and methods of the invention is thalassemia. In certain embodiments, the pathological condition that is treated and/or prevented by the compounds, pharmaceutical compositions, and methods of the invention is a liver disease (e.g., hepatitis B, hepatitis C, and liver cirrhosis). In certain embodiments, the pathological condition that is treated and/or prevented by the compounds, pharmaceutical compositions, and methods of the invention is a heart disease (e.g., cardiomyopathy, coronary heart disease, inflammatory heart disease, ischemic heart disease, valvular heart disease, hypertensive heart disease, and atherosclerosis). In certain embodiments, the pathological condition that is treated and/or prevented by the compounds, pharmaceutical compositions, and methods of the invention is a pancreas disease. In certain embodiments, the pathological condition that is treated and/or prevented by the compounds, pharmaceutical compositions, and methods of the invention is diabetes.

Moreover, the compounds, pharmaceutical compositions, and methods of the present invention may be useful in the treatment and/or prevention of metal overload where the metal is not iron. All metals described herein are contemplated for chelation by the inventive compounds. In certain embodiments, the metal is aluminum. In certain embodiments, the metal is Tl(II), Cr(III), Co(III), Sb(III), Mo(III), or Ce(III). In certain embodiments, the metal is a monovalent metal (e.g., Tl(I), Cu(I), Ag(I), Na(I), K(I), or Hg(I)). In certain embodiments, the metal is a divalent metal (e.g., Fe(II), Mg(II), Ca(II), Sr(II), Ni(II), Mn(II), Co(II), Cu(II), Zn(II), Cd(II), Hg(II), or Pb(II)). In certain embodiments, the metal is a tetravalent metal (e.g., Pb(IV) or Ce(IV)). In certain embodiments, the metal is a pentavalent metal (e.g., Sb(V)). In certain embodiments, the metal is a hexavalent metal (e.g., Cr(VI), Mo(VI), W(VI), or U(VI)).

In certain embodiments, the metal overload is aluminum overload, chromium overload, magnesium overload, calcium overload, strontium overload, nickel overload, manganese overload, cobalt overload, copper overload, zinc overload, silver overload, sodium overload, potassium overload, cadmium overload, mercury overload, lead overload, molybdenum overload, tungsten overload, or actinide overload (e.g., uranium overload). In certain embodiments, the metal overload is trivalent metal overload. In certain embodiments, the metal overload is aluminum overload. In certain embodiments, the metal overload is Cr(III) overload, Mo(III) overload, or Co(III) overload). In certain embodiments, the metal overload is monovalent metal overload (e.g., Cu(I) overload, Ag(I) overload, Na(I) overload, K(I) overload, or Hg(I) overload). In certain embodiments, the metal overload is divalent metal overload (e.g., Mg(II) overload, Ca(II) overload, Sr(II) overload, Ni(II) overload, Mn(II) overload, Co(II) overload, Cu(II) overload, Zn(II) overload, Cd(II) overload, Hg(II) overload, or Pb(II) overload). In certain embodiments, the metal overload is tetravalent metal overload (e.g., Pb(IV) overload). In certain embodiments, the metal overload is pentavalent metal overload. In certain embodiments, the metal overload is hexavalent metal overload (e.g., Cr(VI) overload, Mo(VI) overload, W(VI) overload, or U(VI) overload).

The inventive compounds, pharmaceutical compositions, and methods may also be useful in treating and/or preventing metal poisoning in a subject. Metal poisoning may be caused by metal toxicity to a subject. For example, metals with little or no endogenous function may find their way into the body of a subject and cause damage. Heavy metal ions such as Hg(II) can replace ions such as Zn(II) in metalloproteins and render them inactive, resulting in serious acute or chronic toxicity that can end in a patient's death or in birth defects. Even more significantly, radioactive isotopes of the lanthanide (e.g., cerium) and actinide (e.g., uranium) series can cause grave illness on an individual exposed to them by mouth, air, or skin contact. Such exposure could result not only from the detonation of a nuclear bomb or a "dirty bomb" composed of nuclear waste, but also from the destruction of a nuclear power facility. In certain embodiments, the metal poisoning is iron poisoning, aluminum poisoning, thallium poisoning, chromium poisoning, magnesium poisoning, calcium poisoning, strontium poisoning, nickel poisoning, manganese poisoning, cobalt poisoning, copper poisoning, zinc poisoning, silver poisoning, sodium poisoning, potassium poisoning, cadmium poisoning, mercury poisoning, lead poisoning, antimony poisoning, molybdenum poisoning, tungsten poisoning, lanthanide poisoning (e.g., cerium poisoning), or actinide poisoning (e.g., uranium poisoning). In certain embodiments, the metal poisoning is iron poisoning (e.g., Fe(II) poisoning or Fe(III) poisoning). In certain embodiments, the metal poisoning is aluminum poisoning. In certain embodiments, the metal poisoning is trivalent metal poisoning (e.g., Fe(III) poisoning, Al(III) poisoning, Tl(III) poisoning, Cr(III) poisoning, Co(III) poisoning, Sb(III) poisoning, Mo(III) poisoning, or Ce(III) poisoning). In certain embodiments, the metal poisoning is monovalent metal poisoning (e.g., Tl(I) poisoning, Cu(I) poisoning, Ag(I) poisoning, Na(I) poisoning, K(I) poisoning, or Hg(I) poisoning). In certain embodiments, the metal poisoning is divalent metal poisoning (e.g., Fe(II) poisoning, Mg(II) poisoning, Ca(II) poisoning, Sr(II) poisoning, Ni(II) poisoning, Mn(II) poisoning, Co(II) poisoning, Cu(II) poisoning, Zn(II) poisoning, Cd(II) poisoning, Hg(II) poisoning, or Pb(II) poisoning). In certain embodiments, the metal poisoning is tetravalent metal poisoning (e.g., Pb(IV) or Ce(IV) poisoning). In certain embodiments, the metal poisoning is pentavalent metal poisoning (e.g., Sb(V) poisoning). In certain embodiments, the metal poisoning is hexavalent metal poisoning (e.g., Cr(VI) poisoning, Mo(VI) poisoning, W(VI) poisoning, or U(VI) poisoning).

The compounds, pharmaceutical compositions, and methods of the invention are also useful in treating and/or preventing oxidative stress in a subject. In a subject who suffers from oxidative stress and thus needs oxidative stress reduction, the iron released from red blood cells of the subject may react with oxygen species produced by inflammatory cells such as neutrophils to produce hydroxyl radicals that cause cell and tissue injury. Chelation and removal of the unmanaged iron may prevent or impede these harmful reactions and, therefore, reduce oxidative stress. A subject in need of oxidative stress reduction can have one or more of the following conditions: decreased levels of reducing agents, increased levels of reactive oxygen species, mutations in or decreased levels of antioxidant enzymes (e.g., Cu/Zn superoxide dismutase, Mn superoxide dismutase, glutathione reductase, glutathione peroxidase, thioredoxin, thioredoxin peroxidase, DT-diaphorase), mutations in or decreased levels of metal-binding proteins (e.g., transferrin, ferritin, ceruloplasmin, albumin, metallothionein), mutated or overactive enzymes capable of producing superoxide (e.g., nitric oxide synthase, NADPH oxidases, xanthine oxidase, NADH oxidase, aldehyde oxidase, dihydroorotate dehydrogenase, cytochrome c oxidase), and radiation injury. Increased or decreased levels of reducing agents, reactive oxygen species, and proteins are determined relative to the amount of such substances typically found in healthy persons. A subject in need of oxidative stress reduction can be suffering from an ischemic episode. Ischemic episodes can occur when there is mechanical obstruction of the blood supply, such as from arterial narrowing or disruption. Myocardial ischemia, which can give rise to angina pectoris and myocardial infarctions, results from inadequate circulation of blood to the myocardium, usually due to coronary artery disease. Ischemic episodes in the brain that resolve within 24 hours are referred to as transient ischemic attacks. A longer-lasting ischemic episode, a stroke, involves irreversible brain damage, where the type and severity of symptoms depend on the location and extent of brain tissue whose access to blood circulation has been compromised. A subject at risk of suffering from an ischemic episode typically suffers from atherosclerosis, other disorders of the blood vessels, increased tendency of blood to clot, or heart disease.

A subject in need of oxidative stress reduction can be suffering from inflammation. Inflammation is a fundamental pathologic process consisting of a complex of cytologic and chemical reactions that occur in blood vessels and adjacent tissues in response to an injury or abnormal stimulation caused by a physical, chemical, or biologic agent. Inflammatory disorders are characterized inflammation that lasts for an extended period (i.e., chronic inflammation) or that damages tissue. Such inflammatory disorders can affect a wide variety of tissues, such as respiratory tract, joints, bowels, and soft tissue. The compounds or pharmaceutical compositions of the invention can be used to treat these pathological conditions. Not wishing to be bound by any theory, it is believed that the compounds of the invention derive their ability to reduce oxidative stress through various mechanisms. In one mechanism, the compound binds to a metal, particularly a redox-active metal (e.g., iron), and fills all of the coordination sites of the metal. When all of the metal coordination sites are filled, it is believed that oxidation and/or reducing agents have a diminished ability to interact with the metal and cause redox cycling. In another mechanism, the compound stabilizes the metal in a particular oxidation state, such that it is less likely to undergo redox cycling. In yet another mechanism, the compound itself has antioxidant activity (e.g., free radical scavenging, scavenging of reactive oxygen or nitrogen species). Desferrithiocin and desazadesferrithiocin, and their derivatives and analogs, are known to have intrinsic antioxidant activity, as described in U.S. Application Publication No. 2004/0044220, published Mar. 4, 2004 and now abandoned; U.S. Application Publication No. 2004/0132789 and now abandoned, published Jul. 8, 2004; International PCT Application Publication No. WO2004/017959, published Mar. 4, 2004; U.S. Application Publication No. 2005/0234113, published Oct. 20, 2005 and now abandoned; U.S. Application Publication No. 2008/0255081, published Oct. 16, 2008 and now abandoned; U.S. Application Publication No. 2003/0236417, published Dec. 25, 2003 and now abandoned; U.S. Patent Application, U.S. Ser. No. 61/576,920, filed Dec. 16, 2011; U.S. Patent Application, U.S. Ser. No. 61/576,913, filed Dec. 16, 2011; and U.S. Pat. Nos. 6,083,966, 6,559,315, 6,525,080, 6,521,652, 7,126,004, 7,531,563, and 8,008,502; each of which are incorporated herein by reference. The compounds of the invention can be used to treat these pathological conditions. In certain embodiments, the pathological condition that may be treated and/or prevented by the compounds, pharmaceutical compositions, and methods of the invention is oxidative stress. In certain embodiments, the compounds, pharmaceutical compositions, and methods of the present invention are useful in the reduction of oxidative stress. In certain embodiments, the pathological condition that may be treated and/or prevented by the compounds, pharmaceutical compositions, and methods of the invention is radiation injury. In certain embodiments, the pathological condition that may be treated and/or prevented by the compounds, pharmaceutical compositions, and methods of the invention is inflammation.

The invention also provides compounds, pharmaceutical compositions, and methods for the treatment of macular degeneration. Without wishing to be bound by a particular theory, the compounds of the invention are able to get into the eye. See, e.g., U.S. Patent Application, U.S. Ser. No. 61/576,920, filed Dec. 16, 2011; U.S. Patent Application, U.S. Ser. No. 61/576,913, filed Dec. 16, 2011, International PCT Application Publication No. WO 2013/090750, published Jun. 20, 2013; and International PCT Application Publication No. WO 2013/090766, published Jun. 20, 2013. The compounds of the invention are then able to chelate and remove iron from the eye thereby preventing $Fe^{+2}$ from generating reactive oxygen species. The local accumulation of iron is thought to contribute to macular degeneration. Therefore, the removal of iron from the eye (including the retina) can prevent and treat macular degeneration. In the treatment of macular degeneration, the compound of the invention or a pharmaceutical composition thereof may be administered systemically or ocularly. In certain embodiments, the compound or composition is administered orally. In other embodiments, the compound or composition is administered to the eye using eyedrops or an ointment suitable for ocular administration.

The compounds of the invention and pharmaceutical compositions thereof are expected to be useful in the treatment of head injury, particularly those involving bleeding into the brain or other parts of the central nervous system. Without wishing to be bound by any particular theory, the compounds of the invention are thought to chelate the iron from red blood cells the blood resulting from the head injury, thereby preventing iron ions from generating reactive oxygen species. In the case of head injury resulting in bleeding into the central nervous system where the vasculature has been compromised a compound being used may or may not have the ability to cross the blood brain barrier. In certain embodiments, the compound being used to treat a head injury in a subject is able to cross the blood brain barrier. In other embodiments, the compounds are not able to cross the blood brain barrier. Certain compounds of the invention have been found in the CSF after systemic administration (po and sc).

Head injuries come in various forms and results from various causes. In certain embodiments, the injury is an injury to the head that penetrates the skull. In other embodiments, the head injury being treated is a closed head injury, which does penetrate the skull. Closed head injuries results from a variety of causes including accidents including vehicular accidents, falls, and assaults. Types of closed head injuries include concussions, brain contusions, diffuse axonal injury, and hemtoma. In certain embodiments, the closed head injury being treated in the present invention includes closed head injuries that result in blood outside the blood vessels of the brain.

The local accumulation of iron from the bleeding is thought to contribute to after effects associated with closed head injury. By assisting the clearance of iron from the brain the effects of the bleeding are minimized.

In the treatment of closed head injury, the compound of the invention or a pharmaceutical composition thereof may be administered systemically, for example, parenterally or orally. In certain embodiments, the compound or composition is administered orally. In other embodiments, the compound or composition is administered parenterally (e.g., intravenously).

Reactive oxygen species have been implicated in the pathogenesis of inflammatory bowel disease (IBD). Grisham et al., "Neutophil-mediated mucosal injury. Role of reactive oxygen metabolites." *Dig. Dis. Sci.* 33:6S-15S, 1988; Allgayer "Clinical relevance of oxygen radicals in inflammatory bowel disease—facts and fashion." *Klin. Wochenschr.* 69:1001-1003, 1991; Ymamada et al. "Role of neutrophil-derived oxidants in the pathogenesis of intestinal inflammation." *Klin. Wocheschr.* 69:988-944, 1991; Babbs, "Oxygen radicals in ulcerative colitis." *Free Radic. Biol. Med.* 13:169-181, 1992. The present invention provides for the treatment or preventon of IBD. DFO, an iron chelator, has been discovered to prevent acetic acid-induced colitis in rats, an animal model of IBD. See, e.g., U.S. Patent Application, U.S. Ser. No. 61/576,920, filed Dec. 16, 2011; U.S. Patent Application, U.S. Ser. No. 61/576,913, filed Dec. 16, 2011; Bergeron et al., "Prevention of Acetic Acid-Induced Colitis by Desferrithiocin Analgos in a Rat Model." *Digestive Diseases and Sciences,* 48(2):399-407, February 2003. The compounds used in the inventive treatment are thought to prevent or eliminate the generation of reactive oxygen species or other longer-lived, more stable radicals that may be responsible for the tissue damage and inflammation seen in subjects with IBD. Another possible mechanism of action of the compounds useful in the invention is the chelation of metal, such as iron, which may contribute to the generation of reactive oxygen species, such as hydroxyl radicals and hydrogen peroxide, that cause cell damage.

The present invention may also be useful in treating a subject diagnosed with IBD. The treatment may be used to treat the subject long term or may be used to treat a subject with a fare up of IBD. A therapeutically effective amount of a compound of the invention or pharmaceutical composition thereof is administered to a subject in need thereof to treat IBD. In certain embodiments, treatment with a compound of the invention leads to reduced levels of reactive oxygen species in the intestines, specifically the intestinal mucosa. The compound or composition thereof may be administered to a subject once or multiple times in the treatment of IBD.

In the treatment of IBD, the compound of the invention or a pharmaceutical composition thereof may be administered systemically, for example, parenterally or orally. In certain embodiments, the compound or composition is administered orally. In other embodiments, the compound or composition is administered parenterally (e.g., intravenously). In certain embodiments, the compound or a composition is administered rectally.

The methods of the present invention are also useful in the treatment and/or prevention of stroke. The inventive treatment typically leads to a better and/or faster recovery from stroke. The stroke being treated may be either an ischemic stroke or a hemorrhagic stroke. In the treatment of an ischemic stroke, a compound of the invention or a pharmaceutical composition thereof is administered to a subject to prevent or minimize the damage due to reperfusion injury after the blood supply to the affected part of the brain is restored. The compound is thought to prevent the generation of reactive oxygen species by either chelating iron responsible for the generation of such species and/or quenching such radical species when they do occur. In hemorrhagic stroke, the compound is thought to work by similar mechanisms although the sequestering of iron from the blood in the brain is probably the predominate mechanism by which the inventive treatment works. The mechanism of action of the compound of the invention is similar to that in the treatment of head injury.

The compound being used in the treatment may have the ability to cross the blood brain barrier. In certain embodiments, when the subject has been diagnosed with an ischemic stroke, the compound used in the treatment can pass through the blood brain barrier.

Moreover, the present invention may be useful in treating a subject after the subject has been diagnosed with having a stroke, or a subject who is susceptible to having a stroke may be administered a compound of the invention or composition thereof to prevent or minimize the stroke's effects. In certain embodiments, the compound is administered as quickly as possible after a subject has been diagnosed with having a stroke. In certain embodiments, the compound is administered to the subject while the stroke is still occurring. In certain embodiments, the compound or a composition thereof is administered to a subject who has a history of strokes or is susceptible to having a stroke because of the subject's underlying medical condition. The compound or composition thereof may be administered once or multiple times in the treatment of stroke.

In the treatment of stroke the compound of the invention or a pharmaceutical composition thereof may be administered systemically, for example, parenterally or orally. In certain embodiments, the compound or composition is administered orally. In other embodiments, the compound or composition is administered parenterally (e.g., intravenously).

The present invention also provides for the treatment of reperfusion injury. Reperfusion injury may occur in any area of the body where the blood supply has been compromised. In certain embodiments, the reperfusion injury being treated occurs in the heart. In other embodiments, the reperfusion injury occurs in the brain, for example, as discussed above in the context of a stroke. The inventive treatment minimizes reperfusion injury once the blood supply to the affects organ or tissue is restored. In the treatment and/or prevention of reperfusion injury, a compound of the present invention or pharmaceutical composition thereof is administered to a subject who is suffering from ischemia of a tissue or organ. Without wishing to be bound by any particular theory, the compound of the invention is thought to prevent the generation of reactive oxygen species by either chelating iron responsible for the generation of such species and/or quenching such radical species when they do occur.

The present invention may be useful in treating a subject after the subject has been diagnosed with ischemia of a particular organ or tissue. A therapeutically effective amount of a compound of the invention or composition thereof is administered to a subject to prevent or minimize reperfusion injury. In certain embodiments, the compound is administered as quickly as possible after a subject has been diagnosed with ischemia. In certain embodiments, the compound is administered to the subject at risk of ischemia. In certain embodiments, the compound or a composition thereof is administered to a subject who is about to undergo a procedure that may lead to ischemia of an organ or tissue (e.g., cardiac surgery). In certain embodiments, the compound or a composition thereof is used to prevent reperfusion injury in a transplanted organ. In certain embodiments, the compound or composition thereof is used to perfuse an isolated organ being prepared for donation. The compound or composition thereof may be administered to a subject once or multiple times in the treatment of reperfusion injury.

In the prevention or treatment of reperfusion injury, the compound of the invention or a pharmaceutical composition thereof may be administered systemically, for example, parenterally or orally. In certain embodiments, the compound or composition is administered orally. In other embodiments, the compound or composition is administered parenterally (e.g., intravenously). In certain embodiments, the compound or a composition is administered locally to the organ or tissue suffering from ischemia.

The inventive compounds, or pharmaceutical compositions thereof, may also be useful in the treatment and/or prevention of a neoplastic disease or preneoplastic condition. A neoplastic disease (i.e., neoplasm) is characterized by an abnormal tissue that grows by cellular proliferation more rapidly than normal tissue. The abnormal tissue continues to grow after the stimuli that initiated the new growth cease. Neoplasms show a partial or complete lack of structural organization and functional coordination with the normal tissue, and usually form a distinct mass of tissue that may be benign or malignant. A malignant neoplastic disease is also known as cancer. Neoplasms can occur, for example, in a wide variety of tissues including brain, skin, mouth, nose, esophagus, lungs, stomach, pancreas, liver, bladder, ovary, uterus, testicles, colon, and bone, as well as the immune system (lymph nodes) and endocrine system (thyroid gland, parathyroid glands, adrenal gland, thymus, pituitary gland, pineal gland). In certain embodiments, the pathological condition that may be treated and/or prevented by the compounds, pharmaceutical compositions, and methods of the invention is a benign neoplastic disease. In certain embodiments, the pathological condition that may be treated and/or prevented by the compounds, pharmaceutical compositions, and methods of the invention is cancer. In certain embodiments, the pathological condition that may be treated and/or prevented by the compounds, pharmaceutical compositions, and methods of the invention is acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; or vulvar cancer (e.g., Paget's disease of the vulva).

A preneoplastic condition precedes the formation of a benign or malignant neoplasm. A precancerous lesion typically forms before a malignant neoplasm. Preneoplastic conditions include, but are not limited to, photodermatitis, x-ray dermatitis, tar dermatitis, arsenic dermatitis, lupus dermatitis, senile keratosis, Paget disease, condylomata, burn scar, syphilitic scar, fistula scar, ulcus cruris scar, chronic ulcer, varicose ulcer, bone fistula, rectal fistula, Barrett esophagus, gastric ulcer, gastritis, cholelithiasis, kraurosis vulvae, nevus pigmentosus, Bowen dermatosis, xeroderma pigmentosum, erythroplasia, leukoplakia, Paget disease of bone, exostoses, ecchondroma, osteitis fibrosa, leontiasis ossea, neurofibromatosis, polyposis, hydatidiform mole, adenomatous hyperplasia, and struma nodosa. The compounds, pharmaceutical compositions, and methods of the present invention can be used to treat and/or prevent these preneoplastic conditions.

Imaging or examining one or more organs, tissues, tumors, or a combination thereof can be conducted after a metal salt of a compound of the invention is administered to a subject. The methods of imaging and examining are intended to encompass various instrumental techniques used for diagnosis, such as x-ray methods (including CT scans and conventional x-ray images), magnetic imaging (magnetic resonance imaging, electron paramagnetic resonance imaging) and radiochemical methods. Typically, the metal salts used in imaging or examining serve as a contrast agent. Therefore in one embodiment the metal complexes or metal salts of compounds of the present invention can be used as contrast agents for example in imaging or examining one or more organs, for example, the gastrointestinal tract. Metals that can serve as contrast agents include gadolinium, iron, manganese, chromium, dysprosium, technetium, scandium, barium, aluminum and holmium, preferably as trications. Radioactive metal salts can be made from isotopes including $^{241}$Am, $^{51}$Cr, $^{60}$Co, $^{57}$Co, $^{58}$Co, $^{64}$Cu, $^{153}$Gd, $^{67}$Ga, $^{198}$Au, $^{113m}$In, $^{111}$In, $^{59}$Fe, $^{55}$Fe, $^{197}$Hg, $^{203}$Hg $^{99m}$Tc, $^{201}$Tl, and $^{169}$Yb, again preferably when the metal is present as a trivalent cation.

EXAMPLES

In order that the invention described herein may be more fully understood, the following examples are set forth. It should be understood that these examples are for illustrative purposes only and are not to be construed as limiting this invention in any manner.

Example 1

Synthesis of the Compounds

Figure 1B:
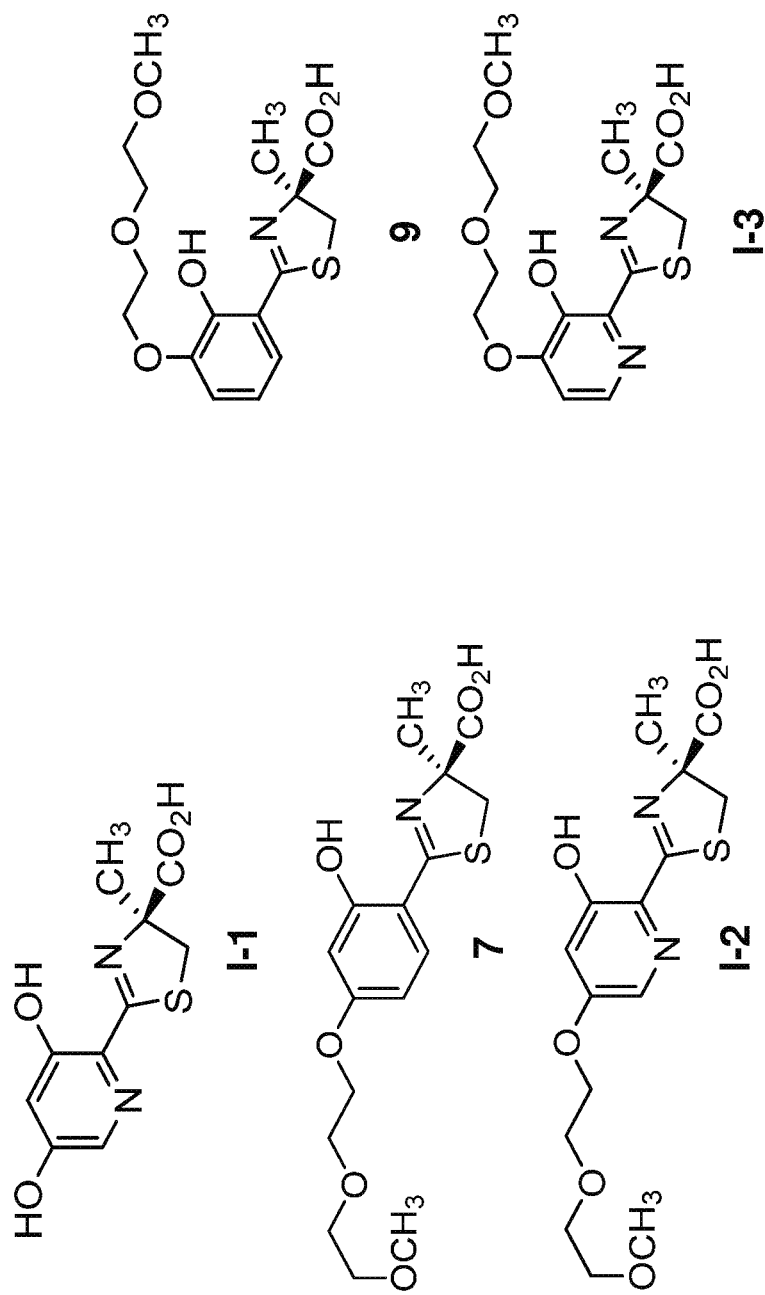
FIG. 1B shows the chemical structures of additional desazadesferrithiocin analogs (7 and 9) and a few examples of inventive desferrithiocin analogs (I-1, I-2, and I-3).

Novel DFT analogs were synthesized, such as (S)-4,5-dihydro-2-(3,5-dihydroxy-2-pyridinyl)-4-methyl-4-thiazolecarboxylic acid, ((S)-5'-(HO)-DFT, I-1), (S)-4,5-dihydro-2-[3-hydroxy-5-(3,6-dioxaheptyloxy)-2-pyridinyl]-4-methyl-4-thiazolecarboxylic acid, ((S)-5'-(HO)-DFT-norPE, I-2), and (S)-4,5-dihydro-2-[3-hydroxy-4-(3,6-dioxaheptyloxy)-2-pyridinyl]-4-methyl-4-thiazolecarboxylic acid, ((S)-4'-(HO)-DFT-norPE, I-3) (the chemical structures shown in FIG. 1B).

The preparation of 5'-hydroxydesferrithiocin (I-1) and its 5'-nor polyether (I-2) began with 2-cyano-3,5-difluoropyridine (11), which was converted to 2-cyano-3,5-dihydroxypyridine (13) in two steps (Scheme 1). Heating 11 with the anion of 4-methoxybenzyl alcohol (NaH, 2.5 equivalents) in DMF (Féau et al., "Preparation and Optical Properties of Novel 3-Alkoxycarbonyl Aza- and Diazacoumarins." *Synth. Commun.* 2010, 40, 3033-3045; Ornelas et al., "An Efficient Synthesis of Highly Functionalized Chiral Lactams." *Tetrahedron Lett.* 2011, 52, 4760-4763) at 95° C. for 18 h gave protected diol 12 in 73% yield. Removal of the 4-methoxybenzyl groups of 12 using excess trifluoroacetic acid (TFA) (White et al., "Total Synthesis of Geodiamolide A, a Novel Cyclodepsipeptide of Marine Origin." *J. Org. Chem.* 1989, 54, 736-738) and pentamethylbenzene (Marriott et al., "Synthesis of the Farnesyl Ether 2,3,5-Trifluoro-6-hydroxy-4-[(E,E)-3,7,11-trimethyldodeca-2,6,10-trien-1-yloxy]nitrobenzene, and Related Compounds Containing a Substituted Hydroxytrifluorophenyl Residue: Novel Inhibitors of Protein Farnesyltransferase, Geranylgeranyltransferase I and Squalene Synthase." *J. Chem. Soc., Perkin Trans.* 2000, 1, 4265-4278) at room temperature for 22 h provided nitrile 13 in quantitative yield. Cyclocondensation of 13 with (S)-2-methyl cysteine (14) in aqueous CH$_3$OH buffered at pH 6 at 75° C. for 45 h followed by esterification of crude acid I-1 with iodoethane and N,N-diisopropylethylamine (DIEA) (1.3 equivalents each) in DMF produced ethyl (S)-4,5-dihydro-2-(3,5-dihydroxy-2-pyridinyl)-4-methyl-4-thiazolecarboxylate (I-1-iii) in 70% yield. Hydrolysis of I-1-iii with aqueous NaOH in CH$_3$OH at room temperature generated (S)-4,5-dihydro-2-(3,5-dihydroxy-2-pyridinyl)-4-methyl-4-thiazolecarboxylic acid (I-1) as a solid in 96% yield. Also, ester I-1-iii was alkylated at the less hindered phenol (Bergeron et al., "The Impact of Polyether Chain Length on the Iron Clearing Efficiency and Physiochemical Properties of Desferrithiocin Analogs." *J. Med. Chem.* 2010, 53, 2843-2853) in the presence of the pyridine nitrogen with tosylate 16 and K$_2$CO$_3$ in refluxing acetone, affording compound precursor I-2-iii in 65% yield. The carboxylate was unmasked under alkaline conditions to give (S)-4,5-dihydro-2-[3-hydroxy-5-(3,6-dioxaheptyloxy)-2-pyridinyl]-4-methyl-4-thiazolecarboxylic acid (I-2) in 97% yield as an oil.

Scheme 1. Exemplary synthesis of I-1 and I-2.

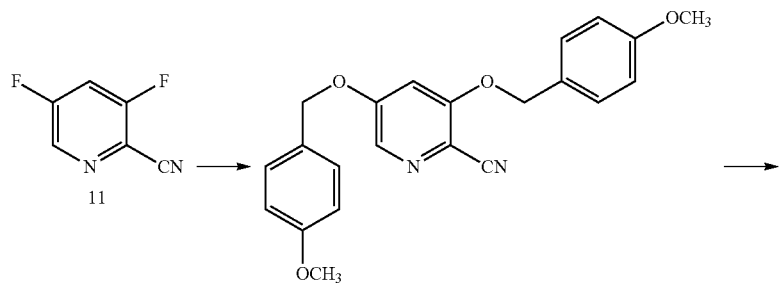

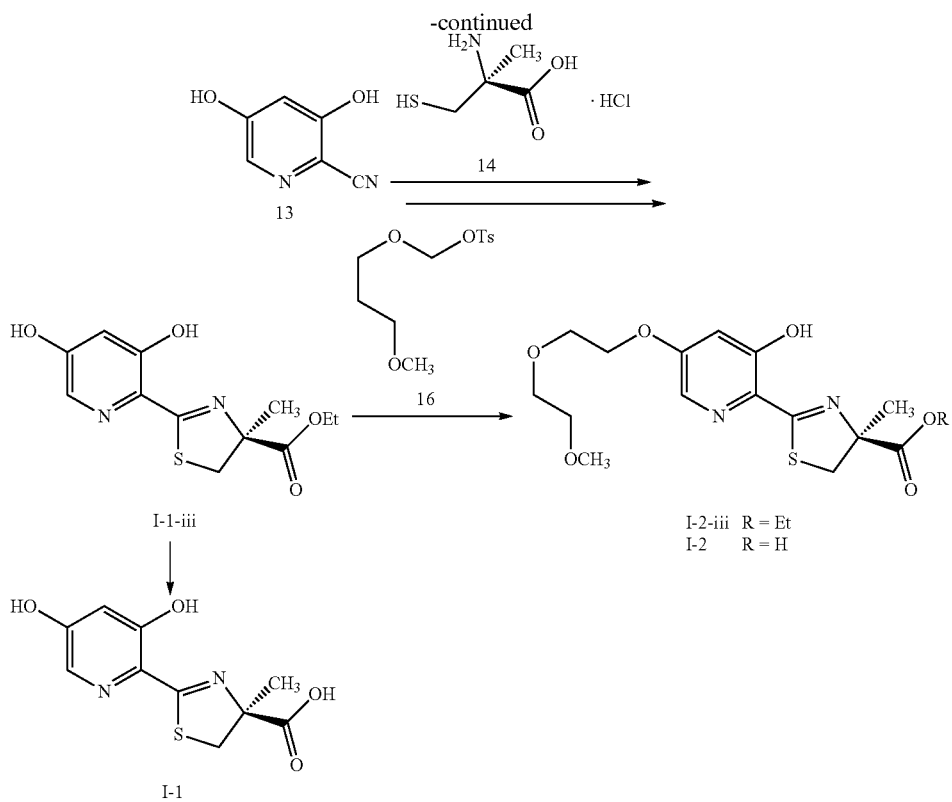

Synthesis of the 4'-nor polyether desferrithiocin analog I-3 (FIG. 1B), an isomer of I-2, started with 2-methyl-3-(benzyloxy)-4-pyridone (18), available in two steps from maltol (Piyamongkol et al., "Novel Synthetic Approach to 2-(1'-Hydroxyalkyl)- and 2-Amido-3-Hydroxypyridin-4-ones." *Tetrahedron* 2001, 57, 3479-3486) (Scheme 2). O-Alkylation of 18 with tosylate 16 and $K_2CO_3$ in refluxing acetonitrile (Li et al., "Synthesis of Coumarin-Appended Pyridyl Tricarbonylrhenium (I) 2,2'-Bipyridyl Complexes with Oligoether Spacer and Their Fluorescence Resonance Energy Transfer Studies." *Organometallics* 2009, 28, 1620-1630) afforded 2-methyl-3-(benzyloxy)-4-(3,6-dioxahepty-loxy)pyridine (19) in 68% yield, which was oxidized to aldehyde 21 by known methodology (Piyamongkol et al., "Novel Synthetic Approach to 2-(1'-Hydroxyalkyl)- and 2-Amido-3-Hydroxypyridin-4-ones." *Tetrahedron* 2001, 57, 3479-3486). Specifically, 19 was treated with 3-chloroper-benzoic acid in $CH_2Cl_2$, and the resulting N-oxide was heated at reflux in acetic anhydride. Cleavage of the acetate ester with base gave the 2-pyridinemethanol 20 in 87% overall yield. Primary alcohol 20 was further oxidized to aldehyde 21 in 83% yield with sulfur trioxide-pyridine complex and $NEt_3$ in DMSO and $CHCl_3$. The oxime 22, generated in 90% yield under standard conditions, was heated at reflux with acetic anhydride, furnishing the corresponding nitrile 23 in 94% yield. Removal of the benzyl-protecting group from 23 by hydrogenolysis (1 atm, 10% Pd—C, $CH_3OH$) in the presence of the cyano group and pyridyl ring produced 4-(3,6-dioxaheptyloxy)-3-hydroxy-2-pyridinecarbonitrile (24) in 81% yield. Heating 24 with amino acid 14 in aqueous $CH_3OH$ buffered at pH 6 generated (S)-4,5-dihydro-2-[3-hydroxy-4-(3,6-dioxaheptyloxy)-2-pyridinyl]-4-methyl-4-thiazolecarboxylic acid (I-3) in 95% yield.

Scheme 2. Exemplary synthesis of I-3.

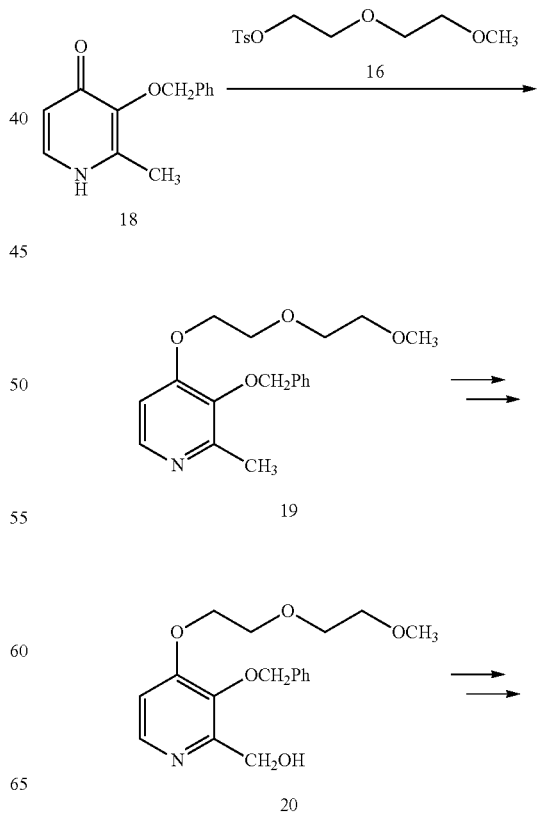

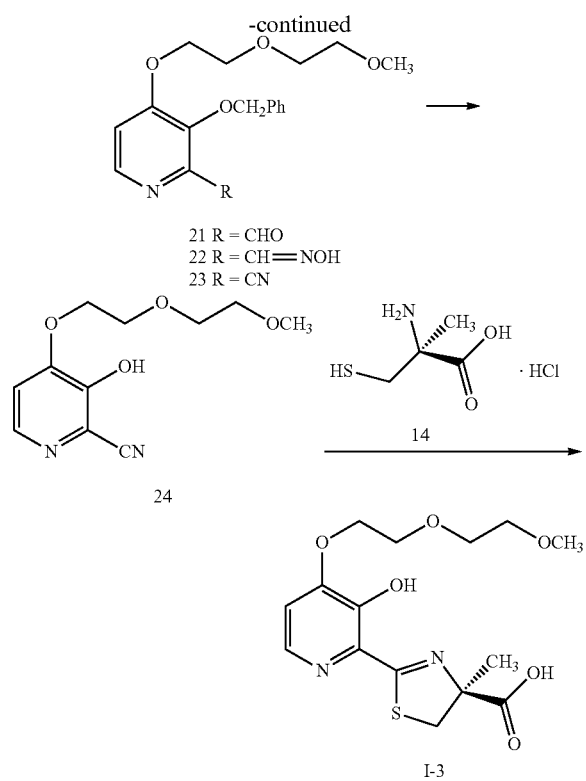

21 R = CHO
22 R = CH=NOH
23 R = CN

24

I-3

Reagents were purchased from Aldrich Chemical Co. (Milwaukee, Wis.). Compound 11 was obtained from Matrix Scientific (Columbia, S.C.). Fisher Optima grade solvents were routinely used. Reactions were run under a nitrogen atmosphere, and organic extracts were dried with sodium sulfate. Silica gel 40-63 from SiliCycle, Inc. (Quebec City, Quebec, Canada) was used for column chromatography. Melting points are uncorrected. Glassware that was presoaked in 3 N HCl for 15 min, washed with distilled water and distilled EtOH, and oven-dried was used during the isolation of I-1, I-2, and I-3. Optical rotations were run at 589 nm (sodium D line) and 20° C. on a Perkin-Elmer 341 polarimeter, with c being concentration in grams of compound per 100 mL of $CHCl_3$. $^1$H NMR spectra were run in $CDCl_3$ at 400 MHz (unless otherwise indicated), and chemical shifts (δ) are given in parts per million downfield from tetramethylsilane. $^{13}$C NMR spectra were measured at 100 MHz (unless otherwise indicated), and chemical shifts (δ) are referenced to the residual solvent resonance of δ 77.16 for $CDCl_3$ (not indicated) or δ 39.52 for DMSO-$d_6$. Coupling constants (J) are in hertz. ESI-FTICR mass spectra are reported. Elemental analyses were performed by Atlantic Microlabs (Norcross, Ga.) and were within ±0.4% of the calculated values. Purity of the compounds is supported by high pressure liquid chromatography (HPLC) 95% for I-1, I-2, and I-3) and by elemental analyses.

3,5-Bis(4-methoxybenzyloxy)pyridine-2-carbonitrile (12). Sodium hydride (60%, 3.66 g, 91.5 mmol) was added to 4-methoxybenzyl alcohol (11.5 mL, 92.6 mmol) in DMF (89 mL). The reaction mixture was stirred for 50 min and was cooled in an ice water bath, followed by addition of 11 (5.13 g, 36.6 mmol). After stirring at room temperature for 30 min and heating at 95-100° C. for 18 h, the reaction was quenched at 0° C. with EtOH and was concentrated by rotary evaporation under high vacuum. The residue was treated with $H_2O$ (250 mL) and extracted with warm EtOAc (400 mL, 2×100 mL). The organic extracts were washed with saturated NaCl (150 mL). Purification by flash column chromatography using 2% acetone/$CH_2Cl_2$ gave 10.11 g of 12 (73%) as a white solid, mp 122-122.5° C.: $^1$H NMR δ 3.81 (s, 3 H), 3.82 (s, 3 H), 5.04 (s, 2 H), 5.11 (s, 2 H), 6.85 (d, 1 H, J=2.0), 6.92 (dd, 4 H, J=8.6, 6.6), 7.31 (d, 4 H, J=8.6), 8.01 (d, 1 H, J=2.0). $^{13}$C NMR δ 55.44, 55.47, 70.98, 71.00, 106.86, 114.41, 115.63, 116.26, 126.83, 126.94, 129.04, 129.56, 131.98, 158.41, 159.10, 160.00, 160.14. HRMS m/z calculated for $C_{22}H_{21}N_2O_4$, 377.1496; (M+H); found: 377.1500. Anal. ($C_{22}H_{20}N_2O_4$) C, H, N.

3,5-Dihydroxy-2-pyridinecarbonitrile (13). Trifluoroacetic acid (477 g) was added over 26 min to 12 (3.448 g, 41.05 mmol) and pentamethylbenzene (38.22 g, 0.2579 mol) with ice bath cooling. The reaction mixture was stirred at room temperature for 22 h, and volatiles were removed by rotary evaporation. The residue was partitioned between cold 2 N NaOH (180 mL) and $Et_2O$ (350 mL) and separated. The $Et_2O$ layer was back extracted with 0.5 N NaOH (80 mL). The combined aqueous phase was extracted with $Et_2O$ (100 mL), cooled in an ice water bath, and combined with cold 2 M HCl (220 mL) and saturated NaCl (100 mL). The aqueous layer was extracted with EtOAc (250 mL, 2×120 mL). The latter organic extracts were washed with saturated NaCl (150 mL) and concentrated in vacuo, giving 3.70 g of 13 (quantitative) as a light tan solid: $^1$H NMR (DMSO-$d_6$) δ 6.80 (d, 1 H, J=2.4), 7.74 (d, 1 H, J=2.0), 10.98 (s, 1 H), 11.39 (s, 1 H). $^{13}$C NMR (DMSO-$d_6$) δ 108.69, 111.17, 116.74, 132.54, 158.10, 159.21. HRMS m/z calculated for $C_6H_3N_2O_2$, 135.0200 (M−H); found: 135.0196. An analytical sample was recrystallized from aqueous EtOH. At >300° C., the sample was dark but not melted. Anal. ($C_6H_4N_2O_2$) C, H, N.

Ethyl (S)-4,5-Dihydro-2-(3,5-dihydroxy-2-pyridinyl)-4-methyl-4-thiazolecarboxylate (I-1-iii). A degassed solution of 0.1 M phosphate buffer (pH 6, 310 mL) and $CH_3OH$ (300 mL) was added to 13 (4.04 g, 29.7 mmol) and 14 (6.95 g, 40.5 mmol). The pH of the reaction solution was adjusted to 6.0 with $NaHCO_3$ (4.92 g, 58.6 mmol). The reaction mixture was heated at 73-76° C. for 45 h with stirring, cooled to 0° C., and reduced in volume by rotary evaporation. The residue was acidified to pH~1 with cold 2 N HCl (61 mL) followed by extraction with EtOAc (300 mL, 2×100 mL). The organic layer was washed with saturated NaCl (100 mL), concentrated in vacuo and dried with toluene, resulting in 6.30 g of I-1. Iodoethane (3.0 mL, 37.5 mmol) and DIEA (6.5 mL, 37.3 mmol) were successively added to I-1 in DMF (130 mL), and the solution was stirred at room temperature for 47 h. After solvent removal under high vacuum, the residue was treated with 12:5 0.5 M HCl/saturated NaCl (170 mL) followed by extraction with EtOAc (150 mL, 4×70 mL). The EtOAc layers were washed with 100 mL portions of 1% $NaHSO_3$ and saturated NaCl, and the solvent was evaporated. Purification by column chromatography using (5% acetone/$CH_2Cl_2$) gave 5.88 g of I-1-iii (70%) as a pale yellow solid, mp 85-87.5° C.: [α] +35.6° (c 0.74). $^1$H NMR δ 1.32 (t, 3 H, J=7.2), 1.69 (s, 3 H), 3.20 (d, 1 H, J=11.7), 3.79 (d, 1 H, J=11.7), 4.27 (q, 2 H, J=7.2), 6.77 (d, 1 H, J=2.4), 7.82 (d, 1 H, J=2.3). $^{13}$C NMR δ 14.23, 24.78, 39.60, 62.33, 83.67, 110.11, 127.71, 130.80, 156.17, 157.79, 173.21, 174.02. HRMS m/z calculated for $C_{12}H_{15}N_2O_4S$, 283.0747 (M+H), 305.0567 (M+Na); found: 283.0751, 305.0573. Anal. ($C_{12}H_{14}N_2O_4S$) C, H, N.

(S)-4,5-Dihydro-2-(3,5-dihydroxy-2-pyridinyl)-4-methyl-4-thiazolecarboxylic Acid (I-1). A solution of 50% (w/w) NaOH (13.7 g, 0.171 mol) in $CH_3OH$ (135 mL) was added to I-1-iii (4.85 g, 17.2 mmol) in $CH_3OH$ (125 mL)

over 13 min at 0° C. The reaction mixture was warmed to room temperature over 19 h, and the bulk of the solvent was removed by rotary evaporation. The concentrate was treated with dilute NaCl (150 mL) and was extracted with Et$_2$O (2×100 mL). The aqueous layer was cooled in ice, acidified with cold 6 N HCl (30 mL), and extracted with EtOAc (250 mL, 2×100 mL). The EtOAc extracts were washed with saturated NaCl (80 mL). Solvent was removed in vacuo, providing 4.18 g of I-1 (96%) as an off white solid, mp 226-227° C. (decomposed): [α] +46.0° (c 0.82, DMF). $^1$H NMR (DMSO-d$_6$) δ 1.58 (s, 3 H), 3.27 (d, 1 H, J=11.7), 3.69 (d, 1 H, J=11.7), 6.72 (d, 1 H, J=2.4), 7.80 (d, 1 H, J=2.0), 10.82 (s, 1 H), 12.32 (s, 1 H), 13.20 (s, 1 H). $^{13}$C NMR (DMSO-d$_6$) δ 24.32, 38.48, 82.98, 108.59, 125.88, 131.13, 156.68, 157.58, 173.30, 173.74. HRMS m/z calculated for C$_{10}$H$_{11}$N$_2$O$_4$S, 255.0434 (M+H), 277.0253 (M+Na), 299.0073 (M−H+2Na), 320.9892 (M−2H+3Na); found: 255.0439, 277.0255, 299.0077, 320.9899. Anal. (C$_{10}$H$_{10}$N$_2$O$_4$S) C, H, N.

Ethyl (S)-4,5-Dihydro-2-[3-hydroxy-5-(3,6-dioxaheptyloxy)-2-pyridinyl]-4-methyl-4-thiazolecarboxylate (I-2-iii). Flame activated K$_2$CO$_3$ (0.72 g, 5.25 mmol) was added to a mixture of 16 (0.96 g, 3.5 mmol) and I-1-iii (0.90 g, 3.19 mmol) in dry acetone (25 mL). The reaction mixture was heated at reflux for 24 h. After cooling to room temperature the solvent was removed by rotary evaporation. The residue was treated with 0.2 N HCl/saturated NaCl (50 mL) and was extracted with EtOAc (4×30 mL). The organic extracts were washed with saturated NaCl (50 mL) and solvent was removed in vacuo. Column chromatography using 1:2:7 CH$_3$OH/hexane/CH$_2$Cl$_2$ furnished 0.80 g of I-2-iii (65%) as a viscous oil: [α] +30.9° (c 1.12). $^1$H NMR δ 1.30 (t, 3 H, J=7.0), 1.67 (s, 3 H), 3.19 (d, 1 H, J=11.3), 3.40 (s, 3 H), 3.56-3.62 (m, 2 H), 3.70-3.75 (m, 2 H), 3.80 (d, 1 H, J=11.7), 3.86-3.93 (m, 2 H), 4.19 (t, 2 H, J=4.7), 4.25 (q, 2 H, J=7.0), 6.80 (d, 1 H, J=2.3), 7.95 (d, 1 H, J=2.3), 12.37 (s, 1 H). $^{13}$C NMR δ 14.23, 24.77, 39.45, 59.25, 62.04, 68.11, 69.46, 70.99, 72.01, 83.84, 107.63, 127.72, 131.49, 157.39, 158.22, 172.87, 173.96. HRMS m/z calculated for C$_{17}$H$_{25}$N$_2$O$_6$S, 385.1428 (M+H), 407.1247 (M+Na); found: 385.1432, 407.1266. Anal. (C$_{17}$H$_{24}$N$_2$O$_6$S) C, H, N.

(S)-4,5-Dihydro-2-[3-hydroxy-5-(3,6-dioxaheptyloxy)-2-pyridinyl]-4-methyl-4-thiazolecarboxylic Acid (I-2). A solution of 50% (w/w) NaOH (1.46 mL, 47.0 mmol) in CH$_3$OH (40 mL) was added dropwise to a solution of I-2-iii (1.66 g, 4.31 mmol) in CH$_3$OH (20 mL) at 0° C. The reaction mixture was stirred at room temperature for 6 h, and the bulk of the solvent was removed under reduced pressure. The residue was treated with dilute NaCl (50 mL) and was extracted with Et$_2$O (2×30 mL). The aqueous layer was cooled in ice, acidified with 2 N HCl to pH=2, and extracted with EtOAc (5×40 mL). Combined EtOAc layers were washed with saturated NaCl (60 mL). Solvent removal in vacuo furnished 1.49 g of I-2 (97%) as a yellow oil: [α] +25.3° (c 0.88). $^1$H NMR δ 1.73 (s, 3 H), 3.22 (d, 1 H, J=12.0), 3.41 (s, 3 H), 3.59-3.61 (m, 2 H), 3.72-3.74 (m, 2 H), 3.83 (d, 1 H, J=11.6), 3.88 (t, 2 H, J=4.8), 4.19 (t, 2 H, J=4.4), 6.84 (d, 1 H, J=2.4), 7.94 (d, 1 H, J=2.4). $^{13}$C NMR δ 24.62, 39.13, 58.98, 67.99, 69.28, 70.63, 71.81, 82.83, 107.67, 126.98, 131.64, 158.15, 158.44, 174.59, 175.94. HRMS m/z calculated for C$_{15}$H$_{21}$N$_2$O$_6$S, 357.1115 (M+H); found: 357.1125. Anal. (C$_{15}$H$_{20}$N$_2$O$_6$S) C, H, N.

2-Methyl-3-(benzyloxy)-4-(3,6-dioxaheptyloxy)pyridine (19). Flame activated K$_2$CO$_3$ (27.6 g, 0.20 mol) and 16 (27.4 g, 0.10 mol) were added to 18 (21.5 g, 0.10 mol) in dry CH$_3$CN (500 mL). The reaction mixture was heated at reflux for 24 h. After cooling to room temperature, the solvent was evaporated by rotary evaporation. The residue was treated with 10% NaCl (200 mL) and was extracted with CH$_2$Cl$_2$ (4×150 mL). The organic extracts were washed with saturated NaCl (300 mL). After solvent was removed in vacuo, column chromatography using 4:4:2 EtOAc/petroleum ether/acetone furnished 21.5 g of 19 (68%) as a colorless viscous oil: $^1$H NMR δ 2.42 (s, 3 H), 3.34 (s, 3 H), 3.51-3.53 (m, 2 H), 3.69-3.71 (m, 2 H), 3.91 (t, 2 H, J=4.8), 4.24 (t, 2 H, J=4.4), 5.02 (s, 2 H), 6.72 (d, 1 H, J=5.6), 7.31-7.40 (m, 3 H), 7.44-7.49 (m, 2 H), 8.12 (d, 1 H, J=5.6). $^{13}$C NMR δ 19.34, 59.16, 67.86, 69.45, 70.92, 71.99, 74.57, 106.68, 128.21, 128.45, 128.49, 137.53, 142.32, 145.41, 153.40, 157.64. HRMS m/z calculated for C$_{18}$H$_{24}$NO$_4$, 318.1700 (M+H); found: 318.1714. Anal. (C$_{18}$H$_{23}$NO$_4$·0.2 H$_2$O) C, H, N.

4-(3,6-Dioxaheptyloxy)-3-(benzyloxy)-2-pyridinemethanol (20). An ice cooled solution of 3-chloroperoxybenzoic acid (3.67 g, 36.0 mmol) in CH$_2$Cl$_2$ (75 mL) was added slowly to 19 (10.4 g, 32.8 mmol) in CH$_2$Cl$_2$ (50 mL) over 15 min at 0° C. The reaction mixture was warmed to room temperature, stirred for 6 h, and diluted with CH$_2$Cl$_2$ (150 mL). The reaction mixture was washed with 5% Na$_2$CO$_3$ (3×100 mL) and saturated NaCl (100 mL) and was concentrated under reduced pressure to give a colorless oil. Acetic anhydride (80 mL, 0.85 mol) was added, and the reaction mixture was heated at 130° C. for 2 h. The solvent was removed under reduced pressure, and the residue was dissolved in H$_2$O (100 mL). The pH of the aqueous solution was adjusted to 8 with 2 N sodium hydroxide, and the aqueous solution was extracted with CH$_2$Cl$_2$ (3×100 mL). The organic fractions were combined, washed with saturated NaCl (100 mL), and concentrated in vacuo. The residue was dissolved in CH$_3$OH, treated with decolorizing charcoal, filtered, and concentrated to yield a brown oil, which was dissolved in EtOH (40 mL). Sodium hydroxide (1 M, 80 mL) was added and the reaction mixture was refluxed for 4 h and cooled. Extraction with CH$_2$Cl$_2$ (4×100 mL), washing with saturated NaCl (100 mL), concentration under reduced pressure, and column chromatography using 10% CH$_3$OH/CHCl$_3$ provided 9.52 g (87%) of 20 as a light brown oil: $^1$H NMR δ 3.34 (s, 3 H), 3.52-3.54 (m, 2 H), 3.69-3.71 (m, 2 H), 3.92 (t, 2 H, J=5.2), 4.28 (t, 2 H, J=4.4), 4.65 (s, 2 H), 5.09 (s, 2 H), 7.32-7.39 (m, 3 H), 7.40-7.44 (m, 2 H), 8.19 (d, 1 H, J=5.6). $^{13}$C NMR δ 59.20, 60.23, 68.13, 69.44, 70.96, 72.04, 74.79, 107.83, 128.49, 128.54, 128.63, 137.15, 140.53, 144.66, 152.98, 157.52. HRMS m/z calculated for C$_{18}$H$_{24}$NO$_5$, 334.1649 (M+H), 356.1468 (M+Na); found: 334.1648, 356.1455. Anal. (C$_{18}$H$_{23}$NO$_5$) C, H, N.

4-(3,6-Dioxaheptyloxy)-3-(benzyloxy)pyridine-2-carboxaldehyde (21). Triethylamine (70 mL, 0.29 mol) followed by DMSO (70 mL) was added to 20 (16.5 g, 49.0 mmol) in CHCl$_3$ (100 mL). Sulfur trioxide-pyridine complex (35 g, 0.22 mol) was slowly added over 35 min to the reaction mixture with ice bath cooling. After warming to room temperature, the reaction mixture was stirred overnight and was diluted with CHCl$_3$ (200 mL). The organic phase was washed with H$_2$O (3×200 mL) and saturated NaCl (100 mL). After solvent was removed in vacuo, column chromatography using 5:5:1 EtOAc/CHCl$_3$/CH$_3$OH furnished 13.61 g of 21 (83%) as a viscous colorless oil: $^1$H NMR δ 3.34 (s, 3 H), 3.52-3.54 (m, 2 H), 3.70-3.72 (m, 2 H), 3.95 (t, 2 H, J=4.4), 4.30 (t, 2 H, J=4.4), 5.24 (s, 2 H), 7.02 (d, 1 H, J=5.2), 7.32-7.39 (m, 3 H), 7.41-7.46 (m, 2 H), 8.39 (d, 1 H, J=5.6), 10.25 (s, 1 H). $^{13}$C NMR δ 59.17, 68.54, 69.23, 70.94, 71.97, 76.24, 111.69, 128.68, 128.75, 128.87, 136.16, 145.87, 146.90, 148.14, 159.49, 189.87. HRMS m/z calculated for $C_{18}H_{21}NNaO_5$, 354.1312 (M+Na); found: 354.1326. Anal. ($C_{18}H_{21}NO_5$) C, H, N.

4-(3,6-Dioxaheptyloxy)-3-(benzyloxy)pyridine-2-carboxaldehyde oxime (22). Hydroxylamine hydrochloride (4.2 g, 60.0 mmol) and NaOAc (5.2 g, 60.0 mmol) were added to a solution of 21 (13.5 g, 40.7 mmol) in $CH_3OH$ (50 mL), and the reaction mixture was heated at reflux for 2 h. The reaction mixture was concentrated by rotary evaporation, and the residue was treated with saturated NaCl (100 mL) and 0.1 M citric acid (100 mL) and then was extracted with EtOAc (2×100 mL). The organic layers were washed with $H_2O$ (100 mL) and saturated NaCl (100 mL). Solvent was removed in vacuo, providing 12.7 g (90%) of 22 as a pale solid, mp 72-73° C.: $^1$H NMR δ 3.34 (s, 3 H), 3.46-3.51 (m, 2 H), 3.64-3.71 (m, 2 H), 3.92 (t, 2 H, J=4.4), 4.27 (t, 2 H, J=4.4), 5.10 (s, 2 H), 6.85 (d, 1 H, J=5.6), 7.29-7.46 (m, 5 H), 8.28 (d, 1 H, J=5.2), 8.46 (s, 1 H). $^{13}$C NMR δ 59.14, 68.12, 69.28, 70.86, 71.94, 75.67, 108.62, 128.42, 128.55, 128.59, 136.70, 143.43, 144.81, 145.23, 146.71, 158.66. HRMS m/z calculated for $C_{18}H_{21}NNaO_5$, 354.1312 (M+Na); found: 352.1326. Anal. ($C_{18}H_{21}NO_5$) C, H, N.

4-(3,6-Dioxaheptyloxy)-3-(benzyloxy)pyridine-2-carbonitrile (23). Compound 22 was dissolved in $Ac_2O$ (40 mL) and heated at reflux for 8 h under a Drierite tube. The reaction mixture was concentrated by rotary evaporation, dissolved in 8% $NaHCO_3$ (100 mL), and extracted with $CHCl_3$ (100 mL, 2×50 mL). Combined organic fractions were washed with 4% $NaHCO_3$ (50 mL) and saturated NaCl (100 mL) followed by solvent removal in vacuo. Purification by flash chromatography eluting with 10% $CH_3OH/CH_2Cl_2$ gave 11.31 g (94%) of 23 as a pale solid, mp 34-35° C.: $^1$H NMR δ 3.34 (s, 3 H), 3.53-3.55 (m, 2 H), 3.70-3.72 (m, 2 H), 3.93 (t, 2 H, J=4.8), 4.27 (t, 2 H, J=4.4), 5.31 (s, 2 H), 6.98 (d, 1 H, J=5.6), 7.31-7.38 (m, 3 H), 7.49-7.52 (m, 2 H), 8.21 (d, 1 H, J=5.2). $^{13}$C NMR δ 59.14, 68.59, 69.09, 70.92, 71.94, 75.84, 111.27, 115.43, 128.60, 128.66, 128.73, 128.84, 135.78, 147.21, 148.28, 158.42. HRMS m/z calculated for $C_{18}H_{20}N_2NaO_4$, 351.1315 (M+Na); found: 351.1325. Anal. ($C_{18}H_{20}N_2O_4$) C, H, N.

4-(3,6-Dioxaheptyloxy)-3-hydroxy-2-pyridinecarbonitrile (24). Palladium on carbon (10%, 0.065 g) was added to a solution of 23 (1.3 g 3.95 mmol) in $CH_3OH$ (15 mL), and the mixture was stirred under $H_2$ at atmospheric pressure for 2 h. The reaction mixture was filtered through Celite®, and the residue was washed with $CH_3OH$ (3×5 mL). The filtrate was concentrated under reduced pressure, and the residue was subjected to column chromatography eluting with 10% $CH_3OH$/EtOAc furnishing 0.80 g (85%) of 24 as a colorless oil: $^1$H NMR δ 3.42 (s, 3 H), 3.61-3.63 (m, 2 H), 3.75-3.77 (m, 2 H), 3.92 (t, 2 H, J=4.8), 4.24 (t, 2 H, J=4.4), 6.91 (d, 1 H, J=4.8), 8.10 (d, 1 H, J=5.6). $^{13}$C NMR δ 58.92, 68.66, 69.05, 70.52, 71.78, 110.68, 115.28, 120.29, 143.49, 148.84, 153.72. HRMS m/z calculated for $C_{11}H_{14}N_2NaO_4$, 261.0846 (M+Na); found: 261.0849. Anal. ($C_{11}H_{14}N_2O_4$) C, H, N.

(S)-4,5-Dihydro-2-[3-hydroxy-4-(3,6-dioxaheptyloxy)-2-pyridinyl]-4-methyl-4-thiazolecarboxylic Acid (I-3). Compound 14 (0.78 g, 4.58 mmol), pH 6 phosphate buffer (30 mL), and $NaHCO_3$ (0.44 g, 5.23 mmol) were successively added to a solution of 24 (0.78 g, 3.27 mmol) in degassed $CH_3OH$ (30 mL). The reaction mixture was heated at 75° C. for 48 h with stirring, cooled to room temperature, and concentrated by rotary evaporation. The residue was dissolved in distilled $H_2O$ (25 mL) and the aqueous layer was acidified with cold 2 N HCl to pH<2 followed by extraction with EtOAc (5×50 mL). Concentration in vacuo resulted in 1.15 g of I-3 (95%) as a light yellow oil: [α] +52.8° (c 0.40). $^1$H NMR δ 1.73 (s, 3 H), 3.24 (d, 1 H, J=11.6), 3.39 (s, 3 H), 3.56-3.58 (m, 2 H), 3.73-3.75 (m, 2 H), 3.85 (d, 1 H, J=11.6), 3.94 (t, 2 H, J=4.8), 4.27 (t, 2 H, J=4.8), 6.88 (d, 1 H, J=5.2), 8.08 (d, 1 H, J=4.8). $^{13}$C NMR δ 24.65, 39.52, 59.08, 68.57, 69.31, 70.87, 71.94, 83.67, 109.81, 133.20, 141.56, 147.16, 154.39, 175.11, 176.26. HRMS m/z calculated for $C_{15}H_{21}N_2O_6S$, 357.1115 (M+H); found: 357.1115. Anal. ($C_{15}H_{20}N_2O_6S$) C, H, N.

Example 2

Stoichiometry of the Complexes of Fe(III) and the Compounds

Earlier studies with 1 by Anderegg and Räber showed the chelator to form a 2:1 complex with Fe(III) (Anderegg et al., "Metal Complex Formation of a New Siderophore Desferrithiocin and of Three Related Ligands." *J. Chem. Soc., Chem. Commun.* 1990, 1194-1196). The cumulative formation constant for this complex was determined to be $4 \times 10^{29}$ $M^{-1}$. Hahn et al. were ultimately able to isolate both the Δ and λ 1-Cr(III) complexes, with chromium serving as a surrogate for Fe(III) (Hahn et al., "Coordination Chemistry of Microbial Iron Transport. 42. Structural and Spectroscopic Characterization of Diastereomeric Cr(III) and Co(III) Complexes of Desferriferrithiocin." *J. Am. Chem. Soc.* 1990, 112, 1854-1860). As expected, the crystal structures of the complexes unequivocally demonstrated a 2:1 ligand to metal ratio. In later studies, Job's plots with 3 (Bergeron et al., "Effects of C-4 Stereochemistry and C-4' Hydroxylation on the Iron Clearing Efficiency and Toxicity of Desferrithiocin Analogues." *J. Med. Chem.* 1999, 42, 2432-2440) and the corresponding desmethyl analog (Bergeron et al., "Desazadesmethyldesferrithiocin Analogues as Orally Effective Iron Chelators." *J. Med. Chem.* 1999, 42, 95-108) also showed that these ligands formed 2:1 complexes with Fe(III). This is in keeping with the fact that the donor groups of the chelators, the aromatic hydroxyl, the thiazoline nitrogen, and the carboxylate are the same as in 1 itself. Furthermore, a comparison of structure 3 (Bergeron et al., "Iron Chelation Promoted by Desazadesferrithiocin Analogs: An Enantioselective Barrier." *Chirality* 2003, 15, 593-599) with 1 reveals that the disposition of the coordinating sites is essentially the same.

Figure 2:
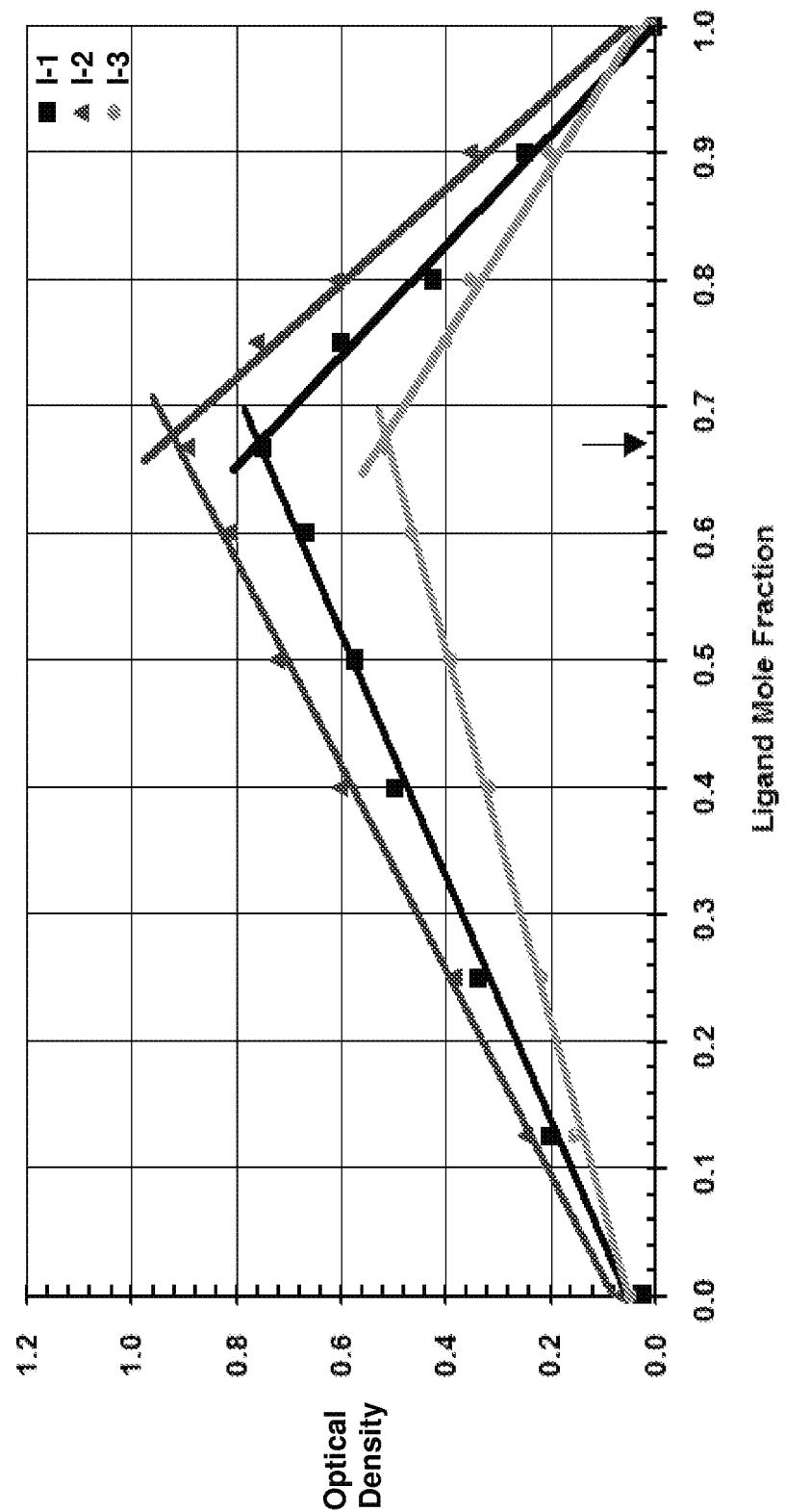
FIG. 2 shows a Job's plot of the Fe(III) complex of DFT analogs I-1, I-2, and I-3. Solutions containing DFT analog/Fe(III) at different ratios were prepared such that [DFT analog]+[Fe(III)]=1.0 mM in Tris-HCl buffer at pH 7.4. The theoretical mole fraction maximum for a 2:1 DFT analog:Fe complex is 0.667 (indicated by an arrow). The observed maxima for I-1, I-2, and I-3 are 0.669, 0.676, and 0.677, respectively. Optical density (y-axis) was determined at 498, 484, and 485 nm for I-1, I-2, and I-3, respectively.

The stoichiometries of the complexes of Fe(III) and DFT analogs I-1, I-2, and I-3 were determined spectrophotometrically using Job's plots (FIG. 2). In each instance, the DFT analogs formed 2:1 complexes with Fe(III). Solutions were monitored at the visible $λ_{max}$ of the Fe(III) complexes (498 nm for I-1, 484 nm for I-2, and 485 nm for I-3). A 100 mM Tris HCl buffer was used to maintain the pH at 7.4. Solutions containing different DFT analog/Fe(III) ratios were prepared by mixing appropriate volumes of 1.0 mM DFT analog solution and 1.0 mM Fe(III)-nitriloacetate (NTA) in Tris-HCl buffer. The 1.0 mM Fe(III)-NTA solution was prepared immediately prior to use by dilution of a 41.6 mM Fe(III)-NTA stock solution with the Tris HCl buffer, whereas the DFT analog stock solution was prepared by dissolving the DFT analog as its monosodium salt in Tris HCl buffer at pH 7.4. The Fe(III)-NTA stock solution was prepared by mixing equal volumes of 90 mM of $FeCl_3$ and 180 mM trisodium NTA. The iron content of the Fe(III)-NTA solution was verified by atomic absorption spectrophotometry (AAS).

Example 3

Partition Properties of the Compounds

The partition values between octanol and water (at pH 7.4, Tris buffer) were determined using a "shake flask" direct method of measuring log $P_{app}$ values (Sangster et al., *Octanol-Water Partition Coefficients: Fundamentals and Physical Chemistry*; John Wiley and Sons: West Sussex, England, 1997; Vol. 2). The fraction of compound in the octanol is then expressed as log $P_{app}$. While the values vary widely (Table 1), one observation stands out: DFT and its analogs are always more hydrophilic than their DADFT counterparts, i.e., 1 vs. 2, I-1 vs. 3, I-2 vs. 7, and I-3 vs. 9. This is likely due to the presence of the aromatic nitrogen, a moderately good hydrogen bond acceptor, on the DFT analogs. Relative to the differences in lipophilicity between DFT and DADFT, fixing a polyether backbone to either the DFT or the DADFT pharmacophore had a much more moderate effect (Table 1).

TABLE 1

Iron-Clearing Efficiency of Desferrithiocin Analogs Administered to Rodents and Primates with the Respective LogP$_{app}$ values.

| Compound Structure | Compound No. | Rodent Iron-Clearing Efficiency[a] (%) | Primate Iron-Clearing Efficiency[c] (%) | LogP$_{app}$ | PR[d] |
|---|---|---|---|---|---|
| *(structure)* | 1 | 5.5 ± 3.2 [93/7] | 16.1 ± 8.5 [78/22] | −1.77 | 2.9 |
| *(structure)* | 2 | 2.7 ± 0.5 [100/0] | 21.5 ± 12.0 [76/24] | −0.34 | 8.0 |
| *(structure)* | 3 | 1.1 ± 0.8 [100/0] | 16.8 ± 7.2 [88/12] | −1.05 | 15.3 |
| *(structure)* | I-1 | 9.0 ± 3.8 [97/3] | 10.0 ± 2.9 [58/42] | −1.68 | 1.1 |
| *(structure)* | 7 | 26.7 ± 4.7[b] [97/3] | 26.3 ± 9.9 [93/7] (capsule) | −0.89 | 1.0 |
|  |  |  | 28.7 ± 12.4 [83/17] (sodium salt) |  | 1.1 |
| *(structure)* | I-2 | 11.7 ± 1.2 [97/3] | 18 ± 5.2 [63/37] | −1.59 | 1.5 |
| *(structure)* | 9 | 15.1 ± 2.0[b] [99/1] | 22.5 ± 6.4 [86/14] | −0.96 | 1.5 |

TABLE 1-continued

Iron-Clearing Efficiency of Desferrithiocin Analogs Administered to Rodents and Primates with the Respective LogP$_{app}$ values.

| Compound Structure | Compound No. | Rodent Iron-Clearing Efficiency$^a$ (%) | Primate Iron-Clearing Efficiency$^c$ (%) | LogP$_{app}$ | PR$^d$ |
|---|---|---|---|---|---|
| [pyridine-thiazoline structure with OCH$_3$, OH, CH$_3$, CO$_2$H groups] | I-3 | 14.2 ± 2.4 [98/2] | 6.1 ± 1.8 (po) [40/60] 16.9 ± 7.3 (sc) [64/36] | −1.38 | 0.4 1.2 |

$^a$ In the rodents [n = 3 (7), 4 (2, I-3), 5 (1, I-1, I-2, 9), or 8 (3)], the compounds were given po at a dose of 150 μmol/kg (1-2) or 300 μmol/kg (3, I-1, 7, I-2, 9, and I-3). The compounds were administered in capsules (7), solubilized in 40% Cremophor RH-40/water (1, 2), or were given as their monosodium salts, prepared by the addition of 1 equiv. of NaOH to a suspension of the free acid in distilled water (3, I-1, I-2, 9, and I-3). The efficiency of each compound was calculated by subtracting the 24 or 48-h iron excretion of control animals from the iron excretion of the treated animals. The number was then divided by the theoretical output; the result is expressed as a percent. The relative percentages of the iron excreted in the bile and urine are in brackets. The iron-clearing efficiency (ICE) data for: 1 is from Bergeron, R. J.; Wiegand, J.; Dionis, J. B.; Egli-Karmakka, M.; Frei, J.; Huxley-Tencer, A.; Peter, H. H. Evaluation of Desferrithiocin and Its Synthetic Analogs as Orally Effective Iron Chelators. J. Med. Chem. 1991, 34, 2072-2078; 2 is from Bergeron et al., "A Comparative Study of the Iron-Clearing Properties of Desferrithiocin Analogs with Desferrioxamine B in a Cebus Monkey Model." Blood 1993, 81, 2166-2173; 3 is from Bergeron et al., "Iron Chelators and Therapeutic Uses." In: Abraham, ed. Burger's Medicinal Chemistry. 6th. Wiley; New York: 2003. pp. 479-561; 7 is from Bergeron et al., "The Impact of Polyether Chain Length on the Iron Clearing Efficiency and Physiochemical Properties of Desferrithiocin Analogs." J. Med. Chem. 2010, 53, 2843-2853; and 9 is from Bergeron et al., "Desferrithiocin Analog Iron Chelators: Iron Clearing Efficiency, Tissue Distribution, and Renal Toxicity." Biometals, 2011, 24, 239-258.
$^b$ICE is based on a 48-h sample collection period.
$^c$In the primates [n = 4 (1, 2, I-1, 7 in capsules, I-2, 9, and I-3), or 6 (3), or 7 (7 as the monosodium salt)], the compounds were given po at a dose of 75 μmol/kg (2, I-1, 7, I-2, 9, and I-3) or 150 μmol/kg (1, 3). Compound I-3 was also given to the primates sc at a dose of 75 μmol/kg. The compounds were administered in capsules (7), solubilized in 40% Cremophor RH-40/water (1, 2), or were given as their monosodium salts, prepared by the addition of 1 equiv of NaOH to a suspension of the free acid in distilled water (1, 2, 3, I-1, 7, I-2, 9, and I-3). The efficiency was calculated by averaging the iron output for 4 days before the compound, subtracting these numbers from the 2-day iron clearance after the administration of the compound, and then dividing by the theoretical output; the result is expressed as a percent. The ICE data for: 1-3 are from Bergeron et al., "Effects of C-4 Stereochemistry and C-4' Hydroxylation on the Iron Clearing Efficiency and Toxicity of Desferrithiocin Analogs." J. Med. Chem. 1999, 42, 2432-2440; 7 is from Bergeron et al., "The Impact of Polyether Chain Length on the Iron Clearing Efficiency and Physiochemical Properties of Desferrithiocin Analogs." J. Med. Chem. 2010, 53, 2843-2853; and 9 is from Bergeron et al., "Desferrithiocin Analog Iron Chelators: Iron Clearing Efficiency, Tissue Distribution, and Renal Toxicity." Biometals, 2011, 24, 239-258. The relative percentages of the iron excreted in the feces and urine are in brackets.
$^d$Performance ratio (PR) is defined as the mean ICE$_{primates}$/ICE$_{rodents}$.

Example 4

Biological Assays of the Compounds

All animal experimental treatment protocols were reviewed and approved by the University of Florida's Institutional Animal Care and Use Committee.

Male Sprague-Dawley rats were procured from Harlan Sprague-Dawley (Indianapolis, Ind.). Male *Cebus apella* monkeys (3.5-4 kg) were obtained from World Wide Primates (Miami, Fl). Ultrapure salts were obtained from Johnson Matthey Electronics (Royston, UK). All hematological and biochemical studies were performed by Antech Diagnostics (Tampa, Fla.). Atomic absorption (AA) measurements were made on a Perkin-Elmer model 5100 PC (Norwalk, Conn.). An R-Rena-strip Lateral-flow Kit for the detection of kidney injury molecule-1 (Kim-1) in rat urine was obtained from BioAssay Works (Ijamsville, Md.). A Chromatoreader ReaScan (Otsuka Electronics Co., Japan) was utilized to read the test strips and to allow for the quantitation of Kim-1 in rat urine.

$^1$H NMR Hydrogen-Deuterium Exchange Study

Compounds 3, I-1, and I-2 were dissolved in 0.1 M pD 7.0 phosphate buffer at a concentration of 5.4 mM: 3 (1.1 mg, 4.34 μmol) and I-1 (1.1 mg, 4.33 μmol) in buffer (0.80 mL) and I-2 (1.8 mg, 5.05 μmol) in buffer (0.933 mL). The ratio of the [3] (unexchanged) to the [3] (original) was measured by the diminution of δ 6.33 (d, H-3', J=2.3) relative to the integration of δ 6.39 (d, H-5', J=9.0) at time points to 104 min. The ratio of the [I-1] (unexchanged) to the [I-1] (original) was measured by the diminution of δ 6.41 (d, H-4', J=2.3) relative to the integration of δ 7.54 (d, H-6', J=2.3) at time points to 16 h. Plots of the natural log of [compound] (unexchanged) versus time are linear, with first order rate constants for 3 and I-1 (Table 2). No change in the 1:1 ratio of δ 6.76 (d, H-4', J=2.0) to δ 7.72 (d, H-6', J=2.3) in I-2 was observed up to 17 h.

TABLE 2

Hydrogen-Deuterium Exchange Rates of Compounds 3, I-1, and I-2.

| Compound No. | Exchange Rate$^a$ (s$^{-1}$) |
|---|---|
| 3 | 5.5 × 10$^{-4}$ |
| I-1 | 3.3 × 10$^{-6}$ |
| I-2 | No exchange |

$^a$The exchange study carried out at 25° C., pH 7.0, in phosphate buffer (0.1 M).

Cannulation of Bile Duct in Non-Iron-Overloaded Rats

The cannulation has been described previously (Bergeron et al., "A Comparative Study of the Iron-Clearing Properties of Desferrithiocin Analogs with Desferrioxamine B in a *Cebus* Monkey Model." Blood 1993, 81, 2166-2173; Bergeron et al., "A Comparative Evaluation of Iron Clearance Models." Ann. N.Y. Acad. Sci. 1990, 612, 378-393). Bile samples were collected from male Sprague-Dawley rats (400-450 g) at 3 h intervals for up to 48 h. The urine sample(s) was taken at 24 h intervals. Sample collection and handling are as previously described (Bergeron et al., "A Comparative Study of the Iron-Clearing Properties of Desferrithiocin Analogs with Desferrioxamine B in a *Cebus* Monkey Model." Blood 1993, 81, 2166-2173; Bergeron et al., "A Comparative Evaluation of Iron Clearance Models." Ann. N.Y. Acad. Sci. 1990, 612, 378-393).

Iron Loading of C. apella Monkeys

The monkeys were iron overloaded with intravenous iron dextran as specified in earlier publications (Bergeron et al., "A Comparative Evaluation of Iron Clearance Models." Ann. N.Y. Acad. Sci. 1990, 612, 378-393; Bergeron et al., "A Comparison of the Iron-Clearing Properties of 1,2-Dimethyl-3-Hydroxypyrid-4-one, 1,2-Diethyl-3-Hydroxypyrid-4-one, and Deferoxamine." Blood 1992, 79, 1882-1890) to provide about 500 mg of iron per kg of body weight; the serum transferrin iron saturation rose to between 70 and 80%. At least 20 half-lives, 60 days (Wood et al., "The Metabolism of Iron-Dextran Given As a Total-Dose Infusion to Iron Deficient Jamaican Subjects." Br. J. Hamaetol. 1968, 14, 119-129), elapsed before any of the animals were used in experiments evaluating iron-chelating agents.

Primate Fecal and Urine Samples

Fecal and urine samples were collected at 24 h intervals and processed as described previously (Bergeron et al., "A Comparative Study of the Iron-Clearing Properties of Desferrithiocin Analogs with Desferrioxamine B in a Cebus Monkey Model." Blood 1993, 81, 2166-2173; Bergeron et al., "A Comparative Evaluation of Iron Clearance Models." Ann. N.Y. Acad. Sci. 1990, 612, 378-393; Bergeron et al., "HBED: A Potential Alternative to Deferoxamine for Iron-Chelating Therapy." Blood 1998, 91, 1446-1452). Briefly, the collections began 4 days prior to the administration of the test compound and continued for an additional 5 days after the compound was given. Iron concentrations were determined by flame absorption spectroscopy as presented in other publications (Bergeron et al., "A Comparative Evaluation of Iron Clearance Models." Ann. N.Y. Acad. Sci. 1990, 612, 378-393; Bergeron et al., "Synthesis and Biological Evaluation of Naphthyldesferrithiocin Iron Chelators." J. Med. Chem. 1996, 39, 1575-1581).

Compound Preparation and Administration: Iron Clearance

In the iron clearing experiments, the rats were given I-1, I-2 and I-3 po at a dose of 300 µmol/kg. The primates were given I-1, I-2 and I-3 po at a dose of 75 µmol/kg; compound I-3 was also given sc at a dose of 75 µmol/kg. The compounds were administered to the rats and primates as their monosodium salts (prepared by the addition of 1 equiv of NaOH to a suspension of the free acid in distilled water). Compound preparation for the rodent urinary Kim-1 excretion studies involving 1, I-1, I-2, and I-3 are described below.

Calculation of Iron-Clearing Efficiency

In the text below, the term "iron-clearing efficiency" (ICE) is used as a measure of the amount of iron excretion induced by a chelator. The ICE, expressed as a percent, is calculated as (compound-induced iron excretion/theoretical iron excretion)×100. To illustrate, the theoretical iron excretion after administration of one millimole of desferrioxamine B mesylate (DFO) (FIG. 3), a hexadentate chelator that forms a 1:1 complex with Fe(III), is one milli-g-atom of iron. Two millimoles of desferrithiocin (DFT) (Table 1), a tridentate iron chelator that forms a 2:1 complex with Fe(III), are required for the theoretical excretion of one milli-g-atom of iron. The theoretical iron outputs of the chelators were generated on the basis of a 2:1 compound:iron complex. The efficiencies in the rats and monkeys were calculated as set forth elsewhere (Bergeron et al., "Effects of C-4 Stereochemistry and C-4' Hydroxylation on the Iron Clearing Efficiency and Toxicity of Desferrithiocin Analogs." J. Med. Chem. 1999, 42, 2432-2440; Bergeron et al., "HBED: A Potential Alternative to Deferoxamine for Iron-Chelating Therapy." Blood 1998, 91, 1446-1452). Data are presented as the mean±the standard error of the mean; p-values were generated via a one-tailed Student's t-test in which the inequality of variances was assumed; and a p-value of <0.05 was considered significant.

Compound Preparation and Administration: Rodent Toxicity/Urinary Kim-1 Excretion Studies The impact of compounds 1, I-1, I-2 and I-3 on urinary Kim-1 excretion were evaluated in rodents. The compounds were administered to the rats po as their monosodium salts, prepared as described above, twice daily at a dose of 237 µmol/kg/dose (474 µmol/kg/d) for up to 7 d. The studies were performed on rats with normal iron stores. The rats were fasted overnight and were given the first dose of the compound first thing in the morning. The rats were fed ~3 h post-dose and had access to food for ~5 h before being fasted overnight.

Collection of Urine for Kim-1 Studies

The rats were housed in individual metabolic cages. Urine samples were collected from the metabolic cages at 24 h intervals. A baseline (day 0) urine sample was collected and assessed for its Kim-1 content; each animal served as its own control. The urine was collected chilled as previously described (Bergeron et al., "Desferrithiocin Analog Iron Chelators: Iron Clearing Efficiency, Tissue Distribution, and Renal Toxicity." Biometals, 2011, 24, 239-258).

Performance of Urinary Kim-1 Studies

The chilled urine was collected, vortexed, and warmed to room temperature; any sediment in the samples was allowed to settle. Kim-1 content was assessed using a Rat Kim-1 Rapid Test Kit according to the manufacturer's instructions. The result was read using a ReaScan Test Reader. The quantity of Kim-1 excreted in the urine per day was calculated by multiplying the concentration of Kim-1 (ng/ml urine)×24-h urine volume, divided by the weight of the animal. The result is expressed as urinary Kim-1 (ng/kg/24 h). Data are presented as the mean±the standard error of the mean; p-values were generated via a one-tailed Student's t-test in which the inequality of variances was assumed; and a p-value of <0.05 was considered significant.

Results

A measure of the amount of iron excretion induced by a chelator is best described by its iron-clearing efficiency (ICE). The ICE, expressed as a percent, is calculated as (compound-induced iron excretion/theoretical iron excretion)×100. To illustrate, the theoretical iron excretion after administration of one millimole of DFO, a hexadentate chelator that forms a 1:1 complex with Fe(III), is one milli-g-atom of iron. Two millimoles of desferrithiocin (DFT, 1) (Table 1), a tridentate chelator that forms a 2:1 complex with Fe(III), are required for the theoretical expression of one milli-g-atom of iron.

The ICE values for compounds 1, 2, 3, 7 and 9 (Table 1) are historical and included for comparative purposes (Bergeron et al., "Effects of C-4 Stereochemistry and C-4' Hydroxylation on the Iron Clearing Efficiency and Toxicity of Desferrithiocin Analogs." J. Med. Chem. 1999, 42, 2432-2440; Bergeron et al., "(S)-4,5-Dihydro-2-(2-hydroxy-4-hydroxyphenyl)-4-methyl-4-thiazolecarboxylic Acid Polyethers: A Solution to Nephrotoxicity." J. Med. Chem. 2006, 49, 2772-2783; Bergeron et al., "Evaluation of Desferrithiocin and Its Synthetic Analogs as Orally Effective Iron Chelators." J. Med. Chem. 1991, 34, 2072-2078; Bergeron et al., "The Impact of Polyether Chain Length on the Iron Clearing Efficiency and Physiochemical Properties of Desferrithiocin Analogs." J. Med. Chem. 2010, 53, 2843-2853; Bergeron et al., "Desferrithiocin Analog Iron Chelators: Iron Clearing Efficiency, Tissue Distribution, and Renal Toxicity." Biometals, 2011, 24, 239-258). The biliary ferrokinetics profiles of compounds 3, I-1, 7, I-2, 9, and I-3 are presented in FIG. 3. Each of the rats in these studies was given a single po dose of the compound at 300 µmol/kg. The biliary ferrokinetics data for compounds 1 and 2 are not included, simply because these animals were dosed at 150 µmol/kg, and the curves are not strictly comparable with the 300 µmol/kg data. These results were published previously (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Evaluation of Desferrithiocin and Its Synthetic Analogs as Orally Effective Iron Chelators." *J. Med. Chem.* 1991, 34, 2072-2078).

DFT (1) given to the rats po at a dose of 150 µmol/kg had an ICE of 5.5±3.2% (Bergeron et al., "Evaluation of Desferrithiocin and Its Synthetic Analogs as Orally Effective Iron Chelators." *J. Med. Chem.* 1991, 34, 2072-2078). Maximum iron clearance (MIC) occurred at 3 h, but deferration had returned to baseline levels by 12 h. The desaza analog of DFT, 2, at 150 µmol/kg had an ICE of 2.7±0.5% (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440). The compound reached MIC at 6 h and had returned to baseline iron excretion by 12 h post-dose.

Figure 3:
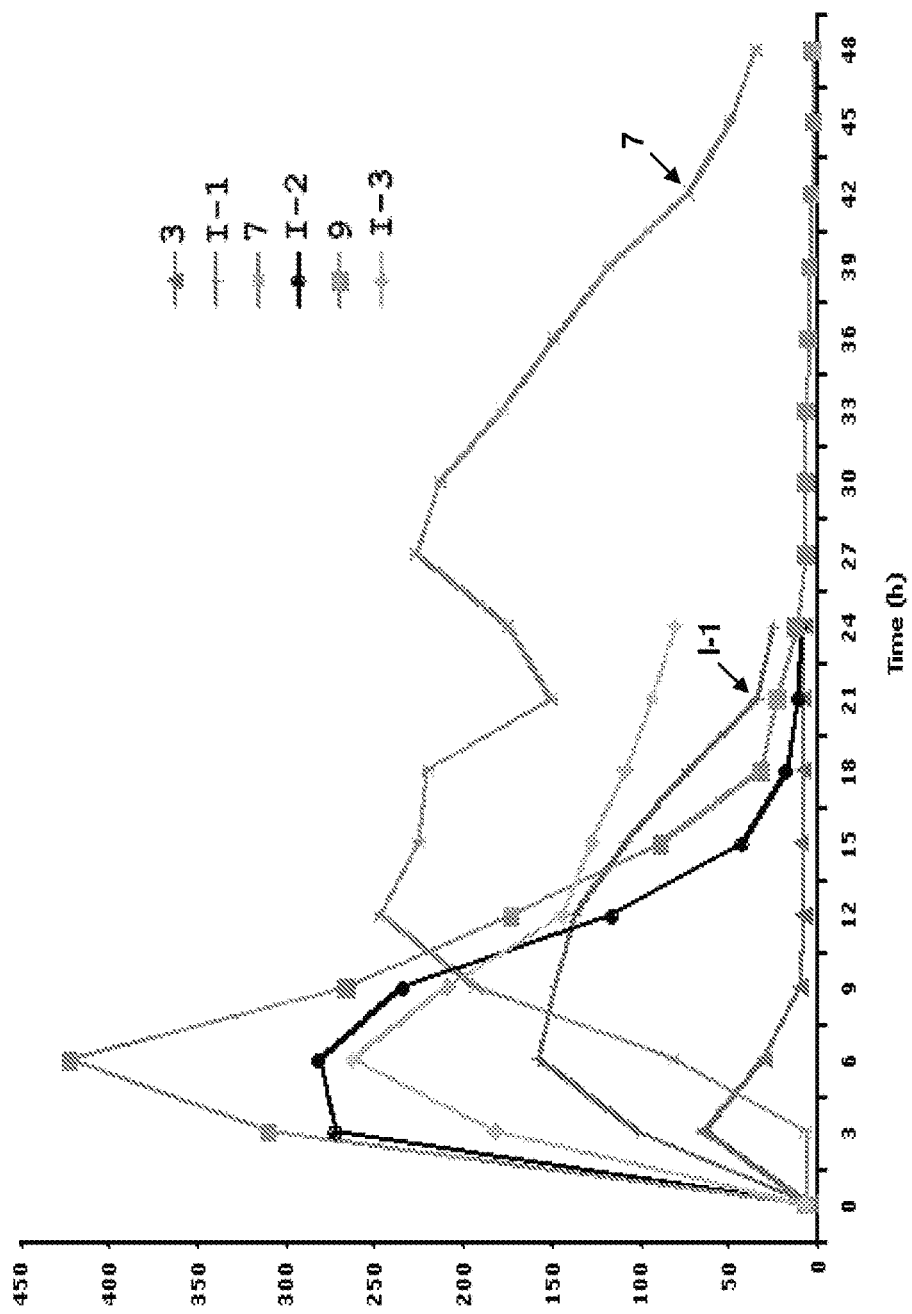
FIG. 3 shows the biliary ferrokinetics of DFT analogs (I-1, I-2, and I-3) and DADFT analogs (3, 7, and 9) in bile duct-cannulated rats. The compounds were given po at 300 µmol/kg.

Compound 3 was the least effective compound, with an ICE of 1.1±0.8% (Bergeron et al., "(S)-4,5-Dihydro-2-(2-hydroxy-4-hydroxyphenyl)-4-methyl-4-thiazolecarboxylic Acid Polyethers: A Solution to Nephrotoxicity." *J. Med. Chem.* 2006, 49, 2772-2783). It presented with an MIC at 3 h; deferration was virtually over at 9 h (FIG. 3). The DFT analog of 3, compound I-1, had an ICE that was significantly better than 3, 9.0±3.8% (p<0.005). MIC occurred at 6 h and its iron decorporation slowly dropped to near baseline levels by 24 h. The most efficient compound, 7, had an ICE of 26.7±4.7% (Bergeron et al., "The Impact of Polyether Chain Length on the Iron Clearing Efficiency and Physiochemical Properties of Desferrithiocin Analogs." *J. Med. Chem.* 2010, 53, 2843-2853). The compound also had a very protracted iron clearance; even though its MIC occurred at around 12 h, it was still active at 48 h. Although the biliary ferrokinetics curve of 7 may appear to be biphasic (FIG. 3), the reason for this unusual line shape is that several animals had temporarily obstructed bile flow. Once the obstruction was resolved, bile volume and overall iron excretion normalized.

The DFT analog I-2 had an ICE that was significantly less than that of 7 (11.7±1.2% vs. 26.7±4.7% for I-2 and 7, respectively, p<0.02). Compound I-2 also achieved MIC earlier than 7 (6 h vs. 12 h, FIG. 3), and the iron clearance induced by I-2 was basically over by 21 h. Finally, DADFT analog 9 (Bergeron et al., "Desferrithiocin Analog Iron Chelators: Iron Clearing Efficiency, Tissue Distribution, and Renal Toxicity." *Biometals,* 2011, 24, 239-258) and its corresponding DFT analog I-3 presented with similar ICEs (~15%), but with very different biliary ferrokinetics (FIG. 3). Both compounds achieved MIC at 6 h. However, while compound 9-induced iron clearance had returned to baseline by 24 h, I-3 was still quite active.

Figure 4:
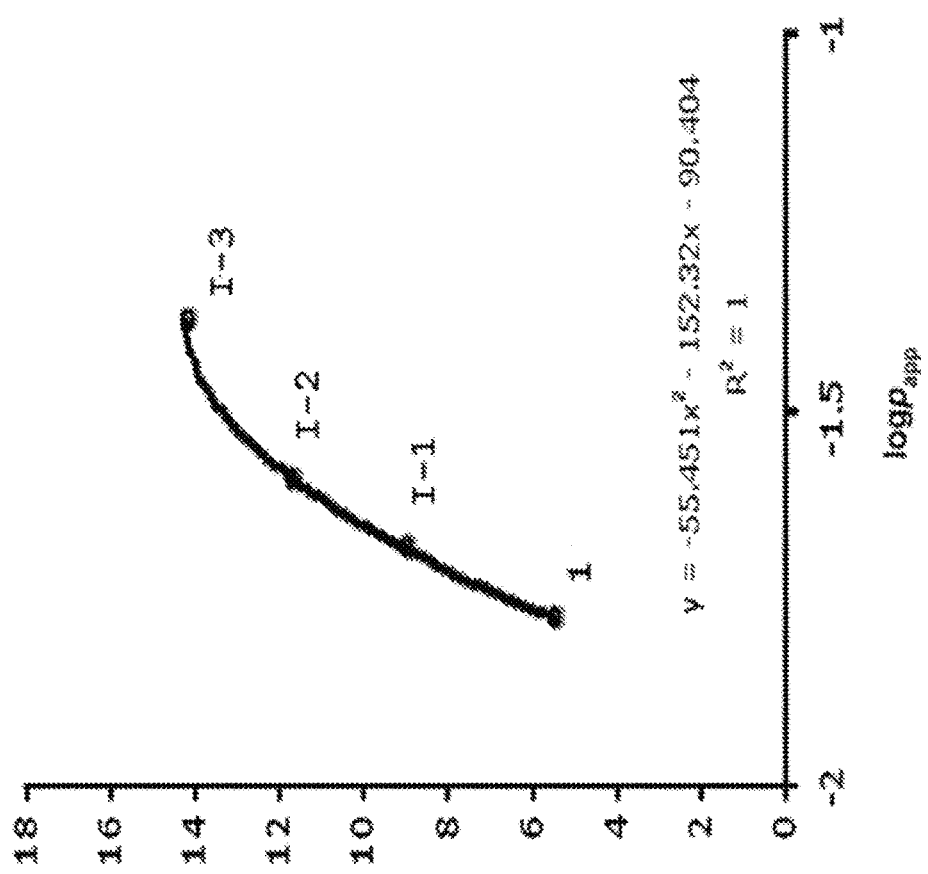
FIG. 4 is a plot showing the iron-clearing efficiency versus log $P_{app}$ for DFT analogs 1, I-1, I-2, and I-3 in bile duct-cannulated rats. Compound 1 was given po at a dose of 150 µmol/kg; compounds I-1, I-2, and I-3 were administered po at 300 µmol/kg.

Finally, there is an excellent correlation between ICE and log $P_{app}$ in rodents amongst the DFT analogs 1, I-1, I-2, and I-3 (FIG. 4). The most lipophilic compounds are also the most active. This ICE vs. log $P_{app}$ pattern has been observed before (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Iron Chelators and Therapeutic Uses." In: Abraham, ed. *Burger's Medicinal Chemistry.* 6th. Wiley; New York: 2003. pp. 479-561; Bergeron et al., "Desferrithiocin Analogs and Nephrotoxicity." *J. Med. Chem.* 2008, 51, 5993-6004). In keeping with previous observations, it appears that the ICE/log $P_{app}$ curve for DFT and its analogs is beginning to turn over with an optimum log $P_{app}$ of around −1.4. This is very different than with the DADFT analogs, in which the optimum log $P_{app}$ was approximately 0.5 (Bergeron et al., "Desferrithiocin Analogs and Nephrotoxicity." *J. Med. Chem.* 2008, 51, 5993-6004).

The primate iron clearance data are provided in Table 1. The ICE values for compounds 1, 2, 3, 7, and 9 have been reported and are included for comparative purposes (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "The Impact of Polyether Chain Length on the Iron Clearing Efficiency and Physiochemical Properties of Desferrithiocin Analogs." *J. Med. Chem.* 2010, 53, 2843-2853; Bergeron et al., "Desferrithiocin Analog Iron Chelators: Iron Clearing Efficiency, Tissue Distribution, and Renal Toxicity." *Biometals,* 2011, 24, 239-258). The compounds were given to the primates po at a dose of 75 µmol/kg (2, I-1, 7, I-2, 9, and I-3) or 150 µmol/kg (1, 3); I-3 was also given to the primates sc at a dose of 75 µmol/kg. Compound 1 was found to have an ICE of 16.1±8.5% (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440). Removal of the pyridine nitrogen to yield 2 increased the ICE to 21.5±12% (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440). However, the increase in ICE was not significant (p>0.05). The introduction of a hydroxyl group at the 4'-position of 2 to provide analog 3 resulted in a compound with an ICE of 16.8±7.2% (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440), which is within error of the ICE found for 1 and 2 (p>0.05). The reintroduction of the pyridine nitrogen into DADFT analog 3 to provide DFT analog I-1 (Table 1) decreased the ICE to 10.0±2.9%, significantly less than its DADFT counterpart, 3, (p<0.05). When a polyether fragment was attached to the 5'-position of I-1 to yield I-2, the ICE increased to 18.0±5.2%, again, less than that achieved by the corresponding DADFT analog 7. Likewise, the ICE of I-3 given po was also less than that of DADFT analog 9 (Table 1). In fact, the DADFT analogs were consistently better deferrating agents in the primates than the corresponding DFT analogs (Table 1).

Several generalizations can be derived from Table 1. The performance ratios, Performance ratio (PR) values (i.e., $ICE_{primate}/ICE_{rodent}$) (Table 1), show that the compounds are either as effective or better at iron clearance in primates than in rodents. The exception to this is compound I-3. The ICE of this compound given po to the primates is 6.1±1.8%, while in the rats is 14.2±2.4%. Its PR value was 0.4, showing it to be far less efficient in primates than rodents. The poor iron clearance in primates relative to rodents was surprising. Two scenarios were evaluated in search of an explanation: compound-plasma binding and a potential GI absorption problem.

A compound-plasma binding experiment was performed in which rodent and primate plasma were incubated separately with compound I-3 at 37° C. for 4 h. Each sample was then passed through a Millipore Amicon Ultra regenerated cellulose filter (3,000 MWCO). The filtrate was assayed for I-3. The results indicated there was little, if any, binding of the compound to either the rodent or the primate plasma. This suggests that compound-plasma binding does not explain the difference in the rodent vs. primate ICE values. However, when primates were given compound I-3 sc, the ICE rose to 16.9±7.3%, which is similar to what was seen in rodents given I-3 orally (Table 1). This observation is consistent with the idea that the primates do not absorb I-3 well when the compound is administered orally.

One of the potential problems with introduction of a second hydroxyl in 1 to produce I-1 or in 2 to generate 3 is the potential for quinone formation owing to the 1,4-relationship between the added hydroxyl and the imine bond. Quinone formation could result in redox cycling and, at a cellular level, untoward side effects. In order to evaluate this, a hydrogen-deuterium exchange study carried out at 25° C., pH 7.0, in phosphate buffer (0.1 M) with compounds 3, I-1, and I-2 (Table 2). The study revealed the 3'-(H) of 3 to be very labile, as was the 3'-(H) of the desmethyl analog of 3 (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440), with less 3'-(H)-deuterium exchange at 4'-(H) with I-1, and none with I-2 (Table 2). The exchange rate order is understandable. The most exchangeable 3'-(H) in 3 still exchanges much faster than the 4'-(H) in I-1, in which an increase in electron density occurs next to the aromatic nitrogen during enolate/enol formation.

In a previous study, 1 was given to rats with normal iron stores po once daily at a dose of 384 µmol/kg/d (100 mg/kg/d). All of the rats were dead by day 5 of a planned 10-d experiment. The compound was found to be severely nephrotoxic (Bergeron et al., "A Comparative Study of the Iron-Clearing Properties of Desferrithiocin Analogs with Desferrioxamine B in a *Cebus* Monkey Model." *Blood* 1993, 81, 2166-2173). The pathologist noted vacuolar changes of the proximal tubules that were diffuse and severe, with multifocal vaculolar degeneration and necrosis. Nevertheless, the compound's remarkable oral activity initiated a series of SAR studies aimed at the development of orally active, nontoxic DFT analogs. This led to the development of 3 (Table 1), which made it to clinical trials (Galanello et al., "A Dose Escalation Study of the Pharmacokinetics, Safety, and Efficacy of Deferitrin, an Oral Iron Chelator in Beta Thalassaemia Patients." *ASH Annu. Meet. Abstr.* 2007, 110, 2669). The compound, when given once daily, cleared iron from the patients and was proceeding forward. Unfortunately, it was discovered that the compound induced proximal tubule nephrotoxicity when it was administered twice daily, and the trial was halted (Galanello et al., "A Dose Escalation Study of the Pharmacokinetics, Safety, and Efficacy of Deferitrin, an Oral Iron Chelator in Beta Thalassaemia Patients." *ASH Annu. Meet. Abstr.* 2007, 110, 2669). The compound was reengineered, and it was determined that, by fixing polyether fragments to the 3'- or 4'-position of 3, e.g., 4 and 5 (FIG. 1), or 7 (Table 1), the renal toxicity virtually disappeared (Bergeron et al., "(S)-4,5-Dihydro-2-(2-hydroxy-4-hydroxyphenyl)-4-methyl-4-thiazolecarboxylic Acid Polyethers: A Solution to Nephrotoxicity." *J. Med. Chem.* 2006, 49, 2772-2783; Bergeron et al., "Design, Synthesis, and Testing of Non-Nephrotoxic Desazadesferrithiocin Polyether Analogs." *J. Med. Chem.* 2008, 51, 3913-3923; Bergeron et al., "The Impact of Polyether Chain Length on the Iron Clearing Efficiency and Physiochemical Properties of Desferrithiocin Analogs." *J. Med. Chem.* 2010, 53, 2843-2853; Bergeron et al., "Desferrithiocin Analog Iron Chelators: Iron Clearing Efficiency, Tissue Distribution, and Renal Toxicity." *Biometals,* 2011, 24, 239-258). This outcome suggested that the introduction of either a hydroxyl group or a polyether fragment directly into DFT itself might reduce the compound's nephrotoxicity. Accordingly, compounds I-1, I-2 and I-3 were synthesized and assessed for their toxicity in rodents relative to 1.

Assessment of chelator-induced impaired renal function has traditionally relied on the detection of a rise in blood urea nitrogen (BUN) and/or serum creatinine (SCr). However, because of the functional reserve of the kidney, these parameters are often unreliable indicators of acute kidney injury; the ultimate answer requires histopathology. The Critical Path Institute's Preventive Safety Testing Consortium (PSTC) has identified kidney injury molecule-1 (Kim-1, rat) or (KIM-1, human) as an early diagnostic biomarker for monitoring acute kidney tubular toxicity (Goodsaid et al., "Novel Biomarkers of Acute Kidney Toxicity." *Clin. Pharmacol. Ther.* 2009, 86, 490-496; Hoffmann et al., "Evaluation of a Urinary Kidney Biomarker Panel in Rat Models of Acute and Subchronic Nephrotoxicity." *Toxicology* 2010, 277, 49-58). Kim-1 is a type 1 transmembrane protein located in the epithelial cells of proximal tubules (Han et al., "Kidney Injury Molecule-1 (KIM-1): A Novel Biomarker for Human Renal Proximal Tubule Injury." *Kidney Int.* 2002, 62, 237-244; Bonventre, "Kidney Injury Molecule-1 (KIM-1): A Urinary Biomarker and Much More." *Nephro. Dial. Transplant* 2009, 24, 3265-3268). After injury, e.g., exposure to a nephrotoxic agent or ischemia, the ectodomain of Kim-1 is shed from the proximal tubular kidney epithelial cells into the urine (Zhou et al., "Comparison of Kidney Injury Molecule-1 and other Nephrotoxicity Biomarkers in Urine and Kidney Following Acute Exposure to Gentamicin, Mercury, and Chromium." *Toxicol. Sci.* 2008, 101, 159-170; Vaidya et al., "Urinary Kidney Injury Molecule-1: A Sensitive Quantitative Biomarker for Early Detection of Kidney Tubular Injury." *Am. J. Physiol. Renal Physiol.* 2006, 290, F517-F529; Bailly et al., "Shedding of Kidney Injury Molecule-1, A Putative Adhesion Protein Involved in Renal Regeneration." *J. Biol. Chem.* 2002 277, 39739-39748). BioAssay Works has recently developed RenaStick, a direct lateral flow immunochromato-graphic assay, which allows for the rapid detection (less than 30 minutes) and quantitation of urinary Kim-1 (rat) or KIM-1 (human) excretion (Vaidya et al., "A Rapid Urine Test for Early Detection of Kidney Injury." *Kidney. Int.* 2009, 76, 108-114). In the present study, rats were treated with 1, I-1, I-2, and I-3 given po twice daily at a dose of 237 µmol/kg/dose (474 µmol/kg/d) for up to 7 d. Urinary Kim-1 levels were assessed at 24-h intervals (FIG. 5). The studies were performed on rats with normal iron stores; each animal served as their own control. The data for compounds 3 and 7 have been reported and are included for comparative purposes (Bergeron et al., "Desferrithiocin Analog Iron Chelators: Iron Clearing Efficiency, Tissue Distribution, and Renal Toxicity." *Biometals,* 2011, 24, 239-258).

None of the rats treated with 1 (n=5) survived the planned 7-d exposure to the compound. Two rats became moribund and were sacrificed after being given the compound for four days. The three remaining animals were found dead the morning of day 6; they had received the compound for 5 days. None of the rodents produced any urine on day 5. The 1-treated rats' baseline (day 0) urinary Kim-1 value was <20 ng/kg/24 h (Figure SA). After one day of 1, the Kim-1 had increased nearly 10-fold, to 192±315 ng/kg/24 h. After three days of 1, the Kim-1 had further increased to 1528±539 ng/kg/24 h. Blood was taken from the two moribund animals immediately prior to sacrifice; the serum was assessed for its BUN and SCr content. The rats' BUN was 139±8 mg/dl (the normal range has been reported to be 9-30 mg/dl (Antech Diagnostics: www.antechdiagnostics.com/#), while their SCr was 5.1±0.3 mg/dl (normal 0.4-1 mg/dl) (Antech Diagnostics: www.antechdiagnostics.com/#). In addition, as no blood was obtained from the three animals that were found dead, these values likely underestimate the actual impact of 1 on these parameters.

Figure 5A:
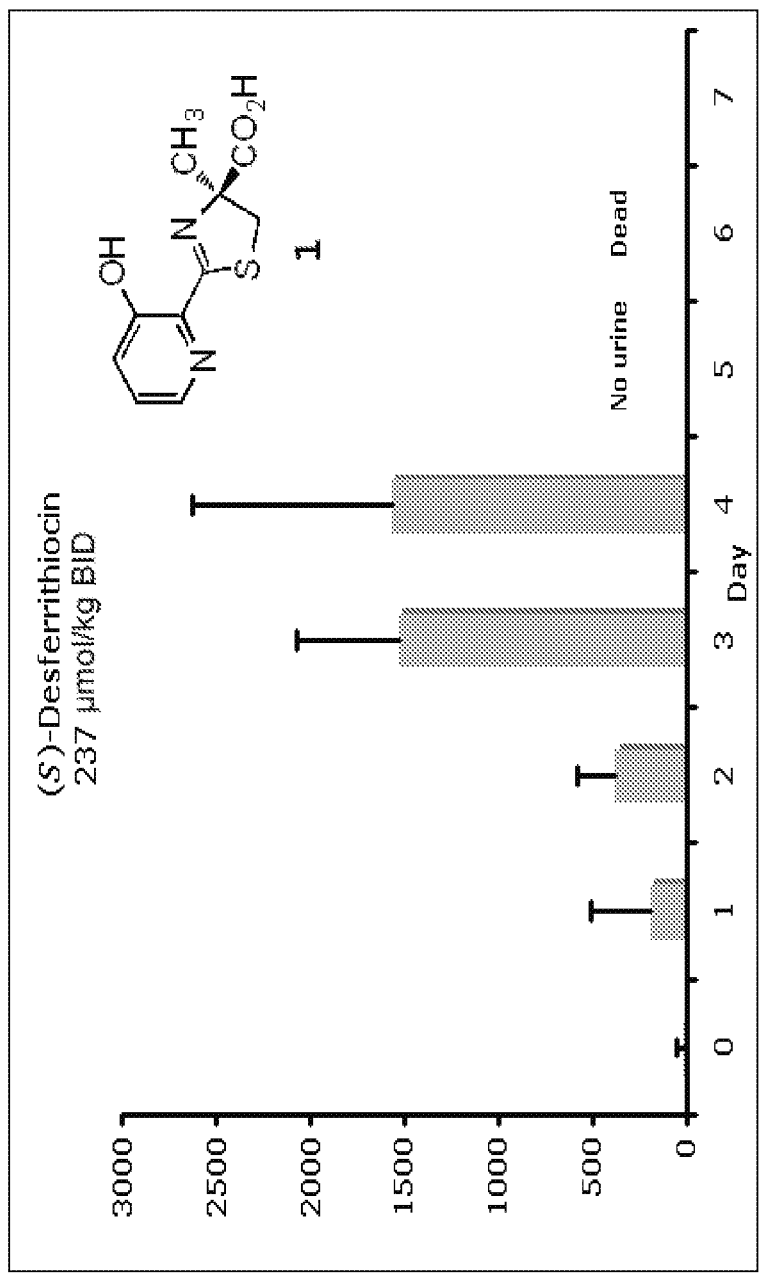
FIG. 5 includes bar graphs showing the urinary excretion of kidney injury molecule-1 (Kim-1), expressed as Kim-1 (ng/kg/24 h) of rats treated with a DFT analog (1 (FIG. 5A), I-1 (FIG. 5C), I-2 (FIG. 5D), or I-3 (FIG. 5F)) or a DADFT analog (3 (FIG. 5B) or 7 (FIG. 5E)). The rats were given the compounds po twice daily (BID) at a dose of 237 µmol/kg/dose (474 µmol/kg/d) for up to 7 d. None of the rats survived the planned 7-d exposure to 1. N=5 for 1, I-1, 7, I-2, and I-3; N=3 for compound 3.
Figure 5B:
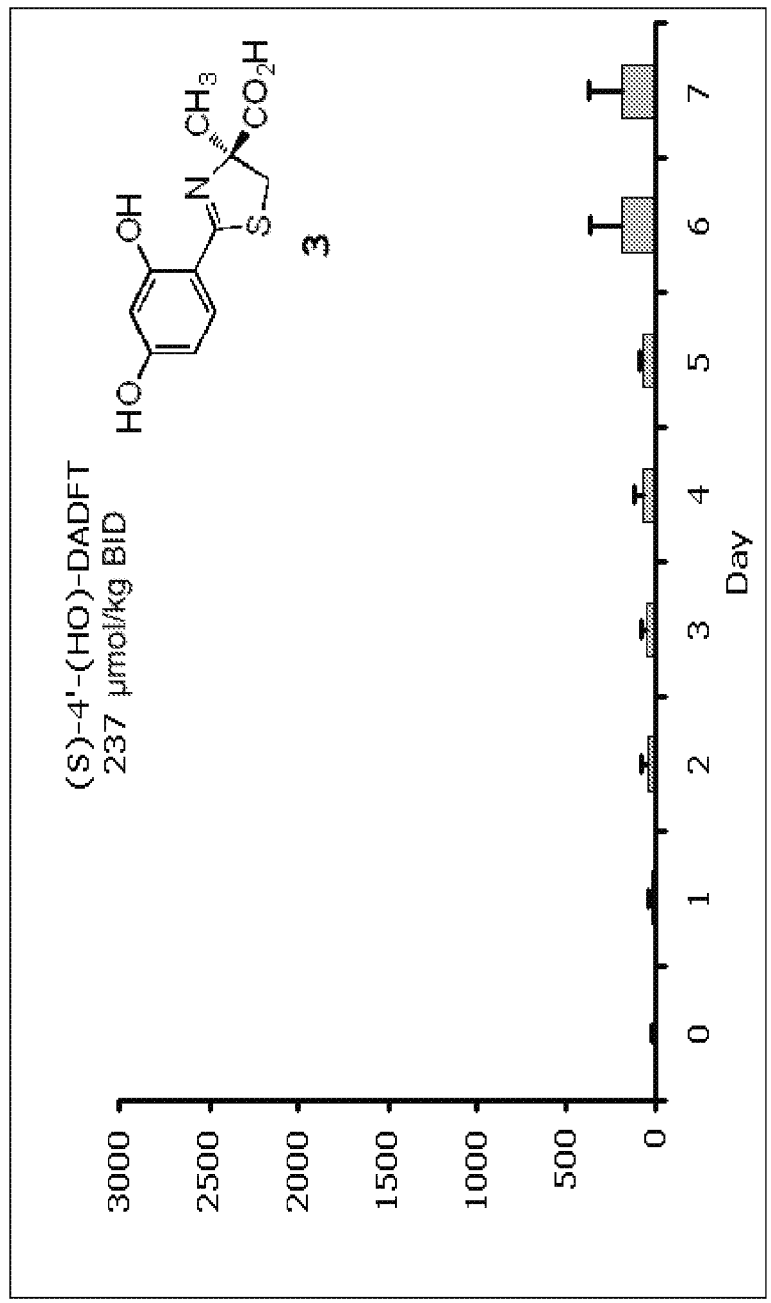

In contrast, in a previous study assessing the impact of 3 on urinary Kim-1 excretion (Bergeron et al., "Desferrithiocin Analog Iron Chelators: Iron Clearing Efficiency, Tissue Distribution, and Renal Toxicity." Biometals, 2011, 24, 239-258), all of the treated rats (n=3) survived the 237 µmol/kg twice daily (474 µmol/kg/d)×7 d dosing period. The rats' baseline (day 0) urinary Kim-1 content was <20 ng/kg/24 h (FIG. 5B). After three days of exposure to 3, the urinary Kim-1 had increased to 69±47 ng/kg/24 h. At the end of the 7 d dosing period, the urinary Kim-1 had further increased to 189±187 ng/kg/24 h (FIG. 5B). The rats were euthanized on day 8; their BUN at that time was 32±13 mg/dl, while their SCr was 1.3±1.0 mg/dl.

Figure 5C:
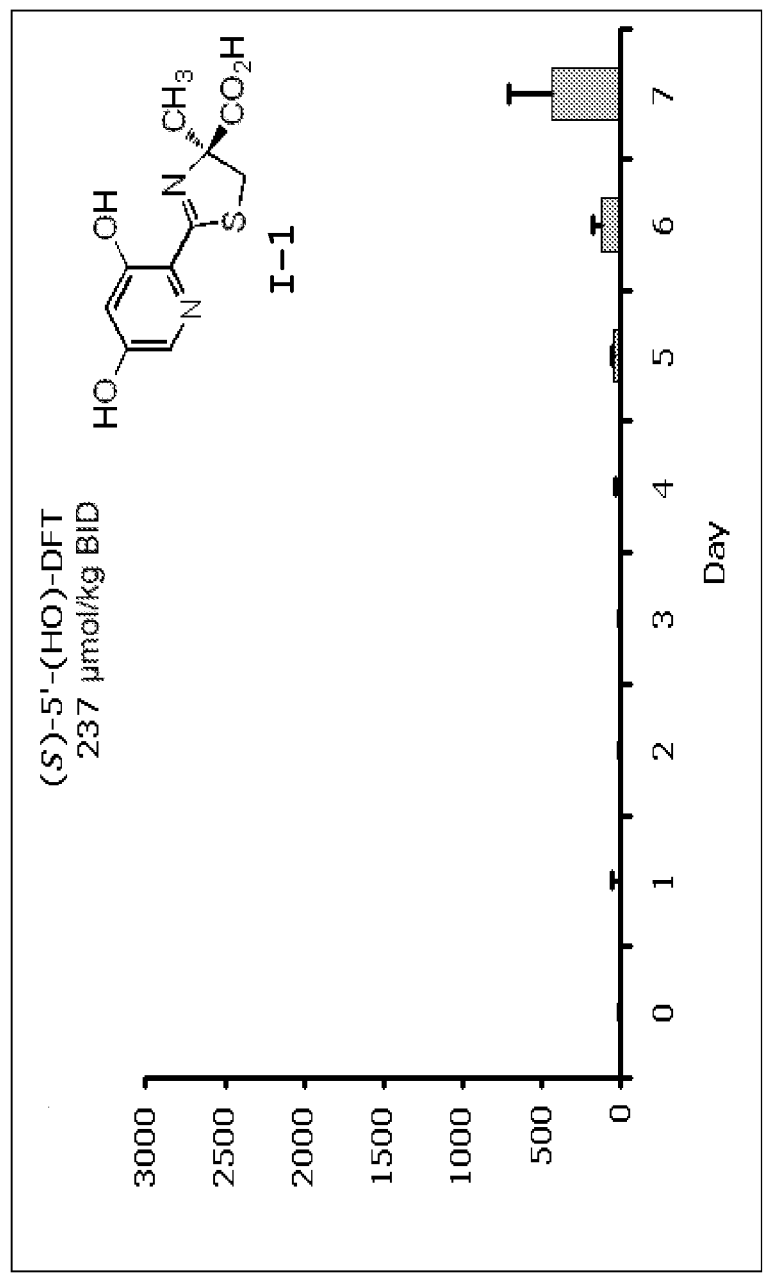

In the present study, all of the animals treated with the corresponding hydroxylated DFT analog, I-1, at 237 µmol/kg twice daily also survived the full 7 d of treatment. The rats' baseline (day 0) urinary Kim-1 content was <20 ng/kg/24 h and remained <50 ng/kg/24 h until day 5 (FIG. 5C). On day 6, the Kim-1 increased to 125±48 ng/kg/24 h, and further increased to 435±269 on day 7 (FIG. 5C). Although the increase in Kim-1 is greater with the I-1-treated rats than with the 3-treated animals, the increase is not statistically significant ($p > 0.05$). The animals were euthanized on day 8; their BUN at that time was 13±2 mg/dl, while their SCr was 0.5±0.1 mg/dl. Thus, simple hydroxylation of the aromatic ring of both DADFT and DFT, e.g., 3 and I-1, respectively, resulted in compounds that were much less toxic than DFT itself.

Figure 5D:
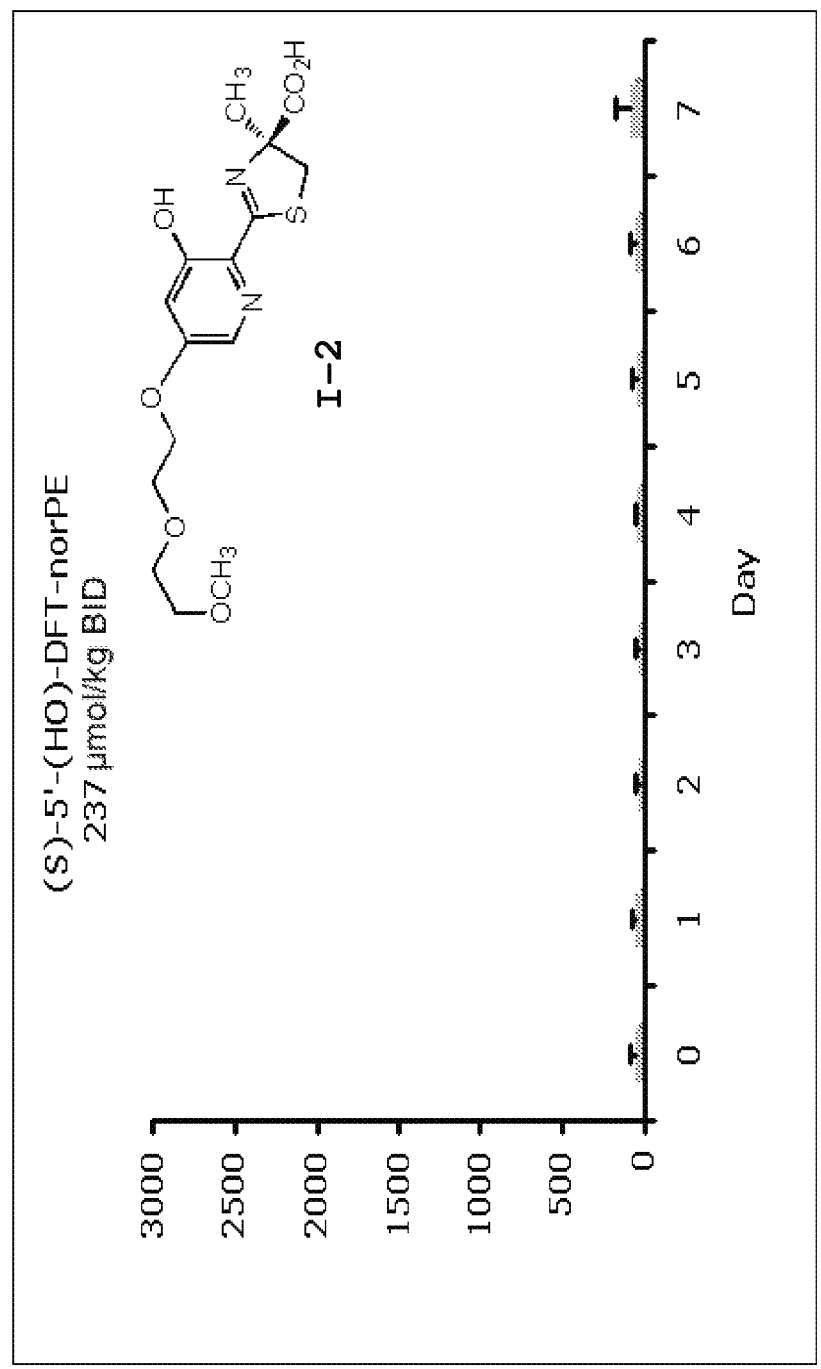
Figure 5E:
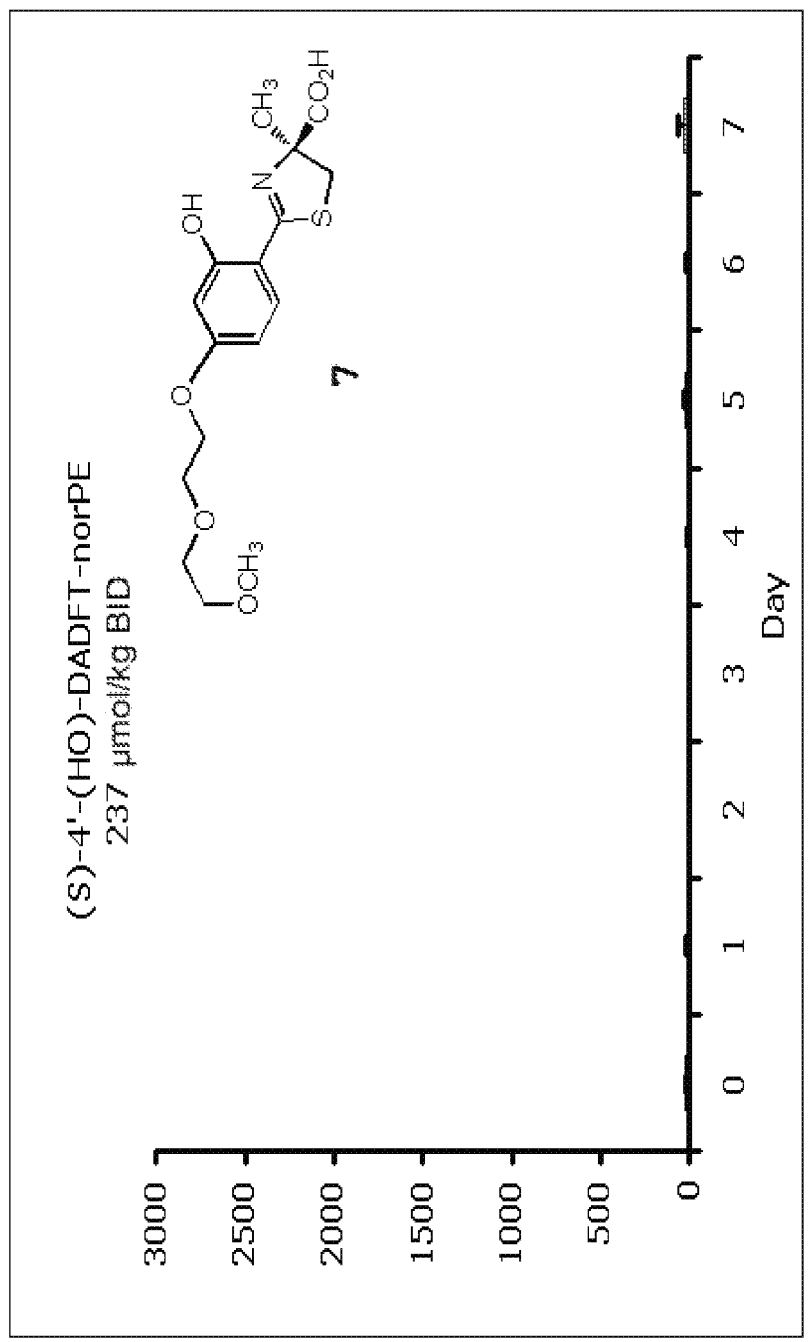

It has previously been demonstrated that introducing a polyether fragment in the 3'-, or 4'-position of the DADFT pharmacophore provided remarkably efficient orally active iron chelators that were much less toxic than 3 (Bergeron et al., "(S)-4,5-Dihydro-2-(2-hydroxy-4-hydroxyphenyl)-4-methyl-4-thiazolecarboxylic Acid Polyethers: A Solution to Nephrotoxicity." J. Med. Chem. 2006, 49, 2772-2783; Bergeron, R. J.; Wiegand, J.; Bharti, N.; Singh, S.; Rocca, J. R. Impact of 3,6,9-Trioxadecyloxy Group on Desazadesferrithiocin Analog Iron Chelators and Organ Distribution. J. Med. Chem. 2007, 50, 3302-3313; Bergeron et al., "Design, Synthesis, and Testing of Non-Nephrotoxic Desazadesferrithiocin Polyether Analogs." J. Med. Chem. 2008, 51, 3913-3923; Bergeron et al., "The Impact of Polyether Chain Length on the Iron Clearing Efficiency and Physiochemical Properties of Desferrithiocin Analogs." J. Med. Chem. 2010, 53, 2843-2853; Bergeron et al., "Desferrithiocin Analog Iron Chelators: Iron Clearing Efficiency, Tissue Distribution, and Renal Toxicity." Biometals, 2011, 24, 239-258). For example, the impact of compound 7 on urinary Kim-1 excretion was determined when the compound was given po: 1) once daily during the course of 28 d toxicity trials; 2) once daily at a dose of 384 µmol/kg/d×10 d, and 3) twice daily at a dose of 237 µmol/kg/dose (474 µmol/kg/d)×7 d (Bergeron et al., "Desferrithiocin Analog Iron Chelators: Iron Clearing Efficiency, Tissue Distribution, and Renal Toxicity." Biometals, 2011, 24, 239-258). All of the rats survived the dosing period. The rats' baseline (day 0) urinary Kim-1 content was <20 ng/kg/24 h and stayed within error of this value for the duration of the compound exposure. The data from the 237 µmol/kg twice daily (474 µmol/kg/d)×7 d regimen (Bergeron et al., "Desferrithiocin Analog Iron Chelators: Iron Clearing Efficiency, Tissue Distribution, and Renal Toxicity." Biometals, 2011, 24, 239-258) are depicted in FIG. 5E. In addition, the BUN and SCr of all of the 7-treated rats were well within the normal range.

Figure 5F:
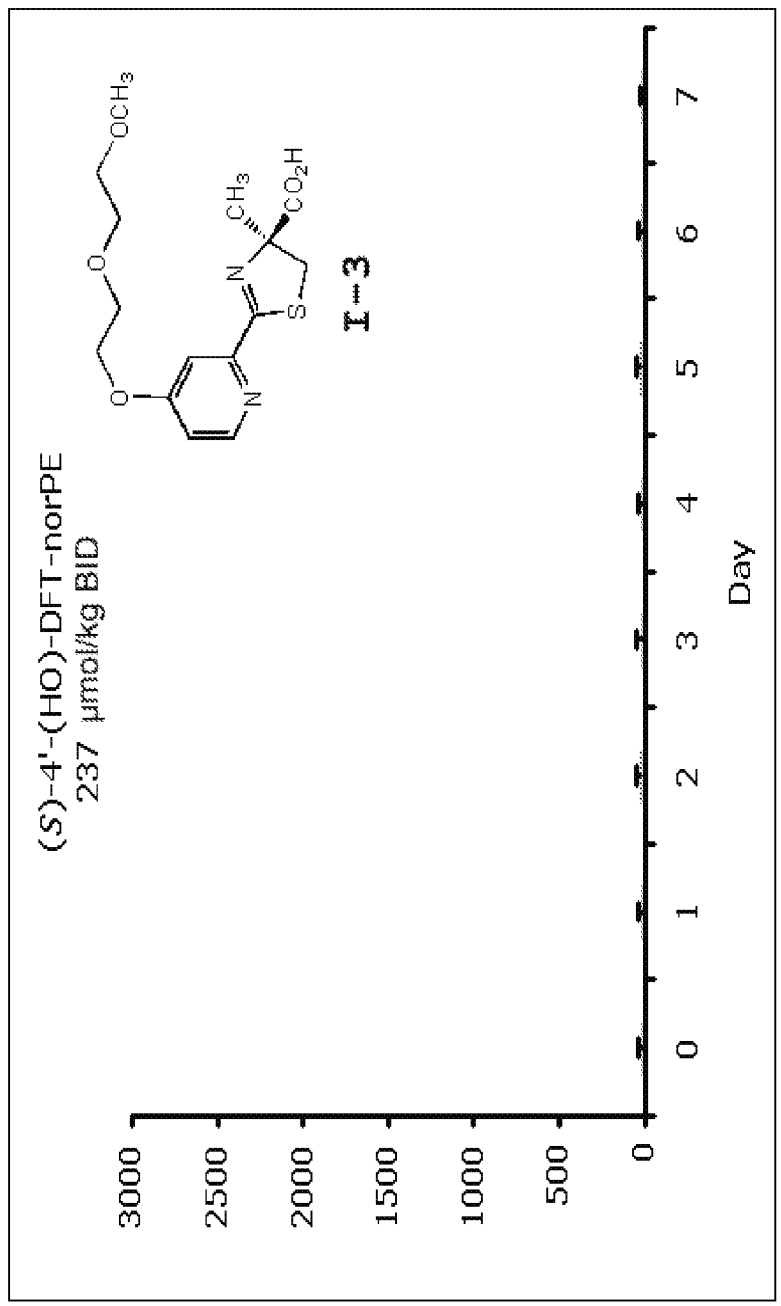

In the present study, the impact was evaluated that affixing a polyether fragment to DFT itself would have on nephrotoxicity. Accordingly, groups of rats (n=5) were given I-2 or I-3 po twice daily at 237 µmol/kg/dose (474 µmol/kg/d)×7 d. All of the animals survived the compound dosing regimen. The animals' urinary Kim-1 excretion remained within error of that of the baseline (day 0) levels (FIGS. 5D and 5F). In addition, the BUN and SCr of all of the I-2- or I-3-treated rats were well within the normal range. Thus, as with the DADFT pharmacophore, fixing a polyether fragment to the DFT framework was an effective tool in further reducing nephrotoxicity.

Conclusion

It was previously demonstrated that the severe nephrotoxicity associated with 1 could be ameliorated by the removal of the pyridine nitrogen of 1 to provide 2, and simple hydroxylation of the aromatic ring of 2 to yield 3 (FIG. 1) (Bergeron et al., "Effects of C-4 Stereochemistry and C-4' Hydroxylation on the Iron Clearing Efficiency and Toxicity of Desferrithiocin Analogs." J. Med. Chem. 1999, 42, 2432-2440; Bergeron et al., "Iron Chelators and Therapeutic Uses." In: Abraham, ed. Burger's Medicinal Chemistry. 6th. Wiley; New York: 2003. pp. 479-561). Further reduction in 3-induced nephrotoxicity, observed when the compound was given po at 237 µmol/kg twice daily, was accomplished by the addition of polyether fragments, e.g., 4, 5, and 7 (FIG. 1 and Table 1) (Bergeron et al., "(S)-4,5-Dihydro-2-(2-hydroxy-4-hydroxyphenyl)-4-methyl-4-thiazolecarboxylic Acid Polyethers: A Solution to Nephrotoxicity." J. Med. Chem. 2006, 49, 2772-2783; Bergeron et al., "Design, Synthesis, and Testing of Non-Nephrotoxic Desazadesferrithiocin Polyether Analogs." J. Med. Chem. 2008, 51, 3913-3923; Bergeron et al., "The Impact of Polyether Chain Length on the Iron Clearing Efficiency and Physiochemical Properties of Desferrithiocin Analogs." J. Med. Chem. 2010, 53, 2843-2853; Bergeron et al., "Desferrithiocin Analog Iron Chelators: Iron Clearing Efficiency, Tissue Distribution, and Renal Toxicity." Biometals, 2011, 24, 239-258). The purpose of the present study was to determine how these same structural modifications to DFT itself would impact the new compounds' ICE and nephrotoxicity. Accordingly, three DFT analogs, I-1, I-2, and I-3, were synthesized and assessed for their lipophilicity, ICE properties in rats and primates, and for their toxicity in rats.

DFT (1) (Table 1) and its analogs were all significantly more water-soluble (lower log $P_{app}$) than the corresponding DADFT analogs, e.g., 1 vs. 2, I-1 vs. 3, I-2 vs. 7, and I-3 vs. 9. There was an excellent correlation between ICE and log $P_{app}$ in rodents amongst the DFT analogs 1, I-1, I-2, and I-3 (FIG. 4), with the more lipophilic compounds having a greater ICE. This trend is in keeping with previous observations that more lipophilic compounds have better ICE properties. The biliary ferrokinetics of the DFT and DADFT compounds in the bile duct-cannulated rats (FIG. 3) have similar temporal properties, except for compound 7. This compound has the highest ICE and a very protracted iron clearance time.

In the primates, the DADFT analogs were consistently better deferration agents than the corresponding DFT analogs (Table 1). The most unusual finding was with compound I-3, a DFT analog with a 4'-(3,6-dioxaheptyloxy) ether functionality fixed to the 4'-position of 1. When the compound was given po to the primates, its ICE was only 6.1±1.8% vs. 14.2±2.4% in the rats, and a PR value of 0.4 (Table 1). However, when the monkeys were given the compound sc, its ICE increased to 16.9±7.3%, with a PR value now at 1.2. This is consistent with the idea that compound I-3 simply was not absorbed well orally in primates.

The effects of structural modification of DFT on its renal toxicity were assessed in rats using a urinary Kim-1 (kidney injury molecule) assay (Vaidya et al., "A Rapid Urine Test for Early Detection of Kidney Injury." *Kidney. Int.* 2009, 76, 108-114), as well as monitoring BUN and SCr. The most notable finding was that fixing a hydroxyl group or a polyether fragment to the DFT aromatic ring resulted in a nearly identical reduction in renal toxicity as seen after the same modification to DADFT (FIG. 5). Although some nephrotoxicity was noted with both hydroxylated DADFT and DFT analogs, 3 and I-1, respectively, the introduction of polyether groups into either pharmacophore resulted in compounds with little to no impact on renal function, e.g., 7, I-2, and I-3 (FIGS. 5E, 5D, and 5F).

In summary, manipulation of the DFT aromatic ring, e.g., hydroxylation, or the introduction of a polyether functionality, can have a marked and unexpected effect on the compound's ICE and renal toxicity (Table 1 and FIG. 5). Although the resulting DFT chelators were generally as effective in the rodents as their DADFT counterparts, they were less active in the primates. However, the tissue distribution of I-1, I-2, and I-3 in rodents remains to be elucidated. Higher levels of these analogs in the critical target organs, i.e., the liver, heart, and pancreas, could easily compensate for their somewhat lower ICE values. Nevertheless, at least one of the DFT polyethers (I-2) was sufficiently effective at iron clearance in rodents (ICE=11.7±1.2%) and primates (ICE=18.0±5.2%) and had an acceptable toxicity profile to merit further studies.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (A):

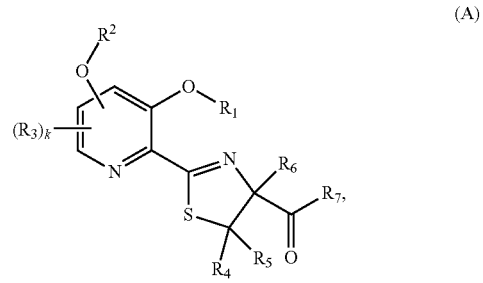

or a pharmaceutically acceptable salt thereof, wherein:
$R_1$ is hydrogen, alkyl, acyl, or an oxygen protecting group;
$R_2$ is $C_{1-12}$ alkyl optionally substituted with one or more substituents independently selected from the group consisting of hydroxyl, unsubstituted alkyloxy, —$CO_2H$, and —$CO_2R_{31}$; acyl; —$[(CH_2)_n$—$O]_x$—$[(CH_2)_n$—$O]_y$—$R"$; or —$[(CH_2)_n$—$O]_x$—$[(CH_2)_n$—$O]_y$—$(CH_2)_n$—$NR_{10}$—$C(=O)O$—$R"$;
$R_{31}$ is substituted or unsubstituted $C_{1-6}$ alkyl;
each occurrence of $R_3$ is independently alkyl, arylalkyl, or —$OR_8$;

$R_4$, $R_5$, and $R_6$ are each independently hydrogen or alkyl;

$R_7$ is —$OR_9$ or —$SR_9$;

$R_8$ is hydrogen, alkyl, acyl, or an oxygen protecting group;

$R_9$ is hydrogen, alkyl, an oxygen protecting group when attached to an oxygen atom, or a sulfur protecting group when attached to a sulfur atom;

$R_{10}$ is hydrogen, alkyl, acyl, or a nitrogen protecting group;

R' is hydrogen or an oxygen protecting group;

R" is hydrogen or acyl;

each occurrence of n is independently an integer from 1 to 8, inclusive;

k is an integer from 0 to 2, inclusive;

x is an integer from 1 to 8, inclusive; and y is an integer from 0 to 8, inclusive.

2. A compound of Formula (A):

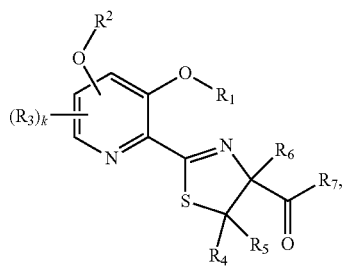

(A)

or a pharmaceutically acceptable salt thereof, wherein:

$R_1$ is hydrogen, alkyl, acyl, an oxygen protecting group,

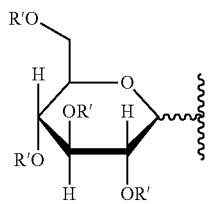

or

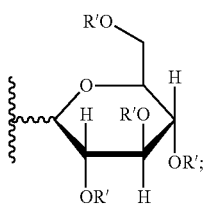

$R_2$ is hydrogen, alkyl, acyl, an oxygen protecting group, —[($CH_2$)$_n$—O]$_x$—[($CH_2$)$_n$—O]$_y$—R", or —[($CH_2$)$_n$—O]$_x$—[($CH_2$)$_n$—O]$_y$—($CH_2$)$_n$—$NR_{10}$—C(=O)O—R";

each occurrence of $R_3$ is independently alkyl, arylalkyl, or —$OR_8$;

$R_4$, $R_5$, and $R_6$ are each independently hydrogen or alkyl;

$R_7$ is —$OR_9$ or —$SR_9$;

$R_8$ is hydrogen, alkyl, acyl, an oxygen protecting group,

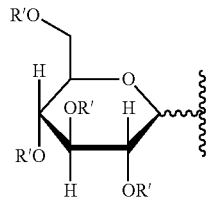

or

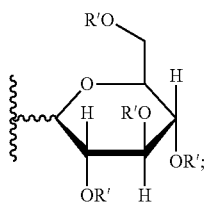

$R_9$ is hydrogen, alkyl,

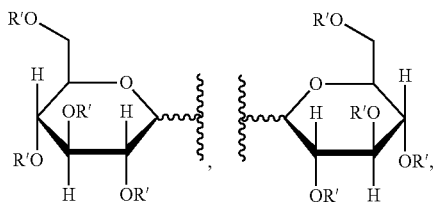

an oxygen protecting group when attached to an oxygen atom, or a sulfur protecting group when attached to a sulfur atom;

$R_{10}$ is hydrogen, alkyl, acyl, or a nitrogen protecting group;

R' is hydrogen or an oxygen protecting group;

R" is hydrogen, alkyl, acyl, an oxygen protecting group,

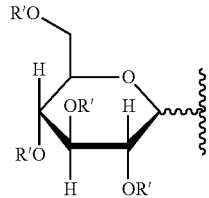

or

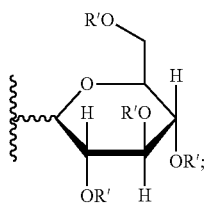

each occurrence of n is independently an integer from 1 to 8, inclusive;
k is an integer from 0 to 2, inclusive;
x is an integer from 1 to 8, inclusive; and
y is an integer from 0 to 8, inclusive;
provided that at least one of $R_1$ and $R_9$ is

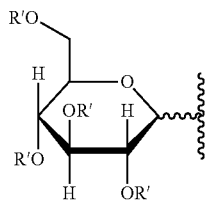

or

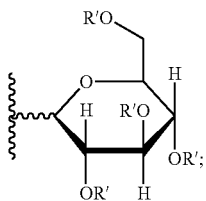

or $R_2$ is $-[(CH_2)_n-O]_x-[(CH_2)_n-O]_y-R''$ or $-[CH_{2n}-O]_x-[(CH_2)_n-O]_y-(CH_2)_n-NR_{10}-C(=O)O-R''$, and R'' is

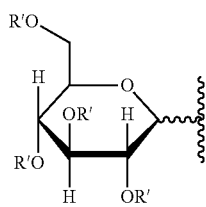

or

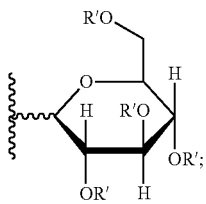

or $R_3$ is $-OR_8$, $R_8$ is

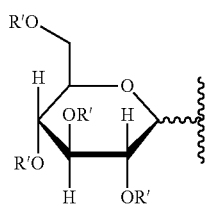

or

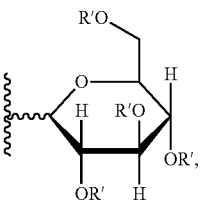

and k is 1 or 2.

3. The compound of claim 1, wherein the compound is of Formula (B):

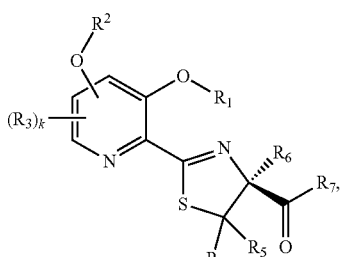

(B)

or a pharmaceutically acceptable salt thereof.

4. The compound of claim 1, wherein the compound is of the formula:

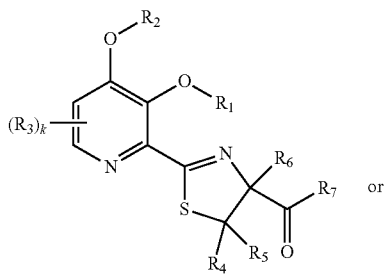

(C)

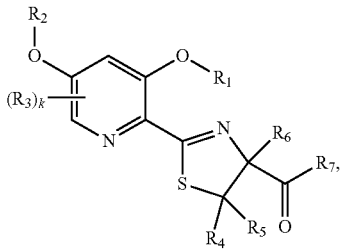

(D)

or a pharmaceutically acceptable salt thereof.

5. The compound of claim 1, wherein the compound is of the formula:

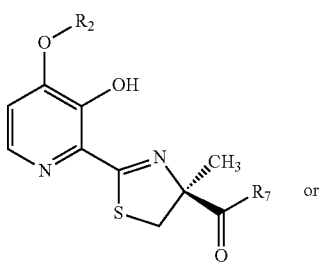

(G)

(H)

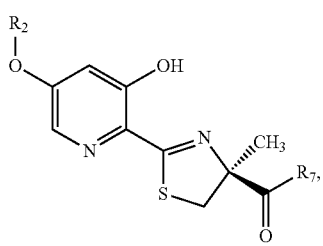

or a pharmaceutically acceptable salt thereof.

6. The compound of claim 1, wherein the compound is of the formula:

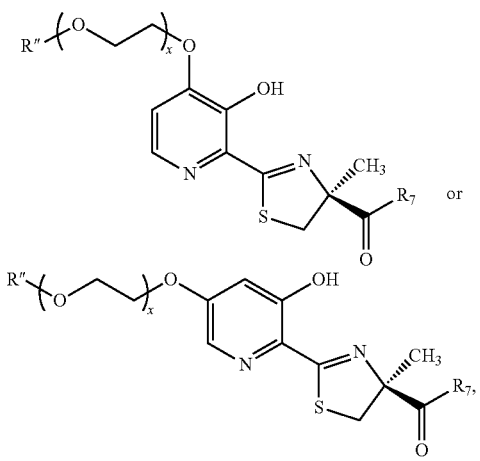

or a pharmaceutically acceptable salt thereof.

7. The compound of claim 1, wherein the compound is of the formula:

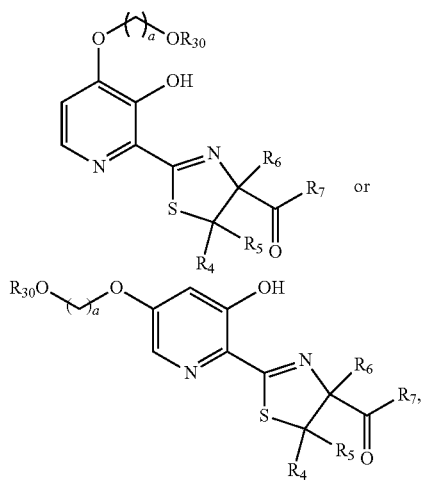

or a pharmaceutically acceptable salt thereof, wherein $R_{30}$ is H or unsubstituted $C_{1-6}$ alkyl; and a is 2, 3, 4, 5, 6, 7, 8, 9, or 10.

8. The compound of claim 7, wherein the compound is of the formula:

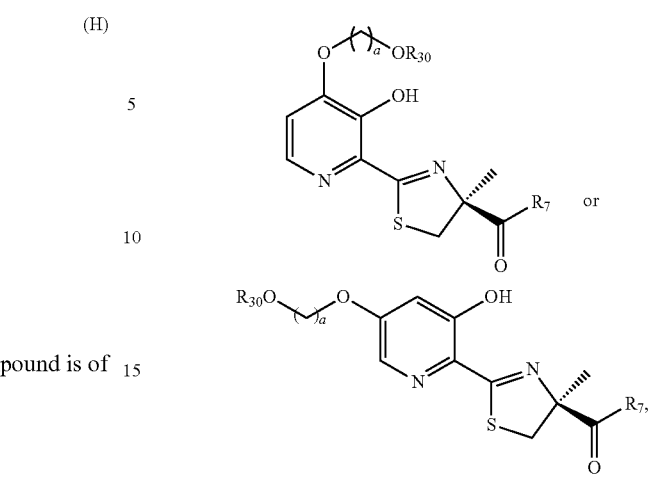

or a pharmaceutically acceptable salt thereof.

9. The compound of claim 1, wherein the compound is of the formula:

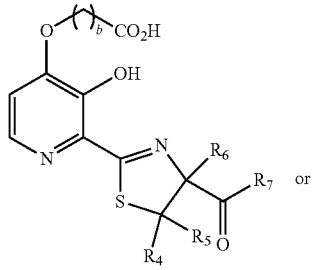

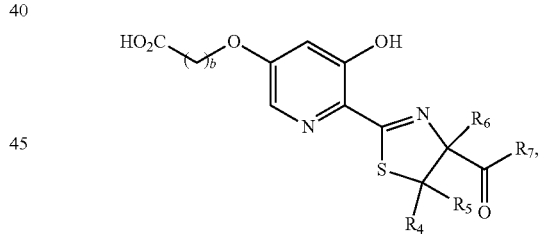

or a pharmaceutically acceptable salt thereof, wherein b is 1, 2, 3, 4, 5, 6, 7, 8, 9, or 10.

10. The compound of claim 9, wherein the compound is of the formula:

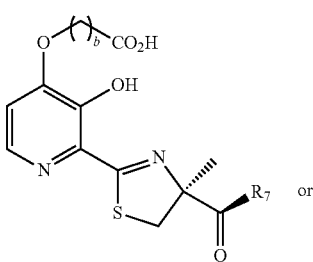

-continued

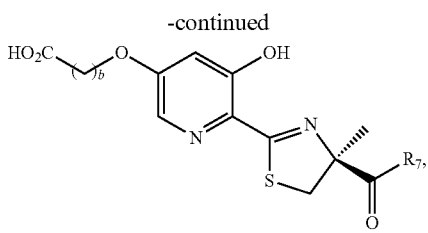

or a pharmaceutically acceptable salt thereof.

11. The compound of claim 1, or a pharmaceutically acceptable salt thereof, wherein $R_2$ is

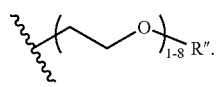

12. The compound of claim 11, or a pharmaceutically acceptable salt thereof, wherein $R_2$ is

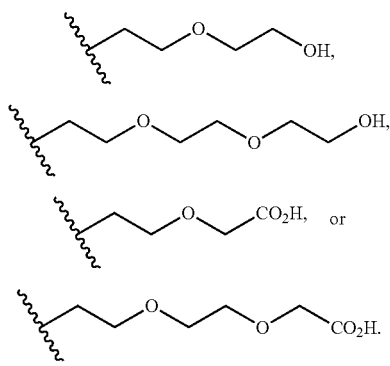

13. The compound of claim 1, or a pharmaceutically acceptable salt thereof, wherein $R_2$ is $C_{1-12}$ alkyl substituted with one or more substituents independently selected from the group consisting of hydroxyl, unsubstituted alkyloxy, —$CO_2H$, and —$CO_2R_{31}$.

14. The compound of claim 1, or a pharmaceutically acceptable salt thereof, wherein $R_4$ and $R_5$ are each hydrogen.

15. The compound of claim 1, or a pharmaceutically acceptable salt thereof, wherein $R_7$ is —$OR_9$.

16. The compound of claim 1, wherein the compound is of the formula:

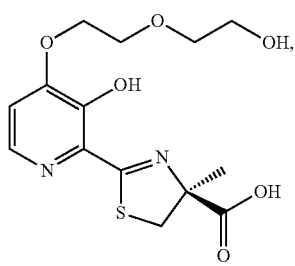

-continued

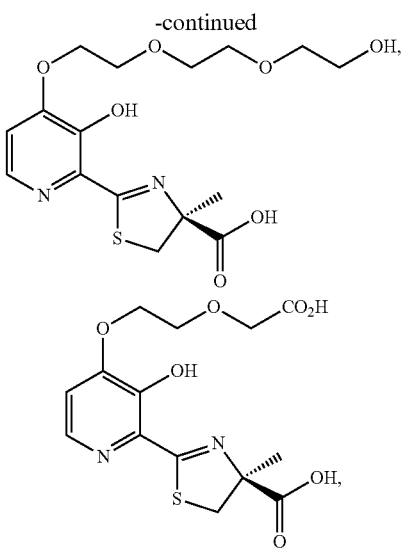

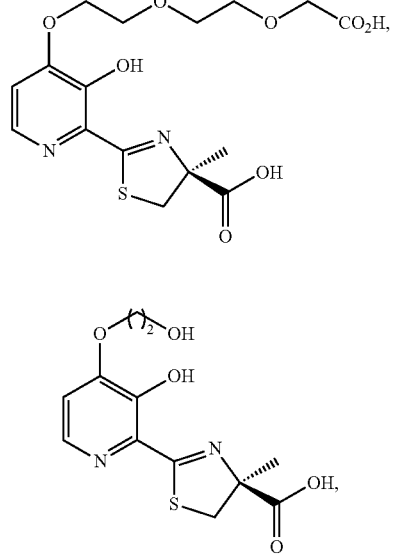

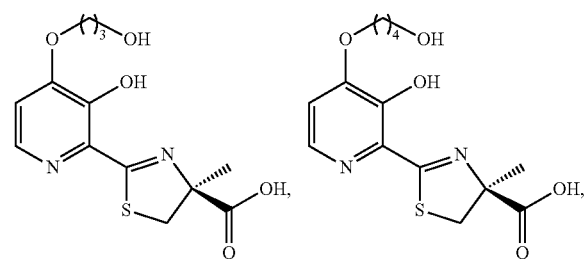

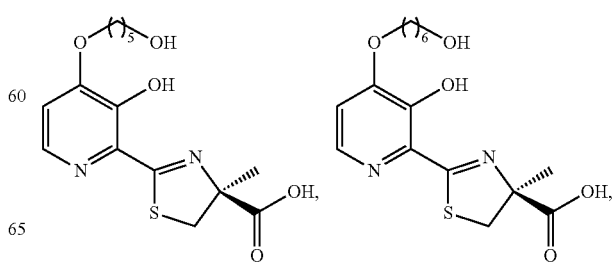

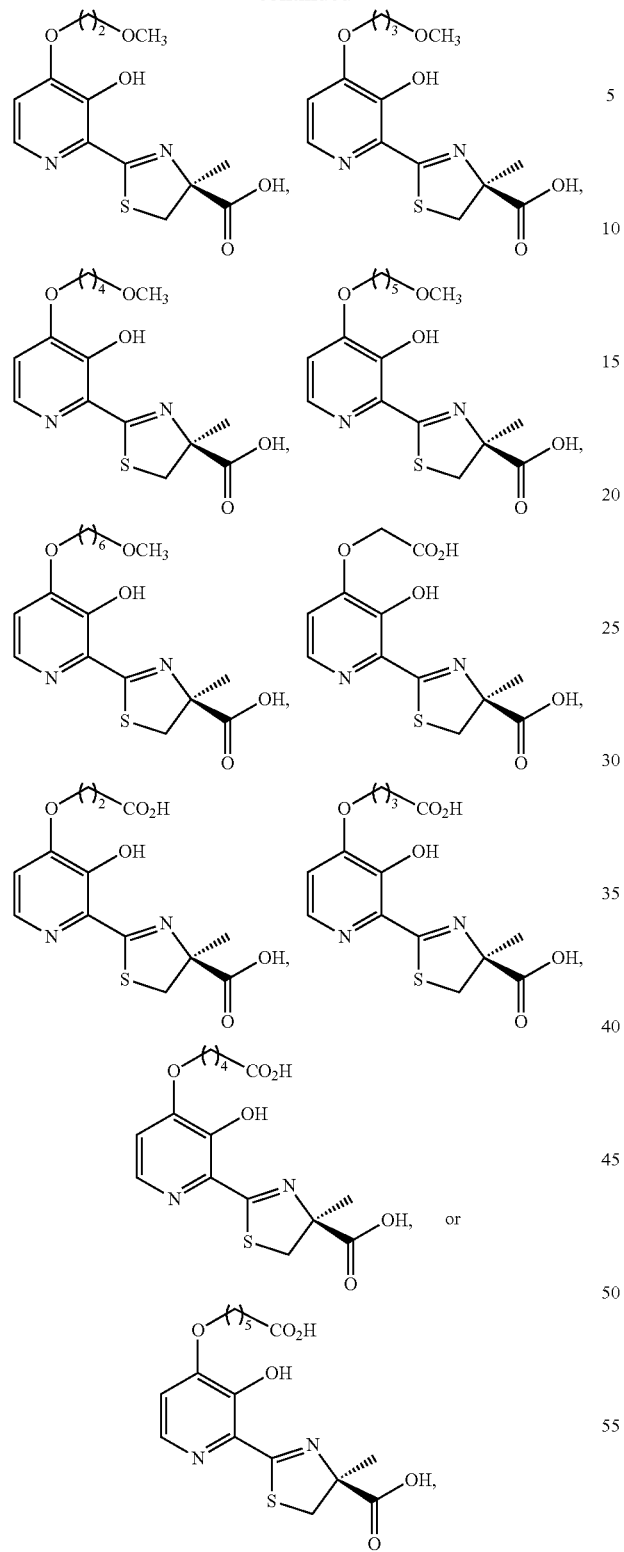
or a pharmaceutically acceptable salt thereof.
17. The compound of claim 1, wherein the compound is of the formula:
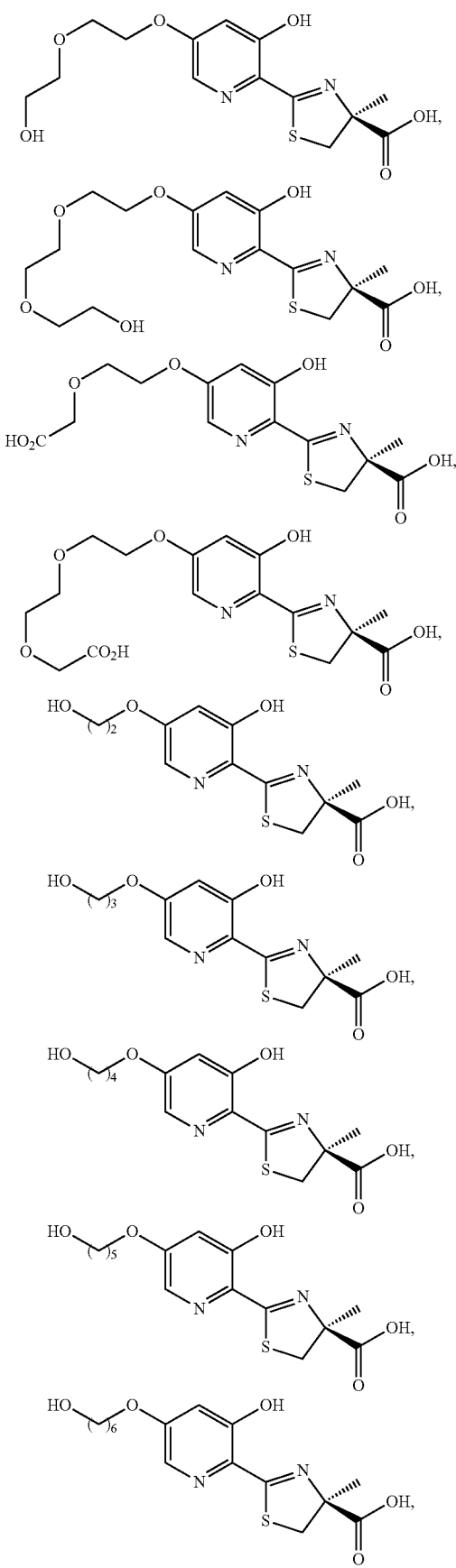

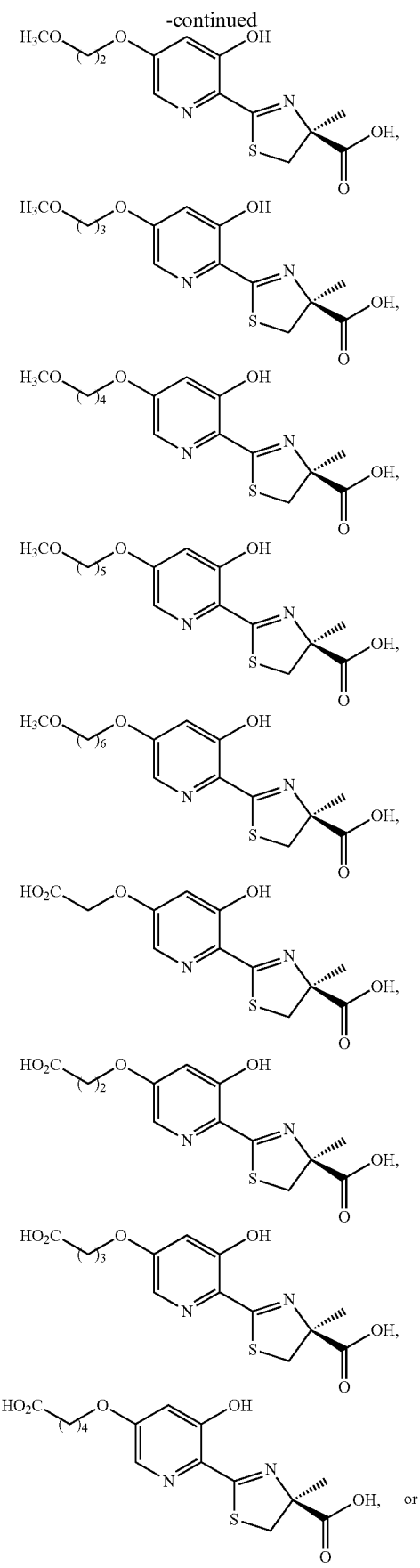

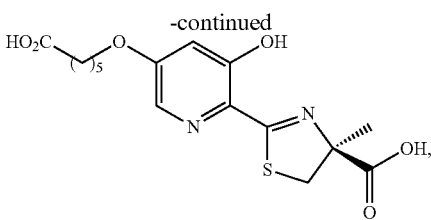

or a pharmaceutically acceptable salt thereof.

18. A pharmaceutical composition comprising a compound of claim 1, or a pharmaceutically acceptable salt thereof, and optionally a pharmaceutically acceptable excipient.

19. A method of treating a pathological condition in a subject in need thereof, the method comprising administering to the subject a therapeutically effective amount of a compound of claim 1, or a pharmaceutically acceptable salt thereof, wherein the pathological condition is iron overload, aluminum overload, lanthanide overload, actinide overload, oxidative stress, transfusional iron overload, thalassemia, primary hemochromatosis, secondary hemochromatosis, diabetes, liver disease, heart disease, radiation injury, Friedreich's ataxia (FRDA), macular degeneration, closed head injury, irritable bowel disease, reperfusion injury, malaria.

20. The compound of claim 1, or a pharmaceutically acceptable salt thereof, wherein $R_1$ is hydrogen.

21. The compound of claim 1, or a pharmaceutically acceptable salt thereof, wherein $R_2$ is unsubstituted $C_{1-12}$ alkyl.

22. The compound of claim 1, or a pharmaceutically acceptable salt thereof, wherein $R_2$ is —$(CH_2)_2$—OH, —$(CH_2)_3$—OH, —$(CH_2)_4$—OH, —$(CH_2)_5$—OH, —$(CH_2)_6$—OH, —$(CH_2)_7$—OH, or —$(CH_2)_8$—OH.

23. The compound of claim 1, or a pharmaceutically acceptable salt thereof, wherein $R_2$ is —$(CH_2)_2$—$OCH_3$, —$(CH_2)_3$—$OCH_3$, —$(CH_2)_4$—$OCH_3$, —$(CH_2)_5$—$OCH_3$, —$(CH_2)_6$—$OCH_3$, —$(CH_2)_7$—$OCH_3$, or —$(CH_2)_8$—$OCH_3$.

24. The compound of claim 1, or a pharmaceutically acceptable salt thereof, wherein $R_2$ is —$CH_2$—$CO_2H$, —$(CH_2)_2$—$CO_2H$, —$(CH_2)_3$—$CO_2H$, —$(CH_2)_4$—$CO_2H$, —$(CH_2)_5$—$CO_2H$, —$(CH_2)_6$—$CO_2H$, or —$(CH_2)_7$—$CO_2H$.

25. The compound of claim 1, or a pharmaceutically acceptable salt thereof, wherein $R_6$ is —$CH_3$.

26. The compound of claim 15, or a pharmaceutically acceptable salt thereof, wherein $R_9$ is hydrogen.

27. The compound of claim 1, wherein the compound is of the formula:

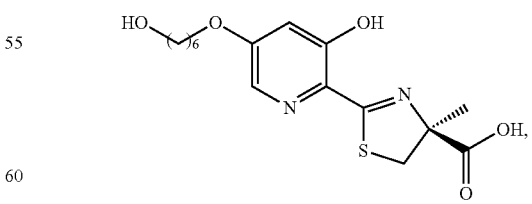

or a pharmaceutically acceptable salt thereof.

28. The method of claim 19, wherein the pathological condition is iron overload.

29. The method of claim 19, wherein the pathological condition is transfusional iron overload.

30. The compound of claim 2, or a pharmaceutically acceptable salt thereof, provided that $R_1$ is

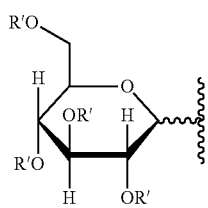

or

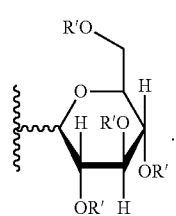

31. The compound of claim 2, or a pharmaceutically acceptable salt thereof, provided that $R_9$ is

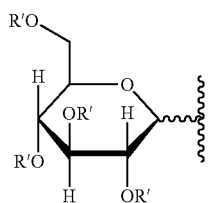

or

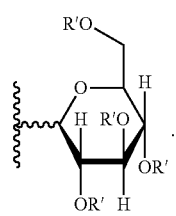

32. The compound of claim 2, or a pharmaceutically acceptable salt thereof, provided that:
$R_2$ is $-[(CH_2)_n-O]_x-[(CH_2)_n-O]_y-R''$ or $-[(CH_2)_n-O]_x-[(CH_2)_n-O]_y-(CH_2)_n-NR_{10}-C(=O)O-R''$; and $R''$ is

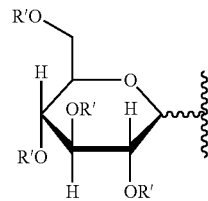

or

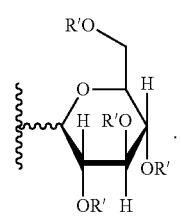

33. The compound of claim 2, or a pharmaceutically acceptable salt thereof, provided that:
$R_3$ is $-OR_8$;
$R_8$ is

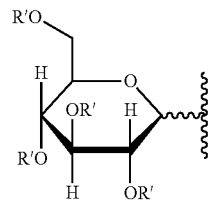

or

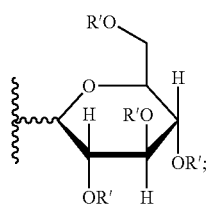

and k is 1 or 2.

34. The compound of claim 2, wherein the compound is of the formula:

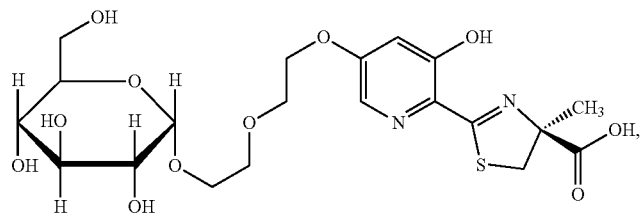

-continued
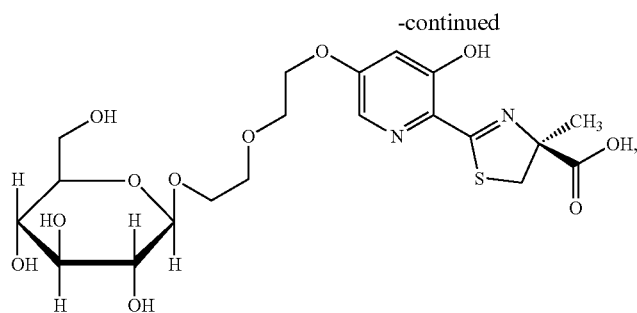
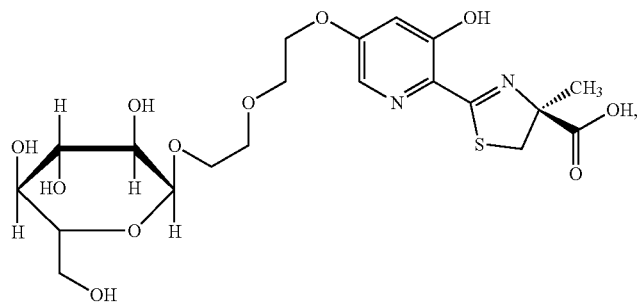
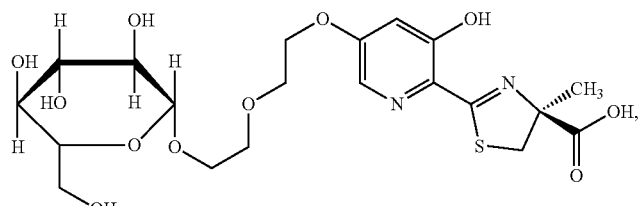
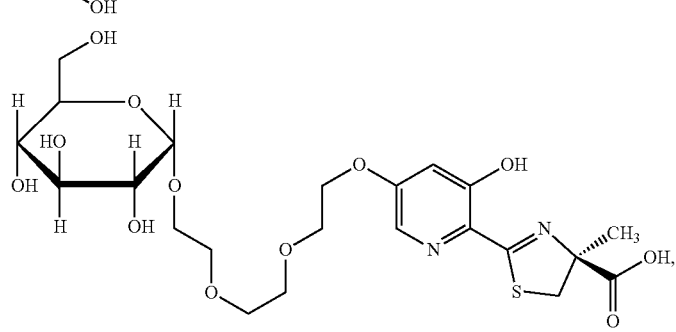
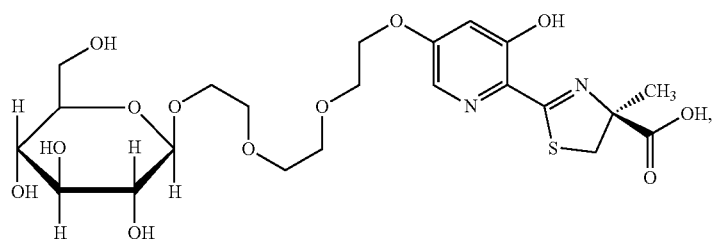
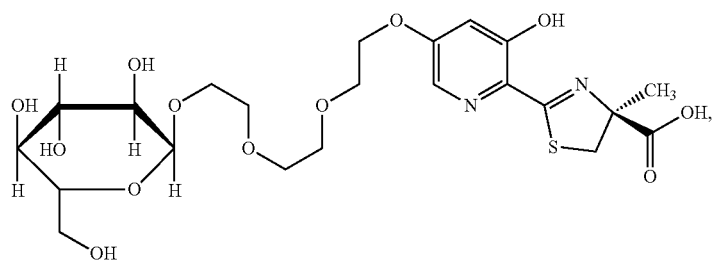

-continued
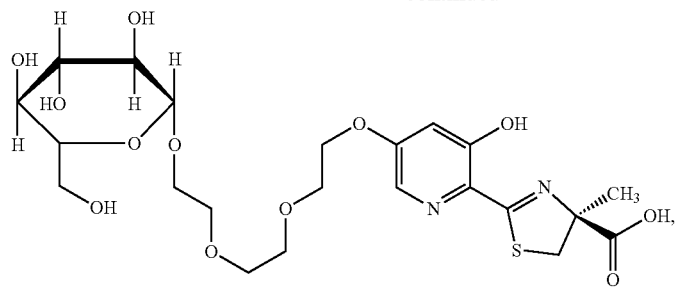
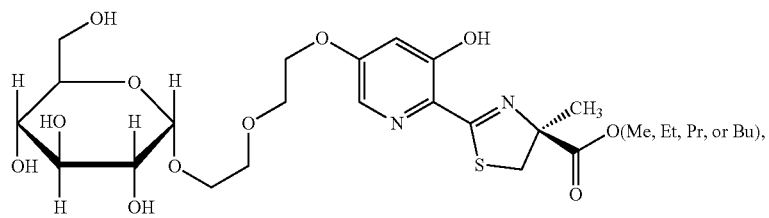
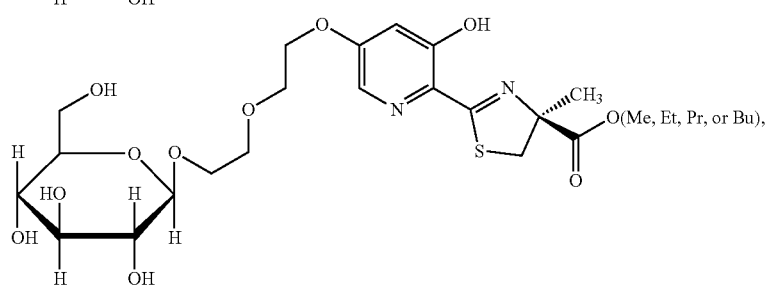
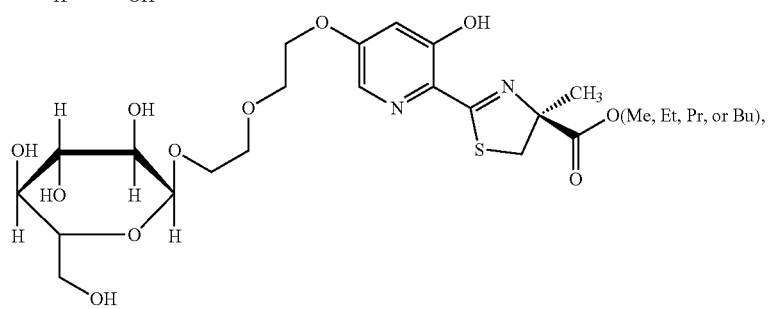
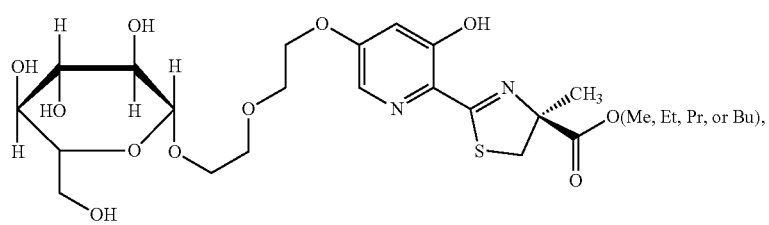
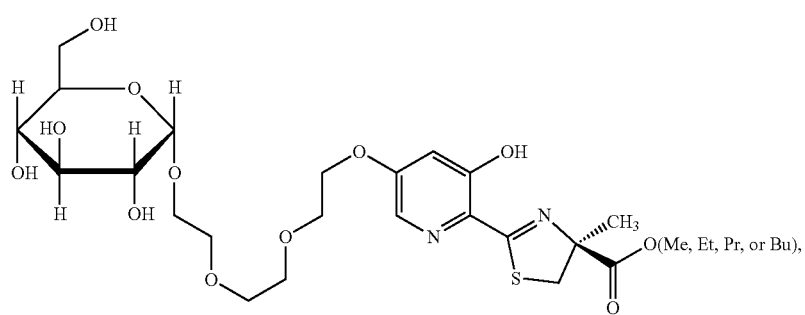

-continued

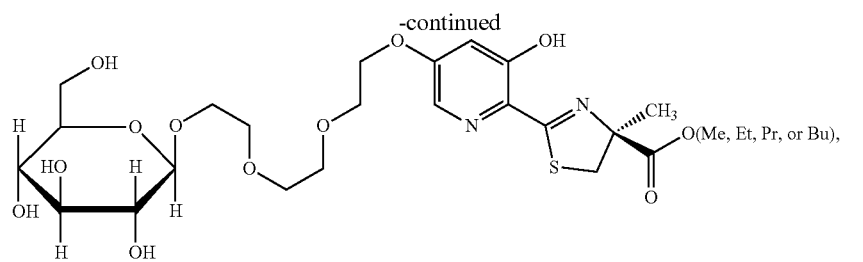

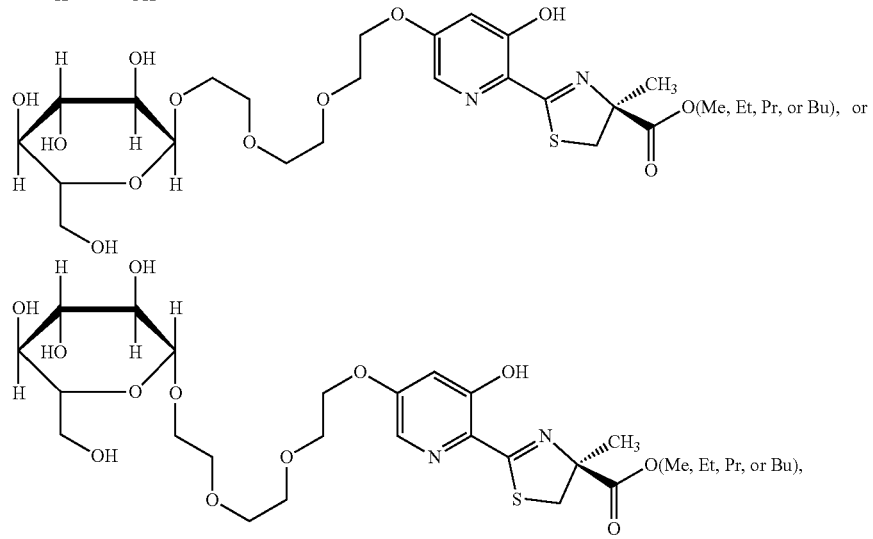

or a pharmaceutically acceptable salt thereof.

35. A pharmaceutical composition comprising a compound of claim 2, or a pharmaceutically acceptable salt thereof, and optionally a pharmaceutically acceptable excipient.

36. A method of treating a pathological condition in a subject in need thereof, the method comprising administering to the subject a therapeutically effective amount of a compound of claim 2, or a pharmaceutically acceptable salt thereof, wherein the pathological condition is iron overload, aluminum overload, lanthanide overload, actinide overload, oxidative stress, transfusional iron overload, thalassemia, primary hemochromatosis, secondary hemochromatosis, diabetes, liver disease, heart disease, radiation injury, Friedreich's ataxia (FRDA), macular degeneration, closed head injury, irritable bowel disease, reperfusion injury, malaria.

* * * * *

UNITED STATES PATENT AND TRADEMARK OFFICE
CERTIFICATE OF CORRECTION

PATENT NO. : 10,010,535 B2
APPLICATION NO. : 15/038188
DATED : July 3, 2018
INVENTOR(S) : Raymond J. Bergeron, Jr.

It is certified that error appears in the above-identified patent and that said Letters Patent is hereby corrected as shown below:

In the Claims

In Claim 19, at Column 198, Line 26, the language "reperfusion injury, malaria." should be changed to: --reperfusion injury, or malaria--.

In Claim 36, at Column 206, Line 39, the language "reperfusion injury, malaria." should be changed to: --reperfusion injury, or malaria--.

Signed and Sealed this
Twenty-sixth Day of May, 2020

Andrei Iancu
*Director of the United States Patent and Trademark Office*